(12) United States Patent
Lennon et al.

(10) Patent No.: US 7,049,270 B2
(45) Date of Patent: May 23, 2006

(54) POTASSIUM GLYPHOSATE FORMULATIONS

(75) Inventors: Patrick J. Lennon, Webster Groves, MO (US); Xiangyang Chen, Chesterfield, MO (US); Graciela B. Arhancet, Creve Coeur, MO (US); Jeanette A. Glaenzer, University City, MO (US); Jane L. Gillespie, St. Louis, MO (US); Jeffrey A. Graham, Wildwood, MO (US); David Z. Becher, St. Louis, MO (US); Daniel R. Wright, St. Louis, MO (US); Henry E. Agbaje, St. Louis, MO (US); Xiaodong C. Xu, Valley Park, MO (US); William Abraham, Wildwood, MO (US); Ronald J. Brinker, Ellisville, MO (US); Norman R. Pallas, Florissant, MO (US); Al S. Wideman, St. Louis, MO (US); Martin D. Mahoney, St. Peters, MO (US); Susan L. Henke, Webster Groves, MO (US)

(73) Assignee: Monsanto Technology LLC, St. Louis, MO (US)

( * ) Notice: Subject to any disclaimer, the term of this patent is extended or adjusted under 35 U.S.C. 154(b) by 185 days.

(21) Appl. No.: 09/926,521

(22) PCT Filed: May 21, 2001

(86) PCT No.: PCT/US01/16550

§ 371 (c)(1),
(2), (4) Date: Apr. 26, 2002

(87) PCT Pub. No.: WO01/89302

PCT Pub. Date: Nov. 29, 2001

(65) Prior Publication Data

US 2003/0104943 A1 Jun. 5, 2003

Related U.S. Application Data

(60) Provisional application No. 60/274,368, filed on Mar. 8, 2001, provisional application No. 60/273,234, filed on Mar. 2, 2001, provisional application No. 60/206,628, filed on May 24, 2000, and provisional application No. 60/205,524, filed on May 19, 2000.

(51) Int. Cl.
*A01N 25/00* (2006.01)
*A01N 57/02* (2006.01)

(52) U.S. Cl. ...................................... 504/206; 504/358

(58) Field of Classification Search ................. 504/206, 504/358
See application file for complete search history.

(56) References Cited

U.S. PATENT DOCUMENTS

| | | | |
|---|---|---|---|
| 3,799,758 A | 3/1974 | Franz | |
| 3,853,530 A | 12/1974 | Franz | |
| 3,977,860 A | 8/1976 | Franz | |
| 4,140,513 A | 2/1979 | Prill | |

(Continued)

FOREIGN PATENT DOCUMENTS

| | | |
|---|---|---|
| DE | 4019362 A1 | 1/1991 |
| DE | 197 52 552 A1 | 6/1999 |
| EP | 0 274 369 B1 | 9/1990 |
| EP | 0 472 310 A1 | 2/1992 |
| EP | 0 290 416 B1 | 6/1993 |
| EP | 0 617 894 A1 | 10/1994 |
| GB | 1 566 770 | 5/1980 |
| GB | 2 267 825 A | 12/1993 |
| WO | WO 95/16352 | 6/1995 |
| WO | WO 95/33379 | 12/1995 |
| WO | WO 97/16969 | 5/1997 |
| WO | WO 97/32476 | 9/1997 |
| WO | WO 97/36494 | 10/1997 |
| WO | WO 98/17109 | 4/1998 |
| WO | WO 98/17113 A1 | 4/1998 |
| WO | WO 98/33384 | 8/1998 |
| WO | WO 98/33385 | 8/1998 |
| WO | WO 00/15037 | 3/2000 |
| WO | WO 00/41567 | 7/2000 |
| WO | WO 00/59302 A1 | 10/2000 |
| WO | WO 01/10210 A2 | 2/2001 |
| WO | WO 01/11957 A1 | 2/2001 |
| WO | WO 01/20987 A1 | 3/2001 |
| WO | WO 02/26036 A1 | 4/2002 |

OTHER PUBLICATIONS

Turner, D. J. "Effects on glyphosate performance of formulation, additives and mixing with other herbicides". Chapter 15 in The Herbicide Glyphosate. Grossbard et al, ed. Butterworths : Boston. P. 221–239. 1985.*
International Search Report for PCT/US 02/15977 dated Oct. 2, 2003.
Research Disclosure Publication No. RDI 15334, Industrial Opportunities Ltd. Homewell–Havant–Hampshire PO91EF, Jan. 1977, United Kingdom.
Annex to Form PCT/ISA/206 of Search Report for PCT/US 01/16550.
International Search Report for PCT/US 01/16550 dated Mar. 5, 2003.
Wyrill, III, J.B. and Burnside, O.C., Glyphosate Toxicity to Common Milkweed and Hemp Dogbane as Influenced by Surfactants, *Weed Science,* May 1977, pp. 275–287, vol. 25, Issue 3.

*Primary Examiner*—S. Mark Clardy
(74) *Attorney, Agent, or Firm*—Senniger Powers; Joseph A. Schaper

(57) ABSTRACT

A herbicidal composition is provided comprising an aqueous solution of N-phosphonomethylglycine, predominantly in the form of the potassium salt thereof, at a concentration of at least 300 g a.e./l of the composition; and a surfactant component in solution or stable suspension, emulsion, or dispersion in the water, comprising one or more surfactants in a total amount of about 20 to about 300 g/l of the composition, wherein the composition has a viscosity of less than about 250 centipoise at 0° C. or a Gardner color value less than 10.

32 Claims, 4 Drawing Sheets

U.S. PATENT DOCUMENTS

| | | | |
|---|---|---|---|
| 4,159,901 A | * 7/1979 | Beestman et al. | 504/206 |
| 4,405,531 A | 9/1983 | Franz | |
| 4,431,765 A | 2/1984 | Doshak et al. | |
| 4,481,026 A | 11/1984 | Prisbylla | |
| 4,507,250 A | 3/1985 | Bakel | |
| 5,118,444 A | 6/1992 | Nguyen | |
| 5,317,003 A | 5/1994 | Kassebaum et al. | |
| 5,389,598 A | 2/1995 | Berk et al. | |
| 5,464,807 A | 11/1995 | Claude et al. | |
| 5,668,085 A | 9/1997 | Forbes et al. | |
| 5,683,958 A | 11/1997 | Berger et al. | |
| 5,703,015 A | 12/1997 | Berger et al. | |
| 5,750,468 A | * 5/1998 | Wright et al. | 504/206 |
| 5,863,863 A | 1/1999 | Hasebe et al. | |
| 6,093,681 A | * 7/2000 | Ward et al. | 504/206 |
| 6,121,199 A | 9/2000 | Berger et al. | |
| 6,184,182 B1 | 2/2001 | Gillespie et al. | |
| 6,313,074 B1 | * 11/2001 | Suzuki et al. | 504/362 |
| 6,667,276 B1 | 12/2003 | Maier et al. | |

* cited by examiner

POTASSIUM GLYPHOSATE FORMULATIONS

FIELD OF THE INVENTION

The present invention relates to aqueous pesticide formulations containing high concentrations of a herbicide, such as the potassium salt of glyphosate, together with surfactants or other adjuvants, including formulations which form anisotropic aggregates (AA) or liquid crystals (LC) on or in the foliage of a plant. More specifically, the present invention relates to glyphosate containing herbicidal formulations containing one or more surfactants that form anisotropic aggregates and/or liquid crystals to facilitate the introduction, uptake and translocation of glyphosate throughout the plant. Methods of killing or controlling unwanted vegetation using such formulations are also described. The invention also relates to novel surfactants and pesticide compositions containing such surfactants.

BACKGROUND OF THE INVENTION

Glyphosate is well known in the art as an effective post-emergent foliar-applied herbicide. In its acid form, glyphosate has a structure represented by formula (1):

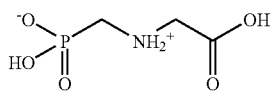
(1)

and is relatively insoluble in water (0.16% by weight at 25° C.). For this reason it is typically formulated as a water-soluble salt.

Monobasic, dibasic and tribasic salts of glyphosate can be made. However, it is generally preferred to formulate glyphosate and apply glyphosate to plants in the form of a monobasic salt. The most widely used salt of glyphosate is the mono(isopropylammonium), often abbreviated to IPA, salt. Commercial herbicides of Monsanto Company having the IPA salt of glyphosate as active ingredient include Roundup®, Roundup® Ultra, Roundup® Xtra and Rodeo® herbicides. All of these are aqueous solution concentrate (SL) formulations and are generally diluted in water by the user prior to application to plant foliage. Another glyphosate salt which have been commercially formulated as SL formulations include the trimethylsulfonium, often abbreviated to TMS, salt, used for example in Touchdown® herbicide of Zeneca (Syngenta).

Various salts of glyphosate, methods for preparing salts of glyphosate, formulations of glyphosate or its salts and methods of use of glyphosate or its salts for killing and controlling weeds and other plants are disclosed in U.S. Pat. No. 4,507,250 to Bakel, U.S. Pat. No. 4,481,026 to Prisbylla, U.S. Pat. No. 4,405,531 to Franz, U.S. Pat. No. 4,315,765 to Large, U.S. Pat. No. 4,140,513 to Prill, U.S. Pat. No. 3,977,860 to Franz, U.S. Pat. No. 3,853,530 to Franz, and U.S. Pat. No. 3,799,758 to Franz. The aforementioned patents are incorporated herein in their entirety by reference.

Among the water soluble salts of glyphosate known in the literature, but never used commercially before the priority filing date hereof, is the potassium salt, having a structure represented by formula (2):

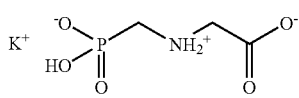
(2)

in the ionic form predominantly present in aqueous solution at a pH of about 4. Glyphosate potassium salt has a molecular weight of 207. This salt is disclosed, for example, by Franz in U.S. Pat. No. 4,405,531 cited above, as one of the "alkali metal" salts of glyphosate useful as herbicides, with potassium being specifically disclosed as one of the alkali metals, along with lithium, sodium, cesium and rubidium. Example C discloses the preparation of the monopotassium salt by reacting the specified amounts of glyphosate acid and potassium carbonate in an aqueous medium.

Very few herbicides have been commercialized as their potassium salts. The Pesticide Manual, 11th Edition, 1997, lists as potassium salts the auxin type herbicides 2,4-DB ((2,4-dichlorophenoxy)butanoic acid), dicamba (3,6-dichloro-2-methoxybenzoic acid), dichlorprop (2-(2,4-dichlorophenoxy)propanoic acid), MCPA ((4-chloro-2-methylphenoxy)acetic acid), and picloram (4-amino-3,5,6-trichloro-2-pyridinecarboxylic acid), the active ingredient of certain herbicide products sold by Dow Agrosciences under the trademark Tordon.

The solubility of glyphosate potassium salt in water is recorded in pending application Ser. No. 09/444,766, filed Nov. 22, 1999, the entire disclosure of which is incorporated herein by reference. As disclosed therein, glyphosate potassium salt has a solubility in pure water at 20° C. of about 54% by weight, that is, about 44% glyphosate acid equivalent (a.e.) by weight. This is very similar to the solubility of the IPA salt. Concentrations expressed as percent by weight herein relate to parts by weight of salt or acid equivalent per 100 parts by weight of solution. Thus a simple aqueous solution concentrate of glyphosate potassium salt can readily be provided at a concentration of, for example, 44% a.e. by weight, comparable to that commercially obtainable with glyphosate IPA salt, as in the aqueous solution concentrate available from Monsanto Company under the name Roundup® D-Pak™. Somewhat higher concentrations can be obtained by slight overneutralization, 5 to 10% for example, of an aqueous solution of glyphosate potassium salt with potassium hydroxide.

A major advantage of the IPA salt over many other salts of glyphosate has been the good compatibility in aqueous solution concentrate formulations of that salt with a wide range of surfactants. As used herein, the term "surfactant" is intended to include a wide range of adjuvants that can be added to herbicidal glyphosate compositions to enhance the herbicidal efficacy thereof, as compared to the activity of the glyphosate salt in the absence of such adjuvant, stability, formulability or other beneficial solution property, irrespective of whether such adjuvant meets a more traditional definition of "surfactant."

Glyphosate salts generally require the presence of a suitable surfactant for best herbicidal performance. The surfactant can be provided in the concentrate formulation, or it can be added by the end user to the diluted spray composition. The choice of surfactant has a major bearing on herbicidal performance. For example, in an extensive study reported in Weed Science, 1977, volume 25, pages 275–287, Wyrill and Burnside found wide variation among surfactants in their ability to enhance the herbicidal efficacy of glyphosate, applied as the IPA salt.

Beyond some broad generalizations, the relative ability of different surfactants to enhance the herbicidal effectiveness of glyphosate is highly unpredictable.

Surfactants tending to give the most useful enhancement of glyphosate herbicidal effectiveness are generally but not exclusively cationic surfactants, including surfactants which form cations in aqueous solution or dispersion at pH levels of around 4–5 characteristic of SL formulations of monobasic salts of glyphosate. Examples are long-chain (typically $C_{12}$ to $C_{18}$) tertiary alkylamine surfactants and quaternary alkylammonium surfactants. An especially common tertiary alkylamine surfactant used in aqueous solution concentrate formulations of glyphosate IPA salt has been the very hydrophilic surfactant polyoxyethylene (15) tallowamine, i.e., tallowamine having in total about 15 moles of ethylene oxide in two polymerized ethylene oxide chains attached to the amine group as shown in formula (3):

(3)

wherein R is a mixture of predominantly $C_{16}$ and $C_{18}$ alkyl and alkenyl chains C); derived from tallow and the total of m+n is an average number of about 15.

For certain applications, it has been found desirable to use a somewhat less hydrophilic alkylamine surfactant, such as one having less than about 10 moles of ethylene oxide, as suggested in U.S. Pat. No. 5,668,085 to Forbes et al., for example polyoxyethylene (2) cocoamine. That patent discloses illustrative aqueous compositions comprising such a surfactant together with the IPA, ammonium or potassium salts of glyphosate. The highest concentration of glyphosate in the potassium salt formulations shown in Table 3 of the '085 patent is 300 g glyphosate a.e./l, with a weight ratio of glyphosate a.e. to surfactant of 2:1.

A class of alkoxylated alkylamines is disclosed in WO 00/59302 for use in herbicidal spray compositions. Potassium glyphosate solutions including various Jeffamine™ EO/PO propylamines or propyldiamines are described therein.

A wide variety of quaternary ammonium surfactants have been disclosed as components of aqueous solution concentrate formulations of glyphosate IPA salt. Illustrative examples are N-methylpolyoxyethylene (2) cocoammonium chloride, disclosed in European Patent No. 0274369, N-methylpolyoxyethylene (15) cocoammonium chloride, disclosed in U.S. Pat. No. 5,317,003, and various quaternary ammonium compounds having formula (4):

$(R^1)(R^2)(R^3)N^+$—$CH_2CH_2O$—$(CH_2CH(CH_3)O)_nH\ Cl^-$ (4)

where $R^1$, $R^2$ and $R^3$ are each $C_{1-3}$ alkyl groups and n is an average number from 2 to 20, disclosed in U.S. Pat. No. 5,464,807.

PCT Publication No. WO 97/16969 discloses aqueous solution concentrate compositions of glyphosate, in the form of the IPA, methylammonium and diammonium salts, comprising a quaternary ammonium surfactant and an acid salt of a primary, secondary or tertiary alkylamine compound.

Other cationic surfactants which have been indicated as useful in aqueous solution concentrate compositions of glyphosate salts include those disclosed in PCT Publication No. WO 95/33379. It is further disclosed in PCT Publication No. WO 97/32476 that highly concentrated aqueous compositions of glyphosate salts can be made with certain of these same cationic surfactants, with the further addition of a defined component that enhances stability of the compositions. Glyphosate salts exemplified therein are the IPA salt and the mono- and diammonium salts.

Among amphoteric or zwitterionic surfactants reported to be useful components of aqueous solution concentrate formulations of glyphosate IPA salt are alkylamine oxides such as polyoxyethylene (10–20) tallowamine oxide, disclosed in U.S. Pat. No. 5,118,444.

Nonionic surfactants are generally reported to be less effective in enhancing herbicidal activity than cationic or amphoteric surfactants when used rBN as the sole surfactant component of SL formulations of glyphosate IPA salt; exceptions appear to include certain alkyl polyglucosides, as disclosed for example in Australian Patent No. 627503, and polyoxyethylene (10–100) $C_{16-22}$ alkylethers, as disclosed in PCT Publication No. WO 98/17109. Anionic surfactants, except in combination with cationic surfactants as disclosed in U.S. Pat. Nos. 5,389,598 and 5,703,015, are generally of little interest in SL formulations of glyphosate IPA salt. The '015 patent discloses a surfactant blend of a dialkoxylated alkylamine and an anionic eye irritancy reducing compound. The surfactant blend is disclosed as being suitable for preparation of aqueous solution concentrate formulations of various glyphosate salts, the potassium salt being included in the list of salts mentioned. Concentrates of the '015 patent contain from about 5 to about 50%, preferably about 35% to about 45% glyphosate a.i. and from about 5 to about 25% surfactant. Further, PCT Publication No. WO 00/08927 discloses the use of certain polyalkoxylated phosphate esters in combination with certain polyalkoxylated amidoamines in glyphosate containing formulations. Potassium is identified as one of several salts of glyphosate noted as being "suitable."

Recently, a class of alkyletheramine, alkyletherammonium salt and alkyletheramine oxide surfactants has been disclosed in U.S. Pat. No. 5,750,468 to be suitable for preparation of aqueous solution concentrate formulations of various glyphosate salts, the potassium salt being included in the list of salts mentioned. It is disclosed therein that an advantage of the subject surfactants when used in an aqueous composition with glyphosate salts is that these surfactants permit the glyphosate concentration of the composition to be increased to very high levels.

It is likely that serious consideration of glyphosate potassium salt as a herbicidal active ingredient has been inhibited by the relative difficulty in formulating this salt as a highly concentrated SL product together with preferred surfactant types. For example, a widely used surfactant in glyphosate IPA salt compositions, namely polyoxyethylene (15) tallowamine of formula (3) above, is highly incompatible in aqueous solution with glyphosate potassium salt. Further, PCT Publication No. WO 00/15037 notes the low compatibility of alkoxylated alkylamine surfactants in general with high-strength glyphosate concentrates. As disclosed therein, in order to "build in" an effective level of surfactant, an alkylpolyglycoside surfactant is required in combination with an alkoxylated alkylamine surfactant to obtain high-strength concentrates containing the potassium salt of glyphosate.

The addition of such alkylpolyglycosides resulted in higher viscosity formulations (as compared to formulations without alkylpolyglycosides). Such an increase in the viscosity of these high-strength formulations is undesirable for various reasons. In addition to being more difficult to conveniently pour from the container or to wash residues therefrom, the deleterious effects resulting from higher viscosity formulations is more dramatically observed with respect to pumping requirements. Increasing volumes of liquid aqueous glyphosate products are being purchased by end-users in large refillable containers sometimes known as shuttles, which typically have an integral pump or connector for an external pump to permit transfer of liquid. Liquid aqueous glyphosate products are also shipped in bulk, in large tanks having a capacity of up to about 100,000 liters. The liquid is commonly transferred by pumping to a storage tank at a facility operated by a wholesaler, retailer or cooperative, from which it can be further transferred to shuttles or smaller containers for onward distribution. Because large quantities of glyphosate formulations are purchased and transported in early spring, the low temperature pumping characteristics of such formulations are extremely important.

When such alkylpolyglycosides (e.g., Agrimul™ APG-2067 and 2-ethyl-hexyl glucoside) are added to a glyphosate concentrate, the formulated product is dark brown in color. It is desirable for a formulated glyphosate product to be lighter in color than the alkylpolyglycoside-containing products as disclosed in WO 00/15037, which have a color value of 14 to 18 as measured by a Gardner colorimeter. When dye is added to a formulated glyphosate product having a Gardner color greater than about 10, the concentrate remains dark brown in color. Concentrates having a Gardner color value of 10 are difficult to dye blue or green as is often desired to distinguish the glyphosate product from other herbicidal products.

It would be desirable to provide a storage-stable aqueous concentrate composition (i.e. formulation) of the potassium salt of glyphosate, or other glyphosate salts other than IPA glyphosate, having an agriculturally useful surfactant content, or that is "fully loaded" with surfactant. These formulations exhibit a reduced viscosity such that they may be pumped with standard bulk pumping equipment at 0° C. at rates of at least 7.5 gallons per minute, usually more than 10 gallons per minute and preferably greater than 12.5 gallons per minute. An "agriculturally useful surfactant content" means containing one or more surfactants of such a type or types and in such an amount that a benefit is realized by the user of the composition in terms of herbicidal effectiveness by comparison with an otherwise similar composition containing no surfactant. By "fully loaded" is meant having a sufficient concentration of a suitable surfactant to provide, upon conventional dilution in water and application to foliage, herbicidal effectiveness on one or more important weed species without the need for further surfactant to be added to the diluted composition.

By "storage-stable," in the context of an aqueous concentrate composition of glyphosate salt further containing a surfactant, is meant not exhibiting phase separation on exposure to temperatures up to about 50° C. for 14–28 days, and preferably not forming crystals of glyphosate or salt thereof on exposure to a temperature of about 0° C. for a period of up to about 7 days (i.e., the composition must have a crystallization point of 0° C. or lower). For aqueous solution concentrates, high temperature storage stability is often indicated by a cloud point of about 50° C. or more. Cloud point of a composition is normally determined by heating the composition until the solution becomes cloudy, and then allowing the composition to cool, with agitation, while its temperature is continuously monitored. A temperature reading taken when the solution clears is a measure of cloud point. A cloud point of 50° C. or more is normally considered acceptable for most commercial purposes for a glyphosate SL formulation. Ideally the cloud point should be 60° C. or more, and the composition should withstand temperatures as low as about −10° C. for up to about 7 days without crystal growth, even in the presence of seed crystals of the glyphosate salt.

A surfactant that is described herein as "compatible" with a glyphosate salt at specified surfactant and glyphosate a.e. concentrations is one that provides a storage-stable aqueous concentrate as defined immediately above containing that surfactant and salt at the specified concentrations.

Users of liquid herbicidal products typically meter the dosage by volume rather than by weight, and such products are usually labeled with directions for suitable use rates expressed in volume per unit area, e.g., liters per hectare (l/ha) or fluid ounces per acre (oz/acre). Thus the concentration of herbicidal active ingredient that matters to the user is not percent by weight, but weight per unit volume, e.g., grams per liter (g/l) or pounds per gallon (lb/gal). In the case of glyphosate salts, concentration is often expressed as grams of acid equivalent per liter (g a.e./l).

Historically, surfactant-containing glyphosate IPA salt products such as Roundup® and Roundup® Ultra herbicides of Monsanto Company have most commonly been formulated at a glyphosate concentration of about 360 g a.e./l. The surfactant-containing glyphosate TMS salt product Touchdown® of Zeneca has been formulated at a glyphosate concentration of about 330 g a.e./l. Products at lower a.e. concentration, i.e., more dilute, are also sold in some markets, but carry a cost penalty per unit of glyphosate they contain, primarily reflecting packaging, shipping and warehousing costs.

Further benefits in cost savings and in convenience to the user are possible if a "fully loaded" aqueous concentrate composition, or at least one having an agriculturally useful surfactant content, can be provided at a glyphosate concentration of at least about 320 g a.e./l, 340 g a.e./l, or significantly more than 360 g a.e./l, for example at least about 420 g a.e./l or more, or at least 440, 450, 460, 470, 480, 490, 500, 510, 520, 530, 540, 550 or 600 g a.e./l or more.

At very high glyphosate a.e. concentrations such as these, a significant problem normally occurs. This is the difficulty in pouring and/or pumping of the aqueous concentrate arising from the high viscosity of the concentrate, especially as manifested at low temperatures. It would therefore be highly desirable to have a highly concentrated aqueous solution of glyphosate potassium salt fully loaded with an agriculturally useful surfactant, such formulation preferably being less viscous than glyphosate potassium salt formulations containing alkylpolyglycoside surfactants, such as those disclosed in PCT Publication No. WO 00/15037.

There is a continuing need for surfactants which are compatible with a pesticidal formulation, such as an aqueous glyphosate herbicidal concentrate The surfactants of the invention include novel surfactants as well as known surfactants not previously used in pesticidal formulations. Surfactants that are particularly compatible with potassium glyphosate or other glyphosate salts other than IPA glyphosate have been identified for formulating concentrates having improved viscosity, storage stability and loading as compared to known glyphosate concentrates.

As will be clear from the disclosure that follows, these and other benefits are provided by the present invention.

SUMMARY OF THE INVENTION

The present invention provides novel surfactants for formulating pesticide compositions such as aqueous herbicidal concentrates containing glyphosate or a salt or ester thereof. It has also been discovered that certain surfactants previously unknown for use in agriculture enhance herbicidal efficacy while remaining compatible with the glyphosate after prolonged storage.

One embodiment of the invention is directed to an aqueous herbicidal concentrate composition comprising glyphosate, predominantly in the form of the potassium salt thereof, in solution in an amount of in excess of 300 grams acid equivalent per liter of the composition, and a surfactant component in solution or stable suspension, emulsion or dispersion, comprising one or more surfactants in a total amount of about 20 to about 300 grams per liter of the composition. The composition either (a) has a viscosity of less than about 250 centipoise at 0° C. at 45/s shear rate, (b) has a Gardner color value of not more than 14 when free of dye or a coloring agent, (c) has a viscosity less than a similarly loaded glyphosate potassium salt composition comprising an alkylpolyglycoside surfactant in combination with an alkoxylated alkylamine surfactant, said alkylpolyglycoside and alkylamine surfactants being present in a weight ratio between about 5:1 and 1:1, (d) controls velvetleaf growth as compared to such a similarly loaded glyphosate potassium salt composition, (e) contains a surfactant component that includes no effective amount of an alkylpolyglycoside and is selected such that the composition remains substantially homogeneous when stored at 50° C. for about 14 to 28 days, or (f) includes a surfactant component that contains an effective amount of alkylpolyglycoside in combination with at least one additional surfactant that contains no effective amount of an alkoxylated alkylamine.

Another embodiment of the invention is directed to such a glyphosate concentrate having a viscosity of less than about 250 centipoise at 0° C. at 45/s shear rate, in which the surfactant component comprises one or more amine or quaternary ammonium salt compounds. Each of the compounds includes an alkyl or aryl substituent having from about 4 to about 16 carbon atoms and not more than ten ethylene oxide linkages within the compound. The compounds are present in an amount which enhances the compatibility of the surfactant component with the glyphosate salt.

The invention is also directed to formulations which form anisotropic aggregates comprised of a surfactant on the waxy cuticle of the foliage of the plant upon which the formulation is applied. Other herbicidal formulations of the present invention form liquid crystals comprised of the surfactant on the waxy cuticle of the foliage of the plant upon which the formulation is applied. Still other herbicidal formulations of the present invention form liquid crystals comprised of the surfactant on the waxy cuticle of the foliage and inside the plant upon which the formulation is applied. It has been found that the formation of anisotropic aggregates and both epicuticular and intracuticular liquid crystals do not depend on the presence or absence of a second surfactant and significantly enhance the performance of the herbicidal formulations of the present invention.

BRIEF DESCRIPTION OF THE DRAWINGS

FIGS. A1 and A2 show a birefringent pattern (A1 at 100× magnification polarized light; A2 at 200× magnification polarized light) of negative fan units, which are typical of hexagonal phase liquid crystals. The formulation which produced these epicuticular liquid crystals was comprised of potassium glyphosate and a mixture of surfactants. Specifically, the formulation comprised a 3:1 weight ratio of glyphosate to surfactant with potassium glyphosate and a mixture of Tomah 1816 E20PA and Witcamine 405 surfactants.

FIGS. B1 and B2 show a birefringent pattern (B1 at 100× magnification polarized light; B2 at 200× magnification polarized light) of fine mosaic patterns, which are typical of lamellar phase liquid crystals. The formulation which produced these epicuticular liquid crystals was comprised of isopropylamine glyphosate and a surfactant. Specifically, the formulation comprise a 3:1 weight ratio of glyphosate to surfactant with isopropylamine glyphosate and Plurafac A38 surfactant.

DETAILED DESCRIPTION OF THE INVENTION

Figure 1A:
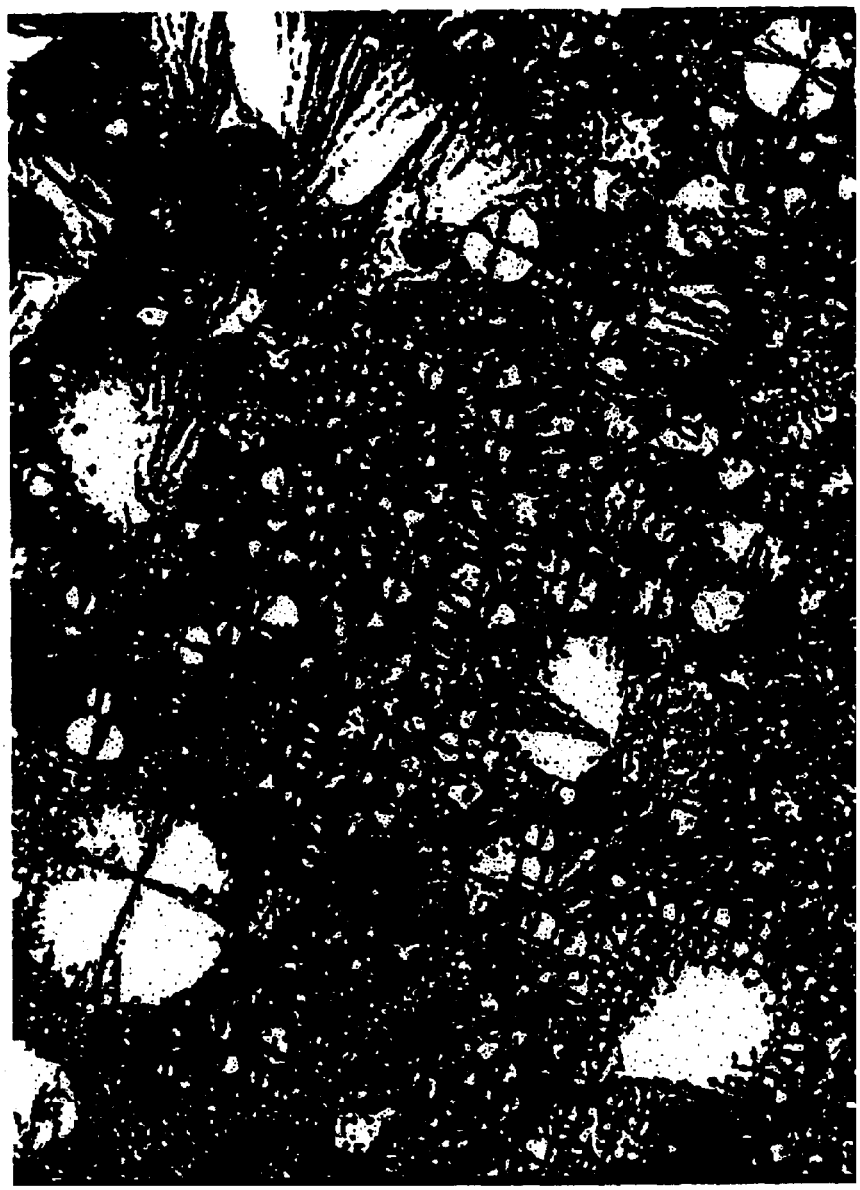
Figure 1B:
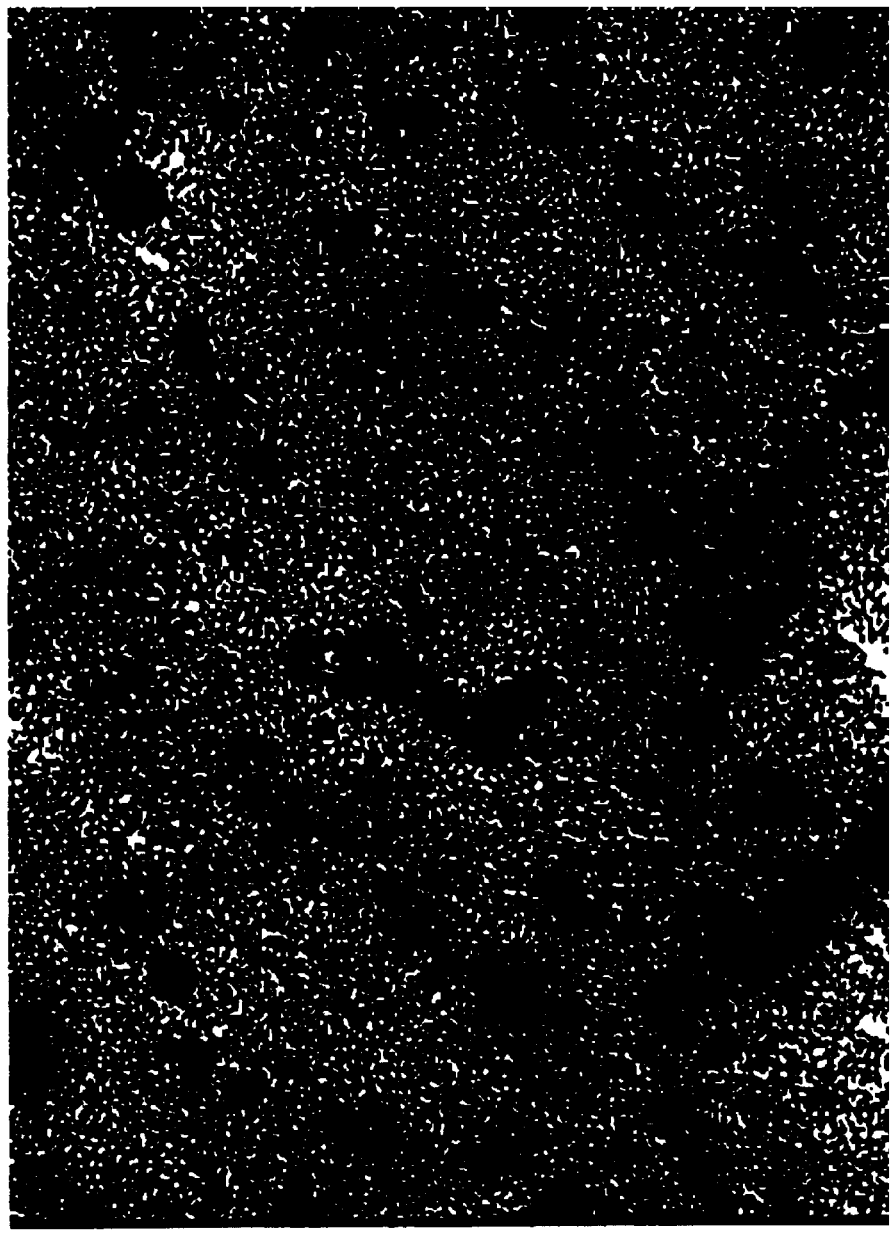
Figure 2A:
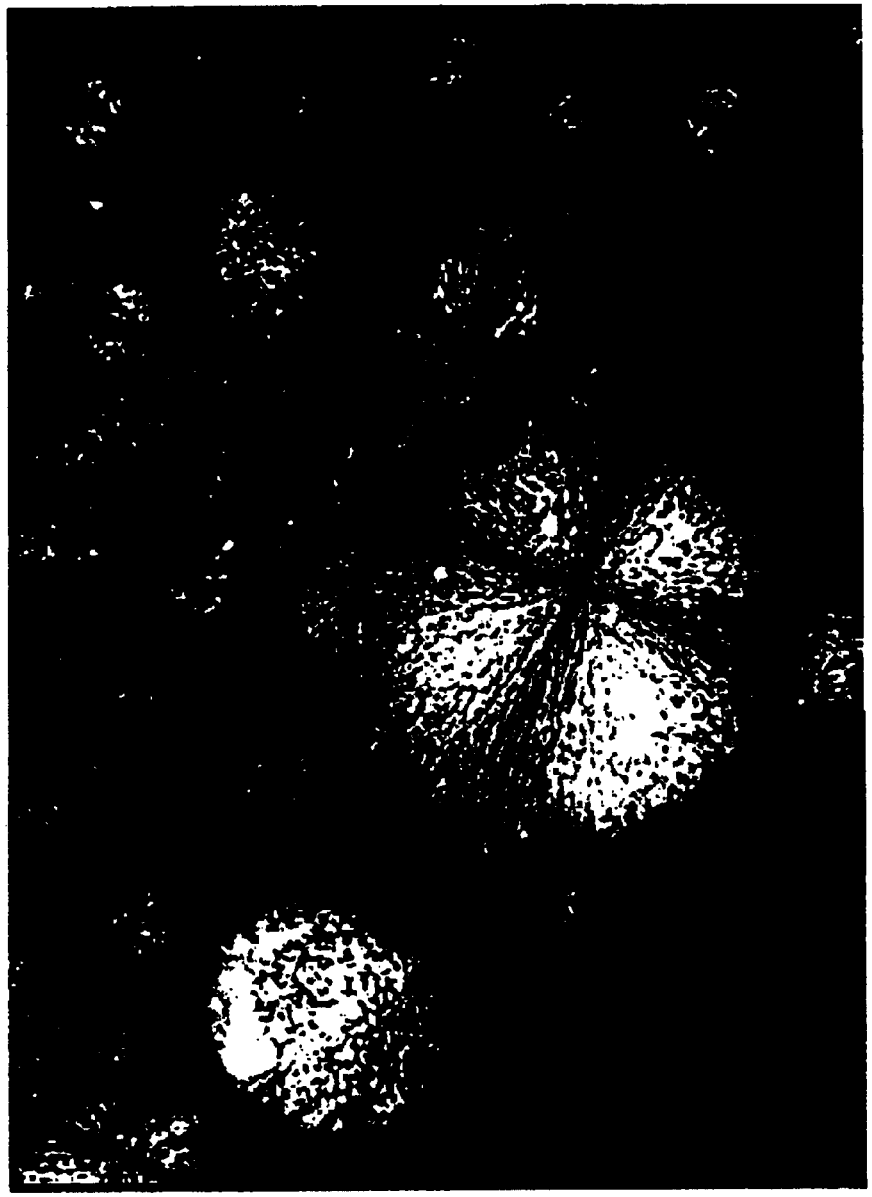
Figure 2B:
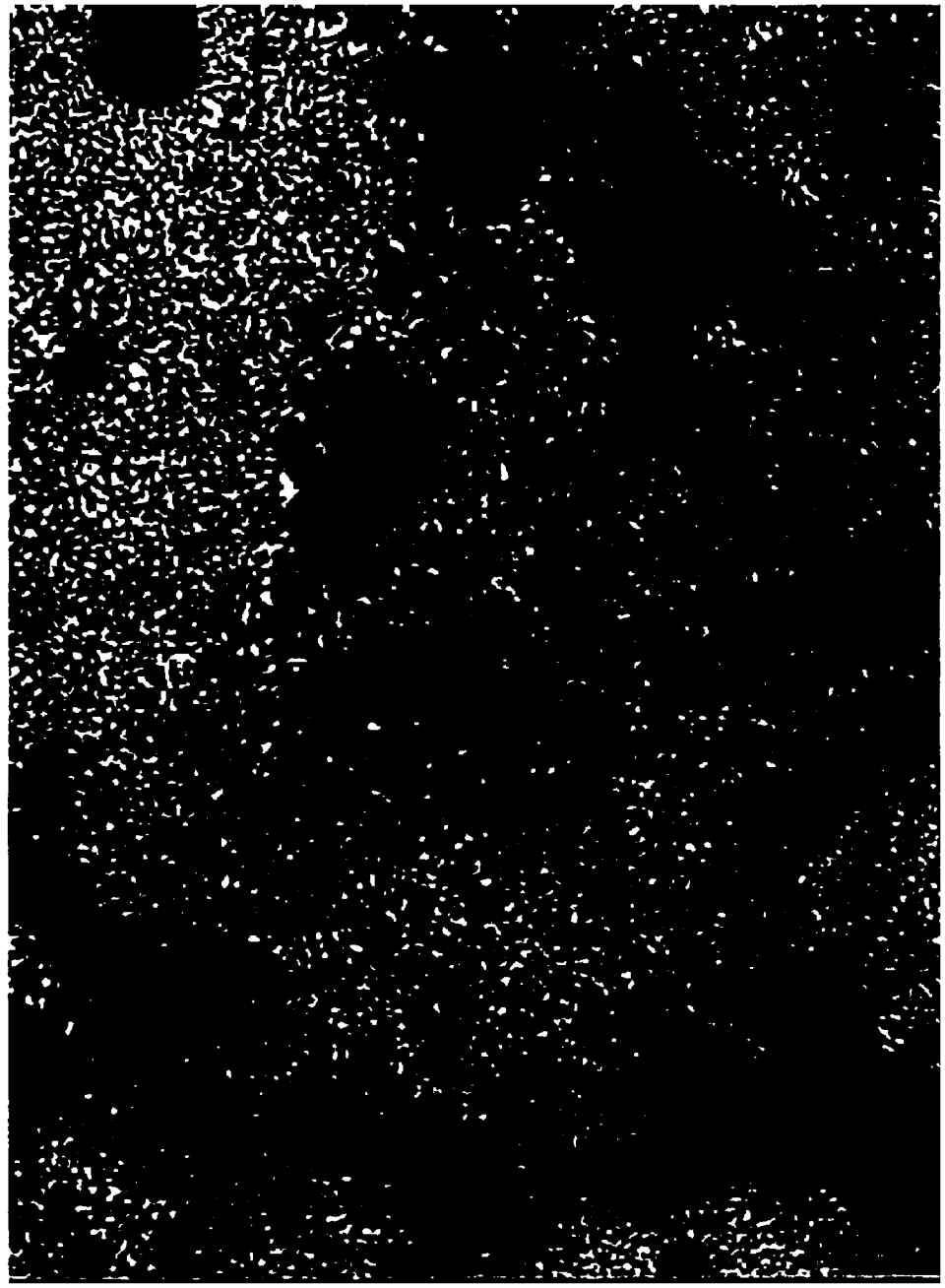

The pesticidal compositions of the invention include aqueous herbicidal compositions of the potassium salt of glyphosate or another glyphosate salt other than IPA glyphosate and a herbicidal efficacy enhancing amount of one or more surfactants. The compositions of the present invention are storage stable over a wide range of temperatures. Compositions of the present invention also exhibit enhanced viscosity characteristics and significantly lighter color as compared to glyphosate potassium salt compositions containing an alkylpolyglycoside surfactant in combination with an alkoxylated alkylamine surfactant. Such "enhanced viscosity" and "enhanced color" formulations are made possible by the selection of a surfactant system that does not include an alkylpolyglycoside surfactant, yet such formulations are still fully loaded so that, upon dilution in water, no additional surfactant is necessary prior to foliar application to attain commercial level performance. It has also been found that alkylpolyglycoside surfactants in combination with surfactants other than alkoxy alkylamine surfactants can be utilized to provide useful glyphosate potassium salt compositions, although without some of the enhanced viscosity characteristics of the more preferred compositions of the present invention that do not contain alkylpolyglycoside surfactants. Further, by controlling the amount of the alkylpolyglycoside present in the glyphosate potassium salt composition, a sufficient amount of alkoxylated alkylamine, or other surfactant described herein, can be utilized to prepare a suitable formulation. Generally, the ratio of alkylpolyglycoside to other surfactant should be between about 1:5 and 5:1, preferably between about 1:5 and 1:1.1, more preferably between about 1:5 and 1:1.2, and most preferably between about 1:5 and 1:1.5. The color of such concentrates is considerably lighter than the concentrates containing greater amounts of alkylpolyglycosides, and is less than 14, preferably less than about 13, 12, 11, 10, 9, 8, 7, 6 or 5.

The herbicidal formulations of the present invention may optionally contain one or more additional surfactants, one or more additional herbicides, and/or other adjuvants or ingredients such as, for example a di-carboxylic acid such as oxalic acid, or a salt or ester thereof. Formulations of the present invention may be prepared on site by the ultimate consumer shortly before application to the foliage of vegetation or weeds to be eliminated or controlled by diluting the aqueous concentrate herbicidal formulations, or by dissolving or dispersing solid particles containing glyphosate. Alternatively, herbicidal formulations of the present invention may be supplied to the ultimate consumer on a "ready to use" basis.

The present invention takes advantage of the high specific gravity of concentrated aqueous solutions of glyphosate potassium salt. Accordingly, at a given percent concentration by weight, an aqueous concentrate composition of glyphosate potassium salt delivers to the user a significantly higher weight of active ingredient per unit volume of the composition than a corresponding composition of glyphosate IPA salt.

In one embodiment of the invention, it has been found that in an aqueous concentrate formulation, an unexpectedly high weight/volume concentration of glyphosate potassium salt can be obtained in the presence of an agriculturally useful surfactant content, with the resulting composition exhibiting acceptable, or in some instance improved, viscosity and storage stability characteristics. The choice of surfactant has been found to be extremely important to achieving these results.

In such embodiment, therefore, the present invention provides an aqueous herbicidal composition comprising:
(1) N-phosphonomethylglycine, predominantly in the form of the ii;) potassium salt thereof, in solution in the water in an amount in excess of about 360 grams N-phosphonomethylglycine acid equivalent per liter of the composition; and
(2) a surfactant component in solution or stable dispersion in the water, comprising one or more surfactants present in an agriculturally useful amount. It is preferred that the surfactant component is selected such that the composition has a viscosity of not greater than about 1000 centipoise at 10° C., a cloud point not lower than about 50° C., and preferably exhibits substantially no crystallization of glyphosate or salt thereof when stored at a temperature of about 0° C. for a period of up to about 7 days. More preferably, the composition has a viscosity of not greater than about 500 centipoise at 45 reciprocal seconds at 10° C., with not greater than 250, 225, 200, 175, 150, 125 or 100 centipoise being most preferred. However, higher viscosities may be acceptable in certain circumstance, such as, for example, where low temperature pumping considerations are not important. The surfactant component, as added to the aqueous herbicidal concentrate composition, is in solution or is a stable suspension, emulsion, or dispersion.

The word "predominantly" in the above context means that at least about 50%, preferably at least about 75% and more preferably at least about 90%, by weight of the glyphosate, expressed as a.e., is present as the potassium salt. The balance can be made up of other salts and/or glyphosate acid but it is preferred that the viscosity, cloud point, and non-crystallization properties of the composition remain within the limits indicated.

As a further aspect of the present invention, a particular class of surfactants has been identified wherein compatibility with glyphosate potassium salt concentrations of greater than 300 g a.e./l to about 600 g a.e./l is unexpectedly high. Accordingly, an embodiment of the invention is a surfactant-containing herbicidal composition as described above wherein the surfactant component predominantly comprises one or more surfactants each having a molecular structure comprising:
(1) a hydrophobic moiety comprising at least one hydrocarbyl or substituted hydrocarbyl group; and
(2) a hydrophilic moiety comprising (i) an amino, ammonium or amine oxide group comprising hydrocarbyl or substituted hydrocarbyl substituents; and/or (ii) a carbohydrate group.

The carbohydrate of the hydrophilic moiety is preferably a sugar such as a monosaccharide, disaccharide or polysaccharide. Preferred sugars include glycosides such as alkyl glycosides, alkyl polyglycosides and aminoglycosides. Surfactants containing on average no more than about two carbohydrate groups per surfactant molecule are preferred.

In such surfactants, the hydrophobic moiety is attached to the hydrophilic moiety in one of the following ways. The terminal atom of the hydrophobic moiety is attached (a) directly to the nitrogen within an amino, ammonium or amine oxide group if present, or (b) directly to the carbohydrate group if present.

In a preferred embodiment, the hydrophobic moiety of the surfactant is a substituted hydrocarbyl group comprising at least one oxyalkylene group in the principle chain. Such substituted hydrocarbyl groups include, for example, alkyloxyalkylene and alkenyloxyalkylene groups containing from one to thirty oxyalkylene groups RO in which R in each of the RO groups is independently $C_2$–$C_4$ alkylene.

In one embodiment of the invention, the surfactant component predominantly comprises one or more surfactants each having a molecular structure comprising:
(1) a hydrophobic moiety having one or a plurality of independently saturated or unsaturated, branched or unbranched, aliphatic, alicyclic or aromatic $C_{3-18}$ hydrocarbyl or hydrocarbylidene groups joined together by 0 to about 7 linkages independently selected from ether, thioether, sulfoxide, ester, thioester and amide linkages, this hydrophobic moiety having in total a number J of carbon atoms where J is about 8 to about 30; and
(2) a hydrophilic moiety comprising:
   (i) an amino group that is cationic or that can be protonated to become cationic, having attached directly thereto 0 to 3 oxyethylene groups or polyoxyethylene chains, these oxyethylene groups and polyoxyethylene chains comprising on average no more than a number E of oxyethylene units per surfactant molecule such that $E+J \leq 50$; and/or
   (ii) an alkyl sugar derivative unit, such as a glycoside, polyglycoside, or aminoglycoide group comprising on average no more than about 2 of the alkyl sugar derivative units per surfactant molecule.

In such surfactants the hydrophobic moiety is attached to the hydrophilic moiety in one of the following ways: (a) directly to an amino group if present, (b) by an ether linkage incorporating an oxygen atom of one of the oxyethylene groups if present or of a terminal oxyethylene unit of one of the polyoxyethylene chains if present, or (c) by an ether linkage to one of the alkyl sugar derivative units if present.

In a preferred embodiment, J is about 8 to about 25, and E+J is no more than 45, preferably no more than 40, and more preferably no more than 28. For example, compound JJJ in Table 4 includes a hydrophobic moiety having 24 total number of carbons and a hydrophilic moiety including 9 total oxyethylene units such that $E+J=33$. Compound C includes 18 carbon atoms (J) in its hydrophobic moiety, and 7 total oxyethylene units (E) such that $E+J=25$.

In one embodiment of the invention, the surfactant component predominantly comprises one or more surfactants each having a molecular structure comprising:
(1) a hydrophobic moiety having one or a plurality of independently saturated or unsaturated, branched or unbranched, aliphatic, alicyclic or aromatic $C_{3-18}$ hydrocarbyl or hydrocarbylidene groups joined together by 0 to about 7 linkages independently selected from ether, thioether, sulfoxide, ester, thioester and amide linkages, this hydrophobic moiety having in total a number J of carbon atoms where J is about 8 to about 18; and
(2) a hydrophilic moiety comprising:
   (i) an amino group that is cationic or that can be protonated to become cationic, having attached directly thereto 0 to 3 oxyethylene groups or polyoxyethylene chains, these oxyethylene groups and polyoxydthylene chains comprising on average no more than a number E of oxyethylene units per surfactant molecule such that $E+J \leq 22$; and/or
   (ii) an alkyl sugar derivative unit, such as a glycoside, polyglycoside, or aminoglycoide group comprising on average no more than about 2 of the alkyl sugar derivative units per surfactant molecule.

In such surfactants the hydrophobic moiety is attached to the hydrophilic moiety in one of the following ways: (a)

directly to an amino group if present, (b) by an ether linkage incorporating an oxygen atom of one of the oxyethylene groups if present or of a terminal oxyethylene unit of one of the polyoxyethylene chains if present, or (c) by an ether linkage to one of the alkyl sugar derivative units if present.

In the context of surfactant content, the expression "predominantly comprises" means that at least about 50%, preferably at least about 75% and more preferably at least about 90%, by weight of the surfactant component is made up of surfactants having the specified features of molecular structure. For the present purpose, the weight or concentration of surfactant component as defined herein does not include essentially non-surfactant compounds that are sometimes introduced with the surfactant component, such as water, isopropanol or other solvents, or glycols (such as ethylene glycol, propylene glycol, polyethylene glycol, etc.).

Without in any way limiting the scope of the present invention, various subclasses of surfactants, defined by formulas (5), and (6) below, are particularly useful in compositions of the invention.

One embodiment of the invention is a herbicidal concentrate composition as described above wherein the surfactant component predominantly comprises one or more chemically stable surfactants having formula (5):

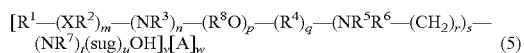

$$[R^1—(XR^2)_m—(NR^3)_n—(R^8O)_p—(R^4)_q—(NR^5R^6—(CH_2)_r)_s—(NR^7)_t(sug)_uOH]_v[A]_w \quad (5)$$

where $R^1$ is hydrogen or $C_{1-18}$ hydrocarbyl, each X is independently an ether, thioether, sulfoxide, ester, thioester or amide linkage, each $R^2$ is independently $C_{2-6}$ hydrocarbylidene, m is an average number of 0 to about 8, the total number of carbon atoms in $R^1$—$(XR^2)_m$ is about 8 to about 24, n is 0 or 1, p is an average number of 0 to about 5, $R^3$, $R^4$, $R^5$, $R^6$ and $R^7$ are independently hydrogen or $C_{1-4}$ hydrocarbyl, $R^8$ is independently $C_2$–$C_4$ alkylene, q is 0 or 1, r is 0 to 4, s is 0 or 1, t is 0 or 1, sug is (i) an open or cyclic structure derived from sugars, such as, for example, glucose or sucrose (referred to herein as a sugar unit), or (ii) a hydroxyalkyl, polyhydroxyalkyl or poly(hydroxyalkyl)alkyl group, u is an average number from 1 to about 2, A is an anionic entity, and v is an integer from 1 to 3 and w is 0 or 1 such that electrical neutrality is maintained. An example of a preferred compound of the type defined by formula 5 is a glucosamine where $R^1$ is $C_8H_{17}$ hydrocarbyl, m, p, q, s, t, and w are 0, n, u and v are 1, $R^3$ is hydrogen, and sug is an open glucose derivative having the structure $CH(OH)CH(OH)CH(OH)CH(OH)CH_2$.

Another embodiment of the invention is a herbicidal concentrate composition as described above wherein the surfactant component predominantly comprises one or more surfactants having formula (6):

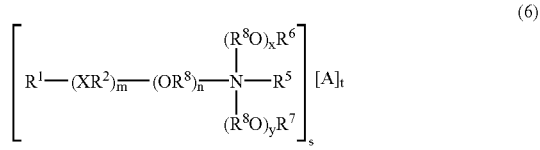

$$\left[ R^1—(XR^2)_{\overline{m}}—(OR^8)_{\overline{n}}—\underset{(R^8O)_yR^7}{\overset{(R^8O)_xR^6}{N}}—R^5 \right]_s [A]_t \quad (6)$$

where $R^1$ is hydrogen or $C_{1-18}$ hydrocarbyl, each X is independently an ether, thioether, sulfoxide, ester, thioester or amide linkage, each $R^2$ is independently $C_{2-6}$ hydrocarbylidene, each $R^8$ is independently $C_2$–$C_4$ alkylene; m is an average. number of 0 to about 9, the total number J of carbon atoms in $R^1$—$(XR^2)_m$ is about 8 to about 18, n is an average number of 0 to about 5, $R^5$ is hydrogen, $C_{1-4}$ alkyl, benzyl, an anionic oxide group or an anionic group —$(CH_2)_uC(O)O$ where u is 1 to 3, $R^6$ and $R^7$ are independently hydrogen, $C_{1-4}$ alkyl or $C_{2-4}$ acyl, x and y are average numbers such that x+y+n is not greater than the number E as defined above, A is an anionic entity and s is an integer from 1 to 3 and t is 0 or 1 such that electrical neutrality is maintained.

It will be appreciated that surfactants conforming to formulas (5) or (6) above include non-restrictively those that can be described as alkyl polyglucosides, alkylaminoglucosides, polyoxyalkylene alkylamines, polyoxalene alkyletheramines, alkyltrimethylammonium salts, alkyldimethylbenzylammonium salts, polyoxyalkylene N-methyl alkylammonium salts, polyoxyalkylene N-methyl alkyletherammonium salts, alkyldimethylamine oxides, polyoxyalkylene alkylamine oxides, polyoxyalkylene alkyletheramine oxides, alkylbetaines, alkylamidopropylamines and the like. In one embodiment of the invention, the average number of oxyalkylene units, such as oxyethylene units, if present, per surfactant molecule is no greater than 22–J where J is as defined above, and the average number of glucose units, if present, per surfactant molecule is no greater than about 2. In another embodiment of the invention, the average number of oxyalkylene units, such as oxyethylene units, if present, per surfactant molecule is no greater than 50–J where J is as defined above, and the average number of glucose units, if present, per surfactant molecule is no greater than about 42.

Illustrative surfactant types that have been found useful in compositions of the invention include the following:

(A) Surfactants corresponding to formula (5) where $R^1$ is a $C_{8-18}$ aliphatic, saturated or unsaturated, linear or branched hydrocarbyl chain, m, n, p, s, t and w are 0, and v is 1. This group includes several commercial surfactants collectively known in the art or referred to herein as "alkyl polyglucosides" or "APGs". Suitable examples are sold by Henkel as Agrimul™ PG-2069 and Agrimul™ PG-2076.

(B) Surfactants corresponding to formula (6) where $R^1$ is a $C_{8-18}$ aliphatic, saturated or unsaturated, linear or branched hydrocarbyl chain and m is 0. In this group $R^1$ alone forms the hydrophobic moiety of the surfactant and is attached directly to the amino function, as in alkylamines, or by an ether linkage formed by the oxygen atom of an oxyalkylene group or the terminal oxygen atom of a polyoxyalkylene chain, as in certain alkyletheramines. Illustrative subtypes having different hydrophilic moieties include:

(1) Surfactants wherein x and y are 0, $R^5$ and $R^6$ are independently $C_{1-4}$ alkyl, $R^7$ is hydrogen and t is 1. This subtype includes (where $R^5$ and $R^6$ are each methyl) several commercial surfactants known in the art or referred to herein as "alkyldimethylamines". Suitable examples are dodecyldimethylamine, available for example from Akzo as Armeen™ DM12D, and cocodimethylamine and tallowdimethylamine, available for example from Ceca as Noram™ DMC D and Noram™ DMS D respectively. Such surfactants are generally provided in non-protonated form, the anion A not being supplied with the surfactant. However, in a glyphosate potassium salt formulation at a pH of about 4–5, the surfactant will be protonated and it will be recognized that the anion A can be glyphosate, which is capable of forming dibasic salts.

(2) Surfactants wherein x and y are 0, $R^5$, $R^6$ and $R^7$ are independently $C_{1-4}$ alkyl and t is 1. This subtype includes (where $R^5$, $R^6$ and $R^7$ are each methyl and A is a chloride ion) several commercial surfactants known in the art or referred to herein as "alkyltrimethylammonium chlorides". A suitable example is cocoalkyl trimethylammonium chloride, available for example from Akzo as Arquad™ C.

(3) Surfactants wherein x+y is 2 or greater, $R^6$ and $R^7$ are hydrogen and t is 1. This subtype includes commercial surfactants known in the art or referred to herein as "polyoxyalkylene alkylamines" (where n is 0 and $R^5$ is hydrogen), certain "polyoxyalkylene alkyletheramines" (where n is 1–5 and $R^5$ is hydrogen), "polyoxyalkylene -methyl alkylammonium chlorides" (where n is 0 and $R^5$ is methyl), and certain "polyoxyalkylene-methyl alkyletherammonium chlorides" (where n is 1–5 and R is methyl). Suitable examples are polyoxyethylene (2) cocoamine, polyoxyethylene (5) tallowamine and polyoxyethylene (10) cocoamine, available for example from Akzo as Ethomeen™ C/12, Ethomeen™ T/15 and Ethomeen™ C/20 respectively; a surfactant conforming, when its amine group is non-protonated, to formula (7):

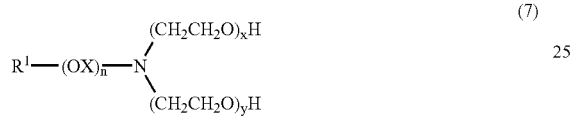

(7)

where $R^1$ is $C_{12-15}$ alkyl, X is ethyl, propyl or methyl ethyl, and x+y is 5, as disclosed in U.S. Pat. No. 5,750,468; and polyoxyethylene (2)N-methyl cocoammonium chloride and polyoxyethylene (2)N-methyl stearylammonium chloride, available for example from Akzo as Ethoquad™ C/12 and Ethoquad™ 18/12 respectively. In cases where $R^5$ is hydrogen, ie., in tertiary as opposed to quaternary ammonium surfactants, the anion A is typically not supplied with the surfactant. However, in a glyphosate potassium salt formulation at a pH of about 4–5, it will be recognized that the anion A can be glyphosate, which is capable of forming dibasic salts.

(4) Surfactants wherein $R^5$ is an anionic oxide group and t is 0. This subtype includes commercial surfactants known in the art or referred to herein as "alkyldimethylamine oxides" (where n, x and y are 0, and $R^6$ and $R^7$ are methyl), certain "alkyletherdimethylamine oxides" (where n is 1–5, x and y are 0, and $R^6$ and $R^7$ are methyl), "polyoxyalkylene alkylamine oxides" (where n is 0, x+y is 2 or greater, and $R^6$ and $R^7$ are hydrogen), and certain "polyoxyalkylene alkyletheramine oxides" (where n is 1–5, x+y is 2 or greater, and $R^6$ and $R^7$ are hydrogen). Suitable examples are cocodimethylamine oxide, sold by Akzo as Aromox™ DMC, and polyoxyethylene (2)cocoamine oxide, sold by Akzo as Aromox™ C/12.

(5) Surfactants wherein $R^5$ is an anionic group —CH$_2$C(O)O (acetate), x and y are 0 and t is 0. This subtype includes commercial surfactants known in the art or referred to herein as "alkylbetaines" (where n is 0, $R^5$ is acetate and $R^6$ and $R^7$ are methyl) and certain "alkyletherbetaines" (where n is 1–5, $R^5$ is acetate and $R^6$ and $R^7$ are methyl). A suitable example is cocobetaine, sold for example by Henkel as Velvetex™ AB-45.

(C) Surfactants corresponding to formula (6) where $R^1$ is a $C_{8-18}$ aliphatic, saturated or unsaturated, linear or branched hydrocarbyl chain, m is 1, X is an ether linkage, $R^2$ is n-propylene and n is 0. In this group $R^1$ together with $OR^2$ forms the hydrophobic moiety of the surfactant which is attached directly by the $R^2$ linkage to the amino function. These surfactants are a subclass of alkyletheramines as disclosed in U.S. Pat. No. 5,750,468. Illustrative subtypes have the different hydrophilic moieties exemplified in (B-1) to (B-5) above. Suitable examples are a surfactant conforming, when its amine group is non-protonated, to formula (8):

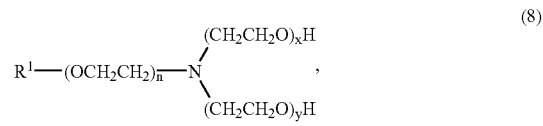

(8)

a surfactant conforming to formula (9):

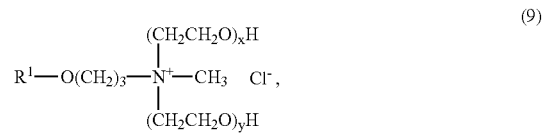

(9)

and a surfactant conforming to formula (10):

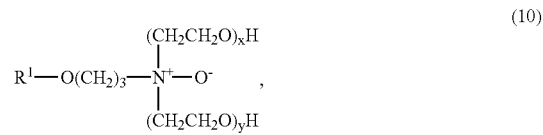

(10)

where, in each of formulas (8), (9) and (10), $R^1$ is $C_{12-15}$ alkyl and x+y is 5, as disclosed in U.S. Pat. No. 5,750,468.

(D) Surfactants corresponding to formula (6) where $R^1$ is a $C_{8-18}$ aliphatic, saturated or unsaturated, linear or branched hydrocarbyl chain, m is 1–5, each $XR^2$ is a group —OCH(CH$_3$)CH$_2$— and n is 0. In this group $R^1$ together with the —OCH(CH$_3$)CH$_2$— groups forms the hydrophobic moiety of the surfactant which is

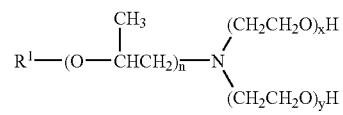

attached directly to the amino function. These surfactants are a further subclass of alkyletheramines as disclosed in U.S. Pat. No. 5,750,468. Illustrative subtypes have the different hydrophilic moieties exemplified in (B-1) to (B-5) above.

(E) Surfactants corresponding to formula (6) where $R^1$ is a $C_{8-18}$ aliphatic, saturated or unsaturated, linear or branched hydrocarbyl chain, m is 1, X is an amide linkage, $R^2$ is n-propylene and n is 0. In this group $R^1$ together with $XR^2$ forms the hydrophobic moiety of the surfactant which is attached directly by the $R^2$ linkage to the amino function. In preferred surfactants of this group, x and y are 0, $R^5$ is hydrogen or $C_{1-4}$ alkyl, $R^6$ and $R^7$ are independently $C_{1-4}$ alkyl and t is 1. A suitable example is cocoamidopropyl dimethylamine propionate, sold for example by McIntyre as Mackalene™ 117.

(F) Surfactants corresponding to formula (6) where $R^1$ is hydrogen, m is 3–8 and each $XR^2$ is a group —OCH$(CH_3)CH_2$—. In this group the polyether chain of —OCH$(CH_3)CH_2$— groups (a polyoxypropylene chain) forms the hydrophobic moiety of the surfactant which is linked directly or via one or more oxyethylene units to the amino function. In preferred surfactants of this group, x and y are 0, $R^5$, $R^6$ and $R^7$ are independently $C_{1-4}$ alkyl and t is 1. These surfactants are a subclass of the polyoxypropylene quaternary ammonium surfactants disclosed in U.S. Pat. No. 5,652,197. In a suitable example, m is 7, n is 1, $R^5$, $R^6$ and $R^7$ are each methyl, and A is chloride.

In surfactants where t is 1, A can be any agriculturally acceptable anion but preferably is chloride, bromide, iodide, sulfate, ethosulfate, phosphate, acetate, propionate, succinate, lactate, citrate or tartrate, or, as indicated above, glyphosate.

In one embodiment of the invention the composition contains a surfactant of a class of alkyletheramines disclosed in U.S. Pat. No. 5,750,468, the disclosure of which is incorporated herein by reference. In a further embodiment, surfactants present are other than alkyletheramines as disclosed in U.S. Pat. No. 5,750,468, the disclosure of which is incorporated herein by reference.

In another embodiment of the invention the composition contains a surfactant having the general formula (11):

$$R^1R^2N(CH_2)_nNR^3R^4 \quad (11)$$

where $R^1$ and $R^2$ are independently a $C_{4-8}$ aliphatic, saturated or unsaturated, linear or branched hydrocarbyl chain, $R^3$ and $R^4$ are independently a $C_{1-4}$ alkyl or hydrogen, and n is greater than 2. A particularly preferred compound of this description is where $R^1$ and $R^2$ are $C_8H_{17}$, n is 3, and $R^3$ and $R^4$ are hydrogen.

In yet another embodiment of the invention the composition contains a surfactant having the general formula (12):

$$R^1R^2N(CH_2CH_2O)_nR^3 \quad (12)$$

where $R^1$ is $C_{8-18}$ aliphatic, saturated or unsaturated, linear or branched hydrocarbyl, $R^2$ and $R^3$ are independently $C_{1-10}$, preferably $C_{1-4}$ alkyl or hydrogen, and n is 1 or greater, preferably 2 to 15. It is believed that at least one compound within this formula has not heretofore been reported in the prior art, and is therefore, a novel compound per se. The structure for this compound is $$CH_3(CH_2)_{17}N(CH_3)(CH_2CH_2O)_7CH_3$$

This novel compound, as well as its use as a pesticidal adjuvant, and in particular with glyphosate, and even more particularly with glyphosate potassium salt, is all within the scope of this invention. Additionally, the hydroxy analogs of the foregoing compound show particularly good compatibility with glyphosate potassium salt formulations.

In other embodiments of the invention, the composition contains a surfactant having one or more of the following the formulas:

$$R^1R^2R^3N^+(CH_2)_nNR^4R^5 \quad (13)$$

where $R^1$ is $C_{8-18}$ aliphatic, saturated or unsaturated, linear or branched hydrocarbyl chain, $R^2$, $R^3$, $R^4$, and $R^5$ are independently a $C_{1-4}$ alkyl or hydrogen, X is an anionic entity, and n is 2 or greater;

$$R^1O(CH_2)_nNR^2R^3 \quad (14)$$

where $R^1$ is a $C_{4-18}$ aliphatic, saturated or unsaturated, linear or branched hydrocarbyl chain, $R^2$ and $R^3$ are independently a $C_{1-4}$ alkyl or hydrogen, and n is equal to 2 or greater;

$$R^1O(CH_2)_mNR^2(CH_2)_nNR^3R^4 \quad (15)$$

where $R^1$ is a $C_{4-18}$ aliphatic, saturated or unsaturated, linear or branched hydrocarbyl chain, $R^2$, $R^3$ and $R^4$ are independently a $C_{1-4}$ alkyl or hydrogen, and m and n are independently equal to 2 or greater;

$$R^1O(CH_2)_mNR^2(CH_2)_nNR^3R^4 \quad (16)$$

where $R^1$ is a $C_{4-18}$ aliphatic, saturated or unsaturated, linear or branched hydrocarbyl chain, $R^2$, $R^3$ and $R^4$ are independently a poly(oxyethylene) chains having a combined total of equal to or greater than 3 moles of ethylene oxide, and m and n are independently equal to 2 or greater;

$$R^1O(CH_2)_mN[(CH_2CH_2O)_nR^2](CH_2)_p[(CH_2CH_2O)_qR^3]_2 \quad (17)$$

where $R^1$ is a $C_{4-18}$ aliphatic, saturated or unsaturated, linear or branched hydrocarbyl chain, $R^2$ and $R^3$ are independently methyl or hydrogen, m and p are independently equal or greater than about 2 and equal to or less than about 6, n and q are independently equal to about 1–10;

$$R^1-X-(CH_2)_n-NR^2R^3 \quad (18)$$

where $R^1$ is a $C_{4-18}$ aliphatic, saturated or unsaturated, linear or branched hydrocarbyl chain, $R^2$ and $R^3$ are independently a $C_{1-4}$ alkyl or hydrogen, X is an amide linkage, and n is equal to 2 or greater;

$$R^1R^2R^3(N^+O^-) \quad (19)$$

where $R^1$ is a $C_{4-18}$ aliphatic, saturated or unsaturated, linear or branched hydrocarbyl chain, and $R^2$ and $R^3$ are independently a $C_{1-4}$ alkyl;

$$R^1-NR^2\text{-carbohydrate} \quad (20)$$

where $R^1$ is a $C_{4-18}$ aliphatic, saturated or unsaturated, linear or branched hydrocarbyl chain, and $R^2$ is a $C_{1-4}$ alkyl or hydrogen and "carbohydrate" is a carbohydrate for example, —$CH_2CH(OH)CH(OH)CH(OH)CH(OH)CH_2OH$. Further, other derivatives, such as, for example, ethoxylated or nonethoxylated alkyl or amide derivatives of amino sugars (particularly 2-aminoglucose) are of particular interest in glyphosate or other herbicide/pesticide formulations. Di-sugar amines are also of particular interest in this regard.

$$R^1-N-[(CH_2)_nNR^2R^3]_2 \quad (21)$$

where $R^1$ is a $C_{4-18}$ aliphatic, saturated or unsaturated, linear or branched hydrocarbyl chain, and $R^2$ and $R^3$ are independently a $C_{1-4}$ alkyl or hydrogen and n is 2 or greater, preferably n is 2 or 3;

$$R^1R^2N(CH_2)_m-O-(CH_2CH_2O)_n-(CH_2)_p-NR^3R^4 \quad (22)$$

where $R^1$, $R^2$, $R^3$ and $R^4$ are independently a $C_{1-4}$ alkyl, polyoxyethylene or hydrogen and m and p are independently 2 or greater, preferably 2 or 3, and n is 1 or greater, preferably 1.

Novel surfactants have been discovered which are particularly suitable for use in formulating pesticide compositions, such as herbicides. The surfactants have been found to be highly compatible with various water soluble salts of glyphosate, especially potassium, ammonium, and diammonium glyphosate. Cationic surfactants suitable in formulating pesticide formulations include:

(a) monoalkoxylated amines having the formula:

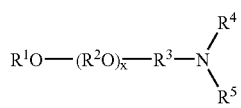
(23)

wherein $R^1$ is hydrogen or hydrocarbyl or substituted hydrocarbyl having at least 7 carbon atoms (preferably containing 8 to about 30 carbon atoms); $R^2$ in each of the x ($R^2O$) and y ($R^2O$) groups is independently $C_2$–$C_4$ alkylene; $R^3$ is a hydrocarbylene or substituted hydrocarbylene having from 2 to about 6 carbon atoms; $R^4$ and $R^5$ are each independently hydrogen, hydrocarbyl or substituted hydrocarbyl having from 1 to about 30 carbon atoms, —$(R^6)_n$—$(R^2O)_y R^7$, or $R^4$ and $R^5$, together with the nitrogen atom to which they are attached, form a cyclic or heterocyclic ring; $R^6$ is hydrocarbylene or substituted hydrocarbylene containing from 1 to about 6 carbon atoms, $R^7$ is hydrogen or a linear or branched alkyl group having 1 to about 4 carbon atoms, n is 0 or 1, and x and y are independently an average number from 1 to about 60, provided, however, that when $R^2$ and $R^3$ in each of the x ($R^2O$) groups is ethylene, $R^1$ is other than unsubstituted alkyl or $R^4$ is other than hydrogen or unsubstituted alkyl when $R^5$ is hydrogen or unsubstituted alkyl, and when $R^2$ and $R^3$ are isopropylene and x is 1, $R^1$ is other than unsubstituted alkyl or $R^4$ is other than —$(R^2O)_y R^7$. In this context, preferred $R^1$, $R^4$, $R^5$ and $R^6$ hydrocarbyl (hydrocarbylene) groups include linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 25 carbon atoms, $R^2$ in each of the x ($R^2O$) groups is independently $C_2$–$C_4$ alkylene, $R^3$ is an ethylene or 2-hydroxypropylene group, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the x ($R^2O$) groups is independently ethylene or propylene, $R^3$ is an ethylene or 2-hydroxypropylene group, $R^4$ and $R^5$ are each independently hydrogen, methyl, or tris(hydroxymethyl)methyl, and x is an average number from about 2 to about 30. Even more preferably, $R^1$ is a linear or branched alkyl group having from about 12 to about 18 carbon atoms, $R^2$ in each of the x ($R^2O$) groups is independently ethylene or propylene, $R^3$ is an ethylene or 2-hydroxypropylene group, $R^4$ and $R^5$ are each independently hydrogen or methyl, and x is an average number from about 4 to about 20. Most preferably, $R^1$ is a linear or branched alkyl group having from about 12 to about 18 carbon atoms, $R^2$ in each of the x ($R^2O$) groups is independently ethylene or propylene, $R^3$ is an ethylene or 2-hydroxypropylene group, $R^4$ and $R^5$ are methyl, and x is an average number from about 4 to about 20.

(b) alkoxylated poly(hydroxyalkyl)amines having the formula:

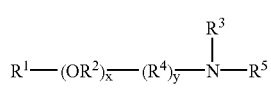
(24)

wherein $R^1$ and $R^3$ are independently hydrogen, hydrocarbyl or substituted hydrocarbyl having from 1 to about 30 carbon atoms, $R^2$ in each of the x ($R^2O$) groups is independently $C_2$–$C_4$ alkylene; $R^4$ is hydrocarbylene or substituted hydrocarbylene having from 1 to about 30 carbon atoms, $R^5$ is hydroxyalkyl, polyhydroxyalkyl, or poly(hydroxyalkyl)alkyl; x is an average number from 0 to about 30, and y is 0 or 1. In this context, preferred $R^1$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) group. Preferred alkoxylated poly(hydroxyalkyl)amines have the formula:

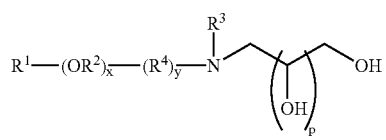
(25)

or

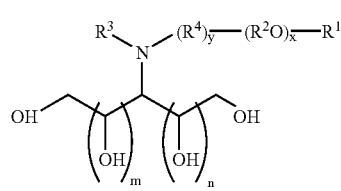
(26)

wherein $R^1$ and $R^3$ are independently hydrogen, hydrocarbyl or substituted hydrocarbyl having from 1 to about 30 carbon atoms, $R^2$ in each of the x ($R^2O$) groups is independently $C_2$–$C_4$ alkylene; $R^4$ is hydrocarbylene or substituted hydrocarbylene having from 1 to about 30 carbon atoms, m and n are independently integers from 0 to about 7, the sum of m and n is not greater than about 7, p is an integer from 1 to about 8, x is an average number from 0 to about 30, and y is 0 or 1. In this context, preferred $R^1$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) group. Preferably, $R^1$ is a linear or branched alkyl or linear or branched alkenyl group having from about 8 to about 30 carbon atoms; $R^2$ in each of the x ($R^2O$) groups is independently $C_2$–$C_4$ alkylene; $R^3$ is hydrogen, a linear or branched alkyl or linear or branched alkenyl group having from 1 to about 30 carbon atoms; $R^4$ is a linear or branched alkylene having from 1 to about 30 carbon atoms, m and n are independently integers from 0 to about 7, the sum of m and n is from about 3 to 7, p is an integer from 1 to about 8, x is an average number from 0 to about 30, and y is 0 or 1. More preferably, $R^1$ is a linear or branched alkyl group having from about 8 to about 22 carbon atoms; $R^2$ in each of the x ($R^2O$) groups is independently ethylene or propylene; $R^3$ is hydrogen, or a linear or branched alkyl group having from 1 to about 6 carbon atoms; $R^4$ is a linear or branched alkylene having from 1 to about 6 carbon atoms, m and n are independently integers from 0 to about 7, the sum of m and n is from about 3 to 7, p is an integer from 1 to about 8, x is an average number from 0 to about 30, and y is 0 or 1. Most preferably, $R^1$ is a linear or branched alkyl group having from about 8 to about 18 carbon atoms; $R^2$ in each of the x ($R^2O$) groups is independently ethylene or propylene; $R^3$ is hydrogen or methyl; m and n are independently integers from 0 to about 7, the sum of m and n is from about 3 to 7, p is an integer from 1 to about 8, x is an average number from 0 to about 30, and y is 0.

(c) di-poly(hydroxyalkyl)amines having the formula:

(27)

wherein $R^1$ and $R^3$ are independently hydrogen or hydrocarbyl or substituted hydrocarbyl having from 1 to about 22 carbon atoms, $R^2$ is hydrocarbylene or substituted hydrocarbylene having from 2 to about 18 carbon atoms, $R^4$ and $R^5$ are independently hydroxyalkyl, polyhydroxyalkyl, or poly(hydroxyalkyl)alkyl, provided, however, that when $R^1$ and $R^3$ are methyl, $R^2$ is other than octylene. In this context, preferred $R^1$, $R^2$ and $R^3$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferred di-poly(hydroxyalkyl)amines have the formula:

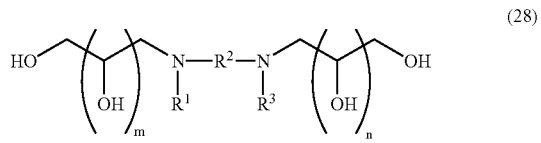

(28)

wherein $R^1$ and $R^3$ are independently hydrogen or hydrocarbyl or substituted hydrocarbyl having from 1 to about 22 carbon atoms, $R^2$ is hydrocarbylene or substituted hydrocarbylene having from 2 to about 18 carbon atoms, and m and n are independently integers from 1 to about 8, provided, however, that when $R^1$ and $R^3$ are methyl, $R^2$ is other than octylene. In this context, preferred $R^1$, $R^2$ and $R^3$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. In one embodiment, $R^1$ and $R^3$ are independently hydrogen or a linear or branched alkyl group having from 1 to about 6 carbon atoms, $R^2$ is a linear or branched alkylene, linear or branched alkenylene, linear or branched alkynylene, arylene, and alkylarylene group having from 9 to about 18 carbon atoms, and m and n are as defined above. In another embodiment, $R^1$ and $R^3$ are independently hydrogen or a linear or branched alkyl group having from 2 to about 22 carbon atoms, $R^2$ is a linear or branched alkylene, linear or branched alkenylene, linear or branched alkynylene, arylene, and alkylarylene group having from 2 to 7 carbon atoms, and m and n are as defined above. Preferably, $R^1$ and $R^3$ are independently hydrogen or a linear or branched alkyl group having from 1 to about 18 carbon atoms, $R^2$ is a linear or branched alkylene or linear or branched alkenylene group having from 2 to about 18 carbon atoms, and m and n are independently integers from 1 to about 8. More preferably, $R^1$ and $R^3$ are independently hydrogen or a linear or branched alkyl group having from 6 to about 12 carbon atoms, $R^2$ is a linear or branched alkylene group having from 2 to about 6 carbon atoms, and m and n are independently integers from about 4 to about 8; or $R^1$ and $R^3$ are independently hydrogen or a linear or branched alkyl group having from 1 to about 4 carbon atoms, $R^2$ is a linear or branched alkylene group having from 2 to about 16 carbon atoms, and m and n are independently integers from about 4 to about 8. Most preferably, $R^1$ and $R^3$ are independently hydrogen or a linear or branched alkyl group having from 6 to about 12 carbon atoms, $R^2$ is ethylene or propylene, and m and n are independently integers from about 4 to about 8; or $R^1$ and $R^3$ are independently hydrogen or a linear or branched alkyl group having from 1 to about 4 carbon atoms, $R^2$ is a linear or branched alkylene group having from 2 to about 12 carbon atoms, and m and n are independently integers from about 4 to about 8.

(d) alkoxylated triamines having the formula:

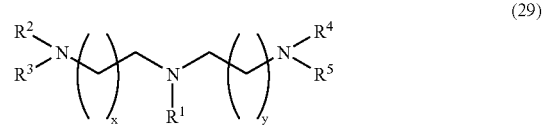

(29)

wherein $R^1$ is hydrocarbyl or substituted hydrocarbyl having from 1 to about 30 carbon atoms; $R^2$, $R^3$, $R^4$ and $R^5$ are independently hydrogen, hydrocarbyl or substituted hydrocarbyl having from 1 to about 30 carbon atoms, or $-(R^8)_s(R^7-O)_nR^6$; $R^6$ is hydrogen, or a linear or branched alkyl group having from 1 to about 4 carbon atoms; $R^7$ in each of the n ($R^7O$) groups is independently $C_2-C_4$ alkylene; $R^8$ is hydrocarbylene or substituted hydrocarbylene having from 1 to about 6 carbon atoms; n is an average number from 1 to about 10; s is 0 or 1; and x and y are independently an integer from 1 to about 4; provided, however, that when $R^1$ is alkyl, $R^2$ is other than hydrogen, x is 3 or 4, or $R^4$ is other than $-(R^7-O)_nR^6$. In this context, preferred $R^1$, $R^2$, $R^3$, $R^4$, $R^5$ and $R^8$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. In one embodiment, $R^2$ is a linear or branched alkyl, linear or branched alkenyl, linear or branched alkynyl, aryl, or aralkyl group having from 1 to about 30 carbon atoms, or $-(R^8)_s(R^7-O)_nR^6$, and the remaining groups are as described above. Preferably, $R^1$ is a linear or branched alkyl or linear or branched alkenyl groups having from about 8 to about 30 carbon atoms, $R^2$, $R^3$, $R^4$ and $R^5$ are independently hydrogen, a linear or branched alkyl or linear or branched alkenyl group having from 1 to about 30 carbon atoms, or $-(R^7-O)_nR^6$, $R^6$ is hydrogen, methyl or ethyl; $R^7$ in each of the n ($R^7O$) groups is independently $C_2-C_4$ alkylene, n is an average number from 1 to about 10, and x and y are independently an integer from 1 to about 4. More preferably, $R^1$ is a linear or branched alkyl group having from about 8 to about 18 carbon atoms, $R^2$, $R^3$, $R^4$ and $R^5$ are independently hydrogen, a linear or branched alkyl group having from 1 to about 6 carbon atoms, or $-(R^7-O)_nR^6$, $R^6$ is hydrogen or methyl, $R^7$ in each of the n ($R^7O$) groups is independently ethylene or propylene, n is an average number from 1 to about 5, and x and y are independently an integer from 1 to about 4. Most preferably, $R^1$ is a linear or branched alkyl group having from about 8 to about 18 carbon atoms, $R^2$, $R^3$, $R^4$ and $R^5$ are independently hydrogen, or $-(R^7-O)_nR^6$, $R^6$ is hydrogen, $R^7$ in each of the n ($R^7O$) groups is independently ethylene or propylene, n is an average number from 1 to about 5, and x and y are independently an integer from 1 to about 4.

(e) monoalkoxylated amines having the formula:

(30)

wherein $R^1$ is a hydrocarbyl or substituted hydrocarbyl group having from 1 to about 30 carbon atoms, $R^2$ is $C_2-C_4$ alkylene, $R^3$ is hydrogen, or a linear or branched alkyl group having from 1 to about 4 carbon atoms, $R^4$ is a linear or branched alkynyl, aryl, or aralkyl group having from 1 to about 30 carbon atoms, and x is an average number from 1 to about 60. In this context, preferred $R^1$ hydrocarbyl or substituted hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from 1 to about 25 carbon atoms, $R^2$ is $C_2$–$C_4$ alkylene, $R^3$ is hydrogen, methyl or ethyl, $R^4$ is a linear or branched alkynyl, aryl, or aralkyl group having from 1 to about 25 carbon atoms, and x is an average number from 1 to about 40. More preferably, $R^1$ is a linear or branched alkyl group having from 8 to about 22 carbon atoms, $R^2$ is ethylene or propylene, $R^3$ is hydrogen or methyl, $R^4$ is a linear or branched alkynyl, aryl, or aralkyl group having from 1 to about 6 carbon atoms, and x is an average number from 1 to about 20. In one embodiment, the compound has the formula shown in Table 4,C.

(f) amine oxides having the formula:

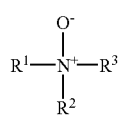

(31)

wherein $R^1$ is hydrocarbyl or substituted hydrocarbyl having from about 8 to about 30 carbon atoms, $R^2$ and $R^3$ are independently —$(R^4O)_xR^5$, $R^4$ in each of the x ($R^4O$) groups is independently $C_2$–$C_4$ alkylene, $R^5$ is hydrogen, or a hydrocarbyl or substituted hydrocarbyl having from 1 to about 30 carbon atoms, x is an average number from 1 to about 50. In this context, preferred $R^1$ and $R^5$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 22 carbon atoms, $R^2$ and $R^3$ are independently —$(R^4O)_xR^5$, $R^4$ in each of the x ($R^4$—O) groups is independently $C_2$–$C_4$ alkylene; $R^5$ is hydrogen or a linear or branched alkyl or linear or branched alkenyl group having from about 1 to about 30 carbon atoms; and x is an average number from 1 to about 20. More preferably, $R^1$ is a linear or branched alkyl group having from about 8 to about 22 carbon atoms, $R^2$ and $R^3$ are independently —$(R^4O)_xR^5$, $R^4$ in each of the x ($R^4$—O) groups is independently ethylene or propylene; $R^5$ is hydrogen or a linear or branched alkyl or linear or branched alkenyl group having from about 1 to about 30 carbon atoms; and x is an average number from 1 to about 10. Most preferably, $R^1$ is a linear or branched alkyl group having from about 8 to about 18 carbon atoms, $R^2$ and $R^3$ are independently —$(R^4O)_xR^5$, $R^4$ in each of the x ($R^4$—O) groups is independently ethylene or propylene; $R^5$ is hydrogen or an alkyl group having from about 8 to about 18 carbon atoms; and x is an average number from 1 to about 5.

(g) an alkoxylated amine oxide having the formula:

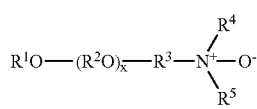

(32)

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2$–$C_4$ alkylene; $R^3$ is a hydrocarbylene or substituted hydrocarbylene having from 2 to about 6 carbon atoms; $R^4$ and $R^5$ are each independently hydrogen, hydrocarbyl or substituted hydrocarbyl having from 1 to about 30 carbon atoms, —$(R^6)_n$—$(R^2O)_yR^7$; $R^6$ is hydrocarbylene or substituted hydrocarbylene containing from 1 to about 6 carbon atoms, $R^7$ is hydrogen or a linear or branched alkyl group having 1 to about 4 carbon atoms, n is 0 or 1, and x and y are independently an average number from 1 to about 60. In this context, preferred $R^1$, $R^4$, $R^5$ and $R^6$ hydrocarbyl (hydrocarbylene) groups include linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 25 carbon atoms, $R^2$ in each of the x ($R^2O$) groups is independently $C_2$–$C_4$ alkylene, $R^3$ is a linear or branched alkylene or alkenylene group having from 2 to about 6 carbon atoms, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the x ($R^2O$) groups is independently ethylene or propylene, $R^3$ is a linear or branched alkylene or alkenylene group having from 2 to about 6 carbon atoms, $R^4$ and $R^5$ are each independently hydrogen, methyl, or tris (hydroxymethyl)methyl, and x is an average number from about 2 to about 30. Even more preferably, $R^1$ is a linear or branched alkyl group having from about 12 to about 18 carbon atoms, $R^2$ in each of the x ($R^2O$) groups is independently ethylene or propylene, $R^3$ is an ethylene, propylene or 2-hydroxypropylene group, $R^4$ and $R^5$ are each independently hydrogen or methyl, and x is an average number from about 4 to about 20. Most preferably, $R^1$ is a linear or branched alkyl group having from about 12 to about 18 carbon atoms, $R^2$ in each of the x ($R^2O$) groups is independently ethylene or propylene, $R^3$ is an ethylene, propylene, or 2-hydroxypropylene group, $R^4$ and $R^5$ are methyl, and x is an average number from about 4 to about 20.

(h) alkoxylated diamines having the formula:

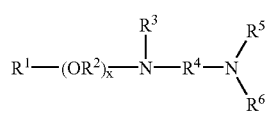

(33)

wherein $R^1$ is hydrocarbyl or substituted hydrocarbyl having from about 8 to about 30 carbon atoms; $R^2$ in each of the x ($R^2O$) groups and the y ($R^2O$) groups is independently $C_2$–$C_4$ alkylene; $R^3$, $R^5$ and $R^6$ are independently hydrogen, hydrocarbyl or substituted hydrocarbyl having from 1 to about 30 carbon atoms, or —$(R^2O)_yR^7$; $R^4$ is hydrocarbylene or substituted hydrocarbylene having from 2 to about 6 carbon atoms, —C(=$NR^{11}$)$NR^{12}R^{13}$—, —C(=O) $NR^{12}R^{13}$—, —C(=S)$NR^{12}R^{13}$—, —C(=$NR^{12}$)—, —C(S)—, or —C(O)—; $R^7$ is hydrogen, or a linear or branched alkyl group having from 1 to about 4 carbon atoms; $R^{11}$, $R^{12}$ and $R^{13}$ are hydrogen, hydrocarbyl or substituted hydrocarbyl having from 1 to about 30 carbon atoms, x is an average number from 1 to about 30; and y is an average number from 1 to about 50, provided, however, that at least one of $R^3$, $R^5$ and $R^6$ is —$(R^2O)_yR^7$, at least one $R^2$ is other than ethylene, $R^4$ is other than unsubstituted propylene, $R^1$ is other than unsubstituted alkyl, or x is from 2 to about 30. In this context, preferred $R^1$, $R^3$, $R^4$, $R^5$ and $R^6$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 22 carbon atoms, $R^2$ in each of the x ($R^2O$) groups and the y ($R^2O$) groups is independently $C_2$–$C_4$ alkylene, $R^3$, $R^5$ and $R^6$ are independently hydrogen, a linear or branched alkyl or linear or branched alkenyl group having from 1 to about 22 carbon atoms, or —($R^2O$)$_y R^7$, $R^4$ is a linear or branched alkylene, linear or branched alkenylene group having from 2 to about 6 carbon atoms, $R^7$ is hydrogen, methyl or ethyl, x is an average number from 1 to about 20, and y is an average number from 1 to about 20. More preferably, $R^1$ is a linear or branched alkyl or linear or branched alkenyl group having from about 8 to about 18 carbon atoms, $R^2$ in each of the x ($R^2O$) groups and the y ($R^2O$) groups is independently ethylene or propylene, $R^3$, $R^5$ and $R^6$ are independently hydrogen, a linear or branched alkyl group having from 1 to about 6 carbon atoms, or —($R^2O$)$_y R^7$, $R^4$ is ethylene, propylene, or 2-hydroxypropylene, $R^7$ is hydrogen or methyl, x is an average number from 1 to about 15, and y is an average number from 1 to about 10. Most preferably, $R^1$ is a linear or branched alkyl or linear or branched alkenyl group having from about 8 to about 18 carbon atoms; $R^2$ in each of the x ($R^2O$) groups and the y ($R^2O$) groups is independently ethylene or propylene; $R^3$, $R^5$ and $R^6$ are independently hydrogen, methyl, or —($R^2O$)$_y R^7$; $R^4$ is ethylene, propylene, or 2-hydroxypropylene, $R^7$ is hydrogen, x is an average number from 1 to about 10; and y is an average number from 1 to about 5.

and (i) dialkoxylated amines having the formula:

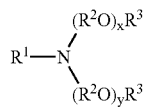

(34)

wherein $R^1$ is a hydrocarbyl or substituted hydrocarbyl having from about 6 to about 30 carbon atoms, or —$R^4 SR^5$, $R^4$ and $R^2$ in each of the x ($R^2O$) and the y ($R^2O$) groups is independently $C_2$–$C_4$ alkylene, $R^3$ is hydrogen, or a linear or branched alkyl group having from 1 to about 4 carbon atoms, $R^5$ is a linear or branched alkyl group having from about 4 to about 15 carbon atoms, and x and y are independently an average number from 1 to about 40. In this context, preferred $R^1$ hydrocarbyl groups are linear or branched alkyl, linear or branched alkenyl, linear or branched alkynyl, aryl, or aralkyl groups. Preferably, $R^1$ is a linear or branched alkynyl, aryl, or aralkyl group having from about 8 to about 30 carbon atoms, $R^2$ in each of the x ($R^2O$) and the y ($R^2O$) groups is independently $C_2$–$C_4$ alkylene, $R^3$ is hydrogen, methyl or ethyl, and x and y are independently an average number from 1 to about 20. More preferably, $R^1$ is a linear or branched alkynyl, aryl, or aralkyl group having from about 8 to about 25 carbon atoms, $R^2$ in each of the x ($R^2O$) and the y ($R^2O$) groups is independently ethylene or propylene, $R^3$ is hydrogen or methyl, and x and y are independently an average number from 1 to about 30. Even more preferably, $R^1$ is a linear or branched alkynyl, aryl, or aralkyl group having from about 8 to about 22 carbon atoms, $R^2$ in each of the x ($R^2O$) and the y ($R^2O$) groups is independently ethylene or propylene, $R^3$ is hydrogen or methyl, and x and y are independently an average number from 1 to about 5.

Nonionic surfactants for use in pesticide formulations include dialkoxylated alcohols having the formula:

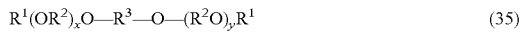

(35)

wherein $R^1$ is independently hydrogen, or a linear or branched alkyl group having from 1 to about 4 carbon atoms, $R^2$ in each of the x ($R^2O$) and the y ($R^2O$) groups is independently $C_2$–$C_4$ alkylene, $R^3$ is hydrocarbylene or substituted hydrocarbylene having from 2 to about 30 carbon atoms, and x and y are independently an average number from 1 to about 60. In this context, preferred $R^3$ hydrocarbylene groups are linear or branched alkylene, linear or branched alkenylene, linear or branched alkynylene, arylene, or aralkylene groups. Preferably, $R^1$ is hydrogen, methyl or ethyl, $R^2$ in each of the x ($R^2O$) and the y ($R^2O$) groups is independently $C_2$–$C_4$ alkylene, $R^3$ is a linear or branched alkylene or linear or branched alkenylene group having from about 8 to about 25 carbon atoms, and x and y are independently an average number from about 1 to about 20. More preferably, $R^1$ is hydrogen or methyl, $R^2$ in each of the x ($R^2O$) and the y ($R^2O$) groups is independently ethylene or propylene, $R^3$ is a linear or branched alkylene or linear or branched alkenylene group having from about 8 to about 18 carbon atoms, and x and y are independently an average number from 1 to about 10. Even more preferably, $R^1$ is hydrogen, $R^2$ in each of the x ($R^2O$) and the y ($R^2O$) groups is independently ethylene or propylene, $R^3$ is a linear or branched alkylene group having from about 8 to about 18 carbon atoms, and x and y are independently an average number from 1 to about 5.

Other surfactants for use in pesticide compositions include compounds of the formula:

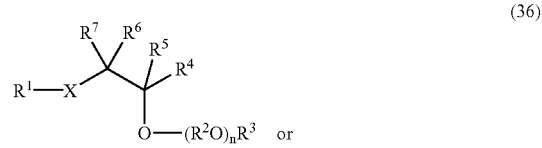

(36)

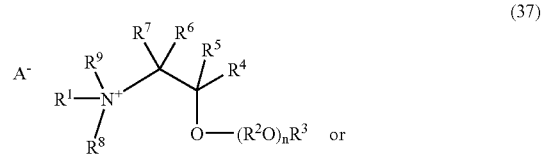

(37)

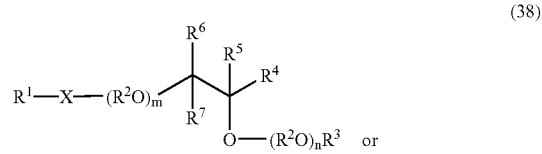

(38)

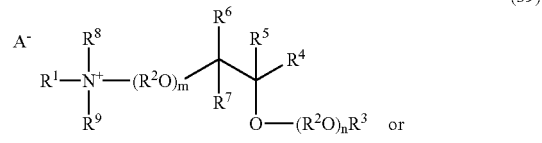

(39)

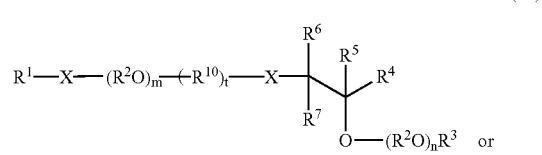

(40)

or or or or or

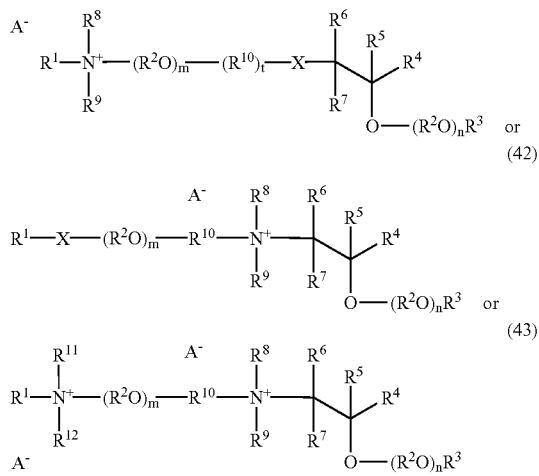

(41)

(42)

(43)

wherein $R^1$, $R^9$, and $R^{12}$ are independently hydrocarbyl or substituted hydrocarbyl having from 1 to about 30 carbon atoms, or $-(R^2O)_pR^{13}$; $R^2$ in each of the m ($R^2O$), n ($R^2O$), p ($R^2O$) and q ($R^2O$) groups is independently $C_2$–$C_4$ alkylene; $R^3$, $R^6$, $R^{11}$, $R^{13}$ and $R^{15}$ are independently hydrogen, or a hydrocarbyl or substituted hydrocarbyl having from 1 to about 30 carbon atoms; $R^4$ is $-(CH_2)_yOR^{13}$ or $-(CH_2)_yO(R^2O)_qR^3$; $R^5$, $R^6$ and $R^7$ are independently hydrogen, hydrocarbyl or substituted hydrocarbyl having from 1 to about 30 carbon atoms, or $R^4$; $R^{10}$ is hydrocarbylene or substituted hydrocarbylene having from 2 to about 30 carbon atoms; $R^{14}$ is hydrocarbyl or substituted hydrocarbyl having from 1 to about 30 carbon atoms, or $-(CH_2)_zO(R^2O)_pR^3$; m, n, p and q are independently an average number from 1 to about 50; X is $-O-$, $-N(R^{14})-$, $-C(O)-$, $-C(O)O-$, $-OC(O)-$, $-N(R^{16})C(O)-$, $-C(O)N(R^{15})-$, $-S-$, $-SO-$, or $-SO_2-$; t is 0 or 1; A– is an agriculturally acceptable anion; and y and z are independently an integer from 0 to about 30. In this context, preferred $R^1$, $R^3$, and $R^5$–$R^{15}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^9$, and $R^{12}$ are independently linear or branched alkyl or alkenyl groups having from 1 to about 22 carbon atoms, or $-(R^2O)_pR^{13}$; $R^2$ in each of the m ($R^2O$), n ($R^2O$), p ($R^2O$) and q ($R^2O$) groups is independently $C_2$–$C_4$ alkylene; $R^3$ is hydrogen, methyl or ethyl; $R^4$ is $-(CH_2)_yOR^{13}$ or $-(CH_2)_yO(R^2O)_qR^3$; $R^8$, $R^{11}$, $R^{13}$ and $R^{15}$ are independently hydrogen, or linear or branched alkyl or alkenyl groups having from 1 to about 22 carbon atoms; $R^4$ is $-(CH_2)_yOR^{13}$ or $-(CH_2)_yO(R^2O)_qR^3$; $R^5$, $R^6$ and $R^7$ are independently hydrogen, linear or branched alkyl or alkenyl groups having from 1 to about 22 carbon atoms, or $R^4$; $R^{10}$ is a linear or branched alkylene or alkenylene group having from 2 to about 18 carbon atoms; $R^{14}$ is a linear or branched alkyl or alkenyl group having from 1 to about 22 carbon atoms, or $-(CH_2)_zO(R^2O)_pR^3$; m, n, p and q are independently an average number from 1 to about 30; X is $-O-$, $-N(R^{14})-$, $-C(O)-$, $-C(O)O-$, $-OC(O)-$, $-N(R^{15})C(O)-$, $-C(O)N(R^{15})-$, $-S-$, $-SO-$, or $-SO_2-$; t is 0 or 1; A– is an agriculturally acceptable anion; and y and z are independently an integer from 0 to about 30. More preferably, $R^1$ is a linear or branched alkyl or alkenyl groups having from about 8 to about 18 carbon atoms, or $-(R^2O)_pR^{13}$; $R^9$ and $R^{12}$ are independently linear or branched alkyl or alkenyl groups having from 1 to about 22 carbon atoms, or $-(R^2O)_pR^{13}$; $R^2$ in each of the m ($R^2O$), n ($R^2O$), p ($R^2O$) and q ($R^2O$) groups is independently ethylene or propylene; $R^3$ is hydrogen or methyl; $R^4$ is $-(CH_2)_yOR^{13}$ or $-(CH_2)_yO(R^2O)_qR^3$; $R^8$, $R^{11}$, $R^{15}$ are independently hydrogen, or linear or branched alkyl or alkenyl groups having from 1 to about 22 carbon atoms; $R^4$ is $-(CH_2)_yOR^{13}$ or $-(CH_2)_yO(R^2O)_qR^3$; $R^5$, $R^6$ and $R^7$ are independently hydrogen, linear or branched alkyl or alkenyl groups having from 1 to about 22 carbon atoms, or $R^4$; $R^{10}$ is a linear or branched alkylene or alkenylene group having from 2 to about 6 carbon atoms; $R^{13}$ is hydrogen, or linear or branched alkyl or alkenyl groups having from about 6 to about 22 carbon atoms; $R^{14}$ is a linear or branched alkyl or alkenyl group having from 1 to about 22 carbon atoms, or $-(CH_2)_zO(R^2O)_pR^3$; m, n, p and q are independently an average number from 1 to about 20; X is $-O-$, $-N(R^{14})-$, $-C(O)-$, $-C(O)O-$, $-OC(O)-$, $-N(R^{15})C(O)-$, $-C(O)N(R^{15})-$, $-S-$, $-SO-$, or $-SO_2-$, t is 0 or 1; A– is an agriculturally acceptable anion; and y and z are independently an integer from 0 to about 10. Most preferably, $R^1$ is a linear or branched alkyl or alkenyl groups having from about 12 to about 18 carbon atoms, or $-(R^2O)_pR^{13}$; $R^9$ and $R^{12}$ are independently linear or branched alkyl or alkenyl groups having from 1 to about 6 carbon atoms, or $-(R^2O)_pR^{13}$; $R^2$ in each of the m ($R^2O$), n ($R^2O$), p ($R^2O$) and q ($R^2O$) groups is independently ethylene or propylene; $R^3$ is hydrogen; $R^4$ is $-(CH_2)_yOR^{13}$ or $-(CH_2)_yO(R^2O)_qR^3$; $R^8$, $R^{11}$, $R^{15}$ are independently hydrogen, or linear or branched alkyl or alkenyl groups having from 1 to about 6 carbon atoms; $R^4$ is $-(CH_2)_yOR^{13}$ or $-(CH_2)_yO(R^2O)_qR^3$; $R^5$, $R^6$ and $R^7$ are independently hydrogen, linear or branched alkyl or alkenyl groups having from 1 to about 22 carbon atoms, or $R^4$; $R^{10}$ is a linear or branched alkylene or alkenylene group having from 2 to about 6 carbon atoms; $R^{13}$ is hydrogen, or linear or branched alkyl or alkenyl groups having from about 6 to about 22 carbon atoms; $R^{14}$ is a linear or branched alkyl or alkenyl group having from 1 to about 22 carbon atoms, or $-(CH_2)_zO(R^2O)_pR^3$; m, n, p and q are independently an average number from 1 to about 5; X is $-O-$ or $-N(R^{14})-$, t is 0 or 1; A– is an agriculturally acceptable anion; and y and z are independently an integer from 1 to about 3.

A surfactant composition of the invention comprises any individual combination of the novel surfactants as described above. The surfactant composition is particularly preferred for use in formulating potassium, diammonium, ammonium, sodium, monoethanolamine, n-propylamine, methylamine, ethylamine, hexamethylenediamine, dimethylamine and/or trimethylsulfonium glyphosate formulations, such as aqueous concentrates. The surfactant composition can be incorporated into a formulation comprising any combination of these glyphosate salts.

Various surfactants not previously used in formulating pesticide compositions have been found to be effective, particularly in formulating aqueous herbicidal concentrates containing potassium or ammonium glyphosate. Cationic surfactants effective in forming pesticide formulations include:

(a) aminated alkoxylated alcohol having the formula:

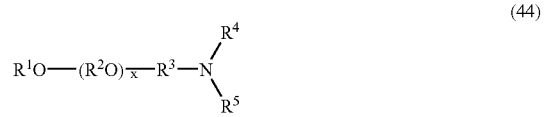

(44)

or

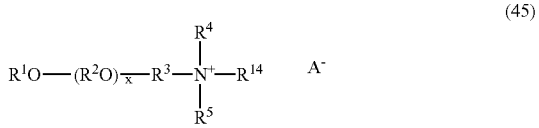

wherein R¹ is hydrocarbyl or substituted hydrocarbyl containing at least 7 carbon atoms (preferably containing 8 to about 30 carbon atoms); R² in each of the x (R²O) and y (R²O) groups is independently $C_2$–$C_4$ alkylene; R³ and R⁶ are each independently hydrocarbylene or substituted hydrocarbylene having from 1 to about 6 carbon atoms; R⁴ is hydrogen, hydrocarbyl or substituted hydrocarbyl having from 1 to about 30 carbon atoms, hydroxy substituted hydrocarbyl, —(R⁶)$_n$—(R²O)$_y$R⁷, —C(=NR¹¹)NR¹²R¹³, —C(=O)NR¹²R¹³, —C(=S)NR¹²R¹³ or together with R⁵ and the nitrogen atom to which they are attached, form a cyclic or heterocyclic ring; R⁵ is hydrogen, hydrocarbyl or substituted hydrocarbyl having from 1 to about 30 carbon atoms, hydroxy substituted hydrocarbyl, —(R⁶)$_n$—(R²O)$_y$R⁷, —C(=NR¹¹)NR¹²R¹³, —C(=O)NR¹²R¹³, —C(=S)NR¹²R¹³, or together with R⁴ and the nitrogen atom to which they are attached, form a cyclic or heterocyclic ring; R⁷ is hydrogen or a linear or branched alkyl group having 1 to about 4 carbon atoms; R¹¹, R¹² and R¹³ are hydrogen, hydrocarbyl or substituted hydrocarbyl, R¹⁴ is hydrogen, hydrocarbyl or substituted hydrocarbyl having from 1 to about 30 carbon atoms, hydroxy substituted hydrocarbyl, (R⁶)$_n$—(R²O)$_y$R⁷, —C(=NR¹¹)NR¹²R¹³, —C(=O) NR¹²R¹³, or —C(=S)NR¹²R¹³, n is 0 or 1, x and y are independently an average number from 1 to about 60, and A– is an agriculturally acceptable anion, provided, however, that when R² and R³ are isopropylene and x is 1, R¹ is other than alkyl or R⁴ is other than —(R²O)$_y$R⁷. In this context, preferred R¹, R³, R⁴, R⁵, R⁶, R¹¹, R¹² and R¹³ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. In one embodiment, R³ is linear alkylene, preferably ethylene, and R¹, R², R⁴ and R⁵ are as previously defined. In another embodiment, R⁴ is H, alkyl, or —R²OR⁷ and R¹, R², R³, R⁵ and R⁷ are as previously defined. In yet another embodiment, R¹ is a linear or branched alkyl or linear or branched alkenyl group having from about 8 to about 25 carbon atoms, R² in each of the x (R²O) groups is independently $C_2$–$C_4$ alkylene, R³ is a linear or branched alkylene group having from 1 to about 6 carbon atoms, R⁴ and R⁵ are each independently hydrogen or a linear or branched alkyl group having from 1 to about 6 carbon atoms, and x is an average number from about 2 to about 30. More preferably, R¹ is a linear or branched alkyl group having from about 12 to about 22 carbon atoms, R² in each of the x (R²O) groups is independently ethylene or propylene, R³ is a linear or branched alkylene group having from 1 to about 4 carbon atoms, R⁴ and R⁵ are each independently hydrogen, methyl, or tris(hydroxymethyl) methyl, and x is an average number from about 2 to about 30. Even more preferably, R¹ is a linear or branched alkyl group having from about 12 to about 18 carbon atoms, R² in each of the x (R²O) groups is independently ethylene or propylene, R³ is ethylene, R⁴ and R⁵ are each independently hydrogen or methyl, and x is an average number from about 4 to about 20. Most preferably, R¹ is a linear or branched alkyl group having from about 12 to about 18 carbon atoms, R² in each of the x (R²O) groups is independently ethylene or propylene, R³ is ethylene, R⁴ and R⁵ are methyl, and x is an average number from about 4 to about 20. Compounds of formula (45) have the preferred groups as described above and R¹⁴ is preferably hydrogen or a linear or branched alkyl or alkenyl group, more preferably alkyl, and most preferably methyl. Preferred monoalkoxylated amines include PEG 13 or 18 $C_{14-15}$ ether propylamines and PEG 7, 10, 15 or 20 $C_{16-18}$ ether propylamines (from Tomah) and PEG 13 or 18 $C_{14-15}$ ether dimethyl propylamines and PEG 10, 15 or 20 or 25 $C_{16-18}$ ether dimethyl propylamines (from Tomah).

(b) hydroxylated amines having the formula:

wherein R¹ is hydrocarbyl or substituted hydrocarbyl having from about 4 to about 30 carbon atoms, R² is hydrogen or hydrocarbyl or substituted hydrocarbyl having from 1 to about 30 carbon atoms, and R³ is hydroxyalkyl, polyhydroxyalkyl, or poly(hydroxyalkyl)alkyl. In this context, preferred R¹ and R² hydrocarbyl groups are linear or branched alkyl, linear or branched alkenyl, linear or branched alkynyl, aryl, or aralkyl groups. Preferably, the hydroxylated amines have the formula:

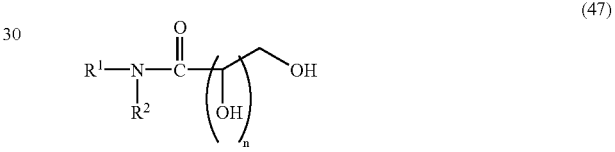

wherein R¹ is hydrocarbyl or substituted hydrocarbyl having from about 4 to about 30 carbon atoms, R² is hydrogen or hydrocarbyl or substituted hydrocarbyl having from 1 to about 30 carbon atoms, and n is 1 to about 8. In this context, preferred R¹ and R² hydrocarbyl groups are linear or branched alkyl, linear or branched alkenyl, linear or branched alkynyl, aryl, or aralkyl groups. Preferably, R¹ is a linear or branched alkyl or linear or branched alkenyl group having from about 8 to about 30 carbon atoms, R² is hydrogen, a linear or branched alkyl or linear or branched alkenyl group having from 1 to about 30 carbon atoms, and n is about 4 to about 8; or R¹ and R² are independently linear or branched alkyl or linear or branched alkenyl groups having from about 4 to about 30 carbon atoms and n is about 4 to about 8. More preferably, R¹ is a linear or branched alkyl or linear or branched alkenyl group having from about 8 to about 22 carbon atoms, R² is hydrogen or a linear or branched alkyl or linear or branched alkenyl group having from 1 to about 6 carbon atoms, and n is about 4 to about 8; or R¹ and R² are independently linear or branched alkyl or linear or branched alkenyl groups having from about 4 to about 8 carbon atoms, and n is about 4 to about 8.

(c) diamines having the formula:

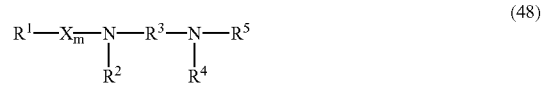

wherein R¹, R² and R⁵ are independently hydrogen or hydrocarbyl or substituted hydrocarbyl having from 1 to about 30 carbon atoms or —R⁸(OR⁹)$_n$OR¹⁰, R³ is hydrocarbylene or substituted hydrocarbylene having from 2 to about 18 carbon atoms, $R^8$ and $R^9$ are individually hydrocarbylene or substituted hydrocarbylene having from 2 to about 4 carbon atoms, $R^4$ and $R^{10}$ are independently hydrogen or hydrocarbyl or substituted hydrocarbyl having from 1 to about 30 carbon atoms, m is 0 or 1, n is an average number from 0 to about 40, X is —C(O)— or —SO$_2$—, and A– is an agriculturally acceptable anion. In this context, preferred $R^1$, $R^3$, $R^4$ and $R^5$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^2$, $R^4$ and $R^5$ are independently hydrogen, a linear or branched alkyl or alkenyl group having from 1 to about 6 carbon atoms, and $R^3$ is a linear or branched alkylene having from 2 to about 6 carbon atoms. More preferably, $R^1$, $R^2$, $R^4$ and $R^5$ are independently hydrogen, or a linear or branched alkyl group having from 1 to about 6 carbon atoms, and $R^3$ is a linear or branched alkylene having from 1 to about 6 carbon atoms. Most preferably, $R^1$, $R^2$, $R^4$, and $R^5$ are independently hydrogen or methyl, and $R^3$ is ethylene or propylene.

(d) mono- or di-ammonium salts having the formula:

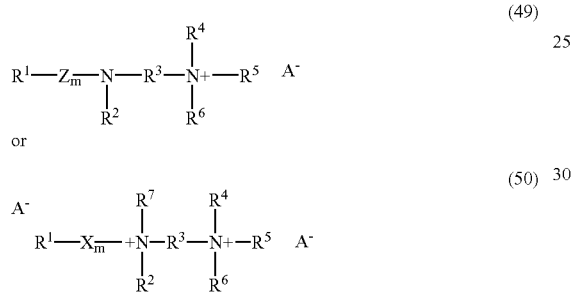

(49)

or (50)

wherein $R^1$, $R^2$, $R^4$, $R^5$ and $R^7$ are independently hydrogen or hydrocarbyl or substituted hydrocarbyl having from 1 to about 30 carbon atoms or —R$^8$(OR$^9$)$_n$OR$^{10}$, $R^6$ is hydrocarbyl or substituted hydrocarbyl having from about 1 to about 30 carbon atoms, $R^3$ is hydrocarbylene or substituted hydrocarbylene having from 2 to about 18 carbon atoms, $R^8$, $R^9$ and $R^{11}$ are individually hydrocarbylene or substituted hydrocarbylene having from 2 to about 4 carbon atoms, $R^{10}$ is hydrogen or hydrocarbyl or substituted hydrocarbyl having from 1 to about 30 carbon atoms, m is 0 or 1, n is an average number from 0 to about 40, X is —C(O)— or —SO$_2$—, Z is —C(O)—, and A– is an agriculturally acceptable anion. In this context, preferred $R^1$, $R^3$, $R^4$, $R^5$, and $R^7$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^2$, $R^4$, $R^5$ and $R^7$ are independently hydrogen, a linear or branched alkyl or alkenyl group having from 1 to about 6 carbon atoms, $R^6$ is a linear or branched alkyl or alkenyl group having from about 8 to about 30 carbon atoms, m is 0 or 1, and $R^3$ is a linear or branched alkylene having from 2 to about 6 carbon atoms. More preferably, $R^1$, $R^2$, $R^4$, $R^5$ and $R^7$ are independently hydrogen, or a linear or branched alkyl group having from 1 to about 6 carbon atoms, $R^6$ is a linear or branched alkyl group having from about 8 to about 22 carbon atoms, m is 0 or 1, and $R^3$ is a linear or branched alkylene having from 1 to about 6 carbon atoms. Most preferably, $R^1$, $R^2$, $R^4$, $R^5$ and $R^7$ are independently hydrogen or methyl, $R^6$ is a linear or branched alkyl group having from about 8 to about 18 carbon atoms, m is 0 or 1, and $R^3$ is ethylene or propylene.

(e) poly(hydroxyalkyl)amines having the formula:

(51)

wherein $R^1$ is hydrocarbyl or substituted hydrocarbyl having from about 4 to about 30 carbon atoms or —R$^4$OR$^5$, $R^2$ is hydrogen or hydrocarbyl or substituted hydrocarbyl having from 1 to about 30 carbon atoms, $R^3$ is hydroxyalkyl, polyhydroxyalkyl, or poly(hydroxyalkyl)alkyl, $R^4$ is hydrocarbylene or substituted hydrocarbylene having from 2 to about 18 carbon atoms, and $R^5$ is hydrogen or hydrocarbyl or substituted hydrocarbyl having from about 1 to about 30 carbon atoms. Preferably, the poly(hydroxyalkyl)amines have the formula:

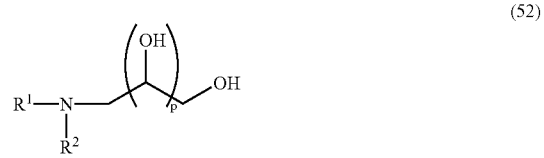

(52)

or

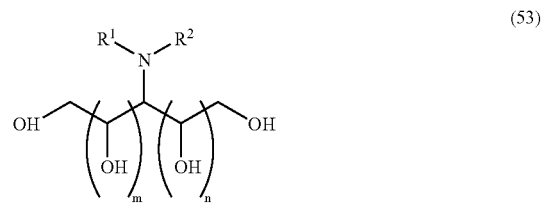

(53)

wherein $R^1$ is hydrocarbyl or substituted hydrocarbyl having from about 4 to about 30 carbon atoms or —R$^3$OR$^4$; $R^2$ is hydrogen or hydrocarbyl or substituted hydrocarbyl having from 1 to about 30 carbon atoms, $R^3$ is hydrocarbylene or substituted hydrocarbylene having from 2 to about 18 carbon atoms, $R^4$ is hydrogen or hydrocarbyl or substituted hydrocarbyl having from about 1 to about 30 carbon atoms, m and n are independently integers from 0 to about 7, the sum of m and n is not greater than about 7, and p is an integer from 1 to about 8. In this context, preferred $R^1$, $R^2$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 30 carbon atoms or —R$^3$OR$^4$, $R^2$ is hydrogen, a linear or branched alkyl or linear or branched alkenyl group having from 1 to about 30 M) carbon atoms, $R^3$ is a linear or branched alkylene or alkenylene group having from 2 to about 6 carbon atoms, $R^4$ is a linear or branched alkyl or alkenyl group having from about 8 to about 22 carbon atoms, m and n are independently integers from 0 to about 7, the sum of m and n is from about 3 to 7, and p is an integer from about 4 to about 8; or $R^1$ and $R^2$ are independently linear or branched alkyl or linear or branched alkenyl groups having from about 4 to about 30 carbon atoms, m and n are independently integers from 0 to about 7, the sum of m and n is from about 3 to 7, and p is an integer from about 4 to about 8. More preferably, $R^1$ is a linear or branched alkyl or linear or branched alkenyl group having from about 8 to about 22 carbon atoms or —R$^3$OR$^4$, $R^2$ is hydrogen or a linear or branched alkyl or linear or branched alkenyl group having from 1 to about 6 carbon atoms, $R^3$ is a linear or branched alkylene or alkenylene group having from 2 to about 6 carbon atoms, $R^4$ is a linear or branched alkyl or alkenyl group having from about 8 to about 18 carbon atoms, m and n are independently integers from 0 to about 7, the sum of m and n is from about 3 to 7, and p is an integer from about 4 to about 8; or $R^1$ and $R^2$ are independently linear or branched alkyl or linear or branched alkenyl groups having from about 4 to about 8 carbon atoms, m and n are independently integers from 0 to about 7, the sum of m and n is from about 3 to 7, and p is an integer from about 4 to about 8. Even more preferably, $R^1$ is a linear or branched alkyl group having from about 8 to about 18 carbon atoms or —$R^3OR^4$, $R^2$ is hydrogen or methyl, m and n are independently integers from 0 to about 4, $R^3$ is a linear or branched alkylene group having from 2 to about 6 carbon atoms, $R^4$ is a linear or branched alkyl group having from about 8 to about 18 carbon atoms, the sum of m and n is about 4, and p is an integer of about 4. Most preferably, $R^1$ is a linear or branched alkyl group having from about 8 to about 18 carbon atoms or —$R^3OR^4$, $R^2$ is methyl, $R^3$ is ethylene, propylene, hydroxyethylene or 2-hydroxypropylene, $R^4$ is a linear or branched alkyl group having from about 8 to about 18 carbon atoms, m and n are independently integers from 0 to about 4, the sum of m and n is about 4, and p is an integer of about 4. Such compounds are commercially available from Aldrich and Clariant.

(f) di-poly(hydroxyalkyl)amine having the formula:

(54)

wherein $R^1$ and $R^3$ are independently hydrogen or hydrocarbyl or substituted hydrocarbyl having from 1 to about 22 carbon atoms, $R^2$ is hydrocarbylene or 1 substituted hydrocarbylene having from 2 to about 18 carbon atoms, and $R^4$ and $R^5$ are independently hydroxyalkyl, polyhydroxyalkyl, or poly(hydroxyalkyl)alkyl. In this context, preferred $R^1$, $R^2$, and $R^3$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, the di-poly(hydroxyalkyl)amine has the formula:

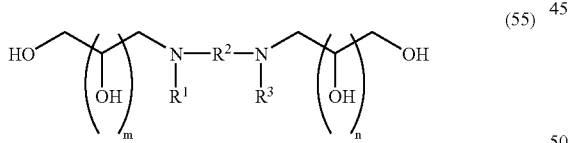

(55)

wherein $R^1$ and $R^3$ are independently hydrogen or hydrocarbyl or substituted hydrocarbyl having from 1 to about 22 carbon atoms, $R^2$ is hydrocarbylene or substituted hydrocarbylene having from 2 to about 18 carbon atoms, and m and n are independently integers from 1 to about 8. In this context, preferred $R^1$, $R^2$, and $R^3$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^3$ are independently hydrogen or a linear or branched alkyl group having from 1 to about 18 carbon atoms, $R^2$ is a linear or branched alkylene or linear or branched alkenylene group having from 2 to about 18 carbon atoms, and m and n are independently integers from 1 to about 8. More preferably, $R^1$ and $R^3$ are independently hydrogen or a linear or branched alkyl group having from 6 to about 12 carbon atoms, $R^2$ is a linear or branched alkylene group having from 2 to about 6 carbon atoms, and m and n are independently integers from about 4 to about 8; or $R^1$ and $R^3$ are independently hydrogen or a linear or branched alkyl group having from 1 to about 4 carbon atoms, $R^2$ is a linear or branched alkylene group having from 2 to about 16 carbon atoms, and m and n are independently integers from about 4 to about 8. Most preferably, $R^1$ and $R^3$ are independently hydrogen or a linear or branched alkyl group having from 6 to about 12 carbon atoms, $R^2$ is ethylene or propylene, and m and n are independently integers from about 4 to about 8; or $R^1$ and $R^3$ are independently hydrogen or a linear or branched alkyl group having from 1 to about 4 carbon atoms, $R^2$ is a linear or branched alkylene group having from 2 to about 12 carbon atoms, and m and n are independently integers from about 4 to about 8.

(g) quaternary poly(hydroxyalkyl)amine salts having the formula:

(56)

wherein $R^1$ is hydrocarbyl or substituted hydrocarbyl having from about 4 to about 30 carbon atoms, $R^2$ and $R^3$ are independently hydrogen or hydrocarbyl or substituted hydrocarbyl having from 1 to about 30 carbon atoms, and $R^4$ is hydroxyalkyl, polyhydroxyalkyl, or poly(hydroxyalkyl)alkyl. In this context, preferred $R^1$, $R^2$, and $R^3$ hydrocarbyl groups are linear or branched alkyl, linear or branched alkenyl, linear or branched alkynyl, aryl, or aralkyl groups. Preferably, the quaternary poly(hydroxyalkyl)amine salts have the formula:

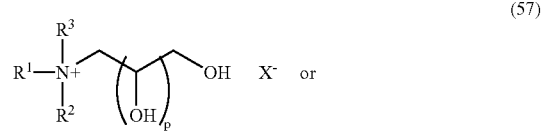

(57)

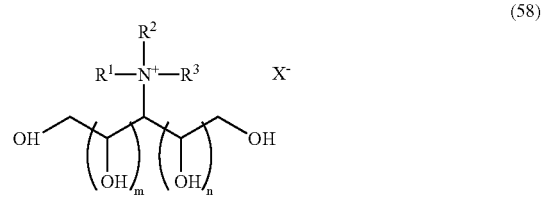

(58)

wherein $R^1$ is hydrocarbyl or substituted hydrocarbyl having from about 4 to about 30 carbon atoms, $R^2$ and $R^3$ are independently hydrogen or hydrocarbyl or substituted hydrocarbyl having from 1 to about 30 carbon atoms, m and n are independently integers from 0 to about 7, the sum of m and n is not greater than about 7, and p is an integer from 1 to about 8. In this context, preferred $R^1$, $R^2$, and $R^3$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, $R^2$ and $R^3$ are independently hydrogen or a linear or branched alkyl or linear or branched alkenyl group having from 1 to about 30 carbon atoms, m and n are independently integers from 0 to about 7, the sum of m and n is from about 3 to 7, and p is an integer from about 4 to about 8; or $R^1$, $R^2$ and $R^3$ are independently linear or branched alkyl or linear or branched alkenyl groups having from about 4 to about 30 carbon atoms, m and n are independently integers from 0 to about 7, the sum of m and n is not greater than about 7, and p is an integer from about 4 to about 8. More preferably, $R^1$ is a linear or branched alkyl or linear or branched alkenyl group having from about 8 to about 22 carbon atoms, $R^2$ and $R^3$ are independently hydrogen or a linear or branched alkyl or linear or branched alkenyl group having from 1 to about 6 carbon atoms, m and n are independently integers from 0 to about 7, the sum of m and n is from about 3 to 7, and p is an integer from about 4 to about 8; or $R^1$, $R^2$ and $R^3$ are independently linear or branched alkyl or linear or branched alkenyl groups having from about 4 to about 8 carbon atoms, m and n are independently integers from 0 to about 7, the sum of m and n is from about 3 to 7, and p is an integer from about 4 to about 8. Even more preferably, $R^1$ is a linear or branched alkyl group having from about 8 to about 18 carbon atoms, $R^2$ and $R^3$ are independently hydrogen or methyl, m and n are independently integers from 0 to about 4, the sum of m and n is about 4, and p is an integer of about 4. Most preferably, $R^1$ is a linear or branched alkyl group having from about 8 to about 18 carbon atoms, $R^2$ and $R^3$ are methyl, m and n are independently integers from 0 to about 4, the sum of m and n is about 4, and p is an integer of about 4.

(h) triamines having the formula:

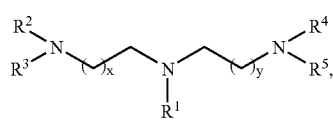

(59)

wherein $R^1$ is hydrocarbyl or substituted hydrocarbyl having from 1 to about 30 carbon atoms; $R^2$, $R^3$, $R^4$ and $R^5$ are independently hydrogen, hydrocarbyl or substituted hydrocarbyl having from 1 to about 30 carbon atoms, or $-(R^8)_s$ $(R^7O)_nR^6$; $R^6$ is hydrogen or a linear or branched alkyl group having from 1 to about 4 carbon atoms, $R^7$ in each of the n ($R^7O$) groups is independently $C_2$–$C_4$ alkylene; $R^8$ is hydrocarbylene or substituted hydrocarbylene having from 1 to about 6 carbon atoms, n is an average number from 1 to about 10, s is 0 or 1, and x and y are independently an integer from 1 to about 4. In this context, preferred $R^1$, $R^2$, $R^3$, $R^4$, $R^5$, and $R^8$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl groups having from about 8 to about 30 carbon atoms, $R^2$, $R^3$, $R^4$ and $R^5$ are independently hydrogen, a linear or branched alkyl or linear or branched alkenyl group having from 1 to about 30 carbon atoms, or $-(R^7-O)_nR^6$, $R^6$ is hydrogen, methyl or ethyl; $R^7$ in each of the n ($R^7O$) groups is independently $C_2$–$C_4$ alkylene, n is an average number from 1 to about 10, and x and y are independently an integer from 1 to about 4. More preferably, $R^1$ is a linear or branched alkyl group having from about 8 to about 18 carbon atoms, $R^2$, $R^3$, $R^4$ and $R^5$ are independently hydrogen, a linear or branched alkyl group having from 1 to about 6 carbon atoms, or $-(R^7-O)_nR^6$, $R^6$ is hydrogen or methyl, $R^7$ in each of the n ($R^7O$) groups is independently ethylene or propylene, n is an average number from 1 to about 5, and x and y are independently an integer from 1 to about 4. Most preferably, $R^1$ is a linear or branched alkyl group having from about 8 to about 18 carbon atoms, $R^2$, $R^3$, $R^4$ and $R^5$ are independently hydrogen, or $-(R^7-O)_nR^6$, $R^6$ is hydrogen, $R^7$ in each of the n ($R^7O$) groups is independently ethylene or propylene, n is an average number from 1 to about 5, and x and y are independently an integer from 1 to about 4. Commercially available triamines include Acros and Clariant Genamin 3119.

Another cationic surfactant effective in any glyphosate formulations is:

(i) diamines having the formula:

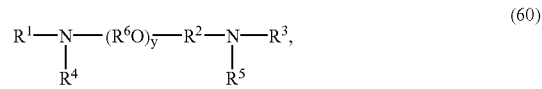

(60)

wherein $R^1$, $R^3$, $R^4$ and $R^5$ are independently hydrogen, hydrocarbyl or substituted hydrocarbyl having from 1 to about 30 carbon atoms, or $-(R^6O)_xR^7$, $R^2$ is hydrocarbylene or substituted hydrocarbylene having from 2 to about 30 carbon atoms, $R^6$ in each of the x ($R^6O$) and y ($R^6O$) groups is independently $C_2$–$C_4$ alkylene, $R^7$ is hydrogen, or a linear or branched alkyl group having from 1 to about 30 carbon atoms, x is an average number from 1 to about 30, and y is an average number from about 3 to about 60, provided, however, that when $R^2$ is ethylene, either y is greater than 4, $R^3$, $R^4$ and $R^5$ are independently hydrogen, a linear or branched alkyl, linear or branched alkenyl, linear or branched alkynyl, aryl, or aralkyl group having from 1 to about 30 carbon atoms or $-(R^6O)_xR^7$, $R^6$ is other than ethylene, or not more than one of $R^1$, $R^3$, $R^4$ and $R^5$ is alkyl or $-(R^6O)_xR^7$. In this context, preferred $R^1$, $R^2$, $R^3$, $R^4$, and $R^5$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^3$, $R^4$ and $R^5$ are independently hydrogen or a linear or branched alkyl or alkenyl group having from about 1 to about 22 carbon atoms or $-(R^6O)_xR^7$, $R^2$ is a linear or branched alkylene or alkenylene group having from about 1 to about 6 carbon atoms, $R^6$ in each of the x($R^6O$) and y ($R^6O$) groups is independently $C_2$–$C_4$ alkylene, $R^7$ is hydrogen, or a linear or branched alkyl group having from 1 to about 4 carbon atoms, x is an average number from 1 to about 30, and y is an average number from 1 to about 60. More preferably, $R^1$, $R^3$, $R^4$ and $R^5$ are independently hydrogen or a linear or branched alkyl group having from about 1 to about 18 carbon atoms or $-(R^6O)_xR^7$, $R^2$ is a linear or branched alkylene group having from about 1 to about 6 carbon atoms, $R^6$ in each of the x ($R^6O$) and y ($R^6O$) groups is independently ethylene or propylene, $R^7$ is hydrogen, or a linear or branched alkyl group having from 1 to about 4 carbon atoms, x is an average number from 1 to about 10, and y is an average number from 1 to about 60. Most preferably, $R^1$ and $R^3$ are independently linear or branched alkyl groups having from about 8 to about 18 carbon atoms and $R^4$ and $R^5$ are independently hydrogen, $R^2$ is a linear or branched alkylene group having from about 1 to about 6 carbon atoms, $R^6$ in each of the x ($R^6O$) and y ($R^6O$) groups is independently ethylene or propylene, $R^7$ is hydrogen, or a linear or branched alkyl group having from 1 to about 4 carbon atoms, x is an average number from 1 to about 10, and y is an average number from 10 to about 50.

(j) mono- or di-quaternary ammonium salts having the formula:

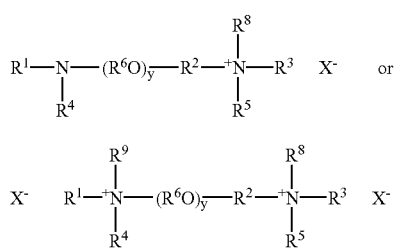

(61)

(62)

wherein $R^1$, $R^3$, $R^4$, $R^5$, $R^8$ and $R^9$ are independently hydrogen, hydrocarbyl or substituted hydrocarbyl having from 1 to about 30 carbon atoms, or $—(R^6O)_xR^7$, $R^2$ is hydrocarbylene or substituted hydrocarbylene having from 2 to about 30 carbon atoms, $R^6$ in each of the x ($R^6O$) and y ($R^6O$) groups is independently $C_2$–$C_4$ alkylene, $R^7$ is hydrogen, or a linear or branched alkyl group having from 1 to about 4 carbon atoms, x is an average number from 1 to about 30, y is an average number from about 3 to about 60, and $X^-$ is an agriculturally acceptable anion. In this context, preferred $R^1$, $R^2$, $R^3$, $R^4$, $R^5$, $R^8$ and $R^9$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^3$, $R^4$, $R^5$, $R^8$ and $R^9$ are independently hydrogen or a linear or branched alkyl or alkenyl group having from about 1 to about 22 carbon atoms or $—(R^6O)_xR^7$, $R^2$ is a linear or branched alkylene or alkenylene group having from about 1 to about 6 carbon atoms, $R^6$ in each of the x($R^6O$) and y ($R^6O$) groups is independently $C_2$–$C_4$ alkylene, $R^7$ is hydrogen, or a linear or branched alkyl group having from 1 to about 4 carbon atoms, x is an average number from 1 to about 30, and y is an average number from 1 to about 60. More preferably, $R^1$, $R^3$, $R^4$, $R^5$, $R^8$ and $R^9$ are independently hydrogen or a linear or branched alkyl group having from about 1 to about 18 carbon atoms or $—(R^6O)_xR^7$, $R^2$ is a linear or branched alkylene group having from about 1 to about 6 carbon atoms, $R^6$ in each of the x ($R^6O$) and y ($R^6O$) groups is independently ethylene or propylene, $R^7$ is hydrogen, or a linear or branched alkyl group having from 1 to about 4 carbon atoms, x is an average number from 1 to about 10, and y is an average number from 1 to about 60. Most preferably, $R^1$ and $R^3$ are independently linear or branched alkyl groups having from about 8 to about 18 carbon atoms and $R^4$, $R^5$, $R^8$ and $R^9$ are independently hydrogen or methyl, $R^2$ is a linear or branched alkylene group having from about 1 to about 6 carbon atoms, $R^6$ in each of the x ($R^6O$) and y ($R^6O$) groups is independently ethylene or propylene, $R^7$ is hydrogen, or a linear or branched alkyl group having from 1 to about 4 carbon atoms, x is an average number from 1 to about 10, and y is an average number from 10 to about 50.

Surfactants effective in formulating potassium, di-ammonium, ammonium, sodium, monoethanolamine, n-propylamine, methylamine, ethylamine, hexamethylenediamine, dimethylamine and/or trimethylsulfonium glyphosate formulations include the nonionic, cationic, anionic and amphoteric surfactants as described below and mixtures thereof.

Cationic surfactants effective in such glyphosate formulations include:

(a) a secondary or tertiary amine having the formula:

(63)

wherein $R^1$ and $R^2$ are hydrocarbyl having from 1 to about 30 carbon atoms, and $R^3$ is hydrogen or hydrocarbyl having from 1 to about 30 carbon atoms. In this context, preferred $R^1$, $R^2$, and $R^3$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, and $R^2$ and $R^3$ are independently hydrogen or a linear or branched alkyl or linear or branched alkenyl group having from 1 to about 6 carbon atoms. More preferably, $R^1$ is a linear or branched alkyl group having from about 12 to about 22 carbon atoms, and $R^2$ and $R^3$ are independently hydrogen, methyl or ethyl. In one embodiment of the amine of formula (CC), $R^1$ is a linear or branched alkyl group having from about 12 to about 22 carbon atoms, and $R^2$ and $R^3$ are independently linear or branched hydroxyalkyl groups having from 1 to about 6 carbon atoms.

In one embodiment, the surfactant has the formula (48) wherein $R^1$ is hydrocarbon or substituted hydrocarbyl having from about 8 to about 30 carbon atoms, $R^2$ is a hydroxyalkyl, polyhydroxyalkyl or poly(hydroxyalkyl)alkyl group, and $R^3$ is hydrogen, hydroxyalkyl, polyhydroxyalkyl or poly(hydroxyalkyl)alkyl. In this context, preferred $R^1$ hydrocarbyl groups are linear or branched alkyl, linear or branched alkenyl, linear or branched alkynyl, aryl, or aralkyl groups. In one embodiment, $R^1$ is a linear or branched alkyl, linear or branched alkenyl, linear or branched alkynyl, aryl, or aralkyl group having from about 8 to about 30 carbon atoms, $R^2$ is a linear or branched hydroxyalkyl group having from 1 to about 6 carbon atoms, and $R^3$ is hydrogen or a linear or branched hydroxyalkyl group having from 1 to about 6 carbon atoms. Preferably, $R^1$ is a linear or branched alkyl, linear or branched alkenyl, linear or branched alkynyl, aryl, or aralkyl group having from about 8 to about 22 carbon atoms, $R^2$ is a linear or branched hydroxyalkyl group having from 1 to about 4 carbon atoms, and $R^3$ is hydrogen or a linear or branched hydroxyalkyl group having from 1 to about 4 carbon atoms. More preferably, $R^1$ is a linear or branched alkyl, linear or branched alkenyl, linear or branched alkynyl, aryl, or aralkyl group having from about 8 to about 18 carbon atoms, $R^2$ is hydroxymethyl or hydroxyethyl, and $R^3$ is hydrogen, hydroxymethyl or hydroxyethyl.

In one embodiment, the secondary or tertiary amines are included in glyphosate concentrates other than IPA glyphosate, such as glyphosate concentrates containing potassium, di-ammonium, ammonium, sodium, monoethanolamine, n-propylamine, methylamine, ethylamine, hexamethylenediamine, dimethylamine, or trimethylsulfonium glyphosate and mixtures thereof, which contain at least about 20 wt. % glyphosate a.e., more preferably at least about 25%, 30%, 35%, 40%, 45%, 50% or 55 wt. % a.e., or at least about 270 g a.e. glyphosate per liter, more preferably at least 300, 360, 400, 420, 440, 460, 480, 500, 520 or 540 g a.e./l.

(b) monoalkoxylated amines having the formula:

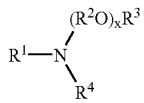
(64)

wherein $R^1$ and $R^4$ are independently hydrocarbyl or substituted hydrocarbyl groups having from 1 to about 30 carbon atoms or $-R^5SR^6$, $R^2$ in each of the x ($R^2O$) groups is independently $C_2-C_4$ alkylene, $R^3$ is hydrogen, or a linear or branched alkyl group having from 1 to about 4 carbon atoms, $R^5$ is a linear or branched alkyl group having from about 6 to about 30 carbon atoms, $R^6$ is a hydrocarbyl or substituted hydrocarbyl group having from 4 to about 15 carbon atoms and x is an average number from 1 to about 60. In this context, preferred $R^1$, $R^4$, and $R^6$ hydrocarbyl groups are linear or branched alkyl, linear or branched alkenyl, linear or branched alkynyl, aryl, or aralkyl groups. In one embodiment, $R^1$ includes from about 7 to about 30 carbon atoms, preferably from about 8 to about 22 carbon atoms, and the remaining groups are as described above. Preferably, $R^1$ and $R^4$ are independently a linear or branched alkyl or linear or branched alkenyl group having from 1 to about 25 carbon atoms, $R^2$ in each of the x ($R^2O$) groups is independently $C_2-C_4$ alkylene, $R^3$ is hydrogen, methyl or ethyl, and x is an average number from 1 to about 40. More preferably, $R^1$ and $R^4$ are independently a linear or branched alkyl group having from 1 to about 22 carbon atoms, $R^2$ in each of the x ($R^2O$) groups is independently ethylene or propylene, $R^3$ is hydrogen or methyl, and x is an average number from 1 to about 30. Even more preferably, $R^1$ is a linear or branched alkyl group having from about 8 to about 22 carbon atoms and $R^4$ is a linear or branched alkyl group having from 1 to about 22 carbon atoms, $R^2$ in each of the x ($R^2O$) groups is independently ethylene or propylene, $R^3$ is hydrogen or methyl, and x is an average number from about 1 to about 10. Most preferably, $R^1$ is a linear or branched alkyl group having from about 16 to about 22 carbon atoms and $R^4$ is methyl, $R^2$ in each of the x ($R^2O$) groups is ethylene, $R^3$ is hydrogen, and x is an average number from about 1 to about 5, or $R^1$ is a linear or branched alkyl group having from about 8 to about 15 carbon atoms and $R^4$ is methyl, $R^2$ in each of the x ($R^2O$) groups is ethylene, $R^3$ is hydrogen, and x is an average number from about 5 to about 10.

In one embodiment, the monoalkoxylated amines are included in glyphosate concentrates other than IPA glyphosate, such as glyphosate concentrates containing potassium, di-ammonium, ammonium, sodium, monoethanolamine, n-propylamine, methylamine, ethylamine, hexamethylenediamine, dimethylamine, or trimethylsulfonium glyphosate and mixtures thereof, which contain at least about 20 wt. % glyphosate a.e., more preferably at least about 25%, 30%, 35%, 40%, 45%, 50% or 55 wt. % a.e., or at least about 270 g a.e. glyphosate per liter, more preferably at least 300, 360, 400, 420, 440, 460, 480, 500, 520 or 540 g a.e./l.

(c) dialkoxylated quaternary ammonium salt having the formula:

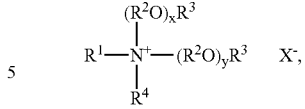
(65)

wherein $R^1$ is hydrocarbyl or substituted hydrocarbyl having from 1 to about 30 carbon atoms, $R^2$ in each of the x ($R^2O$) and y ($R^2O$) groups is independently $C_2-C_4$ alkylene, $R^3$ is hydrogen, or a linear or branched alkyl group having from 1 to about 4 carbon atoms, $R^4$ is hydrogen or hydrocarbyl or substituted hydrocarbyl having from 1 to about 30 carbon atoms, x and y are independently an average number from 1 to about 40, and X− is an agriculturally acceptable anion. In this context, preferred $R^1$ and $R^4$ hydrocarbyl groups are linear or branched alkyl, linear or branched alkenyl, linear or branched alkynyl, aryl, or aralkyl groups. Preferably, $R^1$ and $R^4$ are independently a linear or branched alkyl or linear or branched alkenyl group having from 1 to about 25 carbon atoms, $R^2$ in each of the x ($R^2O$) and y ($R^2O$) groups is independently $C_2-C_4$ alkylene, $R^3$ is hydrogen, methyl or ethyl, and the sum of x and y is an average number from about 2 to about 30. More preferably, $R^1$ and $R^4$ are independently a linear or branched alkyl group having from 1 to about 22 carbon atoms, $R^2$ in each of the x ($R^2O$) and y ($R^2O$) groups is independently ethylene or propylene, $R^3$ is hydrogen or methyl, and the sum of x any y is an average number from about 2 to about 20. Even more preferably, $R^1$ is a linear or branched alkyl group having from about 8 to about 22 carbon atoms and $R^4$ is a linear or branched alkyl group having from 1 to about 22 carbon atoms, $R^2$ in each of the x ($R^2O$) and y ($R^2O$) groups is independently ethylene or propylene, $R^3$ is hydrogen or methyl, and x is an average number from about 2 to about 20. Most preferably, $R^1$ is a linear or branched alkyl group having from about 8 to about 22 carbon atoms and $R^4$ is a linear or branched alkyl group having from 1 to about 6 carbon atoms, $R^2$ in each of the x ($R^2O$) and y ($R^2O$) groups is independently ethylene or propylene, $R^3$ is hydrogen or methyl, and x is an average number from about 2 to about 15, or $R^1$ and $R^4$ are independently a linear or branched alkyl group having from about 8 to about 22 carbon atoms, $R^2$ in each of the x ($R^2O$) and y ($R^2O$) groups is independently ethylene or propylene, $R^3$ is hydrogen or methyl, and x is an average number from about 5 to about 15. Preferred dialkoxylated quaternary ammonium surfactants include Ethoquad™ C12 (a PEG 2 coco methyl ammonium chloride from Akzo Nobel), PEG 5 coco methyl ammonium chloride, PEG 5 tallow methyl ammonium chloride, PEG 5 ditallow ammonium bromide, and PEG 10 ditallow ammonium bromide.

In one embodiment, the dialkoxylated quaternary ammonium salts are included in glyphosate concentrates other than IPA glyphosate, such as glyphosate concentrates containing potassium, di-ammonium, ammonium, sodium, monoethanolamine, n-propylamine, methylamine, ethylamine, hexamethylenediamine, dimethylamine, or trimethylsulfonium glyphosate and mixtures thereof, which contain at least about 20 wt. % glyphosate a.e., more preferably at least about 25%, 30%, 35%, 40%, 45%, 50% or 55 wt. % a.e., or at least about 270 g a.e. glyphosate per liter, more preferably at least 300, 360, 400, 420, 440, 460, 480, 500, 520 or 540 g a.e./l.

(d) monoalkoxylated quaternary ammonium salts having the formula:

(66)

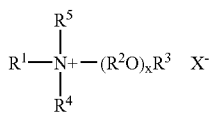

wherein $R^1$ and $R^5$ are independently hydrogen or hydrocarbyl or substituted hydrocarbyl having from 1 to about 30 carbon atoms, $R^4$ is hydrocarbyl or substituted hydrocarbyl having from 1 to about 30 carbon atoms, $R^2$ in each of the x ($R^2$O) groups is independently $C_2$–$C_4$ alkylene, $R^3$ is hydrogen, or a linear or branched alkyl group having from 1 to about 30 carbon atoms, x is an average number from 1 to about 60, and X– is an agriculturally acceptable anion. In this context, preferred $R^1$, $R^4$, and $R^5$ hydrocarbyl groups are linear or branched alkyl, linear or branched alkenyl, linear or branched alkynyl, aryl, or aralkyl groups. Preferably, $R^1$, $R^4$ and $R^5$ are independently a linear or branched alkyl or linear or branched alkenyl group having from 1 to about 25 carbon atoms, $R^2$ in each of the x ($R^2$O) groups is independently $C_2$–$C_4$ alkylene, $R^3$ is hydrogen, methyl or ethyl, and x is an average number from 1 to about 40. More preferably, $R^1$, $R^4$ and $R^5$ are independently a linear or branched alkyl group having from 1 to about 22 carbon atoms, $R^2$ in each of the x ($R^2$O) groups is independently ethylene or propylene, $R^3$ is hydrogen or methyl, and x is an average number from 1 to about 30. Even more preferably, $R^1$ is a linear or branched alkyl group having from about 8 to about 22 carbon atoms, $R^2$ in each of the x ($R^2$O) groups is independently ethylene or propylene, $R^3$ is hydrogen or methyl, $R^4$ and $R^5$ are independently a linear or branched alkyl group having from 1 to about 22 carbon atoms, and x is an average number from 1 to about 30. Even more preferably, $R^1$ is a linear or branched alkyl group having from about 8 to about 22 carbon atoms, $R^2$ in each of the x ($R^2$O) groups is independently ethylene or propylene, $R^3$ is hydrogen or methyl, $R^4$ and $R^5$ are independently a linear or branched alkyl group having from 1 to about 6 carbon atoms, and x is an average number from about 5 to about 25. Most preferably, $R^1$ is a linear or branched alkyl group having from about 16 to about 22 carbon atoms, $R^2$ in each of the x ($R^2$O) groups is independently ethylene or propylene, $R^3$ is hydrogen or methyl, $R^4$ and $R^5$ are independently a linear or branched alkyl group having from 1 to about 3 carbon atoms, and x is an average number from about 5 to about 25. Preferred monoalkoxylated quaternary ammonium surfactants include PEG 7 $C_{18}$ dimethyl ammonium chloride and PEG 22 $C_{18}$ dimethyl ammonium chloride.

In one embodiment, the monoalkoxylated quaternary ammonium salts are included in glyphosate concentrates other than IPA glyphosate, such as glyphosate concentrates containing potassium, di-ammonium, ammonium, sodium, monoethanolamine, n-propylamine, methylamine, ethylamine, hexamethylenediamine, dimethylamine, or trimethylsulfonium glyphosate and mixtures thereof, which contain at least about 20 wt. % glyphosate a.e., more preferably at least about 25%, 30%, 35%, 40%, 45%, 50% or 55 wt. % a.e., or at least about 270 g a.e. glyphosate per liter, more preferably at least 300, 360, 400, 420, 440, 460, 480, 500, 520 or 540 g a.e./l.

(e) quaternary ammonium salts having the formula:

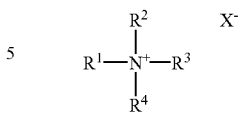

(67)

wherein $R^1$, $R^3$ and $R^4$ are independently hydrogen or hydrocarbyl or substituted hydrocarbyl having from 1 to about 30 carbon atoms, $R^2$ is hydrocarbyl or substituted hydrocarbyl having from 1 to about 30 carbon atoms, and X– is an agriculturally acceptable anion. In this context, preferred $R^1$, $R^2$, $R^3$, and $R^4$ hydrocarbyl groups are linear or branched alkyl, linear of branched alkenyl, linear or branched alkynyl, aryl, or aralkyl groups. Preferably, $R^1$ is a linear or branched alkyl or linear or branched alkenyl group having from about 8 to about 30 carbon atoms, and $R^2$, $R^3$ and $R^4$ are independently a linear or branched alkyl or linear or branched alkenyl group having from 1 to about 30 carbon atoms. More preferably, $R^1$ is a linear or branched alkyl or linear or branched alkenyl group having from about 8 to about 22 carbon atoms, and $R^2$, $R^3$ and $R^4$ are independently a linear or branched alkyl or linear or branched alkenyl group having from 1 to about 6 carbon atoms. Even more preferably, $R^1$ is a linear or branched alkyl group having from about 8 to about 16 carbon atoms, and $R^2$, $R^3$ and $R^4$ are independently a linear or branched alkyl group having from 1 to about 6 carbon atoms. Most preferably, $R^1$ is a linear or branched alkyl group having from about 8 to about 14 carbon atoms, and $R^2$, $R^3$ and $R^4$ are methyl. Preferred commercially available quaternary ammonium surfactants include Arquad™ C-50 (a dodecyl trimethyl ammonium chloride from Akzo Nobel) and Arquad™ T-50 (a tallow trimethyl ammonium chloride from Akzo Nobel).

In one embodiment, the quaternary ammonium salts are included in glyphosate concentrates other than IPA glyphosate, such as glyphosate concentrates containing potassium, di-ammonium, ammonium, sodium, monoethanolamine, n-propylamine, methylamine, ethylamine, hexamethylenediamine, dimethylamine, or trimethylsulfonium glyphosate and mixtures thereof, which contain at least about 20 wt. % glyphosate a.e., more preferably at least about 25%, 30%, 35%, 40%, 45%, 50% or 55 wt. % a.e., or at least about 270 g a.e. glyphosate per liter, more preferably at least 300, 360, 400, 420, 440, 460, 480, 500, 520 or 540 g a.e./l.

(f) ether amines having the formula:

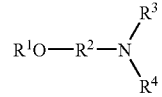

(68)

wherein $R^1$ is hydrocarbyl or substituted hydrocarbyl having from 1 to about 30 carbon atoms; $R^2$ is hydrocarbylene or substituted hydrocarbylene having from 2 to about 30 carbon atoms; $R^3$ and $R^4$ are independently hydrogen, hydrocarbyl or substituted hydrocarbyl having from 1 to about 30 carbon atoms, or —($R^5$O)$_x$$R^6$, $R^5$ in each of the x($R^5$—O) groups is independently $C_2$–$C_4$ alkylene, $R^6$ is hydrogen, or a linear or branched alkyl group having from 1 to about 4 carbon atoms, and x is an average number from 1 to about 50. In this context, preferred $R^1$, $R^2$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl, linear or branched alkenyl, linear or branched alkynyl, aryl, or aralkyl group having from 8 to about 25 carbon atoms, $R^2$ is a linear or branched alkylene or alkenylene group having from 2 to about 30 carbon atoms, $R^3$ and $R^4$ are independently hydrogen, a linear or branched alkyl, linear or branched alkenyl, linear or branched alkynyl, aryl, or aralkyl group having from 1 to about 30 carbon atoms, or —$(R^5O)_xR^6$, $R^5$ in each of the x ($R^5O$) groups is independently $C_2$–$C_4$ alkylene, $R^6$ is hydrogen, methyl or ethyl, and x is an average number from 1 to about 30. More preferably, $R^1$ is a linear or branched alkyl or alkenyl group having from 8 to about 22 carbon atoms, $R^2$ is a linear or branched alkylene or alkenylene group having from 2 to about 6 carbon atoms, $R^3$ and $R^4$ are independently hydrogen, a linear or branched alkyl or alkenyl group having from 1 to about 6 carbon atoms, or —$(R^5O)_xR^6$, $R^5$ in each of the x ($R^5O$) groups is independently ethylene or propylene, $R^6$ is hydrogen or methyl, and x is an average number from 1 to about 15. Most preferably, $R^1$ is a linear or branched alkyl or alkenyl group having from 8 to about 18 carbon atoms, $R^2$ is ethylene or propylene, $R^3$ and $R^4$ are independently hydrogen, methyl, or —$(R^5O)_xR^6$, $R^5$ in each of the x ($R^5O$) groups is independently ethylene or propylene, $R^6$ is hydrogen, and x is an average number from 1 to about 5.

In one embodiment, the ether amines are included in glyphosate concentrates other than IPA glyphosate, such as glyphosate concentrates containing potassium, di-ammonium, ammonium, sodium, monoethanolamine, n-propylamine, methylamine, ethylamine, hexamethylenediamine, dimethylamine, or trimethylsulfonium glyphosate and mixtures thereof, which contain at least about 20 wt. % glyphosate a.e., more preferably at least about 25%, 30%, 35%, 40%, 45%, 50% or 55 wt. % a.e., or at least about 270 g a.e. glyphosate per liter, more preferably at least 300, 360, 400, 420, 440, 460, 480, 500, 520 or 540 g (g) diamines having the formula:

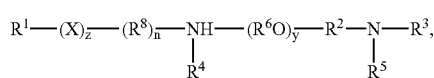
(69)

wherein $R^1$, $R^3$, $R^4$ and $R^5$ are independently hydrogen, hydrocarbyl or substituted hydrocarbyl having from 1 to about 30 carbon atoms, or —$(R^6O)_xR^7$; $R^2$ and $R^8$ are independently hydrocarbylene or substituted hydrocarbylene having from 2 to about 30 carbon atoms, $R^6$ in each of the x ($R^6O$) and y ($R^6O$) groups is independently $C_2$–$C_4$ alkylene, $R^7$ is hydrogen, or a linear or branched alkyl group having from 1 to about 30 carbon atoms, x is an average number from 1 to about 30, X is —O—, —N($R^6$)—, —C(O)—, —C(O)O—, —OC(O)—, —N($R^9$)C(O)—, —C(O)N($R^9$)—, —S—, —SO—, or —$SO_2$—, y is 0 or an average number from 1 to about 30, n and z are independently 0 or 1, and $R^9$ is hydrogen or hydrocarbyl or substituted hydrocarbyl. In this context, preferred $R^1$, $R^2$, $R^3$, $R^4$, $R^5$ and $R^9$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^4$ are independently a linear or branched alkyl or linear or branched alkenyl group having from about 1 to about 22 carbon atoms, $R^2$ and $R^8$ are independently linear or branched alkylene groups having from about 2 to about 25 carbon atoms, $R^3$ and $R^5$ are each independently hydrogen or a linear or branched alkyl group having from 1 to about 6 carbon atoms and n, y and z are 0; or $R^1$, $R^2$, $R^3$ and $R^4$ are independently hydrogen or a linear or branched alkyl or alkenyl group having from about 1 to about 6 carbon atoms, $R^2$ is a linear or branched alkylene or alkenylene group having from about 8 to about 25 carbon atoms, and n, y and z are 0; or $R^1$, $R^2$, $R^3$ and $R^4$ are independently hydrogen or a linear or branched alkyl or alkenyl group having from about 1 to about 6 carbon atoms, $R^2$ is a linear or branched alkylene or alkenylene group having from about 1 to about 6 carbon atoms, $R^8$ in each of the y ($R^6O$) groups is independently $C_2$–$C_4$ alkylene, y is an average number from 1 to about 20 and n and z are 0; or $R^1$ and $R^3$ are independently a linear or branched alkyl or linear or branched alkenyl group having from about 8 to about 22 carbon atoms, $R^2$ is a linear or branched alkylene group having from about 2 to about 25 carbon atoms; and $R^4$ and $R^5$ are each independently hydrogen, a linear or branched alkyl or alkenyl group having from 1 to about 6 carbon atoms, or —$(R^6O)_xR^7$, $R^6$ in each of the x ($R^6O$) groups is independently $C_2$–$C_4$ alkylene, $R^7$ is hydrogen, or a linear or branched alky group having from 1 to about 4 carbon atoms, x is an average number from 1 to about 30, and n, y and z are 0; or $R^1$ is a linear or branched alkyl or linear or branched alkenyl group having from about 1 to about 22 carbon atoms, $R^2$ is a linear or branched alkylene group having from about 2 to about 25 carbon atoms, $R^3$, $R^4$ and $R^5$ are each independently hydrogen or a linear or branched alkyl group having from 1 to about 6 carbon atoms, X is —C(O)— or —$SO_2$—, n and y are 0 and z is 1. More preferably, $R^1$ and $R^4$ are independently a linear or branched alkyl or linear or branched alkenyl group having from about 4 to about 18 carbon atoms, $R^2$ is a linear or branched alkylene group having from about 2 to about 6 carbon atoms, $R^3$ and $R^5$ are each independently hydrogen or a linear or branched alkyl group having from 1 to about 6 carbon atoms, and n, y and z are 0; or $R^1$, $R^2$, $R^3$ and $R^4$ are independently hydrogen or a linear or branched alkyl group having from about 1 to about 6 carbon atoms, $R^2$ is a linear or branched alkylene group having from about 8 to about 25 carbon atoms, and y is 0; or $R^1$, $R^2$, $R^3$ and $R^4$ are independently hydrogen or a linear or branched alkyl group having from about 1 to about 6 carbon atoms, $R^2$ is a linear or branched alkylene group having from about 1 to about 6 carbon atoms, $R^6$ in each of the y ($R^6O$) groups is independently ethylene or propylene, y is an average number from 1 to about 10 and n and z is 0; or $R^1$ and $R^3$ are independently a linear or branched alkyl group having from about 8 to about 22 carbon atoms, $R^2$ is a linear or branched alkylene group having from about 2 to about 6 carbon atoms, and $R^4$ and $R^5$ are each independently hydrogen, a linear or branched alkyl group having from 1 to about 6 carbon atoms, or —$(R^6O)_xR^7$, $R^6$ in each of the x ($R^6O$) groups is independently ethylene or propylene, $R^7$ is hydrogen or methyl, x is an average number from 1 to about 15, and n, y and z are 0; or $R^1$ is a linear or branched alkyl group having from about 1 to about 22 carbon atoms, $R^2$ is a linear or branched alkylene group having from about 2 to about 6 carbon atoms, $R^3$, $R^4$ and $R^5$ are each independently hydrogen, X is —C(O)— or —$SO_2$—, n and y are 0 and z is 1. Preferred diamines include Gemini 14-2-14, Gemini 14-3-14, Gemini 10-2-10, Gemini 10-3-10, Gemini 10-4-10, and Gemini 16-2-16 ($C_{10}$, $C_{14}$ or $C_{16}$ ethylene, propylene or butylene N-methyl diamines from Monsanto), Ethoduomeens™, and Jeffamine™ EDR-148.

In one embodiment, the diamines are included in glyphosate concentrates other than IPA glyphosate, such as glyphosate concentrates containing potassium, di-ammonium, ammonium, sodium, monoethanolamine, n-propylamine, methylamine, ethylamine, hexamethylenediamine, dimethylamine, or trimethylsulfonium glyphosate and mixtures thereof, which contain at least about 20 wt. % glyphosate a.e., more preferably at least about 25%, 30%, 35%, 40%, 45%, 50% or 55 wt. % a.e., or at least about 270 g a.e. glyphosate per liter, more preferably at least 300, 360, 400, 420, 440, 460, 480, 500, 520 or 540 g a.e./l.

(h) amine oxides having the formula:

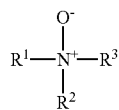

(70)

wherein $R^1$, $R^2$ and $R^3$ are independently hydrogen, hydrocarbyl or substituted hydrocarbyl, $-(R^4O)_xR^5$, or $-R^6(OR^4)_xOR^5$; $R^4$ in each of the x ($R^4O$) groups is independently $C_2-C_4$ alkylene, $R^5$ is hydrogen, or a linear or branched alkyl group having from 1 to about 30 carbon atoms, $R^6$ is hydrocarbylene or substituted hydrocarbylene having from 2 to about 6 carbon atoms, x is an average number from 1 to about 50, and the total number of carbon atoms in $R^1$, $R^2$ and $R^3$ is at least 8. In this context, preferred $R^1$, $R^2$, $R^3$, and $R^6$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^2$ are independently hydrogen, a linear or branched alkyl or linear or branched alkenyl group having from 1 to about 30 carbon atoms, or $-(R^4O)_xR^5$; $R^3$ is a linear or branched alkyl or linear or branched alkenyl group having from about 8 to about 30 carbon atoms, $R^4$ in each of the x ($R^4O$) groups is independently $C_2-C_4$ alkylene; $R^5$ is hydrogen, methyl or ethyl, and x is an average number from 1 to about 30. More preferably, $R^1$ and $R^2$ are independently hydrogen, or a linear or branched alkyl group having from 1 to about 6 carbon atoms, and $R^3$ is a linear or branched alkyl group having from about 8 to about 22 carbon atoms; or $R^1$ and $R^2$ are independently $-(R^4O)_xR^5$, $R^3$ is a linear or branched alkyl group having from about 8 to about 22 carbon atoms, $R^4$ in each of the x ($R^4O$) groups is ethylene or propylene, $R^5$ is hydrogen or methyl, and x is an average number from 1 to about 10. Most preferably, $R^1$ and $R^2$ are independently methyl, and $R^3$ is a linear or branched alkyl group having from about 8 to about 18 carbon atoms; or $R^1$ and $R^2$ are independently $-(R^4O)_xR^5$, $R^3$ is a linear or branched alkyl group having from about 8 to about 18 carbon atoms, $R^4$ in each of the x ($R^4O$) groups is ethylene or propylene, $R^5$ is hydrogen, and x is an average number from 1 to about 5. Commercially available amine oxide surfactants include Chemoxide L70.

In one embodiment, the amine oxides are included in glyphosate concentrates other than IPA glyphosate, such as glyphosate concentrates containing potassium, di-ammonium, ammonium, sodium, monoethanolamine, n-propylamine, methylamine, ethylamine, hexamethylenediamine, dimethylamine, or trimethylsulfonium glyphosate and mixtures thereof, which contain at least about 20 wt. % glyphosate a.e., more preferably at least about 25%, 30%, 35%, 40%, 45%, 50% or 55 wt. % a.e., or at least about 270 g a.e. glyphosate per liter, more preferably at least 300, 360, 400, 420, 440, 460, 480, 500, 520 or 540 g a.e./l.

(i) dialkoxylated amines having the formula:

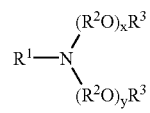

(71)

wherein $R^1$ is a linear or branched alkyl, linear or branched alkenyl, linear or branched alkynyl, aryl, or aralkyl group having from about 6 to about 30 carbon atoms, or $-R^4SH$, $R^2$ in each of the x ($R^2O$) and the y ($R^2O$) groups is independently $C_2-C_4$ alkylene, $R^3$ is hydrogen, or a linear or branched alkyl group having from 1 to about 4 carbon atoms, $R^4$ is a linear or branched alkyl group having from about 6 to about 30 carbon atoms, and x and y are independently an average number from 1 to about 40. Preferably, $R^1$ is a linear or branched alkyl or linear or branched alkenyl group having from about 8 to about 30 carbon atoms, $R^2$ in each of the x ($R^2O$) and the y ($R^2O$) groups is independently $C_2-C_4$ alkylene, $R^3$ is hydrogen, methyl or ethyl, and x and y are independently an average number from 1 to about 20. More preferably, $R^1$ is a linear or branched alkyl group having from about 8 to about 25 carbon atoms, $R^2$ in each of the x ($R^2O$) and the y ($R^2O$) groups is independently ethylene or propylene, $R^3$ is hydrogen or methyl, and x and y are independently an average number from 1 to about 10. Even more preferably, $R^1$ is a linear or branched alkyl group having from about 8 to about 22 carbon atoms, $R^2$ in each of the x ($R^2O$) and the y ($R^2O$) groups is independently ethylene or propylene, $R^3$ is hydrogen or methyl, and x and y are independently an average number from 1 to about 5. Preferred commercially available dialkoxylated amines include Trymeen™ 6617 (from Cognis) and Ethomeen™ C/12, C/15, C/20, C/25, T/12, T/15, T/20 and T/25 (from Akzo Nobel).

Such dialkoxylated amines are preferably used in potassium glyphosate concentrates containing at least 550 grams a.e. per liter of potassium glyphosate, and more preferably at least 560, 570 or 580 grams a.e. per liter of potassium glyphosate. It is preferred that such potassium glyphosate concentrates contain from about 550 to about 600 grams a.e. per liter of potassium glyphosate.

Alternatively, the dialkoxylated amines are preferably formulated in potassium glyphosate concentrates containing at least 320 grams a.e. per liter of potassium glyphosate, that are free of alkyl polyglycosides, or that only contain alkyl polyglycosides having a light color of less than 10, preferably less than 9, 8, 7, 6, or 5 as measured using a Gardner colorimeter. In one embodiment, such concentrates include at least 330, 340, 350, 360, 370, 380, 390, 400, 410, 420, 430, 440, 450, 460, 470, 480, 490, 500, 510, 520, 530, 540, 550, 560, 570 or 580 grams a.e. per liter of potassium glyphosate. It is preferred that such potassium glyphosate concentrates contain from about 400 to about 600 grams a.e. per liter of potassium glyphosate, more preferably from about 450 to about 600, about 500 to about 600, about 540 to about 600 or about 550 to about 600 grams a.e. per liter of potassium glyphosate.

Alternatively, the dialkoxylated amines are preferably incorporated in potassium glyphosate concentrates containing from about 20 to about 150 grams per liter of total surfactant in the formulation, more preferably from about 20 to about 130 grams per liter. In another embodiment, the dialkoxylated amines are incorporated in potassium glyphosate concentrates containing from about 20 to about 150 grams per liter of total surfactant in the formulation and at least 320 grams a.e. per liter of potassium glyphosate, more preferably at least 330, 340, 350, 360, 370, 380, 390, 400, 410, 420, 430, 440, 450, 460, 470, 480, 490, 500, 510, 520, 530, 540, 550, 560, 570 or 580 grams a.e. per liter of potassium glyphosate. It is preferred that such potassium glyphosate concentrates contain from about 400 to about 600 grams a.e. per liter of potassium glyphosate, more preferably from about 450 to about 600, about 500 to about 600, about 540 to about 600 or about 550 to about 600 grams a.e. per liter of potassium glyphosate.

and (j) aminated alkoxylated alcohols having the following chemical structure:

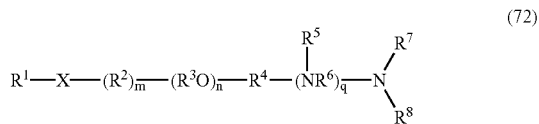

(72)

wherein $R^1$, $R^7$, $R^8$, and $R^9$ are each independently hydrogen, hydrocarbyl or substituted hydrocarbyl having from 1 to about 30 carbon atoms, or $-(R^{11})_s(R^3O)_vR^{10}$; X is $-O-$, $-OC(O)-$, $-C(O)O-$, $-N(R^{12})C(O)-$, $-C(O)N(R^{12})-$, $-S-$, $-SO-$, $-SO_2-$ or $-N(R^9)-$; $R^3$ in each of the n ($R^3O$) groups and the v ($R^3O$) groups is independently $C_2-C_4$ alkylene; $R^{10}$ is hydrogen, or a linear or branched alkyl group having from 1 to about 30 carbon atoms; n is an average number from 1 to about 60; v is an average number from 1 to about 50; $R^2$ and $R^{11}$ are each independently hydrocarbylene or substituted hydrocarbylene having from 1 to about 6 carbon atoms; $R^4$ is hydrocarbylene or substituted hydrocarbylene having from 2 to about 6 carbon atoms; $R^{12}$ is hydrogen or hydrocarbyl or substituted hydrocarbyl having from 1 to about 30 carbon atoms; m and s are each independently 0 or 1; $R^6$ is hydrocarbylene or substituted hydrocarbylene having from 2 to about 30 carbon atoms, $-C(=NR^{12})-$, $-C(S)-$, or $-C(O)-$; q is an integer from 0 to 5; and $R^5$ is hydrogen or hydrocarbyl or substituted hydrocarbyl having from 1 to about 30 carbon atoms. In this context, preferred $R^1$, $R^2$, $R^4$, $R^5$, $R^6$, $R^7$, $R^8$, $R^9$, $R^{11}$ and $R^{12}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups.

In one embodiment, the aminated alkoxylated alcohols are included in glyphosate concentrates other than IPA glyphosate, such as glyphosate concentrates containing potassium, di-ammonium, ammonium, sodium, monoethanolamine, n-propylamine, methylamine, ethylamine, hexamethylenediamine, dimethylamine, or trimethylsulfonium glyphosate and mixtures thereof, which contain at least about 20 wt. % glyphosate a.e., more preferably at least about 25%, 30%, 35%, 40%, 45%, 50% or 55 wt. % a.e., or at least about 270 g a.e. glyphosate per liter, more preferably at least 300, 360, 400, 420, 440, 460, 480, 500, 520 or 540 g a.e./l.

A subclass of such cationic surfactants includes a monoalkoxylated amine having the formula:

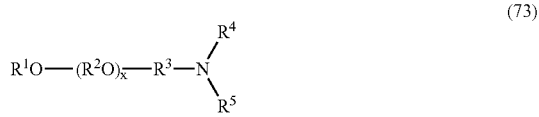

(73)

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2-C_4$ alkylene; $R^3$ is hydrocarbylene or substituted hydrocarbylene having from 2 to about 30 carbon atoms; $R^4$ and $R^5$ are each independently hydrogen, hydrocarbyl or substituted hydrocarbyl having from 1 to about 30 carbon atoms, $-(R^6)_n-(R^2O)_yR^7$, or $R^4$ and $R^5$, together with the nitrogen atom to which they are attached, form a cyclic or heterocyclic ring; $R^6$ is hydrocarbylene or substituted hydrocarbylene having from 1 to about 30 carbon atoms; $R^7$ is hydrogen or a linear or branched alkyl group having 1 to about 4 carbon atoms, n is 0 or 1, x and y are independently an average number from 1 to about 60. In this context, preferred $R^1$, $R^3$, $R^4$, $R^5$, and $R^6$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 25 carbon atoms, $R^2$ in each of the x ($R^2O$) groups is independently $C_2-C_4$ alkylene, $R^3$ is a linear or branched alkylene group having from 2 to about 20 carbon atoms, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the x ($R^2O$) groups is independently ethylene or propylene, $R^3$ is a linear or branched alkylene group having from 2 to about 6 carbon atoms, $R^4$ and $R^5$ are each independently hydrogen, methyl, or tris(hydroxymethyl)methyl, and x is an average number from about 2 to about 30. Even more preferably, $R^1$ is a linear or branched alkyl group having from about 12 to about 18 carbon atoms, $R^2$ in each of the x ($R^2O$) groups is independently ethylene or propylene, $R^3$ is ethylene or propylene, $R^4$ and $R^5$ are each independently hydrogen, methyl or tris(hydroxymethyl)methyl, and x is an average number from about 4 to about 20. Most preferably, $R^1$ is a linear or branched alkyl group having from about 12 to about 18 carbon atoms, $R^2$ in each of the x ($R^2O$) groups is independently ethylene or propylene, $R^3$ is ethylene, $R^4$ and $R^5$ are, methyl, and x is an average number from about 4 to about 20. Preferred monoalkoxylated amines include PEG 13 or 18 $C_{14-15}$ ether propylamines and PEG 7, 10, 15 or 20 $C_{16-18}$ ether propylamines (from Tomah) and PEG 13 or 18 $C_{14-15}$ ether dimethyl propylamines and PEG 10, 15 or 20 or 25 $C_{16-18}$ ether dimethyl propylamines (from Tomah) and Surfonic™ AGM-550 from Huntsman.

In one embodiment, the monoalkoxylated amines are included in glyphosate concentrates other than IPA glyphosate, such as glyphosate concentrates containing potassium, di-ammonium, ammonium, sodium, monoethanolamine, n-propylamine, methylamine, ethylamine, hexamethylenediamine, dimethylamine, or trimethylsulfonium glyphosate and mixtures thereof, which contain at least about 20 wt. % glyphosate a.e., more preferably at least about 25%, 30%, 35%, 40%, 45%, 50% or 55 wt. % a.e., or at least about 270 g a.e. glyphosate per liter, more preferably at least 300, 360, 400, 420, 440, 460, 480, 500, 520 or 540 g a.e./l.

Quaternary ammonium, sulfonium and sulfoxonium salts are also effective cationic surfactants in forming potassium glyphosate concentrates and have a chemical structure:

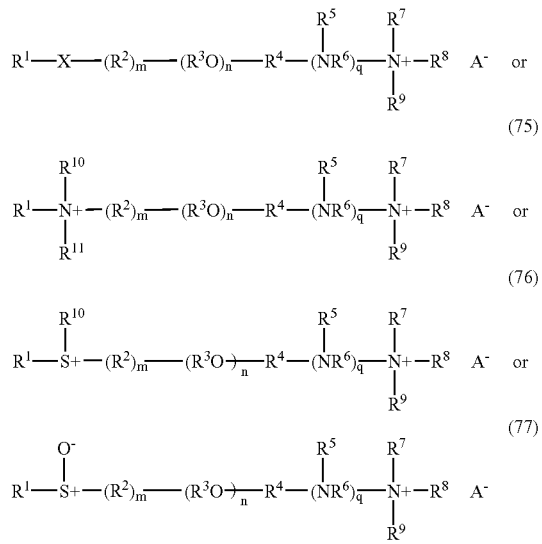

(74), (75), (76), (77)

wherein $R^1$, $R^7$, $R^8$, $R^9$, $R^{10}$ and $R^{11}$ are independently hydrogen, hydrocarbyl or substituted hydrocarbyl having from 1 to about 30 carbon atoms, or $—(R^{13})_s(R^3O)_vR^{12}$; X is $—O—$, $—OC(O)—$, $—N(R^{14})C(O)—$, $—C(O)N(R^{14})—$, $—C(O)O—$, or $—S—$; $R^3$ in each of the n ($R^3O$) groups and v ($R^3O$) groups is independently $C_2$–$C_4$ alkylene; $R^{12}$ is hydrogen, or a linear or branched alkyl group having from 1 to about 30 carbon atoms; n is an average number from 1 to about 60; v is an average number from 1 to about 50; $R^2$ and $R^{13}$ are each independently hydrocarbylene or substituted hydrocarbylene having from 1 to about 6 carbon atoms; m and s are each independently 0 or 1; $R^4$ is hydrocarbylene or substituted hydrocarbylene having from 2 to about 6 carbon atoms; $R^6$ is hydrocarbylene or substituted hydrocarbylene having from 2 to about 30 carbon atoms, $—C(=NR^{12})—$, $—C(S)—$, or $—C(O)—$; $R^{14}$ is hydrogen or hydrocarbyl or substituted hydrocarbyl having from 1 to about 30 carbon atoms, q is an integer from 0 to 5; $R^5$ is hydrogen or hydrocarbyl or substituted hydrocarbyl having from 1 to about 30 carbon atoms; and each $A^-$ is an agriculturally acceptable anion. In this context, preferred $R^1$, $R^2$, $R^4$, $R^5$, $R^6$, $R^7$, $R^8$, $R^9$, $R^{10}$, $R^{11}$, $R^{13}$, and $R^{14}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups.

Another cationic surfactant effective in any glyphosate formulations is a diamine or diammonium salt having the formula:

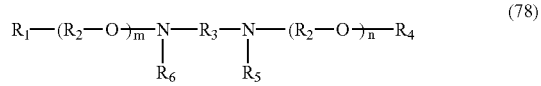

(78)

-continued

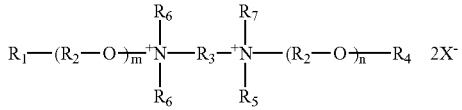

(79)

wherein $R^1$, $R^4$, $R^5$, $R^6$, $R^7$, and $R^8$ are independently hydrogen or hydrocarbyl or substituted hydrocarbyl having from 1 to about 30 carbon atoms, $R^2$ in each of the m ($R^2O$) and n ($R^2O$) groups and $R^9$ are independently $C_2$–$C_4$ alkylene, $R^3$ is hydrocarbylene or substituted hydrocarbylene having from about 2 to about 6 carbon atoms or $—(R^2O)_pR_9—$, m and n are individually an average number from 0 to about 50, and p is an average number from 0 to about 60. In this context, preferred $R^1$, $R^3$, $R^4$, $R^5$, $R^6$, $R^7$ and $R^8$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. In one embodiment of formula (DA), $R^3$ is hydrocarbylene having from about 2 to about 6 carbon atoms, and the remaining groups are as defined above.

Preferred nonionic surfactants for such glyphosate concentrates include alkoxylated alcohols having the formula:

(80)

wherein $R^1$ is hydrocarbyl or substituted hydrocarbyl having from 1 to about 30 carbon atoms, $R^2$ in each of the x ($R^2O$) groups is independently $C_2$–$C_4$ alkylene, $R^3$ is hydrogen, or a linear or branched alkyl group having from 1 to about 4 carbon atoms, and x is an average number from 1 to about 60. In this context, preferred $R^1$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, $R^2$ in each of the x ($R^2O$) groups is independently $C_2$–$C_4$ alkylene, $R^3$ is hydrogen, methyl or ethyl, and x is an average number from about 5 to about 50. More preferably, $R^1$ is a linear or branched alkyl group having from about 8 to about 25 carbon atoms, $R^2$ in each of the x ($R^2O$) groups is independently ethylene or propylene, $R^3$ is hydrogen or methyl, and x is an average number from about 8 to about 40. Even more preferably, $R^1$ is a linear or branched alkyl group having from about 12 to about 22 carbon atoms, $R^2$ in each of the x ($R^2O$) groups is independently ethylene or propylene, $R^3$ is hydrogen or methyl, and x is an average number from about 8 to about 30. Preferred commercially available alkoxylated alcohols include Procol™ LA-15 (from Protameen), Brij™ 35, Brij™ 76, Brij™ 78, Brij™ 97 and Brij™ 98 (from Sigma Chemical Co.), Neodol™ 25-12 (from Shell), Hexotol™ CA-10, Hexotol™ CA-20, Hexotol™ CS-9, Hexotol™ CS-15, Hexotolo™ CS-20, Hexotol™ CS-25, Hexotol™ CS-30, and Plurafac™ A38 (from BASF), ST-8303 (from Cognis), and Arosurf™ 66 E20 (from Witco/Crompton).

In one embodiment, the alkoxylated alcohols are included in glyphosate concentrates other than IPA glyphosate, such as glyphosate concentrates containing potassium, di-ammonium, ammonium, sodium, monoethanolamine, n-propylamine, methylamine, ethylamine, hexamethylenediamine, dimethylamine, or trimethylsulfonium glyphosate and mixtures thereof, which contain at least about 20 wt. % glyphosate a.e., more preferably at least about 25%, 30%, 35%, 40%, 45%, 50% or 55 wt. % a.e., or at least about 270 g a.e. glyphosate per liter, more preferably at least 300, 360, 400, 420, 440, 460, 480, 500, 520 or 540 g a.e./l.

Other nonionic surfactants for use in such glyphosate formulations include alkoxylated dialkylphenols having the formula:

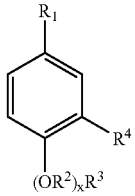
(81)

wherein $R^1$ and $R^4$ are independently hydrogen, or a linear or branched alkyl group having from 1 to about 30 carbon atoms and at least one of $R^1$ and $R^4$ is an alkyl group, $R^2$ in each of the x ($R^2O$) groups is independently $C_2$–$C_4$ alkylene, $R^3$ is hydrogen, or a linear or branched alkyl group having from 1 to about 4 carbon atoms, and x is an average number from 1 to about 60. Preferably, $R^1$ and $R^4$ are independently linear or branched alkyl groups having from 8 to about 30 carbon atoms, $R^2$ in each of the x ($R^2O$) groups is independently $C_2$–$C_4$ alkylene, $R^3$ is hydrogen, methyl or ethyl, and x is an average number from about 5 to about 50. More preferably, $R^1$ and $R^4$ are independently linear or branched alkyl groups having from about 8 to about 22 carbon atoms, $R^2$ in each of the x ($R^2O$) groups is independently ethylene or propylene, $R^3$ is hydrogen or methyl, and x is an average number from about 8 to about 40. Even more preferably, $R^1$ and $R^4$ are independently linear or branched alkyl groups having from about 8 to about 16 carbon atoms, $R^2$ in each of the x ($R^2O$) groups is independently ethylene or propylene, $R^3$ is hydrogen or methyl, and x is an average number from about 10 to about 30. Preferred commercially available alkoxylated dialkylphenols include ethoxylated dinonyl phenols such as Surfonic™ DNP 100, Surfonic™ DNP 140, and Surfonic™ DNP 240 (from Huntsman).

In one embodiment, the phenols are included in glyphosate concentrates other than IPA glyphosate, such as glyphosate concentrates containing potassium, di-ammonium, ammonium, sodium, monoethanolamine, n-propylamine, methylamine, ethylamine, hexamethylenediamine, dimethylamine, or trimethylsulfonium glyphosate and mixtures thereof, which contain at least about 20 wt. % glyphosate a.e., more preferably at least about 25%, 30%, 35%, 40%, 45%, 50% or 55 wt. % a.e., or at least about 270 g a.e. glyphosate per liter, more preferably at least 300, 360, 400, 420, 440, 460, 480, 500, 520 or 540 g a.e./l.

Preferred anionic surfactants effective in forming potassium glyphosate formulations include saturated carboxylic acids such as butyric, caproic, caprylic, capric, lauric, palmitic, myristic or steacri acid, and unsaturated carboxylic acids such as palmitoleic, oleic, linoleic or linolenic acid. Preferred carboxylic acids include palmitic, oleic or stearic acid. Other preferred anionic surfactants include alkyl sulfates such as sodium lauryl sulfate, and alkyl alkoxylated phosphates having the formulae:

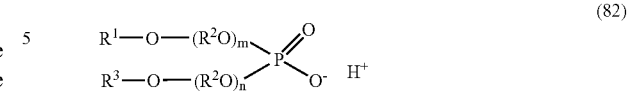
(82)

wherein $R^1$ and $R^3$ are independently a linear or branched alkyl, linear or branched alkenyl, linear or branched alkynyl, aryl, or aralkyl group having from about 4 to about 30 carbon atoms; $R^2$ in each of the m ($R^2O$) and the n ($R^2O$) groups is independently $C_2$–$C_4$ alkylene; and m and n are independently from 1 to about 30; or

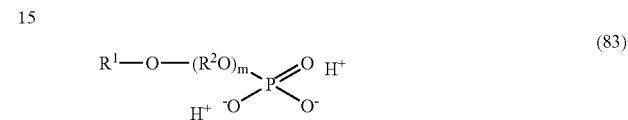
(83)

wherein $R^1$ is a linear or branched alkyl, linear or branched alkenyl, linear or branched alkynyl, aryl, or aralkyl group having from about 8 to about 30 carbon atoms; $R^2$ in each of the m ($R^2O$) groups is independently $C_2$–$C_4$ alkylene; and m is from 1 to about 30. Representative alkyl alkoxylated phosphates include oleth-10 phosphate, oleth-20 phosphate and oleth-25 phosphate.

Exemplary surfactants that may be used in accordance with the present invention include the following species:

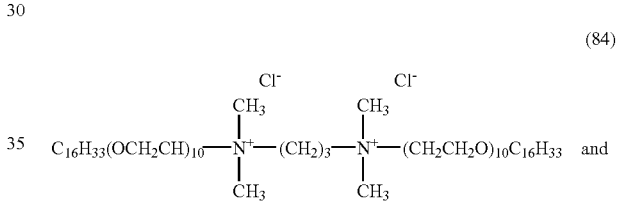
(84)

and

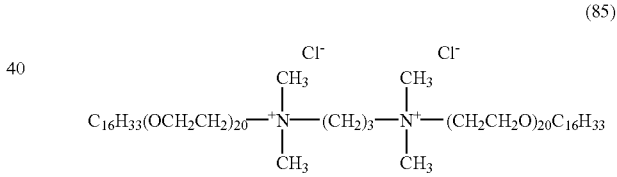
(85)

In either aqueous concentrated formulations or dry formulations of the present invention, the ratio (by weight) of the glyphosate a.e. to the surfactant is typically in the range of from about 1:1 to about 20:1, preferably from about 2:1 to about 10:1, more preferably from about 2:1 to about 8:1, still more preferably from about 2:1 to about 6:1, and still more preferably from about 3:1 to about 6:1.

The density of any glyphosate-containing formulation of the invention is preferably at least 1.210 grams/liter, more preferably at least about 1.215, 1.220, 1.225, 1.230, 1.235, 1.240, 1.245, 1.250, 1.255, 1.260, 1.265, 1.270, 1.275, 1.280, 1.285, 1.290, 1.295, 1.300, 1.305, 1.310, 1.315, 1.320, 1.325, 1.330, 1.335, 1.340, 1.345, 1.350, 1.355, 1.360, 1.365, 1.370, 1.375, 1.380, 1.385, 1.390, 1.395, 1.400, 1.405, 1.410, 1.415, 1.420, 1.425, 1.430, 1.435, 1.440, 1.445, or 1.450 grams/liter.

As further discussed herein, other additives, adjuvants, or ingredients may be introduced into the formulations of the present invention to improve certain properties of the resulting formulations. Although the formulations of the present invention generally show good overall stability and viscosity properties without the addition of any further additives, the addition of a solubilizer (also commonly referred to as a cloud point enhancer or stabilizer) can significantly improve the properties of the formulations of the present invention. Suitable solubilizers for use with the novel formulations of the present invention include, for example, cocoamine (Armeen C), dimethylcocoamine (Arquad DMCD), cocoammonium chloride (Arquad C), PEG 2 cocoamine (Ethomeen C12), PEG 5 tallowamine (Ethomeen T15), and PEG 5 cocoamine (Ethomeen C15), all of which are manufactured by Akzo Nobel (California).

Additionally, it has been found that the addition of a $C_4$ to $C_{16}$ alkyl or aryl amine compound, or the corresponding quaternary ammonium compound, greatly enhances the compatibility of certain glyphosate salts (e.g., potassium or isopropylamine) with surfactants that otherwise exhibit low or marginal compatibility at a given glyphosate loading. Suitable alkyl or aryl amine compounds may also contain 0 to about 5 EO groups. Preferred alkylamine compounds include $C_6$ to $C_{12}$ alkylamines having 0 to 2 EO groups. Similarly, etheramine compounds having 4 to 12 carbons and 0 to about 5 EO groups, as well as the corresponding quaternary ammonium compounds, also enhance the compatibility of such formulations. In one embodiment, the compounds which enhance the compatibility of such surfactants include amines or quaternary ammonium salts having the formula:

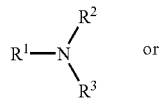

(86)

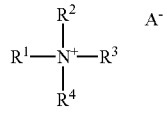

(87)

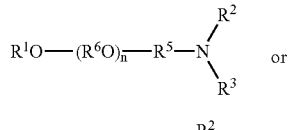

(88)

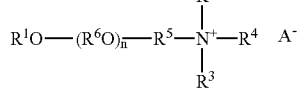

(89)

wherein $R^1$ is linear or branched alkyl or aryl having from about 4 to about 16 carbon atoms, $R^2$ is hydrogen, methyl, ethyl, or —(CH$_2$CH$_2$O)$_x$H, $R^3$ is hydrogen, methyl, ethyl, or —(CH$_2$CH$_2$O)$_y$H wherein the sum of X and y is not more than about 5; $R^4$ is hydrogen or methyl; $R^6$ in each of the n (R$^6$O) groups is independently $C_2$–$C_4$ alkylene; $R^5$ is hydrocarbylene or substituted hydrocarbylene having from 2 to about 6 carbon atoms; and A– is an agriculturally acceptable anion.

Also provided by the present invention is a herbicidal method comprising diluting with a suitable volume of water a herbicidally effective volume of a composition as provided herein to form an application composition, and applying the application composition to foliage of a plant or plants.

Definitions

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The term "hydrocarbylene" as used herein describes radicals joined at two ends thereof to other radicals in an organic compound, and which consist exclusively of the elements carbon and hydrogen. These moieties include alkylene, alkenylene, alkynylene, and arylene moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

The "substituted hydrocarbylene" moieties described herein are hydrocarbylene moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

Unless otherwise indicated, the alkyl groups described herein are preferably lower alkyl containing from one to 18 carbon atoms in the principal chain and up to 30 carbon atoms. They may be straight or branched chain or cyclic and include methyl, ethyl, propyl, isopropyl, n-butyl, isobutyl, hexyl, 2-ethylhexyl, and the like.

Unless otherwise indicated, the alkenyl groups described herein are preferably lower alkenyl containing from two to 18 carbon atoms in the principal chain and up to 30 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to 18 carbon atoms in the principal chain and up to 30 carbon atoms. They may be straight or branched chain and include ethynyl, propynyl, butynyl, isobutynyl, hexynyl, and the like.

The terms "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "aralkyl" as used herein denotes a group containing both alkyl and aryl structures such as benzyl.

As used herein, the alkyl, alkenyl, alkynyl, aryl and aralkyl groups can be substituted with at least one atom other than carbon, including moieties in which a carbon chain atom is substituted with a hetero atom such as nitrogen, oxygen, silicon, phosphorous, boron, sulfur, or a halogen atom. These substituents include hydroxy, nitro, amino, amido, nitro, cyano, sulfoxide, thiol, thioester, thioether, ester and ether, or any other substituent which can increase the compatibility of the surfactant and/or its efficacy enhancement in the potassium glyphosate formulation without adversely affecting the storage stability of the formulation.

The terms "halogen" or "halo" as used herein alone or as part of another group refer to chlorine, bromine, fluorine, and iodine. Fluorine substituents are often preferred in surfactant compounds.

Unless otherwise indicated, the term "hydroxyalkyl" includes alkyl groups substituted with at least one hydroxy group, and includes bis(hydroxyalkyl)alkyl, tris (hydroxyalkyl)alkyl and poly(hydroxyalkyl)alkyl groups. Preferred hydroxyalkyl groups include hydroxymethyl ($-CH_2OH$), and hydroxyethyl ($-C_2H_4OH$), bis (hydroxymethyl)methyl ($-CH(CH_2OH)_2$), and tris (hydroxymethyl)methyl ($-C(CH_2OH)_3$).

The term "cyclic" as used herein alone or as part of another group denotes a group having at least one closed ring, and includes alicyclic, aromatic (arene) and heterocyclic groups.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocylo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like, and non-aromatic heterocyclics such as tetrahydrofuryl, tetrahydrothienyl, piperidinyl, pyrrolidino, etc. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, thioester, thioether, ketal, acetal, ester and ether.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, thioether, thioester, ketal, acetal, ester and ether.

The term "acyl," as used herein alone or as part of another group, denotes the moiety formed by removal of the hydroxyl group from the group $-COOH$ of an organic carboxylic acid, e.g., $RC(O)-$, wherein R is $R^1$, $R^1O-$, $R^1R^2N-$, or $R^1S-$, $R^1$ is hydrocarbyl, heterosubstituted hydrocarbyl, or heterocyclo and $R^2$ is hydrogen, hydrocarbyl or substituted hydrocarbyl.

The term "acyloxy," as used herein alone or as part of another group, denotes an acyl group as described above bonded through an oxygen linkage ($-O-$), e.g., $RC(O)O-$ wherein R is as defined in connection with the term "acyl."

The term "pesticide" includes chemicals and microbial agents used as active ingredients of products for control of crop and lawn pests and diseases, animal ectoparasites, and other pests in public health. The term also includes plant growth regulators, pest repellants, synergists, herbicide safeners (which reduce the phytotoxicity of herbicides to crop plants) and preservatives, the delivery of which to the target may expose dermal and especially ocular tissue to the pesticide. Such exposure can arise by drift of the pesticide from the delivery means to the person performing the application of the pesticide or being present in the vicinity of an application.

When a maximum or minimum "average number" is recited herein with reference to a structural feature such as oxyethylene units or glucoside units, it will be understood by those skilled in the art that the integer number of such units in individual molecules in a surfactant preparation typically varies over a range that can include integer numbers greater than the maximum or smaller than the minimum "average number". The presence in a composition of individual surfactant molecules having an integer number of such units outside the stated range in "average number" does not remove the composition from the scope of the present invention, so long as the "average number" is within the stated range and other requirements are met.

As indicated above, concentrated aqueous solutions of glyphosate potassium salt have been found to have exceptionally high specific gravity. Table 1 shows, by way of example, specific gravities measured for 30% glyphosate a.e. by weight solutions of the potassium salt of glyphosate by comparison with organic ammonium and other salts of current or previous commercial interest. Specific gravities are measured using a Mettler DA-300 Density/Specific Gravity Meter.

TABLE 1

Specific gravity (20/15.6° C.) of 30% a.e. by weight glyphosate monobasic salt solutions.

| Salt | Specific Gravity |
|---|---|
| potassium | 1.2539 |
| monoethanolammonium (MEA) | 1.2357 |
| isopropylammonium (IPA) | 1.1554 |
| n-propylammonium | 1.1429 |
| methylammonium | 1.1667 |
| ethylammonium | 1.1599 |
| ammonium | 1.1814 |
| trimethylsulfonium (TMS) | 1.1904 |

Thus 1 liter of 30% a.e. by weight glyphosate potassium salt solution at 20° C. contains approximately 376 g glyphosate a.e./l, whereas 1 liter of 30% a.e. by weight glyphosate IPA salt solution at 20° C. contains approximately 347 g glyphosate a.e./l. In other words, at equal a.e. weight concentration, the potassium salt solution delivers about 8% more glyphosate a.e. per liter.

The higher specific gravity of solutions of the potassium salt becomes of particular value in surfactant-containing solutions, where the maximum glyphosate concentration is constrained not only by the limit of solubility of the potassium salt in water but also by the limits of surfactant compatibility. In such solutions, the advantages of the potassium salt can mean that (a) a higher maximum glyphosate a.e. weight/volume concentration is achieved than with the IPA salt in the presence of the same compatible surfactant at the same percent surfactant concentration, (b) at given weight/volume concentrations of glyphosate a.e. and surfactant, improved storage-stability is achieved over a corresponding composition prepared with the IPA salt, and/ or (c) at given weight/volume concentrations of glyphosate a.e. and surfactant, improved pouring and pumping properties are achieved over a corresponding composition prepared with the IPA salt.

The advantages of compositions of the present invention are reduced as glyphosate concentration is decreased and are only marginal at a glyphosate concentration lower than about 360 g a.e./l, i.e., lower than the concentration found in such commercial glyphosate IPA salt products as Roundup® herbicide. In preferred compositions of the invention, glyphosate concentration is not lower than 400 g a.e./l or about 420 g a.e./l, in particularly preferred compositions not lower than about 440, 460 or 480 g a.e./l, for example about 480 to about 540 g a.e./l. It is believed that the upper limit of glyphosate concentration in a storage-stable surfactant-containing composition of the invention is in excess of about 650 g a.e./l, this limit being a consequence of the solubility limit of glyphosate potassium salt in water, compounded by further limitation due to the presence of surfactant.

It is expected that the closer to this upper limit of glyphosate concentration, the less the amount of surfactant that can be accommodated. In some instances, this small amount of surfactant is likely to be inadequate to give reliable enhancement of the herbicidal efficacy of the glyphosate to an acceptable degree. However, Win certain special-purpose applications where the composition is to be diluted with a relatively small amount of water, for plant treatment at a volume of, for example, about 10 to about 50 l/ha, the surfactant concentration in a concentrate composition of the invention can usefully be as low as about 20 g/l. Such special-purpose applications include rope-wick, control droplet application and ultra-low-volume aerial spraying. For general-purpose application, typically by spraying following dilution with about 50 to about 1000 l/ha, most commonly about 100 to about 400 l/ha, of water, the surfactant concentration in a concentrate composition of the invention is preferably about 60 to about 300 g/l, and more preferably about 60 to 200 g/l.

The herbicidal formulations of the present invention include at least one surfactant that, in combination with glyphosate or a salt or ester thereof and upon application of the formulation to a plant or an application mixture prepared by dilution of the formulation with water, forms anisotropic aggregates comprising the surfactant on the foliage (epicuticular wax) of the plant. In some formulations of the present invention, a surfactant, in combination with glyphosate or a salt or ester thereof and upon application of the formulation to a plant or an application mixture prepared by dilution of the formulation with water, forms liquid crystals comprising the surfactant on the foliage of the plant (epicuticular wax). In other formulations of the present invention, a surfactant, in combination with glyphosate or a salt or ester thereof and upon application of the formulation to a plant or an application mixture prepared by dilution of the formulation with water forms liquid crystals comprising the surfactant both on the foliage of the plant (epicuticular wax) and with the plant itself (intracuticular liquid crystals). In other formulations of the present invention, a herbicidal formulation comprising an aqueous mixture containing glyphosate or a salt or ester thereof and a surfactant contains liquid crystals comprising the surfactant.

Suitable salt forms of glyphosate which may be used in accordance with the formulations of the present invention include, for example, alkali metal salts, for example sodium and potassium salts, ammonium salts, di-ammonium salts idle such as dimethylammonium, alkylamine salts, for example dimethylamine and isopropylamine salts, alkanolamine salts, for example ethanolamine salts, alkylsulfonium salts, for example trimethylsulfonium salts, sulfoxonium salts, and mixtures or combinations thereof. Various commercial glyphosate formulations sold to date by Monsanto Company include ammonium salts, sodium salts, and isopropylamine salts. Glyphosate formulations sold to date by Zeneca have included trimethylsulfonium salts. Especially preferred glyphosate salts useful in the novel formulations of the present invention include the potassium salt, isopropylamine salt, ammonium salt, di-ammonium salt, sodium salt, monoethanolamine salt, and trimethylsulfonium salt. The potassium salt, sodium salt, ammonium salt and di-ammonium salts are preferred as formulations of these glyphosate salts are most likely to form liquid crystals.

In addition to the glyphosate or salt or ester thereof, the herbicidal formulations of the present invention also comprise at least one surfactant. In one embodiment of the present invention, the nature of the surfactant and the composition of the herbicidal formulation is such that upon application of the formulation to a plant or an application mixture prepared by dilution of the formulation with water, anisotropic aggregates comprising the surfactant are formed on the waxy cuticle (epicuticular) of the plant. These anisotropic aggregates are formed on the foliage of the plant regardless whether a second surfactant is present in the formulation. The anisotropic aggregates may form immediately upon application to the foliage of the plant, or may form as water is evaporated from the formulation present upon the foliage after application. Further, anisotropic aggregates may also form in the concentrate herbicidal formulations.

To determine whether a herbicidal formulation comprising glyphosate or a salt or ester thereof and a surfactant forms anisotropic aggregates on the foliage of a plant comprising the surfactant, the following birefringence testing procedure may be utilized.

First, a wax-coated slide is prepared. A preferred wax for preparing the slide is a blend of carnauba wax and beeswax in a weight/weight ratio of approximately 10:1, respectively. A clear wax mixture is prepared consisting of about 5% carnauba wax and about 0.5% beeswax in isopropanol, and is maintained at a temperature of approximately 82° C. The end of a glass 2.4 cm×7.2 cm microscope slide is immersed perpendicularly in the wax mixture to a depth of approximately one-third of the length of the slide. After about 10 to 15 seconds, the slide is very slowly and steadily withdrawn from the wax mixture and allowed to cool, leaving a wax layer deposited on both faces of the slide.

Visual examination of the slide can give a preliminary indication of the thickness and uniformity of the wax coating. If imperfections are evident the slide is rejected. If the slide shows no obvious imperfections, the wax coating is carefully removed from one face of the slide by wiping with acetone. Further evaluation of the acceptability of the wax-coated slide for the test is done by examining the slide under a microscope. The slide is selected for use in the test if, on microscopic examination using a 4.9× objective, the wax coating is uniformly thick and there is uniform density of wax particles across the slide. Preference is for a coating that has few observable wax particles and exhibits a very dark field when examined under polarized light.

The next stage in the procedure is to conduct the test. For this purpose, samples of the glyphosate herbicidal formulation containing one or more surfactants are diluted, if necessary, to 15% to 20% by weight of the glyphosate acid equivalent. A reference sample is prepared consisting of 41% by weight of glyphosate IPA salt in aqueous solution.

The following instrumentation, or equivalent, items are required or useful for the test procedure:

Nikon SMZ-10A stereoscopic microscope equipoed for polarized light observation, photomicrography, and video observation and recording.

3CCD MTI camera.

Diagnostic Instruments 150 IL-PS power supply.

Sony Trinitron color video monitor, model PVM-1353MD.

Mitsubishi time-lapse video cassette recorder, model HS-S5600.

Hewlett Packard Pavillion 7270 computer, with Windows 95 and Image-Pro Plus version 2.0 electronic imaging program installed.

Hewlett Packard Deskjet 870Cse printer.

For testing, a wax-coated slide, prepared and selected as described above, is positioned on the microscope stage, with the system set to provide transmitted light, both straight and polarized. A 1 microliter drop of the sample to be tested is applied to the wax surface using a thoroughly cleaned 1 microliter Hamilton syringe. This and subsequent operations are followed through the microscope at 4.9× objective. Duplicate or triplicate tests are done for each composition. Numerous tests can be conducted simultaneously on a single slide. Progression of change in the microscopic appearance of the sample is observed through the microscope and recorded at designated time intervals. Useful intervals are 1 minute, 10 minutes, 2 hours and greater than 24 hours after application of the drop to the wax surface. Observations can also be made at intermediate times to capture possible significant transitions occurring at such times.

The temperature of the wax layer tends to increase with prolonged exposure to the microscope light. In many cases it has been determined that this does not significantly interfere with the results obtained. However, in some cases temperature does affect the outcome of the test and in such cases it is preferred to illuminate the sample only for the short periods necessary to make observations, so that the temperature of the wax layer remains close to ambient temperature.

At dark field (polarized light) the wax layer is observed for birefringence, and at light field the character of the drop surface is observed, at each time interval. The following records are preferably made:

birefringence (y/n);

time of initial appearance of birefringence;

character of the birefringence;

appearance of drop surface as composition "dries";

degree of spread of the drop;

effects of temperature (warming of the slide) if any;

other noticeable changes.

Optionally, images are recorded at significant times using the 3CCD MTI camera and the Image-Pro Plus program as documentation of observed changes. Tests may if desired also be recorded on video, especially during the first 15 minutes. In addition to images captured using 4.9× objective, overall-field views using 0.75 objective can be recorded to provide clear comparisons of different samples tested on the same slide. A particularly useful parameter for observing anisotropic aggregates is the observation of birefringence (y/n) 5–20 minutes after deposition of the test drop on the wax-coated slide.

Herbicidal formulations of the present invention that form epicuticular anisotropic aggregates have substantially improved performance over herbicidal formulations currently available. Without being bound to a particular theory, it is believed that the epicuticular anisotropic aggregates may create or enlarge hydrophilic channels through the epicuticular waxy surface of the plant cuticle. These created or enlarged transcuticular channels through the waxy surface may facilitate the mass transfer of glyphosate through the epicuticular wax of the plant cuticle and into the plant more rapidly than in a system without anisotropic aggregates. It is further believed that the majority of the anisotropic aggregates present on the epicuticular surface are present in a form other than a simple micelle, such as a bilayer or multilamellar structure as they tend to form complex structures such as cylindrical, discotic, or ribbon like structures. "Majority" means that more than 50% by weight of the surfactant is present in the form of complex aggregates other than simple micelles. Preferably, more than 75% by weight of the surfactant is present in the form of complex aggregates other than simple micelles. The anisotropic aggregates of the present invention typically have a diameter of at least about 20 nanometers, preferably at least about 30 nanometers.

Regarding the formation of anisotropic aggregates comprising a surfactant in the presence of glyphosate, critical packing parameter (P), which is defined as:

$$P=V/lA$$

where V is the volume of the hydrophobic tail of the molecule, l is the effective length of the hydrophobic tail, and A is the area occupied by the hydrophilic headgroup, may be an important aspect. It is believed that amphiphilic substances useful in forming anisotropic aggregates have a critical packing parameter greater than about $1/3$.

In a preferred embodiment wherein anisotropic aggregates are formed on epicuticular wax of the plant cuticle, the surfactant comprising the anisotropic aggregates is an amphiphilic substance comprising a compound having a cationic headgroup and a hydrophobic tail. Without being bound to a particular theory, it is believed that the cationic group enhances the initial adhesion to the leaf surface, since the majority of the such surfaces carry an overall negative charge. Further, it is believed that the cationic group contributes to the hydrophilicity of the transcuticular channels in the epicuticular wax formed or enlarged by the surfactants of the present invention. Cationic groups attract water molecules which further enlarge the hydrophilic channels and thereby provide an improved pathway of entry for glyphosate, which is polar.

Surfactants that are effective in forming anisotropic aggregates in the presence of glyphosate include nonionic, cationic, anionic and amphoteric surfactants and mixtures thereof.

Mixtures of surfactants as described above are also effective in forming anisotropic aggregates. Preferred mixtures include an alkoxylated alcohol nonionic surfactant and a dialkoxylated quaternary ammonium, monoalkoxylated quaternary ammonium, quaternary ammonium, dialkoxylated amine, diamine, or alkyl choline halide (e.g., lauryl choline chloride) cationic surfactant. Other preferred mixtures contain: a phospholipid amphoteric surfactant and a dialkoxylated amine or dialkoxylated quaternary ammonium cationic surfactant, a fluorinated quaternary ammonium surfactant such as Fluorad™ 754, or an alkoxylated alcohol nonionic surfactant; or a carboxylic acid anionic surfactant and a dialkoxylated amine cationic surfactant. Examples of such preferred mixtures include Hetoxol™ CS-20 (a PEG 20 $C_{16}$–$C_{18}$ alcohol from Heterene) and Ethomeen™ T/20 (a 10 EO tallowamine from Akzo Nobel), Hetoxol™ CS-20 and Ethomeen™ T/25 (a 15 EO tallowamine from Akzo Nobel), Hetoxol™ CS-25 (a PEG 25 $C_{16}$–$C_{18}$ alcohol from Heterene) and Ethomeen™ T/20, Hetoxol™ CS-25 and Ethomeen™ T/25, Brij™ 78 (a PEG 20 $C_{18}$ alcohol from Sigma Chemical Company) and Ethomeen™ T/20, Brij™ 78 and Ethomeen™ T/25, Brij™ 78 and Ethoquad™ T/20 (a PEG 10 tallow methyl ammonium chloride from Akzo Nobel), Brij™ 78 and Ethoquad™ T/25 (a PEG 15 tallow methyl ammonium chloride from Akzo Nobel), Plurafac™ A38 (a PEG 27 $C_{16}$–$C_8$ alcohol from Basf) and Ethomeen™ T/20, Plurafac™ A38 and Ethomeen™ T/25, Plurafac™ A38 and Ethoquad™ T/20, Plurafac™ A38 and Ethoquad™ T/25, ST 8303 (a PEG 14 $C_{16}$ alcohol from Cognis) and Ethoquad™ T/25, Arosurf™ 66 E10 (a PEG 10 iso$C_{18}$ alcohol from Witco/Crompton) and Ethoquad™ T/25, Arosurf™ 66 E20 (a PEG 20 iso$C_{18}$ alcohol from Witco/Crompton) and Ethoquad™ T/25, Arosurf™ 66 E20 and Ethomeen™ T/25, Hetoxol™ CS-20 and Ethomeen™ T/15 (a 5 EO tallowamine from Akzo Nobel), Hetoxol™ CS-20 and Ethomeen™ T/30 (a 20 EO tallowamine from Akzo Nobel), Hetoxol™ CS-20 and Ethomeen™ T/35 (a 25 EO tallowamine from Akzo Nobel), Hetoxol™ CS-20 and Ethomeen™ T/40 (a 30 EO tallowamine from Akzo Nobel), Hetoxol™ CS-20 and Trymeen™ 6647 (a PEG 50 stearylamine from Cognis), Hetoxol™ CS-15 (a PEG 15 $C_{16}$–$C_{18}$ alcohol from Heterene) and Ethomeen™ T/25, Hetoxol™ CS-20 and a PEG 22 dimethyl quaternary ammonium chloride, Hetoxol™ CS-20 and lecithin, Hetoxol™ CS-25 and lecithin, Hetoxol™ CS-20 and Arquad™ C-50 (a dodecyl trimethyl ammonium chloride from Akzo Nobel), Hetoxol™ CS-20 and lauryl choline chloride, Hetoxol™ CS-15 and lauryl choline chloride, Procol™ LA 15 (a PEG 15 $C_{12}$ alcohol from Protameen) and Ethoquad™ T25, Hetoxol™ CS-20 and a PEG 7 dimethyl quaternary ammonium chloride, Hetoxol™ CS-20 and Gemini™ 10-2-10 (a $C_{10}$ ethylene N-methyl diamine from Monsanto), Hetoxol™ CS-20 and Gemini™ 10-3-10 (a $C_{10}$ propylene N-methyl diamine from Monsanto), Hetoxol™ CS-20 and Gemini™ 10-4-10 (a $C_{10}$ butylene N-methyl diamine from Monsanto), Hetoxol™ CS-20 and Gemini™ 14-2-14 (a $C_{14}$ ethylene N-methyl diamine from Monsanto), Hetoxol™ CS-20 and Gemini™ 14-3-14 (a $C_{14}$ propylene N-methyl diamine from Monsanto), palmitic acid and Ethomeen™ T/25, lecithin and Ethomeen™ T/25, lecithin and Ethoquad™ T/25, lecithin and Ethomeen™ T/20, lecithin and Ethoquad™ T/20, and lecithin and Fluorad™ FC 754 (a fluorinated alkyl quaternary ammonium chloride from 3M). Some of the above mixtures are synergistic, in that they are mixtures of surfactants which, when tested individually, did not form anisotropic aggregates.

The herbicidal formulations of the present invention including glyphosate and a surfactant that forms anisotropic aggregates on a waxy plant surface may be prepared as aqueous concentrated formulations comprising at least about 50 g glyphosate a.e./L, more preferably at least about 250 g glyphosate a.e./L, still more preferably at least about 300, 360, 380, 400, 440, 480, 500, 540, or 600 g glyphosate a.e./L. One example of a preferred aqueous concentrate glyphosate formulation contains the isopropylamine or potassium salt of glyphosate at about 360 g glyphosate a.e./L, or about the same level as currently used by Monsanto Corporation in its commercial formulation of Roundup® herbicide. Another preferred aqueous concentrate glyphosate formulation contains the isopropylamine or potassium salt of glyphosate at about 300 to about 600, preferably at about 400 to about 600, about 440 to about 600, about 440 to about 480, about 480 to about 600, or about 480 to about 540 g glyphosate a.e./L.

On a weight basis, stable aqueous concentrate compositions of the present invention including a surfactant that forms anisotropic aggregates on the cuticle surface can be made with glyphosate at a concentration of at least about 35, 40, 41, 42, 43, 44, 45, 46, 47, 48, 49, or 50% a.i. A concentration of about 35 to about 50% a.e., about 40 to about 50% a.i., about 45 to about 50% a.i., or more is preferred, particularly for potassium glyphosate.

In another embodiment, concentrated formulations which form anisotropic aggregates on the waxy surface of plants may be dry formulations which may be in the form of powders, pellets, tablets or granules. These dry formulations are typically dispersed or dissolved into water prior to use. Preferably, there are no substantially water insoluble constituents present at substantial levels in the such formulations such that the formulations are substantially water soluble. Dry water-soluble or water-dispersable formulations of the present invention typically comprise from about 20% to about 80% (by weight) glyphosate a.e., preferably from about 50% to about 80% (by weight) glyphosate a.e., and most preferably from about 60% to about 75% (by weight) glyphosate a.e.

In dry formulations of the present invention, the glyphosate itself may provide the support for other formulation constituents, or there may be additional inert ingredients which provides such support. One example of an inert support ingredient that may be used in accordance with the present invention is ammonium sulfate. It will be recognized by one skilled in the art that as used herein, the term "dry" does not imply that dry formulations of the present invention are 100% free of water. Typically, dry formulations of the present invention comprise from about 0.5% to about 5% (by weight) water. It is preferred that the dry formulations of the present invention contain less than about 1% (by weight) water.

Dry, water soluble or water dispersable formulations in accordance with the present invention can be produced by any process known in the art, including spray drying, fluid-bed agglomeration, pan granulation, or extrusion. In dry formulations, glyphosate may be present as a salt, or as an acid. Formulations containing glyphosate acid may optionally contain an acid acceptor such as an ammonium or alkali metal carbonate or bicarbonate, ammonium dihydrogen phosphate or the like so that upon dissolution or dispersion in water by the user a water soluble salt of glyphosate is produced.

Typically, herbicidal compositions of the present invention that are ready to be applied directly to foliage can be made with a glyphosate concentration of from about 1 to about 40 grams acid equivalent per liter, preferably from about 2 to about 18 grams acid equivalent per liter, more preferably from about 4 to about 11 grams acid equivalent per liter. One skilled in the art will recognize that various factors influence the application rate of glyphosate required for a desired result.

Any convenient and herbicidal activity enhancing amount of the surfactant which comprises anisotropic aggregates on the waxy surface of a plant may be used in the glyphosate formulations of the present invention. Preferably, the surfactant is present in the concentrated glyphosate formulations of the present invention in a concentration of from about 25 to about 250 g/L, more preferably from about 50 to about 200 g/L. Although higher concentrations of the surfactant can be incorporated into the glyphosate formulations of the present invention, for economical reasons it is generally more suitable to use the concentration ranges set forth above. Herbicidal formulations of the present invention that are ready to be applied directly to foliage can be made with a surfactant concentration of from about 0.1 g/L to about 10 g/L, preferably from about 1 g/L to about 5 g/L.

In some herbicidal formulations of the present invention, the nature of the surfactant and the composition of the herbicidal formulation is such that upon application of the formulation to a plant or an application mixture prepared by dilution of the formulation with water, liquid crystals comprising the surfactant are formed on the foliage of the plant (epicuticular liquid crystals). In other words, liquid crystals comprising the surfactant form to create or enlarge hydrophilic channels through the epicuticular wax of the plant cuticle. An important feature of the herbicidal formulations of the present invention is that the surfactant be able to form liquid crystals in the presence of glyphosate on a waxy, porous substrate such as a leaf cuticle to produce transcuticular hydrophilic channels epicuticularly through the waxy cuticle. A distinguishing characteristic of the surfactants which comprise the liquid crystals in the presence of glyphosate is the tendency of the surfactant molecules to align themselves along a common axis in an ordered manner. Typically, liquid crystals have a higher degree of order than isotropic solutions and are much more fluid than solid crystals. Fluidity of liquid crystals may be an important factor in the improved translocation of glyphosate throughout the plant.

Many of the surfactants discussed herein which form liquid crystals on the cuticle surface in the presence of glyphosate to facilitate translocation of the glyphosate throughout the infrastructure of the plant do not form liquid crystals in the concentrated glyphosate solutions at concentrations typically found to be commercially viable. Typically, these surfactants form liquid crystals in the dried down glyphosate/surfactant deposit that forms from drops or spraying of the diluted formulation onto the plant cuticle surface. Generally, and without being bound to a particular theory, it appears that the formation of liquid crystals in the concentrated glyphosate solution itself is not necessarily important or related (although in some circumstances it may be helpful) to the formation of liquid crystals on and in the plant surface. Typically, it is more important that liquid crystals comprised of the surfactant form as a dry-down deposit on the leaf surface. However, in some formulations liquid crystals may form in the concentrated glyphosate/surfactant solutions and on and in the leaf, but not in the diluted spray mixture.

As previously mentioned, the formation of liquid crystals epicuticularly may result from the drying down of glyphosate and surfactant containing droplets applied to the plant. Several environmental factors including air temperature, humidity, and wind speed may affect how quickly liquid crystals form in and on the plant. In some situations, the liquid crystals may actually be formed by phase separation from the main droplet on the foliage. Although the surfactants listed herein form liquid crystals in the presence of glyphosate, it is believed that it is preferable for surfactant molecules to have a molecular weight of less than about 2500. When the molecular weight of the surfactant is in excess of 2500, liquid crystals may still form but not be quite as effective and efficient in the translocation of glyphosate as lower molecular weight surfactants.

The liquid crystals comprising a surfactant in the presence of glyphosate epicuticularly are typically lyotropic liquid crystals; that is the formation of liquid crystals is typically induced by the presence of a solvent, in this case water. The mesophases of the liquid crystals depend not only on the solvent present, but also on temperature. Lyotropic liquid crystals comprising a surfactant in the presence of glyphosate that form transcuticular hydrophilic channels have been observed in hexagonal formation, reversed hexagonal formation, and lamellar and multilamellar formations having at least about 20 to about 30 or more separate, distinct layers. It may be possible to also have lyotropic liquid crystals in a cubical form. Also, both smectic and nematic forms of liquid crystals comprised of a surfactant in the presence of glyphosate have been observed. In the herbicidal formulations of the present invention, liquid crystals form regardless of the presence or absence of a second surfactant.

Further, some surfactants in the presence of glyphosate may form wormlike micelles, another class of organized structures in liquid form which may facilitate the translocation of glyphosate through the waxy cuticle and into the plant. Wormlike micelles are typically less organized than liquid crystals but still have sufficient organization to form hydrophilic channels on and in the plant to facilitate the translocation of glyphosate through the plant. Typically, surfactants that are sufficiently "flexible" will form these types of wormlike micelles.

To determine the onset concentration of glyphosate and surfactants in dry down deposits that are liquid crystal in nature, the following testing procedure may be utilized. The experiments are conducted under 50% relative humidity and 24° C. The isolated cuticles are prepared according to the protocol described herein. A liquid crystal forming glyphosate formulation, which contains a certain amount of glyphosate salts (e.g. potassium), a liquid crystal forming surfactant (e.g. $C_{16-18}$ ether EO 15 dimethyl propylamine), are placed on pre-prepared isolated leaf cuticles as 1 microliter droplets and observed under a polarized microscope for the on-set of birefringence. In a separate experiment, those droplets that show birefringenece are examined and confirmed to show characteristic liquid crystal patterns.

Once the onset of birefringence is observed, the droplets are scraped from the cuticle as quickly as possible, dissolved in 1 ml of 99.9% (nominal) $D_2O$ and transferred into a 5 mm NMR tube. The spectra can be acquired using a Varian Unity Inova 400 MHZ spectrometer equipped with a 5 mm Nalorac pulse tune probe. For example, a 30 degree pulse may be used to acquire scans with an appropriate recycle time. The determination may be made by the integration of the glyphosate doublet signal and the water signal.

The concentration of the glyphosate in these droplets has been determined to be 37% (+/−6%) according to this method. However, it is noted that the evaporation of the water from the drying down droplets is relatively fast (in minutes). Therefore, results may vary from 37% to 50% w/wt. depending upon the skill of the technician performing the task of transferring from the cuticle to the NMR tube.

To determine whether a herbicidal formulation comprising glyphosate or a salt or ester thereof and a surfactant forms liquid crystals comprising the surfactant on the foliage of a plant, the following high resolution polarized microscopy birefringence testing procedure may be utilized. This high resolution birefringence test is capable of distinguishing liquid crystal phase formations and their characteristic microfine textures from other types of anisotropic aggregates or solid crystals precipitated out of solution due to water evaporation. The test procedure is as follows.

Prior to testing for birefringence, a cuticle from greenhouse grown velvetleaf (*Abutilon theophrasti*) is isolated for testing. Other suitable plants that can be used to supply a test cuticle include prickly sida, giant ragweed, and morningglory. To isolate the cuticle, stock solutions of glacial acetic acid and sodium acetate are prepared. The glacial acetic acid stock solution has a concentration of between about 1 to about 5% (weight/weight), and the sodium acetate stock solution has a concentration of between about 1 and about 5% (weight/weight). The stock solutions are mixed together to form a buffered solution having a pH of from about 4.2 to about 4.6.

After the buffer solution is prepared, an enzyme solution is prepared. Typically, the enzyme solution will be prepared at or very near the time of cuticle isolation for maximum effectiveness. The enzyme solution is prepared by adding about 1 to about 5% (weight/weight) and about 0.1 to about 0.5% (weight/weight) cellulase in water. Typically, the pectinase has an activity of 3600 units/gram and cellulase has an activity of about 10,600 units/gram. The enzyme solution is then sterile infiltrated and ready for use or storage.

A healthy leaf from the source plant is removed and its backside is abraded with fine sea sand. The leaf is then throughly rinsed with the buffer solution as prepared above and a healthy section of the leaf is cut out for cuticle isolation. The cut portion of the leaf is infiltrated with the freshly prepared enzyme solution and held at a temperature of from about 30° C. to about 35° C. for about 1 hour or until the leaf cuticle detaches from the leaf tissue substrate. After detachment, the cuticle is carefully removed from the buffered solution and thoroughly rinsed with deionized water and stored in a buffer solution having a pH of about 4 to 6 in an area having a humidity of about 30% to about 75% and a temperature of about 20 to about 30° C. until use. Typically, the cuticle is stored in the controlled environment for at least about 24 hours to allow it to reach equilibrium with its environment.

After a cuticle has been isolated, it is used for the test to determine whether a specific herbicidal formulation containing glyphosate and a surfactant forms liquid crystals comprising the surfactant on the waxy cuticle. The cuticle is transferred to a glass slide and examined under a microscope (without any polarized light) for cracks and other damage. If cracks or other damage are identified on the surface of the cuticle, it is discarded. Once a suitable cuticle is observed, it is further examined under a microscope (at 7.5× magnification) with polarized light to ensure that a dark field is observed. If small areas of crystalline wax are noted on the cuticle surface, these areas are carefully avoided during testing.

After observing the cuticle for defects, the glass slide is connected to a heating/cooling circuit which is capable of regulating the temperature of the glass plate during testing. Heat is applied to the glass plate and the cuticle is allowed to reach equilibrium with the temperature of the glass plate 15° C. to about 35° C. After equilibrium is reached, a sample of the test solution is prepared. The sample may either be in diluted or concentrated form, although it is preferred that the sample be in a diluted form such that the glyphosate concentration (a.e.) is in the range of about 1% to about 10% (weight/weight) in the test sample and the glyphosate to surfactant ratio is in the range of about 1 to 1 to about 10:1 (weight/weight), preferably about 3:1 (weight/weight). A drop of the aqueous test sample is placed on the cuticle and observed under polarized light (7.5× magnification) transmitted through the cuticle. Images of the sample droplets on the cuticle tare recorded and stored in a computer connected to a video monitor using Flash Point 128 Software at a present time interval. The images are then digitized using Image Pro by Media Cybernetics.

In each test, sample droplets are duplicated onto two nearly identical cuticles. If birefringence is observed under the polarized microscope at 7.5× magnification, the sample is transferred immediately to a polarized microscope having magnification capabilities of 100× magnification to 400× magnification. With this microscope, at 200× magnification, characteristic liquid crystal patterns can be seen and distinguished from solid crystals or other birefringent materials. If liquid crystals are observed under the high power magnification, the sample formulation forms epicuticular liquid crystals on the foliage of the plant.

Herbicidal formulations of the present invention containing glyphosate or a salt or ester thereof form epicuticular liquid crystals have substantially improved performance over herbicidal formulations currently available, and may be superior to herbicidal formulations which simply form anisotropic aggregates epicuticularly. Without being bound to a particular theory, it appears that the formation of liquid crystals on the epicuticular portion of a plant form or enlarge hydrophilic channels through the waxy cover of foliage. These created or enlarged hydrophilic channels may substantially increase the mass transfer of glyphosate through the waxy cuticle and into the plant.

Surfactants that are effective in forming epicuticular liquid crystals in the presence of glyphosate include nonionic, cationic, and amphoteric surfactants and mixtures thereof.

Mixtures of surfactants as described above are also effective in forming epicuticular liquid crystals. Preferred mixtures include an alkoxylated alcohol nonionic surfactant and a dialkoxylated quaternary ammonium, monoalkoxylated quaternary ammonium, or dialkoxylated amine cationic surfactant. Other preferred mixtures contain a phospholipid amphoteric surfactant and an alkoxylated alcohol nonionic surfactant. Examples of such preferred mixtures include Hetoxol™ CS-20 (a PEG 20 $C_{16}$–$C_{18}$ alcohol from Heterene) and Ethomeen™ T/20 (a 10 EO tallowamine from Akzo Nobel), Hetoxol™ CS-20 and Ethomeen™ T/25 (a 15 EO tallowamine from Akzo Nobel), Hetoxol™ CS-25 (a PEG 25 $C_{16}$–$C_{18}$ alcohol from Heterene) and Ethomeen™ T/20, Hetoxol™ CS-25 and Ethomeen™ T/25, Brij™ 78 (a PEG 20 $C_{18}$ alcohol from Sigma Chemical Company) and Ethomeen™ T/20, Brij™ 78 and Ethomeen™ T/25, Brij™ 78 and Ethoquad™ T/20 (a PEG 10 tallow methyl ammonium chloride from Akzo Nobel), Brij™ 78 and Ethoquad™ T/25 (a PEG 15 tallow methyl ammonium chloride from Akzo Nobel), Plurafac™ A38 (a PEG 27 C16–$C_{18}$ alcohol from Basf) and Ethomeen™ T/20, Plurafac™ A38 and Ethomeen™ T/25, Plurafac™ A38 and Ethoquad™ T/20, Plurafac™ A38 and Ethoquad™ T/25, ST 8303 (a PEG 14 $C_{16}$ alcohol from Cognis) and Ethoquad™ T/25, Arosurf™ 66 E10 (a PEG 10 iso$C_{18}$ alcohol from Witco/Crompton) and Ethoquad™ T/25, Arosurf™ 66 E20 (a PEG 20 iso$C_{18}$ alcohol from Witco/Crompton) and Ethoquad™ T/25, Arosurf™ 66 E20 and Ethomeen™ T/25, Hetoxol™ CS-20 and Ethomeen™ T/15 (a 5 EO tallowamine from Akzo Nobel), Hetoxol™ CS-20 and Ethomeen™ T/30 (a 20 EO tallowamine from Akzo Nobel), Hetoxol™ CS-20 and Ethomeen™ T/35 (a 25 EO tallowamine from Akzo Nobel), Hetoxol™ CS-20 and Ethomeen™ T/40 (a 30 EO tallowamine from Akzo Nobel), Hetoxol™ CS-20 and Trymeen™ 6617 (a PEG 50 stearylamine from Cognis), Hetoxol™ CS-15 (a PEG 15 $C_{16}$–$C_{18}$ alcohol from Heterene) and Ethomeen™ T/25, Hetoxol™ CS-20 and a PEG 22 dimethyl quaternary ammonium chloride, Hetoxol™ CS-20 and lecithin, and Hetoxol™ CS-25 and lecithin. Some of the above mixtures are synergistic, in that they are mixtures of surfactants which, when tested individually, did not form anisotropic aggregates and/or epicuticular liquid crystals.

In some herbicidal formulations of the present invention, the nature of the surfactant and the composition of the herbicidal formulation is such that upon application of the formulation to a plant or an application mixture prepared by dilution of the formulation with water, liquid crystals comprising the surfactant are formed both on the foliage of the plant (epicuticular liquid crystals) and in the foliage of the plant (intracuticular liquid crystals). In other words, liquid crystals comprising the surfactant form to create or enlarge hydrophilic channels through the epicuticular wax of the plant cuticle and also form inside of the plant (intracuticular) to form pathways deep inside of the plant which may significantly enhance translocation of glyphosate throughout the plant pathways. These transcuticular pathways may be responsible for the increase efficacy such formulations provide. An important feature of the herbicidal formulations of the present invention which form both epicuticular and intracuticular liquid crystals is that the surfactant is able to form liquid crystals both on and in the plant.

Many of the surfactants discussed herein which form liquid crystals on the cuticle surface and within the plant in the presence of glyphosate to facilitate translocation of glyphosate throughout the infrastructure of the plant may not form liquid crystals in the concentrate glyphosate solutions at concentrations typically found to be commercially viable. Typically, these surfactants form liquid crystals in the dried down glyphosate/surfactant deposit that forms from drops or spraying of the diluted formulation onto the plant cuticle surface. Generally, and without being bound to a particular theory, it appears that the formation of liquid crystals in the concentrated glyphosate solution itself is not necessarily important or related (although in some circumstance it may be helpful) to the formation of liquid crystals on and in the plant surface. Typically, it is more important that liquid crystals comprised of the surfactant form as a dry-down deposit on the leaf surface. However, in some formulations liquid crystals may form in the concentrated glyphosate/surfactant solutions and on and in the leaf, but not in the diluted spray mixture.

As previously mentioned, the formation of liquid crystals epicuticularly and intracuticularly may result from the drying down of glyphosate and surfactant containing droplets applied to the plant. Several environmental factors including air temperature, humidity, and wind speed may affect how quickly liquid crystals form in and on the plant. In some situations, the liquid crystals may actually be formed by phase separation from the main droplet. Although the surfactants listed herein form liquid crystals in the presence of glyphosate, it is believed that it is preferable for surfactant molecules to have a molecular weight of less than about 2500. When the molecular weight of the surfactant is in excess of about 2500, liquid crystals may still form in and on the plant, but may not be as effective and efficient in the translocation of glyphosate as lower molecular weight surfactants.

The liquid crystals comprising a surfactant in the presence of glyphosate epicuticularly and intracuticularly are typically lyotropic liquid crystals; that is the formation of liquid crystals is typically induced by the presence of a solvent, such as water. The mesophases of the liquid crystals depend not only on the solvent, but may also be temperature dependent. Lyotropic liquid crystals comprising a surfactant in the presence of glyphosate epicuticularly and intracuticularly have been observed in cubical formation, hexagonal formation, reversed hexagonal formation, and lamellar and multilamellar formations having at least about 20 to about 30 or more separate layers. Also, both smectic and nematic forms of liquid crystals comprised of a surfactant in the presence of glyphosate have been observed both epicuticularly and intracuticularly. In the herbicidal formulations of the present invention, both epicuticular and intracuticular liquid crystals comprising a surfactant in the presence of glyphosate form regardless of the presence or absence of a second surfactant.

In some formulations of the present invention comprising glyphosate and a surfactant which forms epicutcular and intracuticular liquid crystals the liquid crystals comprise a stratified array of the surfactant molecules such that the hydrophilic moieties of the surfactant molecules in one stratum of the stratified array is oriented toward the hydrophilic moieties of the surfactant molecules in a second stratum of the stratified array. The liquid crystals of the present invention, both epicuticular and intracuticular, may form this type of stratified array and may have numerous layers as discussed above.

In some formulations of the present invention comprising glyphosate and a surfactant which forms epicuticular and intracuticular liquid crystals the liquid crystals may orient themselves in a stratified array such that lipophilic moieties of the surfactant molecules of one stratum of the stratified array are in contact with a hydrophobic surface on the foliage of a plant that the formulation is applied to. Further, the surfactant molecules of one stratum of the stratified array may be in contact with a hydrophobic surface located within a cuticle of a plant that the formulation is applied to.

Further, some surfactants in the presence of glyphosate may form wormlike micelles, another class of organized structures in liquid form which may facilitate the translocation of glyphosate through the waxy cuticle and into and throughout the plant, both epicuticularly and intracuticularly. Wormlike micelles organization to form hydrophilic channels on and in the plant to facilitate the introduction and translocation of glyphosate in and throughout the plant. Typically, surfactants that are sufficiently "flexible" will form these types of wormlike micelles.

Although the present invention is directed primarily at aqueous concentrate formulations of the potassium salt of glyphosate, such aqueous concentrate formulations can optionally further comprise one or more additional pesticides, such as for example, water-soluble herbicidal active ingredients, including without restriction water-soluble forms of acifluorfen, asulam, benazolin, bentazon, bialaphos, bispyribac, bromacil, bromoxynil, carfentrazone, chloramben, clopyralid, 2,4-D, 2,4-DB, dalapon, dicamba, dichlorprop, diclofop, difenzoquat, diquat, endothall, fenac, fenoxaprop, flamprop, fluazifop, fluoroglycofen, fluroxypyr, fomesafen, fosamine, glufosinate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, paraquat, picloram, sulfamic acid, 2,3,6-TBA, TCA and triclopyr.

An embodiment of the invention therefore is an herbicidal aqueous concentrate composition comprising glyphosate predominantly in the form of the potassium salt thereof, and a second anionic herbicide predominantly in the form of a potassium or other agriculturally acceptable salt or acid thereof, the total concentration of the glyphosate and the second anionic herbicide together being about 360 to about 570 g a.e./l, the composition further comprising a surfactant component, selected in accordance with the invention, at a concentration of about 20 to about 300 g/l.

In this embodiment, it is preferred that the weight/weight ratio of glyphosate a.e. to the second anionic herbicide be not less than about 1:1, for example from about 1:1 to about 200:1, preferably between 1:1 to about 30:1. The second anionic herbicide is preferably selected from the group consisting of acifluorfen, bialaphos, carfentrazone, clopyralid, 2,4-D, 2,4-DB, dicamba, dichlorprop, glufosinate, MCPA, MCPB, mecoprop, methylarsonic acid, nonanoic acid, picloram, triclopyr and herbicides of the imidazolinone class, including imazameth, imazamethabenz, imazamox, imazapic, imazapyr, imazaquin and imazethapyr.

Also embraced by the present invention are liquid concentrate formulations having an aqueous phase wherein glyphosate is present predominantly in the form of the potassium salt thereof, and a non-aqueous phase optionally containing a second herbicidal active ingredient that is relatively water-insoluble. Such formulations illustratively include emulsions (including macro- and microemulsions, water-in-oil, oil-in-water and water-in-oil-in-water types), suspensions and suspoemulsions. The non-aqueous phase can optionally comprise a microencapsulated component, for example a microencapsulated herbicide. In formulations of the invention having a non-aqueous phase, the concentration of glyphosate a.e. in the composition as a whole is nonetheless within the ranges recited herein for aqueous concentrate formulations.

Illustrative water-insoluble herbicides that can be used in such formulations include acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlomitrofen, chlorotoluron, chlorpropham, chlorsulfuron, chlorthal-dimethyl, chlorthiamid, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flumiclorac-pentyl, flumioxazin, fluometuron, fluorochloridone, fluoroglycofen-ethyl, flupoxam, flurenol, fluridone, fluroxypyr-1-methylheptyl, flurtamone, fluthiacet-methyl, fomesafen, halosulfuron, haloxyfop-methyl, hexazinone, imazosulfuron, indanofan, isoproturon, isouron, isoxaben, isoxaflutole, isoxapyrifop, lactofen, lenacil, linuron, mefenacet, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, simazine, sirnetryn, sulcotrione, sulfentrazone, sulfometuron, sulfosulfuron, tebutam, tebuthiuron, terbacil, terbumeton, terbuthylazine, terbutryn, thenylchlor, thiazopyr, thifensulfuron, thiobencarb, tiocarbazil, tralkoxydim, triallate, triasulfuron, tribenuron, trietazine, trifluralin, triflusulfuron and vemolate. It is preferred that the weight/weight ratio of glyphosate a.e. to such water-insoluble herbicide be not less than 1:1, for example from about 1:1 to about 200:1, preferably between 1:1 to about 30:1.

Excipient ingredients other than the above-defined surfactant component can optionally be present in a composition of the invention, so long as the cloud point and non-crystallization properties of the composition remain in accordance with the invention. Such additional excipient ingredients include conventional formulation additives such as dyes, thickeners, crystallization inhibitors, antifreeze agents including glycols, foam moderating agents, antidflft agents, compatibilizing agents, etc.

A type of excipient ingredient often used in glyphosate formulations is an inorganic salt such as ammonium sulfate, included to enhance herbicidal activity, or consistency of herbicidal activity, of the glyphosate. As the content of inorganic salt in the formulation needed to provide such enhancement is typically relatively high, often greater than the amount of glyphosate present, it will seldom be useful to add such salt to a composition of the invention. The amount of ammonium sulfate, for example, that could be accommodated in a storage-stable aqueous composition containing glyphosate potassium salt at a concentration of at least 360 g a.e./l would be so small as to bring no substantial benefit. An alternative, therefore, is to include a small amount of a synergist such as an anthraquinone compound or a phenyl-substituted olefin compound as disclosed in International Publication Nos. WO 98/33384 and WO 98/33385 respectively.

To determine whether a herbicidal formulation comprising glyphosate or a salt or ester thereof and a surfactant forms liquid crystals comprising a surfactant on the foliage of a plant and in the foliage of a plant, the following procedures are utilized. First, the surfactant/glyphosate formulation is tested as described above to determine whether liquid crystals form epicuticulariy on the plant foliage. If it is determined that epicuticular liquid crystals do form on the plant foliage, the following testing procedure using high resolution polarized microscopy is utilized to determine whether liquid crystals also form intracuticularly.

In determining whether intracuticular liquid crystals form, fruit cuticles such as pear cuticles or tomato cuticles are typically used because they are highly robust. The isolation of the fruit cuticle is performed similarly to that of a broadleaf cuticle described above with certain modifications. Typically, the enzyme utilized to remove the fruit cuticle is pectinase (10,000 activity units per 100 mL). The concentration of the enzyme solution is typically from about 10% to about 30% weighttweight and the final enzyme solution typically contains activity of about 50 to about 200 units/mL. The fruit cuticle in incubated with the enzyme at room temperature for a period of about 1 hour or more to detach the fruit cuticle. After detachment of the cuticle, it is thoroughly rinsed and washed prior to use.

To determine whether intracuticular liquid crystals form with a surfactanttglyphosate formulation, a fruit cuticle as described above is used along Gside a control system in which the substrate is a non-porous hydrophobic material such as parafilm. The fruit cuticle is positioned on a supporting gel agar which rests on a supporting mesh, typically comprised of carbon fibers. The cuticle/agar/mesh composition is then placed on a glass slide. The parafilm is also mounted on the glass slide in this manner.

Herbicidal formulations of interest containing a surfactant and glyphosate are deposited on the cuticle and on the parafilm. When the onset of liquid crystal formulation is observed under a polarized light at 100× magnification as described above, both the cuticle and the parafilm control are wiped away either by hand or by mechanical means with a foam tip at room temperature. Typically, the liquid crystals formed on the parafilm are easily wiped away. Both the parafilm control and the fruit cuticle, after wiping, are left to achieve equilibrium for between about 24 and about 48 hours in a controlled environment (temperature between 20 to about 25° C., humidity 50% to 75%)

After equilibrium has been achieved with the parafilm control and the fruit cuticle, the area where the formulation deposits were made are again rigorously wiped by hand or mechanically with a foam tip. After wiping, the cuticle and parafilm are again examined under 100× magnification polarized light for liquid crystal formation. If the microfine texture is observed after the second wiping procedure, this is an indication of intracuticular liquid crystal formation as these liquid crystals have not been removed after two wiping cycles. Further, additional wiping may be conducted on the fruit cuticles showing liquid crystal formation to further evidence that the liquid crystals cannot be wiped off as they are intracuticular. After the second wiping, the inventors have not seen any formation of liquid crystals on any of the parafilm controls observed.

Typically, only a very small amount of solubilizer will be required to impart improved formulation characteristics. Generally, only a ratio of about 50:1 (by weight), more preferably about 25:1, still more preferably about 10:1, and most preferably about 8:1 ethoxylated etheramine surfactant to solubilizer is required. One skilled in the art will recognize that various factors may influence the amount of solubilizer required to impart the desired characteristics. The solubilizer may also be included in the formulation at a lower ratio at which it may not function as a solubilizer but will enhance efficacy, such as a surfactant to solubilizer ratio of about 5:1, about 4:1, about 3:1, about 2:1 or about 1:1.

Further, the addition of a solubilizer imparts improved viscosity characteristics on concentrated formulations of the present invention. It is preferred that sufficient solubilizer be added to the formulation to produce a formulation having a viscosity of less than 1000 c.p. at 0° C. at 45/s shear rate, even more preferably less than about 500 c.p. at 0° C. at 45/s shear rate, and most preferably less than about 300 c.p. at 0° C. at 45/s shear rate. In a preferred embodiment, the herbicidal formulations of the present invention have a viscosity of from about 100 c.p. at 0° C. at 45/s shear rate to about 500 c.p. at 0° C. at 45/s shear rate. The novel formulations of the present invention require only a small amount of solubilizer to produce these desired viscosities.

Another ingredient that can optionally be added to the glyphosate herbicidal formulations of the present invention to further improve the herbicidal effectiveness and related herbicidal properties is a di-carboxylic acid or salt of a di-carboxylic acid. Suitable di-carboxylic acids that may be added to the herbicidal formulations comprising glyphosate or a salt or ester thereof and a surfactant as described herein include, for example, oxalic acid, malonic acid, succinic acid, glutaric acid, maleic acid, adipic acid, and fumaric acid, and combinations or mixtures thereof, with oxalic acid being preferred. Also, in addition to, or in place of the di-carboxylic acid, salts of the aforementioned di-carboxylic acids may be incorporated into the herbicidal formulations of the present invention to improve herbicidal performance. Suitable salts include, for example, alkali metal salts such as potassium salts, alkanolamine salts and lower alkylamine salts. Preferred salts include potassium oxalate, dipotassium oxalate, sodium oxalate, disodium oxalate, diammonium oxalate, diethanolamine oxalate, dimethylamine oxalate, alkanolamine salts of oxalic acid, and lower alkylamine salts of oxalic acid.

Formulations containing a di-carboxylic acid such as oxalic acid or a di-carboxylic acid salt such as potassium oxalate, typically contain a sufficient amount of di-carboxylic acid/di-carboxylic acid salt to enhance the resulting efficacy of the herbicidal formulation. Typically, the weight ratio of total surfactant to carboxylic acid/carboxylic acid salt may be from about 1:1 to about 50:1, more preferably 5:1 to 40:1 and most preferably from about 5:1 to about 20:1. This ratio of total surfactant to carboxylic acid/carboxylic acid salt significantly enhances the herbicidal performance of the resulting herbicidal formulation.

The di-carboxylic acid or salt thereof which can be added to herbicidal formulations of the present invention to improve efficacy are suitable for use with glyphosate, or salts or esters thereof. Suitable glyphosate salts include those listed above, specifically isopropylamine salt, potassium salt, and trimethylammonium salt.

The present invention also includes a method for killing or controlling weeds or unwanted vegetation comprising the steps of diluting a liquid concentrate in a convenient amount of water to form a tank mix and applying a herbicidally effective amount of the tank mix to the foliage of the weeds or unwanted vegetation. Similarly included in the invention is the method of killing or controlling weeds or unwanted vegetation comprising the steps of diluting a solid particulate concentrate in a convenient amount of water to form a tank mix and applying a herbicidally effective amount of the tank mix to the foliage of the weeds or unwanted vegetation.

In a herbicidal method of using a composition of the invention, the composition is diluted in a suitable volume of water to provide an application solution which is then applied to foliage of a plant or plants at an application rate sufficient to give a desired herbicidal effect. This application rate is usually expressed as amount of glyphosate per unit area treated, e.g., grams acid equivalent per hectare (g a.e./ha). What constitutes a "desired herbicidal effect" is, typically and illustratively, at least 85% control of a plant species as measured by growth reduction or mortality after a period of time during which the glyphosate exerts its full herbicidal or phytotoxic effects in treated plants. Depending on plant species and growing conditions, that period of time can be as short as a week, but normally a period of at least two weeks is needed for glyphosate to exert its full effect.

The selection of application rates that are herbicidally effective for a composition of the invention is within the skill of the ordinary agricultural scientist. Those of skill in the art will likewise recognize that individual plant conditions, weather and growing conditions, as well as the specific active ingredients and their weight ratio in the composition, will influence the degree of herbicidal effectiveness achieved in practicing this invention. With respect to the use of glyphosate compositions, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate salts are used to control a very wide variety of plants worldwide, and it is believed the potassium salt will prove no different from other salts of glyphosate in this regard.

Particularly important annual dicotyledonous plant species for control of which a composition of the invention can be used are exemplified without limitation by velvetleaf (*Abutilon theophrasti*), pigweed (*Amaranthus* spp.), buttonweed (*Borreria* spp.), oilseed rape, canola, indian mustard, etc. (*Brassica* spp.), commelina (*Commelina* spp.), filaree (*Erodium* spp.), sunflower (*Helianthus* spp.), morningglory (*Ipomoea* spp.), kochia (*Kochia scoparia*), mallow (*Malva* spp.), wild buckwheat, smartweed, etc. (*Polygonum* spp.), purslane (*Portulaca* spp.), russian thistle (*Salsola* spp.), sida (*Sida* spp.), wild mustard (*Sinapis arvensis*) and cocklebur (*Xanthium* spp.).

Particularly important annual monocotyledonous plant species for control of which a composition of the invention can be used are exemplified without limitation by wild oat (*Avena fatua*), carpetgrass (*Axonopus* spp.), downy brome (*Bromus tectorum*), crabgrass (*Digitara* spp.), barnyardgrass (*Echinochloa crusgalii*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (*Phalaris* spp.), foxtail (*Setaria* spp.), wheat (*Triticum aestivum*) and corn (*Zea mays*).

Particularly important perennial dicotyledonous plant species for control of which a composition of the invention can be used are exemplified without limitation by mugwort (*Artemisia* spp.), milkweed (*Asclepias* spp.), canada thistle (*Cirsium arvense*), field bindweed (*Convolvulus arvensis*) and kudzu (*Pueraia* spp.).

Particularly important perennial monocotyledonous plant species for control of which a composition of the invention can be used are exemplified without limitation by brachiaria (*Brachiaria* spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (*Phragmites* spp.), johnsongrass (*Sorghum halepense*) and cattail (*Typha* spp.).

Other particularly important perennial plant species for control of which a composition of the invention can be used are exemplified without limitation by horsetail (*Equisetum* spp.), bracken (*Pteridium aquilinum*), blackberry (*Rubus* spp.) and gorse (*Ulex europaeus*).

If desired, the user can mix one or more adjuvants with a composition of the invention and the water of dilution when preparing the application composition. Such adjuvants can include additional surfactant and/or an inorganic salt such as ammonium sulfate with the aim of further enhancing herbicidal efficacy. However, under most conditions a herbicidal method of use of the present invention gives acceptable efficacy in the absence of such adjuvants.

In a particular contemplated method of use of a composition of the invention, the composition, following dilution in water, is applied to foliage of crop plants genetically transformed or selected to tolerate glyphosate, and simultaneously to foliage of weeds or undesired plants growing in close proximity to such crop plants. This method of use results in control of the weeds or undesired plants while leaving the crop plants substantially unharmed. Crop plants genetically transformed or selected to tolerate glyphosate include those whose seeds are sold by Monsanto Company or under license from Monsanto Company bearing the Roundup Ready® trademark. These include, without restriction, varieties of cotton, soybean, canola, sugar beet, wheat and corn.

Plant treatment compositions can be prepared simply by diluting a concentrate composition of the invention in water. Application of plant treatment compositions to foliage is preferably accomplished by spraying, using any conventional means for spraying liquids, such as spray nozzles, atomizers or the like. Compositions of the invention can be used in precision farming techniques, in which apparatus is employed to vary the amount of pesticide applied to different parts of a field, depending on variables such as the particular plant species present, soil composition, etc. In one embodiment of such techniques, a global positioning system operated with the spraying apparatus can be used to apply the desired amount of the composition to different parts of a field.

A plant treatment composition is preferably dilute enough to be readily sprayed using standard agricultural spray equipment. Useful spray volumes for the present invention can range from about 10 to about 1000 liters per hectare (l/ha) or higher, by spray application.

EXAMPLES

The following Examples are provided for illustrative purposes only and are not intended to limit the scope of the present invention. The Examples will permit better understanding of the invention and perception of its advantages and certain variations of execution.

Example A

Preparation of Glyphosate Potassium Salt

To a glass container of approximately 4 liter capacity was added 1264.1 grams of glyphosate acid with an assay of 95.7%. The container was placed in an ice/water bath to provide cooling. The container was equipped with an overhead stirrer with a propeller blade approximately one half the diameter of the container. A commercial 45% potassium hydroxide solution (VWR Scientific Products) was added. The addition rate was controlled to avoid obvious boiling of the resulting solution. The stirrer height was adjusted as the volume of the liquid changed to insure good mixing. A total of 966.2 grams of potassium hydroxide solution were added. The concentration was adjusted by the addition of 195.3 grams of deionized water. Stirring was continued for approximately 1 hour. The final yield was 2418.4 grams which represents a weight loss of 7.2 grams. The calculated assay was 50.0% glyphosate acid or 61% of potassium glyphosate and the calculated neutralization was 108%. The pH of a 10% dilution in deionized water was 4.76. The density of the resulting solution at 20° C. was approximately 1.4661 grams/milliliter and the volume of 1000 grams at 20° C. was therefor approximately 682 ml. This corresponds to a weight/volume concentration of about 730 grams/liter.

Example B

Preparation of Comparative Formulations and Formulations of the Present Invention Surfactant-containing compositions 2-01 to 2-13 are prepared as described below. Each contains glyphosate potassium salt, and was prepared using the 50% a.e. potassium glyphosate solution from Example A, above. Comparative compositions containing glyphosate potassium salt, an alkylpolyglycoside, and alkoxylated alkylamine surfactants (Compositions 2.01–2.05) were prepared so as to duplicate the compositions set forth for Examples 1, 2, 3, 7, and 15 of PCT Publication No. WO 00/15037, respectively.

Sample Preparation: To a 4 ounce (117 ml) jar is added approximately 80 grams of the potassium glyphosate solution from Example A. To this is added the appropriate ratio of adjuvant and water. To some samples a small amount of phosphoric acid was added to adjust the pH to between 4.9 and 5.1. The resulting mixture is stirred with a magnetic stirrer (Cole-prmer, Chicago, Ill.) until a single phase is obtained. In the case of materials that were viscous and consequently could not be mixed with the magnetic stirrer, the material was rolled on a roller mill (US Stoneware, Manwah, N.J.) until the surfactant was dissolved. The material was allowed to stand overnight and observed to insure that it was a single phase and free of air bubbles.

The density was then determined using a Mettler DA-300 Density Meter and the concentrations in grams per liter was calculated.

Cloud points were measured by heating a small amount of the material in a test tube until the solution became hazy or cloudy then removing the test tube from the heat and observing the temperature at which the solution became clear on cooling. The temperature at which the solution became clear is noted as the cloud point.

Viscosities were measured using a Haake Model VT500 (Haake, Inc., Karisruhe Germany) equipped with the appropriate MV series cup and bob sensor system at a shear rate of 45 sec$^{-1}$. The temperature was varied with the attached water bath. For a few samples for which insufficient sample was available the viscosities were measured with a Brookfield Model DV-II equipped with a Small Sample Adapter (Brookfield Laboratories, Inc., Stoughton, Mass.).

TABLE 2

Composition of Formulations of Example B (2.01 through 2.05)

| | 2.01 (Z1) | | 2.02 (Z2) | | 2.03 (Z3) | | 2.04 (Z7) | | 2.05 (Z15) | |
|---|---|---|---|---|---|---|---|---|---|---|
| | % | % Active | % | % Active | % | % Active | % | % Active | % | % Active |
| Potassium Glyphosate (50%) | 78.63 | 39.33 | 74.58 | 37.29 | 69.48 | 34.74 | 69.52 | 34.76 | 78.50 | 39.29 |
| Agrimu PG 2067 | 15.60 | 10.92 | 12.85 | 9.00 | 17.73 | 12.41 | 12.15 | 8.50 | 13.50 | 9.45 |
| Ethomeen C/15 | 3.65 | | 3.45 | | 3.86 | | 7.72 | | 3.81 | |
| Propylene Glycol | 0.00 | | 0.00 | | 0.00 | | 0.00 | | 1.96 | |
| Water | 2.09 | | 9.12 | | 8.93 | | 10.61 | | 4.11 | |
| | 100.00 | | 100.00 | | 100.00 | | 100.00 | | 100.00 | |
| Density (g/cc) 20° C. | | 1.3793 | | 1.3509 | | 1.3408 | | 1.3288 | | 1.3824 |
| g/l glyphosate ae | | 542 g/l | | 504 g/l | | 466 g/l | | 462 g/l | | 543 g/l |
| Total Surfactant Solids | 14.6 | 201 g/l | 12.45 | 168 g/l | 16.3 | 218 g/l | 16.22 | 216 g/l | 13.3 | 183 g/l |
| Cloud Point | >90° C. | | >90° C. | | | | | | | |

| Haake Viscosity | Temp (° C.) | cPs | Temp (° C.) | cPs | Temp (° C.) | cPs | Temp (° C.) | cPs | Temp (° C.) | CPs |
|---|---|---|---|---|---|---|---|---|---|---|
| | 25 | 556 | 25 | 135 | 25 | 229 | 25 | 116 | 25 | 208 |
| | 15 | 758 | 15 | 209 | 15 | 394 | 15 | 150 | 15 | 432 |
| | 10 | 1205 | 10 | 226 | 10 | 457 | 10 | 209 | 10 | 501 |
| | 5 | 1488 | 5 | 312 | 5 | 630 | 5 | 226 | 5 | 580 |
| | 0 | 1877 | 0 | 335 | 0 | 668 | 0 | 271 | 0 | 1035 |
| | −5 | 2733 | −5 | 485 | −5 | 880 | −5 | 398 | −5 | 1266 |

TABLE 3

Composition of Formulations of Example B (2.06 through 2.13)

| | 2.06 | | 2.07 | | 2.08 | | 2.09 | |
|---|---|---|---|---|---|---|---|---|
| | % | Active | % | Active | % | Active | % | Active |
| Potassium Glyphosate 50% | 74.56 | 37.28% | 69.06 | 34.53% | 73.40 | 36.70% | 69.40 | 34.70% |
| Huntsman Surfonic AGM 550 | 12.46 | | 16.07 | | 13.69 | | 0.00 | |
| Ethomeen C/15 | 0.00 | | 0.00 | | 0.00 | | 0.00 | |
| Ethoquad C/12 | 0.00 | | 0.00 | | 0.00 | | 22.19 | 16.20% |
| Tomah E-D-17-5 | 0.00 | | 0.00 | | 0.00 | | 0.00 | |
| Phosphoric Acid | 0.00 | | 0.48 | | 0.82 | | 0.00 | |
| Water | 12.98 | | 14.39 | | 12.09 | | 8.41 | |
| | 100.00 | | 100.00 | | 100.00 | | 100.00 | |
| Density (g/cc) 20° C. | 1.3238 | | 1.3019 | | 1.3264 | | 1.2932 | |
| g/l glyphosate ae | | 494 | | 449 | | 487 | | 449 |

TABLE 3-continued

Composition of Formulations of Example B (2.06 through 2.13)

| | | | | | | | | |
|---|---|---|---|---|---|---|---|---|
| Total Surfactant Solids | 12.46 | 165 g/l | 16.1 | 209 g/l | 13.7 | 182 g/l | 16.2 | 209 g/l |
| Cloud Point | 70° C. | | 55° C. | | 55° C. | | >90° C. | |

| Haake Viscosity | Temp (° C.) | cPs | Temp (° C.) | cPs | Temp (° C.) | cPs | Temp (° C.) | cPs |
|---|---|---|---|---|---|---|---|---|
| | 25 | 43 | 25 | 73 | 25 | 70 | 25 | 3 |
| | 15 | 55 | 15 | 102 | 15 | 82 | 15 | 15 |
| | 10 | 91 | 10 | 122 | 10 | 131 | 10 | 29 |
| | 5 | 125 | 5 | 144 | 5 | 177 | 5 | 33 |

| | 2.10 | | 2.11 | | 2.12 | | 2.13 | |
|---|---|---|---|---|---|---|---|---|
| | % | Active | % | Active | % | Active | % | Active |
| Potassium Glyphosate 50% | 78.36 | 39.18% | 72.80 | 36.40% | 74.58 | 37.29% | 74.00 | 37.00% |
| Huntsman Surfonic AGM 550 | 0.00 | | 9.11 | | 9.60 | | 0.00 | |
| Ethomeen C/15 | 14.55 | | 0.00 | | 3.46 | | 0.00 | |
| Ethoquad C/12 | 0.00 | | 0.00 | | 0.00 | | 0.00 | |
| Tomah E-D-17-5 | 0.00 | | 0.00 | | 0.00 | | 12.51 | |
| Phosphoric Acid | 2.37 | | 0.00 | | 0.00 | | 0.00 | |
| Water | 4.72 | | 18.09 | | 12.94 | | 13.49 | |
| | 100.00 | | 100.00 | | 100.00 | | 100.00 | |
| Density (g/cc) 20° C. | 1.3493 | | 1.3085 | | 1.3215 | | 1.3349 | |
| g/l glyphosate ae | | 529 | | 476 | | 493 | | 494 |
| Total Surfactant Solids | 14.6 | 196 | 9.10 | 119 | 12.50 | 165 | 12.51 | 167 |
| Cloud Point | >90° C. | | 60° C. | | 75° C. | | >90° C. | |

| Haake Viscosity | Temp (° C.) | cPs | Temp (° C.) | cPs | Temp (° C.) | cPs | Temp (° C.) | cPs |
|---|---|---|---|---|---|---|---|---|
| | 25 | | 25 | | 25 | 32 | 25 | 54 |
| | 15 | 541 | 15 | 33 | 15 | 61 | 15 | 112 |
| | 10 | 531 | 10 | 36 | 10 | 109 | 10 | 123 |
| | 5 | 613 | 5 | 46 | 5 | 113 | 5 | 160 |

TABLE 4

Surfactants used in Example C

| Surfactant | Chemical Structure | Trade name and supplier |
|---|---|---|
| A | 2-ethylhexylamine structure (CH₃(CH₂)₃CH(C₂H₅)CH₂NH₂) | 104-75-6 (Aldrich) |
| B | $C_{16}H_{37}$—N(CH₃)₂ type tertiary amine | Pfaltz & Bauer (www.pfaltzandbauer.com) |
| C | $C_{18}H_{37}$—N with methyl and $(CH_2CH_2O)_7CH_3$ substituents | not commercially available (prepared in accordance with Example D, above) |

TABLE 4-continued

Surfactants used in Example C

| Surfactant | Chemical Structure | Trade name and supplier |
|---|---|---|
| D | $C_{18}H_{37}-N(-(EO)_{4.4}H)(-CH_3)$ | not commercially available (prepared by the ethoxylation of N-methyloctadecylamine) |
| E | $C_{18}H_{37}-N(-(EO)_{5.3}H)(-CH_3)$ | not commercially available (prepared by the ethoxylation of N-methyloctadecylamine |
| F | $(C_4H_9)_2N-CH_2CH_2CH_2-NH_2$ | 102-83-0 (Aldrich) |
| G | $(C_4H_9)_2N-CH_2CH_2CH_2-N(CH_3)_2$ | CAS 62478-76-6 not commercially available) |
| H | $(C_8H_{17})_2N-CH_2CH_2CH_2-NH_2$ | CAS 64184-58-3 (not commercially available) |
| I | dimethyl quaternary ammonium bromide with decyl chain and NMe₂ substituent | CAS 123714-89-9 (not commercially available) |
| J | $(C_8-C_{10})-O-CH_2CH_2CH_2-NH_2$ | PA-1214 (Tomah) |
| K | branched alkyl-$O-CH_2CH_2CH_2-NH_2$ | PA 10 (Tomah) |
| L | 2-ethylhexyl-$O-CH_2CH_2CH_2-NH_2$ | PA-12EH (Tomah) |
| M | branched alkyl-$O-CH_2CH_2CH_2-N((EO)_mH)((EO)_nH)$, m+n=5 | E-17-5 (Tomah) |
| N | $C_{12-14}-O-CH_2CH(CH_3)-O-CH_2CH(CH_3)-N((EO)_mH)((EO)_nH)$, m+n=5 | Surfonic AGM - 550 (Huntsman Petrochemical Corp.) |
| O | $(C_8-C_{10})-O-CH_2CH_2CH_2-NH-CH_2CH_2CH_2-NH_2$ | DA-1214 (Tomah) |
| P | $(C_{12}-C_{14})-O-CH_2CH_2CH_2-NH-CH_2CH_2CH_2-NH_2$ | DA-1618 (Tomah) |
| Q | $(C_{14}-H_{29})-O-CH_2CH_2CH_2-NH-CH_2CH_2CH_2-NH_2$ | DA-18 (Tomah) |

TABLE 4-continued
Surfactants used in Example C
| Surfactant | Chemical Structure | Trade name and supplier |
|---|---|---|
| R | 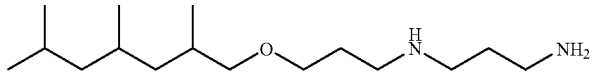 | DA-14 (Tomah) |
| S | 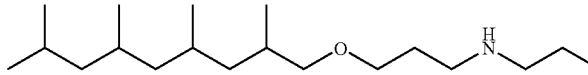 | DA-17 (Tomah) |
| T | 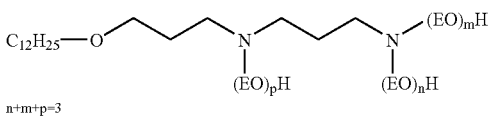<br>n+m+p=3 | B1910-5 (Witco) |
| U | <br>Total EO = 6 | B1910-6 (Witco) |
| V | 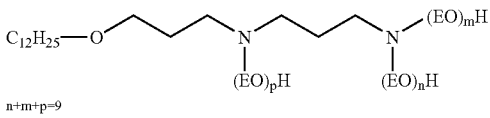<br>n+m+p=9 | B1910-9 (Witco) |
| W | 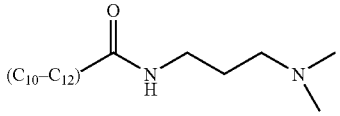 | Mackine 101 |
| X | 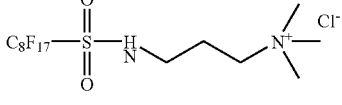 | Fluorad FC-754 |
| Y | 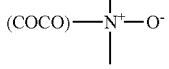 | Chemoxide L70 |
| Z | $C_{11}C_{10+}C_{9+}$—O-(glucoside) | Agrimul APG 2069 |
| AA | 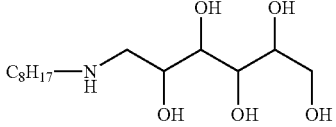 | 23323-37-7 (Aldrich) |
| BB | 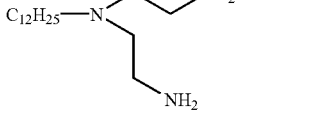 | 4182-44-9 (Acros) |
| CC | 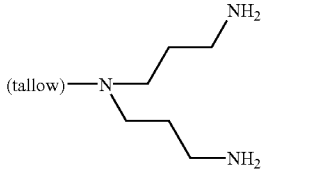 | Genamin 3119(Clariant)<br>CAS 85632-63-9 |

TABLE 4-continued

Surfactants used in Example C

| Surfactant | Chemical Structure | Trade name and supplier |
|---|---|---|
| DD | $H_2N-CH_2CH_2-O-CH_2CH_2-O-CH_2CH_2-NH_2$ | Jeffamine EDR-148 |
| EE | (tallow)—N$^+$(O$^-$)((EO)$_m$H)((EO)$_n$H), n+m=5 | Custom B-1965-F (Witco) |
| FF | 2-ethylhexyl-N(CH$_2$CH$_2$OH)$_2$ | 6637025 |
| GG | $C_{12}H_{25}$—N$^+$(CH$_3$)$_3$ | |
| HH | $C_{18}H_{37}$—N(CH$_3$)—(CH$_2$CH$_2$O)$_{5.9}$H | 6801342 |
| II | $C_{12}H_{25}$—N(CH$_3$)—(CH$_2$CH$_2$O)$_{7.5}$H | 6801343 |
| JJ | (C$_8$H$_{17}$)$_2$N—(CH$_2$)$_3$—N(CH$_3$)$_2$ | NBP6476266 |
| KK | CH$_3$NH—(CH$_2$)$_{12}$—NHCH$_3$ | 208540-68-5 |
| LL | 2-ethylhexyl-O-(CH$_2$)$_3$-N((EO)$m$H)((EO)$n$H), n+m=5 | 6801357 |
| MM | 2-ethylhexyl-O-(CH$_2$)$_3$-N((EO)$m$H)((EO)$n$H), n+m=7 | 6801359 |
| NN | $C_{12}H_{25}$-O-(CH$_2$)$_3$-N((EO)$n$)((EO)$m$) | Witco Exp-5388-48 (MON 59124) |
| OO | $C_8F_{17}$—S(=O)$_2$—NH—(CH$_2$)$_3$—N(CH$_3$)$_2$ | S. Auinbauh ck CAS |

TABLE 4-continued
Surfactants used in Example C
| Surfactant | Chemical Structure | Trade name and supplier |
|---|---|---|
| PP | 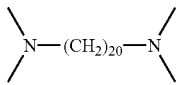 $n+m=5$ | Witco custom B-1965-F |
| QQ | 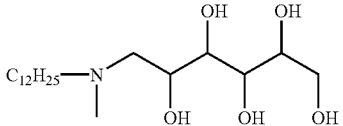 | 6747747 |
| RR | 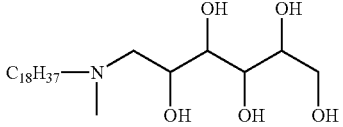 | 6788433 |
| SS | 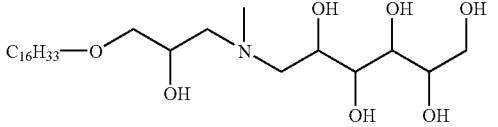 | 6788438 |
| TT | 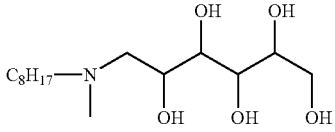 | 6916805 |
| UU | 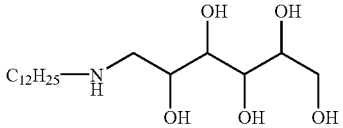 | 6788445 |
| VV | 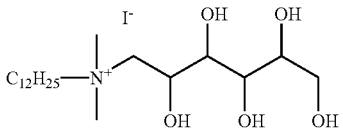 | Clariant |
| WW | 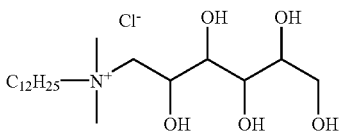 | 6788437 |
| XX | 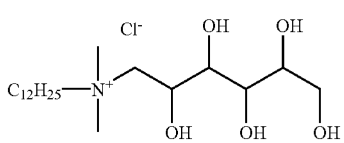 | 6788449 |
| YY | 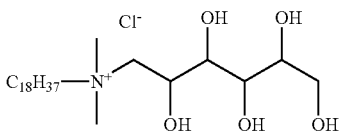 | 6788440 |

TABLE 4-continued

Surfactants used in Example C

| Surfactant | Chemical Structure | Trade name and supplier |
|---|---|---|
| ZZ | $H_3C-N(-(CH_2)_{12}-N(-CH_3)(-CH_2CHOH-CHOH-CHOH-CHOH-CH_2OH))(-CH_2CHOH-CHOH-CHOH-CHOH-CH_2OH)$ | 6788462 |
| AAA | $C_6H_{13}-N(-(CH_2)_3-N(-C_6H_{13})(-CH_2CHOH-CHOH-CHOH-CHOH-CH_2OH))(-CH_2CHOH-CHOH-CHOH-CHOH-CH_2OH)$ | 6788468 |
| BBB | $C_6H_{13}-N(-(CH_2)_8-N(-C_6H_{13})(-CH_2CHOH-CHOH-CHOH-CHOH-CH_2OH))(-CH_2CHOH-CHOH-CHOH-CHOH-CH_2OH)$ | 6788476 |
| CCC | $C_8H_{17}-N(-(CH_2)_3-N(-C_8H_{17})(-CH_2CHOH-CHOH-CHOH-CHOH-CH_2OH))(-CH_2CHOH-CHOH-CHOH-CHOH-CH_2OH)$ | 6788465 |
| DDD | $C_{12}H_{25}-N((EO)_nH)-(CH_2)_3-N((EO)_mH)-C_{12}H_{25}$; EO = 9 | 6916412 |
| EEE | $C_8H_{17}-NH-C(CH_2OH)_3$ | 6747783 |
| FFF | $C_{12}H_{25}-NH-C(CH_2OH)_3$ | 6788460 |
| GGG | $C_{12}H_{25}-(OCH_2CH_2)_4NHCH_3$ | 6566722 |
| HHH | $C_{12}H_{25}-(OCH_2CH_2)_4N(CH_3)_2$ | 6747786 |
| III | $C_{16}H_{33}-(EO)_{10}N(CH_3)_2$ | 6866748 |
| JJJ | (tallow)-$(PO)_2(EO)_9N(CH_3)_2$ | 6866733 |

TABLE 4-continued

Surfactants used in Example C

| Surfactant | Chemical Structure | Trade name and supplier |
|---|---|---|
| KKK | $(C_{16}H_{33})-(OCH_2CH_2)_{10}NH(CH_2)_3NH_2$ | 6866729 |
| LLL | $(C_{16}H_{33})-(EO)_{10}-N(CH_3)-CH_2CH_2-NH-CH_3$ | 6866759 |
| MMM | $(C_{16}H_{33})-(EO)_{10}-N(CH_3)-CH_2CH_2-N(CH_3)_2$ | 6866758 |
| NNN | $(C_{16}H_{33})-(EO)_{10}NH-CH_2-CH(OH)-CH_2-NH_2$ | |
| OOO | $C_{16}H_{33}-(OCH_2CH_2)_{10}-N(Me)-CH_2-CH(OH)-CH(OH)-CH(OH)-CH(OH)-CH_2OH$ | 6866730 |
| PPP | $CH_3(CH_2)_{15}-(OCH_2CH_2)_{20}-N(Me)-CH_2-CH(OH)-CH(OH)-CH(OH)-CH(OH)-CH_2OH$ | 6866782 |
| QQQ | $CH_3(CH_2)_{15}-(OCH_2CH_2)_{20}-N(Me)-CH_2-CH(OH)-CH_2OH$ | 6866787 |
| RRR | $C_{12}H_{25}-N(Me)-CH_2-CH(O-(EO)mH)-CH_2-O-(EO)nH$; $m+n=5$ | 6801387 |
| SSS | $C_{12}H_{25}-N(Me)-CH_2-CH(O-(EO)mH)-CH_2-O-(EO)nH$; $m+n=10$ | 6801389 |
| TTT | $C_{18}H_{37}-N(Me)-CH_2-CH(O-(EO)mH)-CH_2-O-(EO)nH$; $m+n=5$ | 6801384 |
| UUU | $C_{18}H_{37}-N(Me)-CH_2-CH(O-(EO)mH)-CH_2-O-(EO)nH$; $m+n=10$ | 6801388 |

TABLE 4-continued

Surfactants used in Example C

| Surfactant | Chemical Structure | Trade name and supplier |
|---|---|---|
| VVV | $C_{12}H_{25}\text{—}^+N\diagup\hspace{-0.5em}\diagdown$ $Cl^-$ | |

The following compounds were not compatible with 31% a.e. potassium glyphosate and 10% surfactant, but were compatible with 31% a.e. diammonium glyphosate and 10% surfactant:

| | | |
|---|---|---|
| WWW | $C_{18}H_{37}\text{—}^+N\diagup\hspace{-0.5em}\diagdown$ $Cl^-$ | |
| XXX | $C_{12}H_{25}\text{—}(OCH_2CH_2)_4\text{—}N^+\diagup\hspace{-0.5em}\diagdown$ $Cl^-$ | |

Example C

Preparation of Representative Sample Compositions of the Invention

For the 31 wt. % a.e. potassium glyphosate/10 wt. % surfactant compositions: 1.550 g of 40 wt. % a.e. aqueous glyphosate potassium salt solution was weighed into a vial. To the same vial, 0.200 g of surfactant was added. Enough deionized water was then added to the contents to bring the total weight to 2.000 g. The mixture was stirred for 2 hours at room temperature and checked to see if a solution had been formed. If a solution was present, the test vial was allowed to stand at room temperature overnight. If a solution was still present, the test vial was placed in a 50° C. oven for 1 week. If no phase separation had occurred in one week, the surfactant being tested was considered "compatible." All of the surfactants identified in Table 4 were compatible at the 31% a.e. potassium/10 wt. % surfactant loading.

For the 37 wt. % a.e. potassium glyphosate/12 wt. % surfactant compositions: 41.1 g of 45 wt. % a.e. aqueous glyphosate potassium salt was weighed to a container. To the same container was added 6.0 g of surfactant and 2.9 g deionized water for a total weight of 50.0 g. The remainder of the protocol is the same as that described for the 31 wt. % samples. The surfactants identified in Table 4 that were compatible at the 37% a.e. potassium/12 wt. % surfactant loading are indicated in Table 5 below.

For the 40 wt. % a.e. potassium glyphosate/10 wt. % surfactant compositions: 1.79 g of 45 wt. % a.e. aqueous glyphosate potassium salt was weighed into a vial. To the same vial was added 0.2 g of surfactant. The remainder of the protocol is the same as that described for the 31 wt. % samples. The surfactants identified in Table 4 that were compatible at the 40% a.e. potassium/10 wt. % surfactant loading are indicated in Table 5 below.

For the 45 wt. % a.e. potassium glyphosate/15 wt. % surfactant compositions: 1.100 g of solid mono potassium glyphosate was weighed into a vial. To the same vial was added 0.300 g surfactant. Enough deionized water was added to the vial to bring the final weight to 2.000 g. The remainder of the protocol is the same as that described for the 31 wt. % samples. The surfactants identified in Table 4 that were compatible at the 45% a.e. potassium/10 wt. % surfactant loading are indicated in Table 5 below.

For the 31 wt. % a.e. $NH_4^+$glyphosate/10 wt. % surfactant compositions:

1.48 g of 41.9 wt % a.e. aqueous glyphosate diammonium (1.7 eq) salt was weighed into a vial. To the same vial was added 0.2 g of surfactant and 0.32 g deionized water. The remainder of the protocol is the same as that described for the 31 wt % potassium glyphosate samples. The surfactants identified in Table 4 that were compatible at the 31% a.e. ammonium/10 wt. % surfactant loading are indicated in Table 5 below.

For the 37 wt. % a.e. $NH_4^+$glyphosate/12 wt. % surfactant compositions:

1.76 g of 41.9 wt % a.e. aqueous glyphosate diammonium (1.7 eq) salt was weighed into a vial. To the same vial was added 0.2 g of surfactant. The remainder of the protocol is the same as that described for the 31 wt % potassium glyphosate samples. The surfactants identified in Table 4 that were compatible at the 37% a.e. ammonium/12 wt. % surfactant loading are indicated in Table 5 below.

Compatibility and viscosity data are listed for selected compositions of Example C in Table 5. It is understood that not all results of all compatibility tests are reported herein. Several surfactants tested (but not reported herein) were not compatible even at the 31 wt. % a.e. loading.

Example D

Preparation of α-methyl-ω-(N-methyloctadecylamino)poly(oxy-1,2-ethanediyl)
Preparation of Intermediate for Compound C of Table 4

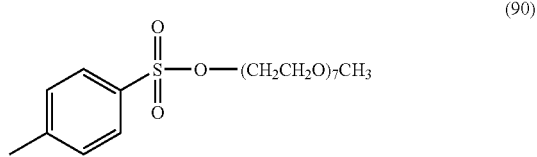

(90)

Hepta(oxythylene)glycol Methyl Ether Tosylate (I):
Hepta(oxyethylene)glycol methyl ether (350 MW avg., 47 g, 1 eq., Aldrich) and triethylamine (17.59 g, 1.3 eq.) were dissolved in anhydrous methylene chloride (20 ml) and placed under a nitrogen atmosphere. p-Toluenesulfonyl chloride (28.16 g, 1.1 eq.) dissolved anhydrous methylene chloride (20 ml) was added slowly, keeping the temperature below 10° C. After stirring for 4 hours at room temperature, the reaction mixture was filtered, and the solvent was removed from the filtrate under reduced pressure to give 64 g of an orange oil, 95% yield. $^1$H NMR d 7.8 (d, 2H), 7.5 (d, 2H), 4.1 (t, 2H), 3.6–3.4 (m, 26H), 3.2 (s, 3H), 2.4 (s, 3H).

Preparation of Compound C of Table 4:
N-methyloctadecyl amine (283 MW, 18.49 g, 2.2 eq.) was dissolved in 200 ml of toluene and then potassium carbonate (4.1 g, 1 eq.) was added. The tosylate (I) (15 g, 1 eq.) was slowly added to the mixture and then the reaction was placed under nitrogen and heated overnight at 80° C. Solids were removed from the completed reaction by filtering over celite. Toluene was removed from the filtrate under reduced pressure. The crude product was chromatographed using methylene chloride/methanol/ammonium hydroxide in the ratio 80:5:1. 16 g of yellow semi-solid (II) was obtained, yield 85%. H NMR, 3.6–3.4p(m, 26H), 3.3p(s, 3H), 2.6p(t, 2H), 2.4p(t, 2H), 2.2p(s, 3H), 1.4p(m, 2H), 1.2p(s, 30H), 0.8p(t, 3H).

TABLE 5

Compatibility and Viscosity Data for Selected 37 wt. % a.e., 40 wt. % a.e. and 45 wt. % a.e. compositions of Example 3.

| Surfactant | Compatible w/37% a.e. K + glyphosate at 12 wt % loading | Viscosity Data 37% a.e. K + glyphosate at 12 wt % loading | Cloud Point Data 37% a.e. K + glyphosate at 12 wt % loading | Compatible w/40% a.e. K + glyphosate at 10% wt loading | Compatible w/45% a.e. K + glyphosate at 15% wt loading | Compatible w/31% a.e. diammonium glyphosate at 10 wt % loading | Compatible w/37% a.e. diammonium glyphosate at 12 wt % loading |
|---|---|---|---|---|---|---|---|
| C | | | | | | No | |
| F | Yes | Haake Vis. 25° C. 57.29 cPs 15° C. 110.89 cPs 10° C. 142.38 cPs 5° C. 173.57 cPs 0° C. 273.01 cPs −5° C. 400.48 cPs | >90° C. | Yes | Yes | | |
| J | Yes | frozen at 10° C. | n.a. | | | | |
| O | Yes | Haake Vis. 25° C. 101.82 cPs 15° C. 118.51 cPs 10° C. 198.34 cPs 5° C. 221.90 cPs 0° C. 467.60 cPs | >90° C. | | | | |
| R | Yes | Haake Vis. 25° C. 1077 cPs 15° C. 1420 cPs 10° C. 1963 cPs 5° C. 2269 cPs 0° C. 2517 cPs −5° C., too thick | >90° C. | | | | |
| W | Yes | Haake Vis. 25° C. 31.49 cPs 15° C. 64.15 cPs 10° C. 76 cPs 5° C. 96.58 cPs 0° C. 146.77 cPs −5° C. 164.23 cPs | >90° C. | Yes | No (Gel) | | |
| AA | Yes | Brookfield Viscosity 10° C., Spindle 31 60 rpm, 60.1 cPs 12 rpm, 52.6 cPs | >90° C. | Yes | Yes | Yes | Yes |
| CC | Yes | Haake Vis. 25° C. 115.18 cPs 15° C. 162.06 cPs 10° C. 274.66 cPs 5° C. 358.87 cPs 0° C. 384.53 cPs −5° C. 646.90 cPs | >90° C. | Yes | No | | |

TABLE 5-continued

Compatibility and Viscosity Data for Selected 37 wt. % a.e., 40 wt. % a.e. and 45 wt. % a.e. compositions of Example 3.

| Surfactant | Compatible w/37% a.e. K + glyphosate at 12 wt % loading | Viscosity Data 37% a.e. K + glyphosate at 12 wt % loading | Cloud Point Data 37% a.e. K + glyphosate at 12 wt % loading | Compatible w/40% a.e. K + glyphosate at 10% wt loading | Compatible w/45% a.e. K + glyphosate at 15% wt loading | Compatible w/31% a.e. diammonium glyphosate at 10 wt % loading | Compatible w/37% a.e. diammonium glyphosate at 12 wt % loading |
|---|---|---|---|---|---|---|---|
| DD | Yes | Haake Vis.<br>25° C.  49.37 cPs<br>15° C.  82.51 cPs<br>10° C.  138.80 cPs<br>5° C.  150.26 cPs<br>0° C.  231.17 cPs<br>−5° C.  397.16 cPs | >90° C. | | | | |
| EE | Yes | Brookfield Vis.<br>10° C., Spindle 31<br>60 rpm, too thick<br>12 rpm, 1420 cp | 40° C. | | | | |
| PP | Yes | Brookfield Vis.<br>10° C., Spindle 31<br>60 rpm, 50.1 cp<br>12 rpm, 37.6 cp | 64° C. | | | | |
| RR | Yes | | | | Yes | Yes | Yes |
| SS | Yes | Brookfield Vis.<br>10° C., Spindle 31<br>60 rpm, 88.2 cp<br>12 rpm, 86.5 cp | | | Yes, but initially a gel that became flowable | No | No |
| UU | Yes | Brookfield Vis.<br>10° C., Spindle 31<br>60 rpm, 113 cp<br>12 rpm, 114 cp | | | | No | No |
| VV | Yes | Brookfield Vis.<br>10° C., Spindle 31<br>60 rpm, 103 cp<br>12 rpm, 107 cp | | | Yes | Yes | Yes |
| XX | No | | | | | Yes | No |
| YY | No | | | | | Yes | No |
| ZZ | Yes | | | | Yes | | |
| AAA | Yes | Brookfield Vis.<br>10° C., Spindle 31<br>60 rpm, 78.2 cp<br>12 rpm, 76.5 cp | | | Yes | Yes | Yes |
| CCC | Yes | | | | Yes | | |
| DDD | | | | | | No | No |
| EEE | Yes | | | | No | Yes | Yes |
| FFF | | | | | | No (gel) | No (gel) |
| HHH | | | | | | No (gel) | |
| KKK | Probably yes, but ambiguous due to minor solids | | | | Yes, but minor solids present, initially a gel that became flowable | | |
| MMM | Yes | | | | | Yes (Very thick) | |
| OOO | Probably yes, but ambiguous due to minor solids | | | | | No (gel) | Yes |
| PPP | No | | | | | No | No |
| QQQ | No | | | | | No | No |
| RRR | Yes | | | | No | Yes | No |
| TTT | Yes (minor solids) | | | | No | | |
| VVV | | | | | | Yes | No (gel) |
| WWW | | | | | | Yes | No (gel) |
| XXX | No | | | | | Yes | No |

It will be noted that the compositions of the invention containing glyphosate potassium salt without alkylpolyglycoside as a component of the surfactant system generally have significantly lower viscosity than similarly loaded glyphosate potassium salt compositions containing APG. The magnitude of this viscosity advantage depends to some extent on the choice and concentration of the particular surfactant(s) employed. For example, the preceding description of specific embodiments of the present invention is not intended to be a complete list of every possible embodiment of the invention. Persons skilled in this field will recognize that modifications can be made to the specific embodiments described here that remain within the scope of the present invention.

Example E

Preparation of Surfactants RRR-UUU

Compounds of the formulae (36) or (37) were prepared

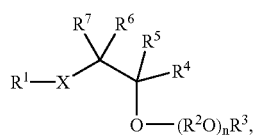
(36)

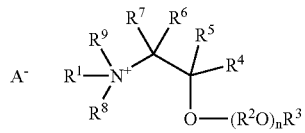
(37)

wherein $R^1$, and $R^9$ are independently hydrocarbyl or substituted hydrocarbyl having from 1 to about 30 carbon atoms, or —$(R^2O)_p R^{13}$; $R^2$ in each of the m $(R^2O)$, n $(R^2O)$, p $(R^2O)$ and q $(R^2O)$ groups is independently $C_2$–$C_4$ alkylene; $R^3$, $R^8$, $R^{13}$ and $R^{15}$ are independently hydrogen, or a hydrocarbyl or substituted hydrocarbyl having from 1 to about 30 carbon atoms; $R^4$ is —$(CH_2)_y OR^{13}$ or —$(CH_2)_y O(R^2O)_q R^3$; $R^5$, $R^6$ and $R^7$ are independently hydrogen, hydrocarbyl or substituted hydrocarbyl having from 1 to about 30 carbon atoms, or $R^4$; $R^{14}$ is hydrocarbyl or substituted hydrocarbyl having from 1 to about 30 carbon atoms, or —$(CH_2)_z O(R^2O)_p R^3$; m, n, p and q are independently an average number from 1 to about 50; X is —O—, —$N(R^{14})$—, —C(O)—, —C(O)O—, —OC(O)—, —$N(R^{15})C(O)$—, —$C(O)N(R^{15})$—, —S—, —SO—, or —$SO_2$—; t is 0 or 1; A- is an agriculturally acceptable anion; and y and z are independently an integer from 0 to about 30.

The compound was prepared by addition of a compound $R^1$—XH to an epoxide in a 1:1 molar ratio in the presence of a base such as diisobutyl aluminum hydride (DIBAL), NaH or a Lewis acid, such as $BF_3Et_2O$, to form intermediate (91) as represented in the reaction scheme shown below:

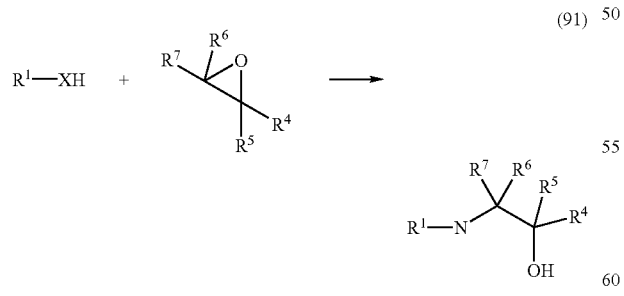
(91)

The compound (91) is then alkoxylated via conventional means to form a compound of formula (36). When X is —$N^+R^8R^9$— in the above reaction scheme, compound (37) is formed.

Alkyl aminopropanediol compounds having the formula (36) were prepared, wherein X is —$N(R^{14})$—, $R^3$, $R^5$, $R^6$ and $R^7$ are hydrogen, $R^2O$ is ethylene, and $R^4$ is —$CH_2O$ $(R^2O)_q R^3$. Ethylene oxide was used for the alkoxylation.

TABLE 6

| Compound | $R_1$ | $R_{14}$ | n + q | Formulation |
|---|---|---|---|---|
| 1a | $C_{18}H_{37}$ | $CH_3$ | 5 | 384 |
| 1b | $C_{18}H_{37}$ | $CH_3$ | 10 | 388 |
| 1c | $C_{18}H_{37}$ | $CH_3$ | 15 | 409 |
| 1d | $C_{18}H_{37}$ | $CH_3$ | 20 | 415 |
| 1e | $C_{18}H_{37}$ | $CH_3$ | 25 | 416 |
| 1f | $C_{12}H_{25}$ | $CH_3$ | 5 | 387 |
| 1g | $C_{12}H_{25}$ | $CH_3$ | 10 | 389 |
| 1h | tallow | H | 15 | 421 |
| 1i | tallow | H | 23 | 423 |
| 1j | tallow | H | 27 | 427 |
| 1k | coco | H | 23 | 425 |
| 1l | coco | H | 30 | 427 |

Alkyl aminopropanol compounds 2a–c having the formula (36), wherein X is —$N(R^{14})$—, $R^3$, $R^5$, $R^6$ and $R^7$ are hydrogen, $R^2O$ is ethylene, and $R^4$ is —$CH_2OCH_2C_6H_5$, were prepared by the reaction of an amine with benzyl glycidol, followed by alkoxylation and deprotection of the benzyl group by conventional catalytic hydrogenation such that $R^4$ is then —$CH_2OR^3$. Ethylene oxide was used for the alkoxylation.

Alkyl aminopropanol compounds 2d–j having the formula (36), wherein X is —$N(R^{14})$—, $R^3$, $R^5$, $R^6$ and $R^7$ are hydrogen, $R^2O$ is ethylene, and $R^4$ is —$CH_2OR^3$, were prepared by the reaction of an amine with a corresponding glycidyl ether, followed by alkoxylation. Ethylene oxide was used for the alkoxylation.

TABLE 7

| Compound | $R_1$ | $R_{14}$ | $R_3$ | n | Formulation |
|---|---|---|---|---|---|
| 2a | $C_{18}H_{37}$ | $CH_3$ | H | 5 | 640 |
| 2b | $C_{18}H_{37}$ | $CH_3$ | H | 10 | 637 |
| 2c | $C_{12}H_{25}$ | $CH_3$ | H | 5 | 639 |
| 2d | $C_{18}H_{37}$ | $CH_3$ | $CH_3$ | 5 | |
| 2e | $C_{18}H_{37}$ | $CH_3$ | $CH_3$ | 15 | |
| 2f | $C_{18}H_{37}$ | $CH_3$ | $CH_3$ | 25 | |
| 2g | $C_{12}H_{25}$ | $CH_3$ | $CH_3$ | 10 | 481 |
| 2h | $C_{12}H_{25}$ | $CH_3$ | $CH_3$ | 15 | 483 |
| 2i | $C_{12}H_{25}$ | $CH_3$ | $CH_3$ | 25 | 485 |
| 2j | $C_{18}H_{37}$ | $CH_3$ | isopropyl | 5 | |
| 2k | $C_{18}H_{37}$ | $CH_3$ | isopropyl | 10 | |
| 2l | $C_{12}H_{25}$ | $CH_3$ | isopropyl | 5 | |
| 2m | $C_{12}H_{25}$ | $CH_3$ | isopropyl | 10 | |

Compounds (38) and (39) were prepared:

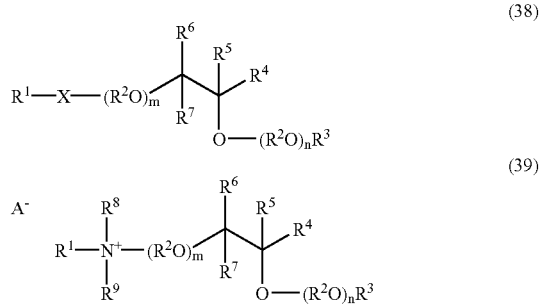
(38)

(39)

wherein $R^1$, and $R^9$ are independently hydrocarbyl or substituted hydrocarbyl having from 1 to about 30 carbon atoms, or —$(R^2O)_p R^{13}$; $R^2$ in each of the m $(R^2O)$, n $(R^2O)$, p $(R^2O)$ and q $(R^2O)$ groups is independently $C_2$–$C_4$ alkylene; $R^3$, $R^8$, $R^{13}$ and $R^{15}$ are independently hydrogen, or a hydrocarbyl or substituted hydrocarbyl having from 1 to about 30 carbon atoms, $R^4$ is —$(CH_2)_yOR^{13}$ or $(CH_2)_yO(R^2O)_qR^3$; $R^5$, $R^6$ and $R^7$ are independently hydrogen, hydrocarbyl or substituted hydrocarbyl having from 1 to about 30 carbon atoms, or $R^4$; $R^{14}$ is hydrocarbyl or substituted hydrocarbyl having from 1 to about 30 carbon atoms, or —$(CH_2)_zO(R^2O)_pR^3$; m, n, p and q are independently an average number from 1 to about 50; X is —O—, —N($R^{14}$)—, —C(O)—, —C(O)O—, —OC(O)—, —N($R^{15}$)C(O)—, —C(O)N($R^{15}$)—, —S—, —SO—, or —$SO_2$—; t is 0 or 1; A– is an agriculturally acceptable anion; and y and z are independently an integer from 0 to about 30.

The compound was prepared by addition of a compound $R^1$—XH to an epoxide in a 1:2 molar ratio in the presence of a base such as diisobutyl aluminum hydride (DIBAL), NaH or a Lewis acid, to form intermediate (92) as represented in the reaction scheme shown below:

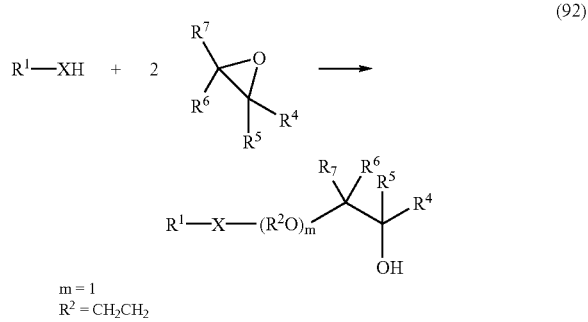

(92)

The compound (92) is then alkoxylated via conventional means to form a compound of formula (38). When X in $R^1$XH is —$N^+R^8R^9$—, the compound of formula (39) is formed.

The number of alkylene oxide groups formed within the main chain of compound (92) depends upon the molar ratio of compound $R^1$—XH to epoxide present during the reaction. If the molar ratio of compound $R^1$—XH to epoxide is 1:3, for example, $R^2$ is —$CH_2CH_2$— and m is 2 in the formula (92). The compound can then be alkoxylated as described above.

Compounds (40), (41), (42) and (43) were prepared:

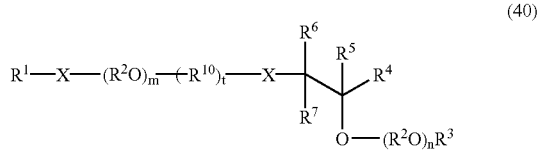

(40)

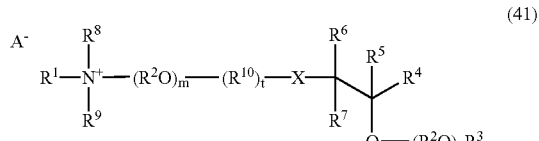

(41)

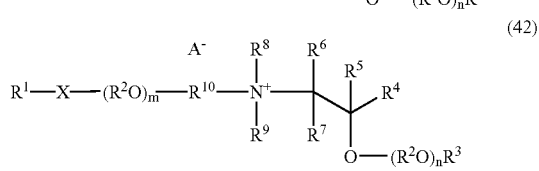

(42)

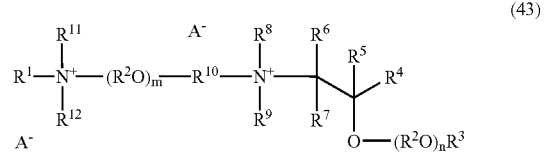

(43)

wherein $R^1$, $R^9$, and $R^{12}$ are independently hydrocarbyl or substituted hydrocarbyl having from 1 to about 30 carbon atoms, or —$(R^2O)_pR^{13}$; $R^2$ in each of the m ($R^2O$), n ($R^2O$), p ($R^2O$) and q ($R^2O$) groups is independently $C_2$–$C_4$ alkylene; $R^3$, $R^8$, $R^{11}$, $R^{13}$ and $R^{15}$ are independently hydrogen, or a hydrocarbyl or substituted hydrocarbyl having from 1 to about 30 carbon atoms; $R^4$ is —$(CH_2)_yOR^{13}$ or —$(CH_2)_yO(R^2O)_qR^3$; $R^5$, $R^6$ and $R^7$ are independently hydrogen, hydrocarbyl or substituted hydrocarbyl having from 1 to about 30 carbon atoms, or $R^4$; $R^{10}$ is hydrocarbylene or substituted hydrocarbylene having from 2 to about 30 carbon atoms; $R^{14}$ is hydrocarbyl or substituted hydrocarbyl having from 1 to about 30 carbon atoms, or —$(CH_2)_zO(R^2O)_pR^3$; m, n, p and q are independently an average number from 1 to about 50; X is —O—, —N($R^{14}$)—, —C(O)—, —C(O)O—, —OC(O)—, —N($R^{15}$)C(O)—, —C(O)N($R^{15}$)—, -S—, —SO—, or —$SO_2$—; t is 0 or 1; A— is an agriculturally acceptable anion; and y and z are independently an integer from 0 to about 30.

Compounds of the formula (40), (41), (42) or (43) were prepared by addition of a compound $R^1$—X—$(R^2O)_n$—XH to an epoxide in a 1:1 molar ratio in the presence of a base such as diisobutyl aluminum hydride (DIBAL) as represented below:

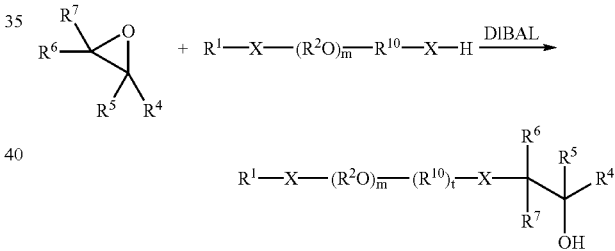

The compound (93) is then alkoxylated via conventional means to form a compound of formula (40). When the starting material includes one quaternary ammonium salt (i.e., one X is —$N^+R^8R^9$—), the compound has the formula (41) or (42). When two quaternary ammonium salts are present in the starting material (i.e., one X is —$N^+R^8R^9$— and the other is —$N^+R^{11}R^{12}$—), a compound of formula (43) is formed.

Example F

Preparation of Gemini Glucitols ZZ, AAA, BBB, CCC of Formula (28)

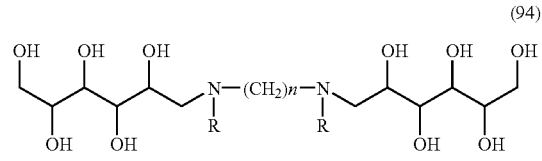

(94)

Compound ZZ:
1,12 methylaminoglucitoldodecane: R=methyl, n=12: 1-deoxy-1-(methylamino)-D-glucitol (195 MW,15 g, 2 eq.,), 1,12 dibromododecane (328 MW, 12.6 g, 1 eq.), sodium bicarbonate (7.1 g, 2.2 eq) and 120 ml anhydrous dimethylformamide, were placed under nitrogen and heated for 17 hours at 70° C. After the reaction was complete, any unreacted sodium bicarbonate was removed by filtration and then DMF was removed from the reaction under reduced pressure. 400 ml of ethyl acetate was added to precipitate the crude product and the mixture was stirred for several hours to remove occluded DMF from the precipitated product. The crude product was recrystallized twice from a 1:1 solution of methanol/water to give 6.68 g white solid or 15% yield. H NMR 300 MHz, MeOD$^4$: 1.25–1.4(broad, 16H), 1.5p (quint, 4H), 2.45p(sept.,4H), 2.55p(d, 4H), 3.6–3.8p (complex, 12H). Analysis: C26H58N2O11: Theory: C, 54.3; H, 10.1; N, 4.8. Found: C, 54.2; H, 9.9; N, 4.5.

Compound AAA
1,6 hexylaminoglucitol propane: R=hexyl, n=3: 1-deoxy-1-(hexylamino)-D-glucitol (265 MW, 15.76 g, 2 eq.), 1,3-dibromopropane (202 MW, 6.0 g, 2 eq.), sodium bicarbonate (5.49 g, 2.2 eq.) and 180 ml anhydrous dimethylformamide, were placed under nitrogen and heated for 17 hours at 70° C. After the reaction was complete, any unreacted sodium bicarbonate was removed by filtration and then DMF was removed from the reaction under reduced pressure. 600 ml of ethyl acetate was added to precipitate the crude product and the mixture was stirred for several hours to remove occluded DMF from the precipitated product.

The solvents were decanted and the product underwent additional drying in a vacuum oven overnight at 80° C. 12 g of yellow semi-solid that was 90% pure. All attempts at recrystallization or chromatography for additional purification were unsuccessful. Yield, 71%. H NMR 500 MHz, MeOD$^4$. 0.9p(t, 6H), 1.25–1.4p (broad, 12H), 1.55p(quint, 4H), 1.75p(quint, 2H), 2.55–2.75p(complex, 12H), 3.6–3.8p (complex, 12H). C NMR 50 MHz, MeOD$^4$: 13.8p, 22.8p, 25.8p, 26.5p 26.2p, 32.0p, 53.0p, 54.5p, 56.8p, 63.8p, 70.0p, 71.2p, 72.0p, 72.5p. 2D-NMR experiments provided conclusive structure confirmation.

Compound CCC
1,8 hexylaminoglucitol octane: R-hexyl, n=8: 1-deoxy-1-(hexylamino)-D-glucitol (265 MW, 15.0 g, 2 eq.), 1,8-dibromooctane (262 MW, 7.68 g, 1 eq.), potassium carbonate (8.56 g, 2.2 eq.) and 180 ml anhydrous dimethylformamide, were placed under nitrogen and heated for 20 hours at 70° C. After the reaction was complete, any unreacted potassium carbonate was removed by filtration and then DMF was removed from the reaction under reduced pressure. 600 ml of ethyl acetate was added to precipitate the crude product and the mixture was stirred for several hours to remove occluded DMF from the precipitated product.

The solvents were decanted and the product underwent additional drying in a vacuum oven overnight at 80° C. Further purification was achieved by dissolving the crude product in a minimum of methanol and discarding any precipitated solids. 13.6 g yellow semi-solid was recovered that was 90% pure. Yield, 38%. H NMR 300 MHz, MeOD$^4$: 0.9p(t, 6H), 1.2–1.4p(broad, 18H), 1.4–1.6p(broad,8H), 2.4–2.6p(complex, 12H), 3.55–3.8(complex, 12H).

Compound BBB
1,8 octylaminoglucitol propane: R=octyl, n=3: 1-deoxy-1-(octylamino-D-glucitol (293 MW, 6.45 g, 2 eq. ), 1,3-dibromopropane (202 MW, 2.2 g, 1 eq.), sodium bicarbonate (2.0 g, 2.2 eq.) and 60 ml anhydrous dimethylformamide, were placed under nitrogen and heated for 17 hours at 70° C. After the reaction was complete, any unreacted sodium bicarbonate was removed by filtration and then DMF was removed from the reaction under reduced pressure. 200 ml of ethyl acetate was added to precipitate the crude product and the mixture was stirred for several hours to remove occluded DMF from the precipitated product. The solvents were decanted and the product underwent additional drying in a vacuum oven overnight at 80° C. 8.88 g white semi-solid that was 90% pure was recovered. All attempts at recrystallization or chromatography for additional purification were unsuccessful. Yield, 64%. H NMR 600 MHz, MeOD$^4$: 0.87p(t, 6H), 1.2–1.35p(broad, 20H), 1.5p(quint., 4H), 1.7p(quint.,2H), 2.5–2.7p(complex, 12H), 3.6–3.8p (complex, 12H). C NMR 600 MHz, MeOD$^4$: 14.6p, 23.7p, 24.55p, 27.4p, 28.6p, 30.4p, 30.8p, 33.0p, 54.0p, 55,8p, 58.2p, 64.8p, 71.7p, 72.5p, 73.0p, 73.8p. 2D NMR experiments provided conclusive structure confirmation.

Example G

Preparation of Compound of Formula (23)

An alkoxylated amine is prepared, wherein the amine has the formula:

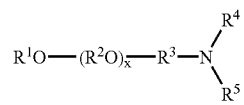

(23)

A commercially available alcohol ethoxylate of choice (such as Brij™ 58) was converted to the corresponding tosylate by treatment with tosyl chloride in the presence of potassium hydroxide. The resulting tosylate was then reacted with an appropriate alkylamine (such as methylamine, benzylamine, dimethylamine, etc.) in anhydrous tetrahydrofuran (THF) at 80° C. overnight to afford the desired product.

Example H

Preparation of Compound of Formula (25)

An alkoxylated poly(hydroxyalkyl)amine having the formula below is prepared as follows:

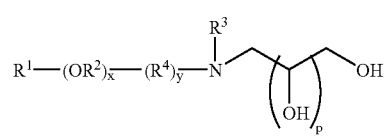

(25)

A commercially available alcohol ethoxylate of choice (such as Brij™ 58) was converted to the corresponding tosylate by treatment with tosyl chloride in the presence of potassium hydroxide. The resulting tosylate was then reacted with an appropriate amine derivative (such as n-alkyl glucamines, etc.) in the presence of anhydrous powdered sodium bicarbonate in refluxing anhydrous ethanol for one to two days to afford the desired product.

Example I

Preparation of Compound of Formula (74)

An alkoxylated quaternary ammonium salt having the formula below is prepared as follows:

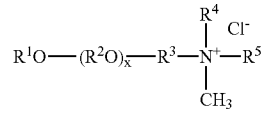

An alkoxylated amine of formula (73) was treated with methyl chloride in anhydrous THF at 50° C. overnight to afford the desired product.

Example J

Preparation of Compound of Formula (32)

An amine oxide was prepared as follows:

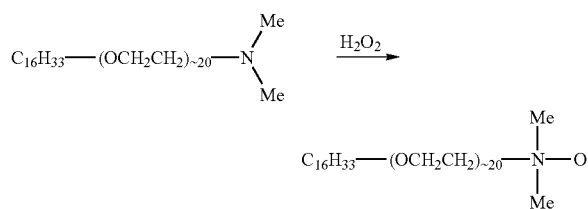

Alkyl alkoxy dimethylamine was oxidized by hydrogen peroxide in methanol at room temperature overnight to afford the desired product.

Example K

Preparation of Compounds of Formula (72)

A guanidine compound of the formula (72) was prepared as follows.

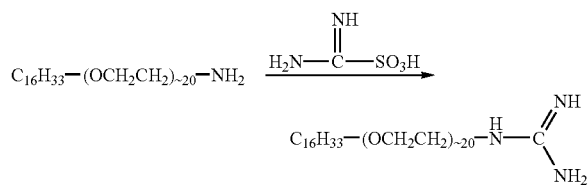

Alkyl alkoxy amine was converted to the desired product by treatment with formamidesulfonic acid in methanol at room temperature overnight.

Another compound of formula (72) was prepared as shown below.

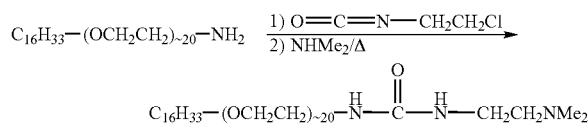

The product was synthesized by acylation of the corresponding amine with chloroethyl isocyanate, followed by replacement of chloride with dimethylamine.

Example L

Preparation of Compounds of Formula (78) and (79)

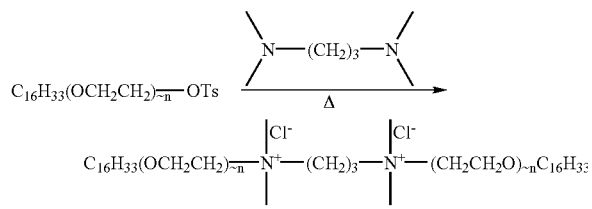

The compound (79) was made by alkylation of tetramethylpropylene diamine with excess of hexadecyl poly(ethylene oxide)tosylate in refluxing ethanol for two days, and purified by DOWEX 50WX2-400 ion exchange resin eluting with 50% concentrated HCl in ethanol.

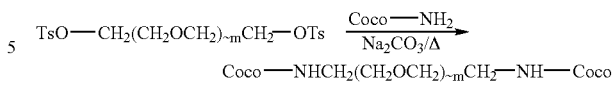

The compound (78) was prepared by alkylation of cocoamine with poly(ethylene oxide)ditosylate in the presence of anhydrous powder sodium carbonate in refluxing ethanol for two days.

Example M

Preparation of Gemini Surfactants of Formula (29)

The compound was prepared by reaction of the corresponding diamines with two equivalents of an acid chloride followed by reduction of the resulting diamide with lithium aluminum hydride (LAH). Alternatively, this compound can be prepared by reaction of the diamine with two equivalents of a long alkyl chain bromide. The Gemini diamines were ethoxylated under standard conditions.

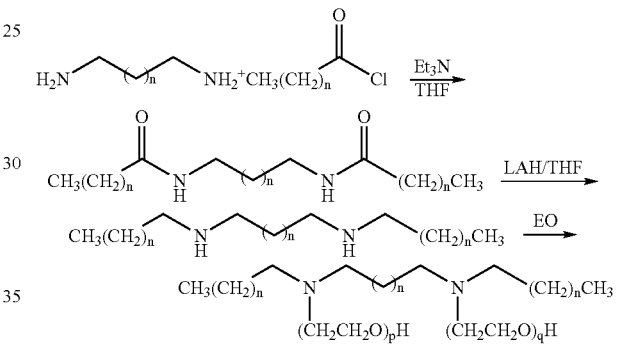

Example N

Preparation of Compound of Formula (26)

A commercially available alcohol ethoxylate is converted to the corresponding tosylate by treatment with tosyl chloride in the presence of potassium hydroxide. D-glucosamine hydrochloride is then reduced in the presence of sodium borohydride and water to give the ring opened glucosamine salt. In the presence of potassium carbonate, the glucosamine is reacted with alkylethoxytosylate to give the desired product as shown below:

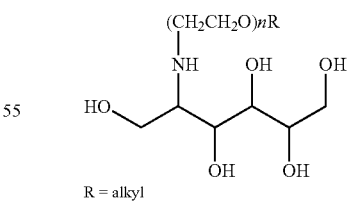

R = alkyl

Example O

Preparation of a Compound of Formula (26)

D-glucosamine hydrochloride is reduced in the presence of sodium borohydride and water to give the ring opened glucosamine salt. The glucosamine salt is neutralized with sodium hydroxide and reacted with an alkylaldehyde of suitable chain length under reducing conditions, i.e., in the presence of ethanol, 4% Pd/C and hydrogen gas at 60 psig and 40° C. to give the desired product as shown below:

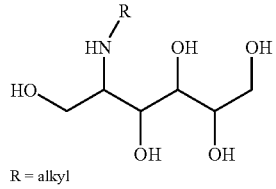

R = alkyl

Alkoxylated compounds of formulae (33), (35), (64) and (71) are prepared by selecting a commercially available starting material, such as a tertiary amine, and alkoxylating the starting material by methods known in the art to form one of the alkoxylated compounds.

Example P

Testing for the Formation of Anisotropic Aggregates and/or Liquid Crystals

Utilizing the various methods disclosed herein for determining whether a surfactant, in the presence of glyphosate, forms an anisotropic aggregate, an epicuticular liquid crystal, and/or an intracuticular liquid crystal, numerous surfactants have been tested by the inventors for the formation of anisotropic aggregates and/or liquid crystals. A number of surfactants in the presence of glyphosate have been tested utilizing a isopropylamine glyphosate formulations while other surfactants have been tested in potassium glyphosate formulations. The table set forth below illustrates the results of the numerous tests.

Nonionic Surfactant having the Formula:
$C_WO-(EO)_xH$
in IPA Glyphosate Formulation:

| w | x | Trade Name | LC intra | LC epi | AA |
|---|---|---|---|---|---|
| 11 | 9 | Neodol 1-9 | N | N | N |
| 12 | 10 | Procol LA-10 | N | N | N |
| 12 | 12 | Procol LA-12 | N | N | N |
| 12 | 15 | Procol LA-15 | N | N | Y |
| 12 (laureth) | 23 | Brij 35 | N | Y | Y |
| 11–15 | 9 | Tergitol 15-S-9 | N | N | N |
| 11–15 | 12 | Tergitol 15-S-12 | N | N | NT |
| 11–15 | 15 | Tergitol 15-S-15 | N | N | NT |
| 12–15 | 12 | Neodol 15-12 | N | N | Y |
| 16 | 2 | Hetoxol CA-2 | N | N | N |
| 16 | 7 | ST-8302 | N | N | N |
| 16 | 10 | Hetoxol CA-10 | N | N | Y |
| 16 | 14 | ST-8303 | N | N | Y |
| 16 | 20 | Hetoxol CA-20 | Y | Y | Y |
| 16–18 | 9 | Hetoxol CS-9 | N | N | Y |
| 16–18 | 15 | Hetoxol CS-15 | N | N | Y |
| 16–18 | 20 | Hetoxol CS-20 | NT | Y | Y |
| 16–18 | 25 | Hetoxol CS-25 | Y | Y | Y |
| 16–18 | 27 | Plurafac A38 | Y | Y | Y |
| 16–18 | 30 | Hetoxol CS-30 | NT | Y | Y |
| 18 | 10 | Brij 76 | N | Y | Y |
| 18 | 20 | Brij 78 | Y | Y | Y |
| iso18 | 10 | Arosurf 66 E10 | N | N | N |
| iso18 | 20 | Arosurf 66 E20 | N | Y | Y |
| 18 (oleath) | 10 | Brij 97 | N | Y | Y |
| 18 (oleath) | 20 | Brij 98 | NT | Y | Y |

Other Nonionic Surfactants in IPA Glyphosate Formulation:

| | LC intra | LC epi | AA |
|---|---|---|---|
| Agrimul PG2069 alkyl polyglucoside | N | N | N |
| Surfonic DNP 80 (PEG 8 dinonyl phenol) | N | N | N |
| Surfonic DNP 100 (PEG 10 dinonyl phenol) | NT | NT | Y |
| Surfonic DNP 140 (PEG 15 dinonyl phenol) | NT | NT | Y |
| Surfonic DNP 240 (PEG 24 dinonyl phenol) | NT | NT | Y |

Cationic Surfactant having the Formula:

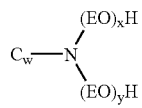

| w | x + y | Trade Name | LC intra | LC epi | AA |
|---|---|---|---|---|---|
| in IPA Glyphosate Formulation: | | | | | |
| coco (8–16) | 2 | Ethomeen G/12 | N | N | N |
| coco | 5 | Ethomeen C/15 | N | N | N |
| coco | 10 | Ethomeen C/20 | N | N | N |
| coco | 15 | Ethomeen C/25 | N | N | N |
| tallow (16–18) | 2 | Ethomeen T/12 | N | N | N |
| tallow | 2 | Armeen T12 | N | N | N |
| tallow | 5 | Ethomeen T/15 | N | N | N |
| tallow | 10 | Ethomeen T/20 | N | N | N |
| tallow | 15 | Ethomeen T/25 | N | N | N |
| stearyl (18) | 50 | Trymeen 6617 | N | Y | Y |
| in Potassium Glyphosate Formulation: | | | | | |
| coco (8–16) | 2 | Ethomeen C/12 | NT | N | Y |
| coco | 5 | Ethomeen C/15 | N | N | N |
| tallow 16–18) | 2 | Armeen T12 | N | N | Y |
| tallow | 5 | Ethomeen T/15 | NT | Y | Y |

Cationic Surfactant having the Formula:

in IPA Glyphosate Formulation:

| w | Trade Name: | LC intra | LC epi | AA |
|---|---|---|---|---|
| tallow (16–18) | Armeen T | N | N | N |

Cationic Surfactant having the Formula:

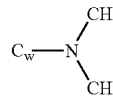

| w | Trade Name: | LC intra | LC epi | AA |
|---|---|---|---|---|

-continued in IPA Glyphosate Formulation:

| | | | | | |
|---|---|---|---|---|---|
| 10 | NA | | N | N | N |
| coco (8–16) | Armeen DMCD | | N | N | N |
| tallow (16–18) | Armeen TMCD | | N | N | N |
| tallow | Armeen DMTD | | N | N | N | in Potassium Glyphosate Formulation:

| | | | | |
|---|---|---|---|---|
| coco (8–16) | Armeen DMCD | N | N | N |
| tallow (16–18) | Armeen DMTD | N | Y | Y |

Cationic Surfactant having the Formula:

$$C_w - N \begin{smallmatrix} C_w \\ \\ H \end{smallmatrix} C_w$$

in IPA Glyphosate Formulation:

| w | Trade Name: | LC intr a | LC epi | AA |
|---|---|---|---|---|
| coco (8–16) | Armeen 2C | N | N | NT |
| tallow (16–18) | Armeen 2T | N | N | Y |

Cationic Surfactant having the Formula:

$$C_w - N \begin{smallmatrix} (EO)_xH \\ \\ CH_3 \end{smallmatrix}$$

in IPA Glyphosate Formulation:

| w | x + y | Trade Name | LC intr a | LC epi | AA |
|---|---|---|---|---|---|
| stearyl (18) | 7 | NA | N | N | N |
| | 22 | Arosurf 66 E2O | N | Y | Y |

Cationic Surfactant having the Formula:

$$C_w - N \begin{smallmatrix} (EO)_xH \\ \\ C_w \end{smallmatrix}$$

in IPA Glyphosate Formulation:

| w | x | Trade Name | LC intr a | LC epi | AA |
|---|---|---|---|---|---|
| coco (8–16) | 5 | NA | N | N | N |
| coco | 10 | NA | N | N | N |
| coco | 15 | NA | N | N | Y |
| coco | 20 | NA | N | N | Y |
| tallow 16–18) | 5 | NA | NT | Y | Y |
| tallow | 10 | NA | NT | Y | Y |
| tallow | 15 | NA | NT | Y | Y |
| tallow | 20 | NA | NT | Y | Y |

Cationic Surfactant having the Formula:

$$C_w - O - (EO)_x - (CH_2)_3 - N \begin{smallmatrix} H \\ \\ H \end{smallmatrix}$$

| w | x | TradeName | LC intr a | LC epi | AA |
|---|---|---|---|---|---| in IPA Glyphosate Formulation:

| | | | | | |
|---|---|---|---|---|---|
| 14–15 | 7 | NA | N | N | NT |
| 14–15 | 13 | NA | NT | Y | Y |
| 14–15 | 18 | NA | NT | Y | Y |
| 16–18 | 7 | NA | N | N | NT |
| 16–18 | 10 | NA | N | N | NT |
| 16–18 | 15 | NA | NT | Y | Y |
| 16–18 | 20 | NA | NT | Y | Y | in Potassium Glyphosate Formulation:

| | | | | | |
|---|---|---|---|---|---|
| isotridecyl oxy | 5 | Tomah E-17-5 | N | N | N |
| 14–15 | 7 | NA | N | N | NT |
| 14–15 | 13 | NA | NT | Y | Y |
| 14–15 | 18 | NA | NT | Y | Y |
| 16–18 | 7 | NA | NT | Y | Y |
| 16–18 | 10 | NA | NT | Y | Y |
| 16–18 | 15 | NA | NT | Y | Y |

Cationic Surfactant having the Formula:

$$C_w - O - (EO)_x - (CH_2)_3 - N \begin{smallmatrix} CH_3 \\ \\ CH_3 \end{smallmatrix}$$

| w | x | TradeName | LC intr a | LC epi | AA |
|---|---|---|---|---|---| in IPA Glyphosate Formulation:

| | | | | | |
|---|---|---|---|---|---|
| 14–15 | 13 | NA | NT | Y | Y | in Potassium Glyphosate Formulation:

| | | | | | |
|---|---|---|---|---|---|
| 14–15 | 18 | NA | NT | Y | Y |
| 16–18 | 15 | NA | NT | Y | Y |

Cationic Surfactant having the Formula:

$$C_w - N^+ \begin{smallmatrix} (EO)_xH \\ \\ (EO)_yH \\ \\ CH_3 \end{smallmatrix} \quad X^-$$

| w | x + y | Trade Name | LC intr a | LC epi | AA |
|---|---|---|---|---|---| in IPA Glyphosate Formulation:

| | | | | | |
|---|---|---|---|---|---|
| coco (8–16) | 2 | Ethoquad C/12 | N | N | NT |
| coco | 5 | NA | N | N | NT |
| coco | 5 | Rewoquat CPEM | N | N | NT |
| tallow 16–18) | 2 | Ethoquad T/12 | N | N | N |
| tallow | 5 | NA | N | N | NT |
| tallow | 10 | Ethoquad T/20 | N | N | NT |
| tallow | 15 | Ethoquad 5/25 | N | N | NT | in Potassium Glyphosate Formulation:

| | | | | | |
|---|---|---|---|---|---|
| coco (8–16) | 2 | Ethoquad C12 | NT | Y | Y |
| coco | 5 | NA | NT | Y | Y |
| tallow (16–18) | 5 | Ethoquad T12 | NT | Y | Y |

Cationic Surfactant having the Formula:

$$C_w - N^+ \begin{smallmatrix} (EO)_xH \\ \\ (EO)_yH \\ \\ C_w \end{smallmatrix} \quad X^-$$

-continued in IPA Glyphosate Formulation:

| w | x + y | Trade Name | LC intra | LC epi | AA |
|---|---|---|---|---|---|
| tallow (16–18) | 5 | NA | NT | Y | Y |
| tallow | 10 | NA | NT | Y | Y |
| tallow | 30 | NA | N | N | N |

Cationic Surfactant having the Formula:

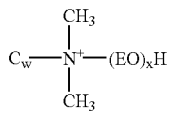

in IPA Glyphosate Formulation:

| w | x | Trade Name | LC intra | LC epi | AA |
|---|---|---|---|---|---|
| 18 | 7 | NA | NT | NT | Y |
| 18 | 22 | NA | NT | NT | Y |

Cationic Surfactant having the Formula:

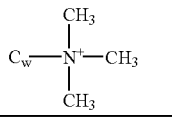

| w | Trade Name | LC intra | LC epi | AA |
|---|---|---|---|---| in IPA Glyphosate Formulation:

| dodecyl (12) | Arquad C-50 | N | N | N |
| tallow (16–18) | Arquad T-50 | N | N | NT | in Potassium Glyphosate Formulation:

| dodecyl (12) | Arquad C-50 | NT | Y | Y |
| tallow (16–18) | Arquad T-50 | NT | Y | Y |

Cationic Surfactant having the Formula:

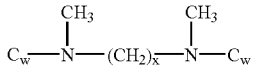

in IPA Glyphosate Formulation:

| w | x | Trade Name | LC intra | LC epi | AA |
|---|---|---|---|---|---|
| 10 | 2 | Gemini 10-2-10 | NT | NT | Y |
| 10 | 3 | Gemini 10-3-10 | NT | NT | Y |
| 10 | 4 | Gemini 10-4-10 | NT | NT | Y |
| 14 | 2 | Gemini 14-2-14 | NT | NT | Y |
| 14 | 3 | Gemini 14-3-14 | NT | NT | Y |
| 16 | 12 | Gemini 16-2-16 | NT | NT | Y |

| Name | LC intra | LC epi | AA |
|---|---|---|---|
| Anionic Surfactant in IPA Glyphosate Formulation: | | | |
| oleth-10 phosphate | N | N | Y |
| oleth-20 phosphate | N | N | Y |
| oleth-25 phosphate | N | N | Y |
| 2-ethylhexyl phosphate | N | N | N |
| laureth-3 phosphate | N | N | N |
| palmitic acid | N | N | Y |
| oleic acid | N | N | Y |
| stearic acid | N | N | Y |
| caprylic acid | NT | NT | N |
| sodium alkylbenzene sulfonate | N | N | NT |
| sodium lauryl sulfate | N | N | Y |
| phosphated aryl ethoxylate | N | N | N |
| phosphate ester, free acid | N | N | N |
| phosphated nonyl phenyl ethoxylate, free acid | N | N | N |

| Trade Name | LC intra | LC epi | AA |
|---|---|---|---|
| Amphoteric Surfactant in an IPA Glyphosate Formulation: | | | |
| Lecithin | N | Y | Y |
| Velvetex ™ BC coco betaine | N | N | N |
| Fluorinated Surfactant in an IPA Glyphosate Formulation: | | | |
| Fluorad ™ 135 alkyl quaternary ammonium iodides | N | N | N |
| Fluorad ™ 754 alkyl quaternary ammonium chlorides | N | N | N |
| Fluorad ™ FC129 potassium fluorinated alkyl carboxylate | N | N | N |
| Fluorad ™ FC-171 fluorinated alkyl alkoxylate | N | N | N |
| Flurorad ™ FC121 ammonium perfluoroalkyl sulfonates | N | N | N |
| Fluowet PL 80 perfluorinated phosphinic/phosphnic acid | N | N | N |

| | LC intra | LC epi | AA |
|---|---|---|---|
| Surfactant Mixtures in IPA Glyphosate Formulation: | | | |
| Hetoxol CA2/Ethomeen T125 | N | N | N |
| ST 8302/Ethoquad T125 | N | N | N |
| ST 8303/Ethoquad T125 | NT | Y | Y |
| Arosurf 66 E/10/Ethoquad T/25 | NT | Y | Y |
| Arosurf 66 E20/Ethoquad T/25 | NT | Y | Y |
| Arosurf 66 E20/Ethomeen T/25 | NT | Y | Y |
| Hetoxol CS20/Ethomeen T/15 | NT | Y | Y |
| Hetoxol CS20/Ethomeen T/20 | Y | Y | Y |
| Hetoxol CS20/Ethomeen T/25 | Y | Y | Y |
| Hetoxol CS20/Ethomeen T/30 | NT | Y | Y |
| Hetoxol CS20/Ethomeen T/35 | NT | Y | Y |
| Hetoxol CS20/Ethomeen T/40 | NT | Y | Y |
| Hetoxol CS20/Trymeen 6617 | N | Y | Y |
| Hetoxol CS20 + Duoquat T-50 | NT | NT | N |
| Hetoxol CS20 + Arquad C-50 | NT | NT | Y |
| Hetoxol CS20 + lauryl choline chloride | NT | NT | Y |
| Hetoxol CS25 + Ethomeen T25 | Y | Y | Y |
| Hetoxol CS15 + Ethomeen T25 | NT | Y | Y |
| Hetoxol CS20 + Ethomeen T20 | Y | Y | Y |
| Hetoxol CS25 + Ethomeen T20 | Y | Y | Y |
| Hetoxol CS15 + lauryl choline chloride | NT | NT | Y |
| Brij 78 + Ethomeen T20 | Y | Y | Y |
| Brij 78 + Ethomeen T25 | Y | Y | Y |
| Brij 78 + Ethoquad T20 | Y | Y | Y |
| Brij 78 + Ethoquad T25 | Y | Y | Y |
| Neodol 1-9/Ethomeen T/25 | N | N | N |
| Agrimul PG 2069/Ethomeen T/25 | N | N | N |
| Tergitol 15-S-9/Ethomeen T/25 | N | N | N |
| Tergitol 15-S-12/Ethomeen T/25 | N | N | N |
| Tergitol 15-S-15/Ethomeen T/25 | N | N | N |
| Procol LA 10 + Ethoquad T25 | NT | NT | N |
| Procol LA 12 + Ethoquad T25 | NT | NT | N |
| Procol La 15 + Ethoquad T25 | NT | NT | Y |
| Hetoxol CS20 + PEG 7 dimethyl ammonium chloride | NT | NT | Y |
| Hetoxol CS20 + PEG 22 dimethyl ammonium chloride | NT | Y | Y |

-continued

| | | | |
|---|---|---|---|
| Plurafac A38 + Ethomeen T25 | Y | Y | Y |
| Plurafac A38 + Ethoquad T25 | Y | Y | Y |
| Plurafac A38 + Ethomeen T20 | Y | Y | Y |
| Plurafac A38 + Ethoquad T20 | Y | Y | Y |
| Hetoxol CS20 + Gemini 10-2-10 | NT | NT | Y |
| Hetoxol CS20 + Gemini 10-3-10 | NT | NT | Y |
| Hetoxol CS20 + Gemini 10-4-10 | NT | NT | Y |
| Hetoxol CS 20 + Gemini 14-2-14 | NT | NT | Y |
| Hetoxol CS 20 + Gemini 14-3-14 | NT | NT | Y |
| Caprylic acid + Ethomeen T25 | NT | NT | N |
| Capric acid + Ethomeen T25 | NT | NT | N |
| Lauric acid + Ethomeen T25 | NT | NT | N |
| Myristic acid + Ethomeen T25 | NT | NT | N |
| Palmitic acid + Ethomeen T25 | NT | NT | Y |
| Oleic acid + Ethomeen T25 | NT | NT | N |
| Lecithin + Ethomeen T25 | N | N | Y |
| Lecithin + Ethoquad T25 | N | N | Y |
| Lecithin + Ethomeen T20 | N | N | Y |
| Lecithin + Ethoquad T20 | N | N | Y |
| Lecithin + Fluorad FC 754 | N | N | Y |
| Lecithin + Hetoxol CS20 | NT | Y | Y |
| Lecithin + Hetoxol CS25 | NT | Y | Y |
| Fluowet PL 80 + Ethomeen T25 | N | N | N |
| Ethoquad C12 + Tergitol 15-S-7 | N | N | N |
| Ethoquad T12 + Tergitol 15-S-7 | N | N | N |
| Ethoquad C12 + Tergitol 15-S-9 | N | N | N |
| Ethoquad T12 + Tergitol 15-S-9 | N | N | N |
| Ethoquad C12 + Tergitol 15-S-12 | N | N | N |
| Ethoquad T12 + Tergitol 15-S-12 | N | N | N |
| Ethoquad C12 + Tergitol 15-S-15 | N | N | N |
| Ethoquad C12 + Arosurf 66 E10 | NT | N | N |
| Ethoquad T12 + Arosurf 66 E10 | NT | N | |
| Surfactant Mixtures in Potassium Glyphosate Formulation: | | | |
| Ethoquad C12 + Tergitol 15-S-7 | NT | Y | Y |
| Ethoquad T12 + Tergitol 15-S-7 | NT | Y | Y |
| Ethoquad C12 + Tergitol 15-S-9 | NT | Y | Y |
| Ethoquad T12 + Tergitol 15-S-9 | NT | Y | Y |
| Ethoquad C12 + Tergitol 15-S-12 | NT | Y | Y |
| Ethoquad T12 + Tergitol 15-S-12 | NT | Y | Y |
| Ethoquad C12 + Tergitol 15-S-15 | NT | Y | Y |
| Ethoquad T12 + Tergitol 15-S-15 | NT | Y | Y |
| Ethoquad C12 + Arosurf 66 E10 | NT | Y | Y |
| Ethoquad T12 + Arosurf 66 E10 | NT | Y | Y |

$C_w$ is an alkyl group having w carbon atoms
X is a chloride anion
EO is ethylene oxide
AA is anisotropic aggregate
LC intra is intracuticular liquid crystal
LC epi is epicuticular liquid crystal
Y is yes
N is no
NT is not tested
NA is not applicable (i.e., no trade name)

An especially preferred herbicide is N-phosphonomethylglycine (glyphosate), a salt, adduct or ester thereof, or a compound which is converted to glyphosate in plant tissues or which otherwise provides glyphosate ion. Glyphosate salts that can be used according to this invention are outlined in U.S. Pat. No. 4,405,531, which is incorporated by reference herein. The glyphosate salts are generally comprised of alkali metals, halogens, organic amines or ammonia, and include, but are not limited to, the following. The mono-, di- and tri- alkali metal salts of potassium, lithium and sodium. Salts of the alkali earth metals calcium, barium, and magnesium. Salts of other metals including copper, manganese, nickel and zinc. The mono-, di- and tri- halide salts of fluorine, chlorine, bromine, and iodine. Monoammonium, alkyl and phenyl ammonium salts, including the mono-, di- and tri- forms, comprising ammonium, methylammonium, ethylammonium, propylammonium, butylammonium and aniline. Alkylamine salts, including the mono-, di- and tri- forms, comprising methylamine, ethylamine, propylamine, butylamine, methylbutylamine, stearylamine and tallowamine. Alkenylamine salts based on ethylene, propylene or butylene. Cyclic organic amine salts including pyridine, piperidine, morpholone, pyrrolidone and picolene. Alkylsulfonium salts of methylsulfonium, ethylsulfonium, propyl sulfonium, and butyl sulfonium. Other salts including sulfoxonium, methoxymethylamine and phenoxyethylamine. Preferred salts of glyphosate include potassium (mono-, di- and tri- forms), sodium (mono-, di- and tri- forms), ammonium, trimethylammonium, isopropylamine, monoethanolamine and trimethylsulfonium.

Because the commercially most important herbicidal derivatives of N-phosphonomethylglycine are certain salts thereof, the glyphosate compositions useful in the present invention will be described in more detail with respect to such salts. These salts are well known and include ammonium, IPA, alkali metal (such as the mono-, di-, and tripotassium salts), and trimethylsulfonium salts. Salts of N-phosphonomethylglycine are commercially significant in part because they are water soluble. The salts listed immediately above are highly water soluble, thereby allowing for highly concentrated solutions that can be diluted at the site of use. In accordance with the method of this invention as it pertains to glyphosate herbicide, an aqueous solution containing a herbicidally effective amount of glyphosate and other components in accordance with the invention is applied to foliage of plants. Such an aqueous solution can be obtained by dilution of a concentrated glyphosate salt solution with water, or dissolution or dispersion in water of a dry (i.e., granular, powder, tablet or briquette) glyphosate formulation.

Exogenous chemicals should be applied to plants at a rate sufficient to give the desired biological effect. These application rates are usually expressed as amount of exogenous chemical per unit area treated, e.g. grams per hectare (g/ha). What constitutes a "desired effect" varies according to the standards and practice of those who investigate, develop, market and use a specific class of exogenous chemicals. For example, in the case of a herbicide, the amount applied per unit area to give 85% control of a plant species as measured by growth reduction or mortality is often used to define a commercially effective rate.

Herbicidal effectiveness is one of the biological effects that can be enhanced through this invention. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The herbicidal effectiveness data set forth herein report "inhibition" as a percentage following a standard procedure in the art which reflects a visual assessment of plant mortality and growth reduction by comparison with untreated plants, made by technicians specially trained to make and record such observations. In all cases, a single technician makes all assessments of percent inhibition within any one experiment or trial. Such measurements are relied upon and regularly reported by Monsanto Company in the course of its herbicide business.

The selection of application rates that are biologically effective for a specific exogenous chemical is within the skill of the ordinary agricultural scientist. Those of skill in the art will likewise recognize that individual plant conditions, weather and growing conditions, as well as the specific exogenous chemical and formulation thereof selected, will affect the efficacy achieved in practicing this invention.

Useful application rates for exogenous chemicals employed can depend upon all of the above conditions. With respect to the use of the method of this invention for glyphosate herbicide, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate or derivatives thereof are used to control a very wide variety of plants worldwide. Such compositions can be applied to a plant in a herbicidally effective amount, and can effectively control one or more plant species of one or more of the following genera without restriction: *Abutilon, Amaranthus, Artemisia, Asclepias, Avena, Axonopus, Borreria, Brachiaria, Brassica, Bromus, Chenepodium, Cirsium, Commelina Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium*, and *Zea*.

Particularly important species for which glyphosate compositions are used are exemplified without limitation by the following:

Annual broadleaves:
velvetleaf (*Abutilon theophrasti*)
pigweed (*Amaranthus* spp.)
buttonweed (*Borreria* spp.)
oilseed rape, canola, indian mustard, etc. (*Brassica* spp.)
commelina (*Commelina* spp.)
filaree (*Erodium* spp.)
sunflower (*Helianthus* spp.)
morningglory (*Ipomoea* spp.)
kochia (*Kochia scoparia*)
mallow (*Malva* spp.)
wild buckwheat, smartweed, etc. (*Polygonum* spp.)
purslane (*Portulaca* spp.)
russian thistle (*Salsola* spp.)
sida (*Sida* spp.)
wild mustard (*Sinapis arvensis*)
cocklebur (*Xanthium* spp.)
Annual narrowleaves:
wild oat (*Avena fatua*)
carpetgrass (*Axonopus* spp.)
downy brome (*Bromus tectorum*)
crabgrass (*Digitaria* spp.)
barnyardgrass (*Echinochloa crus-galli*)
goosegrass (*Eleusine indica*)
annual ryegrass (*Lollum multiflorum*)
rice (*Oryza sativa*)
ottochloa (*Ottochloa nodosa*)
bahiagrass (*Paspalum notatum*)
canarygrass (*Phalaris* spp.)
foxtail (*Setaria* spp.)
wheat (*Triticum aestivum*)
corn (*Zea mays*)
Perennial broadleaves:
mugwort (*Artemisia* spp.)
milkweed (*Asclepias* spp.)
canada thistle (*Cirsium arvense*)
field bindweed (*Convolvulus arvensis*)
kudzu (*Pueraria* spp.)
Perennial narrowleaves:
brachiaria (*Brachiaria* spp.)
bermudagrass (*Cynodon dactylon*)
yellow nutsedge (*Cyperus esculentus*)
purple nutsedge (*C. rotundus*)
quackgrass (*Elymus repens*)
lalang (*Imperata cylindrica*)
perennial ryegrass (*Lolium perenne*)
guineagrass (*Panicum maximum*)
dallisgrass (*Paspalum dilatatum*)
reed (*Phragmites* spp.)
johnsongrass (*Sorghum halepense*)
cattail (*Typha* spp.)
Other perennials:
horsetail (*Equisetum* spp.)
bracken (*Pteridium aquilinum*)
blackberry (*Rubus* spp.)
gorse (*Ulex europaeus*)

Thus, the method of the present invention, as it pertains to glyphosate herbicide, can be useful on any of the above species.

Effectiveness in greenhouse tests, usually at exogenous chemical rates lower than those normally effective in the field, is a proven indicator of consistency of field performance at normal use rates. However, even the most promising composition sometimes fails to exhibit enhanced performance in individual greenhouse tests. As illustrated in the Examples herein, a pattern of enhancement emerges over a series of greenhouse tests; when such a pattern is identified this is strong evidence of biological enhancement that will be useful in the field.

The compositions of the present invention can be applied to plants by spraying, using any conventional means for spraying liquids, such as spray nozzles, atomizers, or the like. Compositions of the present invention can be used in precision farming techniques, in which apparatus is employed to vary the amount of exogenous chemical applied to different parts of a field, depending on variables such as the particular plant species present, soil composition, and the like. In one embodiment of such techniques, a global positioning system operated with the spraying apparatus can be used to apply the desired amount of the composition to different parts of a field.

The composition at the time of application to plants is preferably dilute enough to be readily sprayed using standard agricultural spray equipment. Preferred application rates for the present invention vary depending upon a number of factors, including the type and concentration of active ingredient and the plant species involved. Useful rates for applying an aqueous composition to a field of foliage can range from about 25 to about 1,000 liters per hectare (l/ha) by spray application. The preferred application rates for aqueous solutions are in the range from about 50 to about 300 l/ha.

Many exogenous chemicals (including glyphosate herbicide) must be taken up by living tissues of the plant and translocated within the plant in order to produce the desired biological (e.g., herbicidal) effect. Thus, it is important that a herbicidal composition not be applied in such a manner as to excessively injure and interrupt the normal functioning of the local tissue of the plant so quickly that translocation is reduced. However, some limited degree of local injury can be insignificant, or even beneficial, in its impact on the biological effectiveness of certain exogenous chemicals.

A large number of compositions of the invention are illustrated in the Examples that follow. Many concentrate compositions of glyphosate have provided sufficient herbicidal effectiveness in greenhouse tests to warrant field testing on a wide variety of weed species under a variety of application conditions.

The spray compositions of Examples 1–70 contained an exogenous chemical, such as glyphosate potassium salt, in addition to the excipient ingredients listed. The amount of exogenous chemical was selected to provide the desired rate in grams per hectare (g/ha) when applied in a spray volume of 93 l/ha. Several exogenous chemical rates were applied for each composition. Thus, except where otherwise indicated, when spray compositions were tested, the concentration of exogenous chemical varied in direct proportion to exogenous chemical rate, but the concentration of excipient ingredients was held constant across different exogenous chemical rates.

Concentrate compositions were tested by dilution, dissolution or dispersion in water to form spray compositions. In these spray compositions prepared from concentrates, the concentration of excipient ingredients varied with that of exogenous chemical.

In the following Examples illustrative of the invention, greenhouse and field tests were conducted to evaluate the relative herbicidal effectiveness of glyphosate compositions. Compositions included for comparative purposes included the following:

Composition 139: which consists of 570 g/l of glyphosate IPA salt in aqueous solution with no added surfactant.

Composition 554: which consists of 725 g/l of glyphosate potassium salt in aqueous solution with no added surfactant.

Composition 754: which consists of 50% by weight of glyphosate IPA salt in aqueous solution, together with surfactant. This formulation is sold by Monsanto Company under the ROUNDUP ULTRAMAX® trademark.

Composition 360: which consists of 41% by weight of glyphosate IPA salt in aqueous solution, together with surfactant. This formulation is sold by Monsanto Company under the ROUNDUP ULTRA® trademark.

Composition 280: which consists of 480 g a.e./l of glyphosate IPA salt in aqueous solution, together with 120 g/l of ethoxylated etheramine surfactant (M121).

Composition 560: which consists of 540 g a.e./l of glyphosate potassium salt in solution, together with 135 g/l of ethoxylated etheramine surfactant (M121).

Composition 553: which consists of 360 g a.e./l of glyphosate IPA salt in solution, together with 111 g/l ethoxylated quaternary surfactant based tallowamine with 25EO, 74 g/l polyoxyethylene 10 EO cetyl ether and 12 g/l myristyl dimethyl amineoxide.

Composition 318: which consists of 487 g a.e./l of glyphosate potassium salt in aqueous solution, together with 65 g/l of ceteth(2PO)(9EO) alcohol alkoxylate, 97 g/l ethoxylated (10EO) tallowamine and 85 g/l n-octylamine.

Composition 765: which consists of 472 g a.e./l of glyphosate potassium salt in aqueous solution, together with 117 g/l cocoamine 5 EO, 52 g/l isostearyl 10 EO and 13 g/l cocoamine.

Various proprietary excipients were used in compositions of the Examples. They may be identified as follows:

| Ref. | Trade Name | Manufacturer | Chemical Description |
|---|---|---|---|
| 1816E | 1816E15PA | | (C16–18)O(CH2CH2O)15(CH2)3NH2 |
| AE10 | Arosurf 66 E-10 | Witco | Ethoxylated branched alkyl 10 EO |
| AGN68 | DF 68(89) | Agnique | Silicone defoamer |
| APG67 | APG 2067 | | Alkyl polyglycoside C8–10 alkyl group and 1.7 glucose groups |
| APG69 | APG 2069 | | Alkyl polyglycoside C8–10 alkyl group and 1.6 glucose groups |
| AR41 | Arphos HE-6641 | Witco | C4EO3 phosphoric acid |
| ARMC | Armeen C | | Mixed C8–16 (coco) alkyl primary amine |
| ARO66 | Arosurf 66 E10 | Witco | PEG-20 isostearyl ether |
| ARQ27 | Arquad T-27W | | 27% solution of tallow trimethylammonium chloride |
| ARQ37 | Arquad 1237W | | Cocotrimethylammonium chloride (37% in water) |
| ARQ50 | Arquad C-50 | Akzo | Coco trimethyl ammonium chloride |
| B1A | B-2050-01A | | Ethoxylated C16–18 linear alcohol 9.4 EO |
| B1B | B-2050-01B | | Alkyloxylated C16–18 linear alcohol 9.4 EO + 2.2 PO |
| B1C | B-2050-01C | | Alkyloxylated C16–18 linear alcohol 9.4 EO + 4.2 PO |
| B1F | B-2050-01F | | Alkyloxylated C16–18 linear alcohol 9.6 EO + 4.4 PO |
| BRI35 | Brij 35 | | Ethoxylated (23 EO) lauryl ether |
| BRI56 | Brij 56 | | Polyoxyethylene (10 EO) cetyl ether |
| BRI58 | Brij 58 | | Polyoxyethylene (20 EO) cetyl ether |
| BRI78 | Brij 78 | | Exthoxylated (20 EO) stearyl ether |
| CETAC | | | Cetyl trimethyl ammonium chloride |
| DUO50 | Duoquat T-50 | Akzo | Alkyl diamine quaternary salt |
| EA175 | | Tomah | EO etheramine |
| ED175 | | Tomah | EO Di-etheramine |
| EMC42 | Emcol CC42 | Witco | Polypropylene glycol-40 diethyl ammonium chloride |
| EMUL | Emulgin L | Cognis | Ceteareth 2 propoxylate 9 ethoxylate |

-continued

| Ref. | Trade Name | Manufacturer | Chemical Description |
|---|---|---|---|
| ETH12 | Ethomeen C12 | Akzo | Ethoxylated cocoamine 2 EO |
| ETH15 | Ethomeen T/15 | Akzo | Ethoxylated tallow amine 5 EO |
| ETH25 | Ethomeen T/25 | Akzo | 15 EO tallow ethoxylate quaternary ammonium chloride |
| EXP0A | EXP B 2030-A | | coco 15 EO benyl quaternary |
| EXP0B | EXP B 2030-B | | tallow 15 EO benyl quaternary |
| EXP0C | EXP B 2030-C | | N,N—C16 dimethyl 14 EO benyl quaternary |
| EXP86 | Experimental 5880-86B | | Propoxylated C16–18 alcohol 10.4 PO |
| GEN2 | Genamin T200NF AV 01/37-2 | Clariant | Monoethoxylated alkylamine C18NMe(EO)7H |
| GEN3 | Genamin T200NF AV 01/37-3 | Clariant | Monoethoxylated alkylamine C18NMe(EO)15H |
| GEN4 | Genamin T200NF AV 01/37-4 | Clariant | Monoethoxylated alkylamine C18NMe(EO)23H |
| HET20 | Hetoxol CS20 | | Ethoxylated (20 EO) C16–C18 ether |
| INT00 | Intermediate PF 8000 | Witco | Phosphate ester tridecanol + 4 EO (C13)O(CH2CH2)4(PO(OH2)) |
| L770 | Silwet L-77 | Witco | hepamethyl trisiloxane 7 EO methyl ether |
| LF700 | Plurafac LF700 | BASF | Alkoxylated C16–C18 alkyl |
| M117 | MON 59117 | | Ethoxylated Ether Amine |
| M121 | MON 58121 | Huntsman Surfonic AGM550 | (C12–14)O(CHCH3CH2)O—(CHCH3CH2)N (EO)x (EO)y x + y = 5 |
| M128 | MON78128 | | Formulation of 480 g a.e./l monoethanolamine glyphosate and 120 g/l M121 |
| M368 | MON 78368 | | Formulation of 357 g a.e./l IPA glyphosate with 57 g/l of EMUL, 85 g/l ethoxylated (10 EO) tallowamine and 57 g/l n-octylamine. |
| M619 | MON68619 | | Formulation of 360 g a.e./l IPA glyphosate with 70 g/l ETH25, 46 g/l BRI56 and 23 g/l CETAC |
| M620 | MON68620 | | Formulation of 360 g a.e./l IPA glyphosate with 83 g/l ETH25, 56 g/l BRI56 and 27 g/l CETAC |
| MPE01 | MPEAE | | EO-etheramine |
| MT13 | M-T4513-2 | Tomah | C14–15 dimethylated etheramine 13 EO |
| NEO25 | Neo 25-9 | | Ethoxylated alcohol with C12–15 hydrophobe and 9 EO |
| NO13 | Nopar 13 | Exxon | Normal parrafin |
| OA | | Fluka | Octyl amine |
| PG069 | APG-2069 | Agrimul APG | C9–C11 alkyl ether glucoside |
| S01 | | | Hexadecyl-eincosa(ethylene oxide) dimethyl amine |
| S02 | | | Hexadecyl-deca(ethylene oxide)-3-amino-propyl-1-amine |
| S03 | | | Hexadecyl/octadecyl(propylene oxide)-nona(ethylene oxide)-dimethylamine |
| S04 | | | Tallow-di(propylene oxide)-nona(ethylene oxide)-dibutylamine |
| S05 | | | Tallow-di(propylene oxide)-nona(ethylene oxide)-3'-amino-propylamine. |
| S06 | | | Tallow-di(propylene oxide)-nona(ethylene oxide)-N-methyl-glucamine |
| S07 | | | Hexadecyl-penta(propylene oxide)-eicosa(ethylene oxide)-dimethylamine |
| S08 | | | Tridecyl-hexa(ethylene oxide)-tri(propylene oxide)-dimethylamine |
| S09 | | | N-methyloctadecylamino glucitol |
| S10 | | | Hexadecyl-eicosa(ethylene oxide) dimethylamine |

-continued

| Ref. | Trade Name | Manufacturer | Chemical Description |
|---|---|---|---|
| S11 | | | Hexadecyl-eicosa(ethylene oxide) Tris |
| S12 | | | Hexadecyl-eicosa(ethylene oxide) methylamine |
| S13 | | | Hexadecyl-deca(ethylene oxide)-N-methyl-glucamine |
| S14 | | | 1-deoxy-1-(octadecylamino)-D-glucitol |
| S15 | | | Tallow-di(propylene oxide)-nona(ethylene oxide)-N-methyl-glucamine |
| S16 | | | N-dodecylglucamine |
| S17 | | | N-methyloctadecylamine glucitol |
| S18 | | | N,N-dimethyloctadecyl glucitol chloro amino quat |
| S19 | | | Ethoxylated cetyl alcohol |
| S20 | | | N-methyldodecylamino glucitol |
| S21 | | | N,N-dimethyldodecyl glucitol chloro amino quat |
| S22 | | | 10 EO isotridecyl phosphate ester (60% monoester) |
| S23 | | | n-hexyl glucamine |
| S24 | | | n-dodecyl glucamine |
| S39 | | | Eicosane-1,20-bis(trimethyl ammonium chloride) |
| S40 | | | Dodecane-1,12-bis(trimethyl ammonium chloride) |
| S41 | | | Hexadecane-1,16-bis(trimethylammonium chloride) |
| S42 | | | N,N-octylglucitol 1,3-propane |
| S43 | | | N,N-dodecylglucitol 1,3-propane |
| S44 | | | N,N-hexylglucitol 1,3-propane |
| S45 | | | N,N'-dioctyl-1,3-diaminopropane octa(ethylene oxide) |
| S46 | | | N,N'-didodecyl-1,3-diaminopropane eicosa(ethylene oxide) |
| S47 | | | N,N'-didecyl-1,3-diaminopropane deca(ethylene oxide) |
| S48 | | | N,N'-didecyl-1,3-diaminopropane octadeca(ethylene oxide) |
| S49 | | | N,N'-didodecyl-1,3-diaminopropane deca(ethylene oxide) |
| S50 | | | N,N'-didodecyl-1,3-diaminopropane eicosa(ethylene oxide) |
| S51 | | | Dodecyl-tetra(ethylene oxide) Tris |
| S52 | | | Tris(hydroxymethyl),N-dodecylaminomethane |
| S53 | | | Dodecyl-tetra(ethylene oxide) dimethyl amine |
| S54 | | | Hexadecyl-deca(ethylene oxide) dimethylamine |
| S55 | | | Dodecyl-tetra(ethylene oxide) trimethyl ammonium chloride |
| S56 | | | Hexadecyl-deca(ethylene oxide) trimethyl ammonium chloride |
| S57 | | | Hexadecyl-eicosa(ethylene oxide) trimethyl ammonium chloride |
| S58 | | | Monoethoxylated alkylamine C18NMe(EO)7.5H |
| S59 | | | Monoethoxylated alkylamine C18NMe(EO)11H |
| S60 | | | N-methyldodecylamino glucitol |
| S61 | | | Ethoxylated cetyl alcohol (10 EO) |
| S62 | | | Hexadecyl-deca(ethyleneoxide)-tris |
| S65 | | | Octylamino glucitol |
| S66 | | | Dodecyl-tetra(ethylene oxide) methylamine |
| S67 | | | Hexadecyl-deca(ethylene oxide) methylamine |
| S68 | | | Hexadecyl-eicosa(ethylene oxide) methylamine |

-continued

| Ref. | Trade Name | Manufacturer | Chemical Description |
|---|---|---|---|
| S71 | | | Bis-[N-hexadecyl-deca(ethylene oxide)-propylene-diammonium chloride |
| S72 | | | Bis-[N-hexadecyl-eicosa(ethylene oxide)-propylene-diammonium chloride |
| S73 | | | 3-(N-dodecyl-methylamino)-1,2-propanediol-penta(ethylene oxide) |
| S74 | | | 3-(N-dodecyl-methylamino)-1,2-propanediol-deca(ethylene oxide) |
| S75 | | | 3-(N-methyl-octadecylamino)-1,2-propanediol-penta(ethylene oxide) |
| S76 | | | 3-(N-methyl-octadecylamino)-1,2-propanediol-deca(ethylene oxide) |
| S77 | | | Hexadecyl/octadecyl-di(propylene oxide)-nona(ethylene oxide)-dimethylamine |
| S78 | | | 1-hydroxy-3-(N-methyl-octadecylamino)-propan-2-ol-penta(ethylene oxide) |
| S79 | | | 1-hydroxy-3-(N-methyl-octadecylamino)-propan-2-ol-nona(ethylene oxide) |
| S80 | | | 1-hydroxy-3-(N-methyl-dodecylamino)-propan-2-ol-penta(ethylene oxide) |
| S81 | | | Hexadecyl-deca(ethylene oxide)-hydroxyethylene-amine |
| S82 | | | Hexadecyl-deca(ethylene oxide)-2'-methylamino-ethylene-N-methyl-amine |
| S83 | | | Hexadecyl-deca(ethylene oxide)-2'-dimethylamino-ethylene-N-methylamine |
| S84 | | | Hexadecyl-deca(ethylene oxide)-3'-amine-2'hydroxypropylamine |
| S85 | | | Ethoxylated methyl stearyl amine 7.5 EO |
| S86 | | | Ethoxylated methyl stearyl amine 5.9 EO |
| S87 | | | Ethoxylated methyl stearyl amine 11 EO |
| S88 | | | (C4H9)2N(CH2)3NH2 |
| S89 | | | (C4H9)2N(CH2)3NMe2 |
| S90 | | | (C4H9)2N + (I−)(CH2)3N + Me3(I−) |
| S91 | | | Eicosa(ethylene oxide)hexadecyl-N,N-dimethylamine |
| S92 | | | Tallow-eicosa(ethylene oxide)-dimethylamine |
| S93 | | | Tallow-pentacosa(ethylene oxide)-dimethylamine |
| S94 | | | Tallow-eicosa(ethylene oxide)-Tris |
| S95 | | | Tallow-pentacosa(ethylene oxide)-Tris |
| S96 | | | deca(ethylene oxide)hexadecyl-N,N-dimethylamine |
| S97 | | | deca(ethylene oxide)eicosyl-N,N-dimethylamine |
| S98 | | | hexadecyl-eicosa(ethylene oxide)-N-methyl-dodecylamine |
| S99 | | | Bis-(Coca-amino)-eicosa(ethylene oxide) |
| S100 | | | 3-tallowamino-1,2-propanediol-pentadeca(ethylene oxide) |
| S101 | | | 3-tallowamino-1,2-propanediol-trieicosa(ethylene oxide) |
| S102 | | | 3-tallowamino-1,2-propanediol-heptaeicosa(ethylene oxide) |
| S103 | | | 3-cocoamino-1,2-propanediol-trieicosa(ethylene oxide) |
| S104 | | | 3-cocoamino-1,2-propanediol-triaconta(ethylene oxide) |
| SC85 | SC1485 | Albermarle | Myristyl dimethyl amine oxide8 |
| SUR10 | Surfonic L12-10 | Huntsman | C10–12 alcohol ethoxylate 10 EO |
| SUR12 | Surfonic L12-12 | Huntsman | C10–12 alcohol ethoxylate 12 EO |
| SUR50 | Surfonic AGM-50 | Huntsman | Alkyl etheramine |

-continued

| Ref. | Trade Name | Manufacturer | Chemical Description |
|---|---|---|---|
| SUR6 | Surfonic L12-6 | Huntsman | C10–12 alcohol ethoxylate 6 EO |
| SUR9 | Surfonic TDA-9 | Huntsman | Tridecyl alcohol 9 EO |
| T003A | B-1910-03 A | | Tallowamine + 10 EO |
| T003B | B-1910-03 B | | Tallowamine + 15 EO |
| T003C | B-1910-03 C | | Tallowamine + 20 EO |
| T003D | B-1910-03 D | | Tallowamine + 25 EO |
| T003E | B-1910-03 E | | Tallowamine + 30 EO |
| T23E2 | T23E1PAE2 | Tomah | Etheramine with a C12–13 linear alcohol hydrophobe with 1 EO and 2 EO on the amine C12–13O(OCH2CH2)CH2CH2CH2—N (EO)x (EO)y x = y = 2 |
| T23E5 | T23E1PAE5 | Tomah | Etheramine with a C12–13 linear alcohol hydrophobe with 1 EO and 5 EO on the amine C12–13O(OCH2CH2)CH2CH2CH2N(EO)x (EO)y x = y = 5 |
| TAM12 | Tomadol 25-12 | | C12–C15 alcohol ethoxylate (11.9 EO) |
| TED5 | E-D-17-5 | Tomah | C13O(CH2)3N(EO)x(CH2)3N(EO)y (EO)z x + y + z = 5 |
| TER9 | Tergitol 15 S-9 | | Ethoxylated (9 EO) C11–15 secondary alcohol |
| TPA0E | DPA-400E | Tomah | Polyethylene glycol 400 converted to a dietheramine (NH2)(CH2)3O(CH2CH2)n(CH2)3—(NH2) |
| TPAE6 | NDPA-14-E6 | Tomah | hexamethylenediol converted into a symmetrical di-etheramine and ethoxylated with 6 EO (Tomah NDPA with 6 EO) |
| TQ14 | Q14-M3 | Tomah | trimethylisodecyloxypropylamine chloride(quternary etheramine) |
| TQ17 | Q17-M3 | Tomah | trimethylisotridecyloxypropylamine chloride(quternary etheramine) |
| VAR02 | Varonic K-202 | Witco | Ethoxylated coco amine 2 EO |
| VAR05 | Varonic K-205 | Witco | Ethoxylated coco amine 5 EO |
| WEX5 | Experimental B1910-5 | Witco | N-dedecyoxypropyl-1,3 diaminopropane 3.4 EO |
| WEX6 | Experimental B1910-6 | Witco | N-dedecyoxypropyl-1,3 diaminopropane 6.1 EO |
| WEX7 | Experimental B1910-7 | Witco | N-dedecyoxypropyl-1,3 diaminopropane 9.5 EO |
| WIT05 | Witcamine TAM 105 | Witco | Ethoxylated tallow amine 10 EO |
| WIT305 | Witcamine TAM 305 | Witco | Coco amine 5 EO |
| WIT60 | Witcamine TAM 60 | | Ethoxylated tallow amine 6 EO |
| WIT80 | Witcamine TAM 80 | Witco | Ethoxylated tallow amine 8 EO |

Except where otherwise indicated, the aqueous spray composition were prepared by mixing the surfactant with the appropriate amount of potassium glyphosate added as a 47.5% (w/w) a.e. solution. The composition was placed in a water bath at 55° C. to 60° C. for about 30 minutes until a clear homogeneous solution was obtained. In some compositions the surfactant was melted before mixing.

The following procedure was used for testing compositions of the Examples to determine herbicidal effectiveness, except where otherwise indicated.

Seeds of the plant species indicated were planted in 88 mm square pots in a soil mix which was previously sterilized and prefertilized with a 14-14-14 NPK slow release fertilizer at a rate of 3.0 kg/m3. The post were placed in a greenhouse with sub-irrigation. About one week after emergence, seedlings were thinned as needed, including removal of any unhealthy or abnormal plants, to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 29° C. during the day and about 21° C. during the night. Plants were sub-irrigated throughout the test to ensure adequate soil moisture levels.

Pots were assigned to different treatments in a fully randomized experimental design with 6 replications. A set of pots was left untreated as a reference against which effects of the treatments could later be evaluated.

Application of glyphosate compositions was made by spraying with a track sprayer fitted with a 9501 E nozzle calibrated to deliver a spray volume of 93 liters per hectare (l/ha) at a pressure of 165 kilopascals (kPa). After treatment, pots were returned to the greenhouse until ready for evaluation.

Treatments were made using dilute aqueous compositions. These could be prepared as spray compositions directly from their ingredients, or by dilution with water of preformulated concentrate compositions.

For evaluation of herbicidal effectiveness, all plants in the test were examined by a single practiced technician, who recorded percent control, a visual measurement of the effectiveness of each treatment by comparison with untreated plants. Control of 0% indicates no effect, and control of 100% indicates that all of the plants are completely dead. The reported % control values represent the average for all replicates of each treatment.

Example 1

Aqueous concentrate compositions were prepared containing glyphosate salt and excipient ingredients as shown in Table 1a.

TABLE 1a

| Comp. | Salt | g/l | Component 1 | g/l | Component 2 | g/l |
|---|---|---|---|---|---|---|
| 734A9M | K | 30 | S16 | 4.5 | PG069 | 5.5 |
| 734B3K | K | 30 | S60 | 4.7 | PG069 | 5.3 |
| 734C1A | K | 30 | S21 | 5.0 | PG069 | 5.0 |
| 734D6O | K | 30 | | | PG069 | 10.0 |
| 734E9D | K | 4.3 | S16 | 1.4 | | |
| 734F2H | K | 30 | S60 | 10.0 | | |
| 734G9W | K | 30 | S21 | 10.0 | | |

Velvetleaf (*Abutilon theophrasti*, ABUTH) and Japanese millet (*Echinochloa crus-galli*, var. frumentae ECHCF) plants were grown and treated by the standard procedures above. The compositions of Table 1a and comparative compositions 139, 553 and 360 were applied. Results, averaged for all replicates of each treatment, are shown in Table 1b and 1c.

TABLE 1b

ABUTH % Control

| Composition | 75 g a.e./ha | 150 g a.e./ha | 225 g a.e./ha | 300 g a.e./ha |
|---|---|---|---|---|
| 139 | 0 | 62.5 | 75.8 | 80.8 |
| 360 | 45.0 | 81.7 | 85.0 | 91.7 |
| 553 | 64.2 | 85.0 | 85.8 | 90.0 |
| 734A9M | 0 | 60.8 | 77.5 | 84.2 |
| 734B3K | 0 | 63.3 | 80.8 | 83.3 |
| 734C1A | 17.5 | 74.2 | 80.8 | 84.2 |
| 734D6O | 10.0 | 61.7 | 78.3 | 71.7 |
| 734E9D | 30.8 | 68.3 | 81.7 | 83.3 |
| 734F2H | 41.7 | 75.8 | 83.3 | 85.8 |
| 734G9W | 30.0 | 79.2 | 84.2 | 87.5 |

TABLE 1c

ECHCF % Control

| Composition | 75 g a.e./ha | 150 g a.e./ha | 225 g a.e./ha | 300 g a.e./ha |
|---|---|---|---|---|
| 139 | 0 | 40.8 | 45.8 | 62.5 |
| 360 | 56.7 | 77.5 | 80.0 | 90.8 |
| 553 | 64.2 | 79.2 | 87.5 | 89.2 |
| 734A9M | 53.3 | 71.7 | 83.3 | 87.5 |
| 734B3K | 35.8 | 70.8 | 85.5 | 89.2 |
| 734C1A | 23.3 | 73.3 | 78.3 | 86.5 |
| 734D6O | 44.2 | 74.2 | 75.8 | 47.5 |
| 734E9D | 24.2 | 66.7 | 68.3 | 73.3 |
| 734F2H | 16.7 | 54.2 | 68.3 | 73.3 |
| 734G9W | 12.5 | 59.2 | 67.5 | 71.7 |

Results for ABUTH and ECHCF: Compositions 734F2H, and 734G9W exhibited similar herbicidal effectiveness to comparative composition 360 on velvetleaf (ABUTH).

Example 2

Aqueous concentrate compositions were prepared containing glyphosate salt and excipient ingredients as shown in Table 2a.

TABLE 2a

| Comp. | Salt | g/l | Component 1 | g/l | Component 2 | g/l |
|---|---|---|---|---|---|---|
| 736A4D | K | 30 | S16 | 2.6 | S22 | 7.4 |
| 736B7S | K | 30 | S09 | 2.8 | S22 | 7.2 |
| 736C8B | K | 30 | S18 | 3.0 | S22 | 7.0 |
| 736D5V | K | 30 | | | S22 | 10.0 |
| 734E1D | K | 4.3 | S16 | 1.4 | | |
| 734F9A | K | 30 | S09 | 10.0 | | |
| 734G3K | K | 30 | S18 | 10.0 | | |

Velvetleaf (ABUTH) and Japanese millet (ECHCF) plants were grown and treated by the standard procedures above. The compositions of Table 2a and comparative compositions 554, 553 and 360 were applied. Results, averaged for all replicates of each treatment, are shown in Table 2b and 2c.

TABLE 2b

ABUTH % Control

| Composition | 75 g a.e./ha | 150 g a.e./ha | 225 g a.e./ha | 300 g a.e./ha |
|---|---|---|---|---|
| 554 | 0 | 8.3 | 41.7 | 55.8 |
| 360 | 0 | 58.3 | 81.7 | 86.7 |
| 553 | 26.3 | 83.3 | 89.2 | 94.2 |
| 736A4D | 0 | 25 | 52.5 | 61.7 |
| 736B7S | 0 | 45 | 65.8 | 74.2 |
| 736C8B | 4.2 | 31.7 | 65 | 80.8 |
| 736D5V | 0 | 5.8 | 50.8 | 64.2 |
| 734E1D | 0 | 32.5 | 66.7 | 75.8 |
| 734F9A | 0 | 44.2 | 68.3 | 77.5 |
| 734G3K | 0 | 42.5 | 70 | 78.3 |

TABLE 2c

ECHCF % Control

| Composition | 75 g a.e./ha | 150 g a.e./ha | 225 g a.e./ha | 300 g a.e./ha |
|---|---|---|---|---|
| 554 | 0 | 8.3 | 18.3 | 39.2 |
| 360 | 10.8 | 71.7 | 75 | 79.2 |
| 553 | 30 | 71.7 | 79.2 | 91.7 |
| 736A4D | 13.3 | 46.7 | 65 | 69.2 |
| 736B7S | 0 | 58.3 | 67.5 | 70 |
| 736C8B | 0 | 58.3 | 66.7 | 75.8 |
| 736D5V | 0 | 26.7 | 53.3 | 67.5 |
| 734E1D | 46.7 | 63.3 | 70 | 71.7 |
| 734F9A | 3.3 | 48.3 | 55.8 | 70 |
| 734G3K | 0 | 28.3 | 62.5 | 68.3 |

Results for ABUTH and ECHCF: All of the compositions exhibited less herbicidal effectiveness than comparative compositions 360 and 553 on ABUTH and ECHCF.

Example 3

Aqueous concentrate compositions were prepared containing glyphosate salt and excipient ingredients as shown in Table 3a.

TABLE 3a

| Comp. | Salt | g/l | Component 1 | g/l | Component 2 | g/l |
|---|---|---|---|---|---|---|
| 664A5A | K | 540 | M121 | 135.02 | | |
| 687A1J | K | 540 | M121 | 101.26 | S23 | 33.75 |
| 687B8S | K | 540 | M121 | 89.92 | S23 | 44.96 |

TABLE 3a-continued

| Comp. | Salt | g/l | Component 1 | g/l | Component 2 | g/l |
|---|---|---|---|---|---|---|
| 687C8L | K | 540 | M121 | 67.50 | S23 | 67.50 |
| 688D3F | K | 540 | M121 | 101.27 | S24 | 33.76 |
| 688E2M | K | 540 | M121 | 89.91 | S24 | 44.96 |
| 688F9D | K | 540 | M121 | 67.51 | S24 | 67.51 |
| 360 | | 360 | | | | |
| 754 | | 445 | | | | |

Velvetleaf (ABUTH) and Japanese millet (ECHCF) plants were grown and treated by the standard procedures above. The compositions of Table 3a and comparative compositions 139, 554, 754 and 360 were applied. Results, averaged for all replicates of each treatment, are shown in Table 3b and 3c.

TABLE 3b

ABUTH % Control

| Composition | 75 g a.e./ha | 100 g a.e./ha | 150 g a.e./ha | 200 g a.e./ha |
|---|---|---|---|---|
| 139 | 16.7 | 40.0 | 61.7 | 73.3 |
| 554 | 9.2 | 30.0 | 47.5 | 60.0 |
| 360 | 66.7 | 71.7 | 92.7 | 96.3 |
| 664A5A | 35.0 | 42.5 | 74.2 | 86.8 |
| 687A1J | 21.7 | 40.0 | 55.0 | 82.5 |
| 687B8S | 21.7 | 31.7 | 73.3 | 78.3 |
| 687C8L | 15.8 | 43.3 | 68.3 | 70.0 |
| 688D3F | 26.7 | 36.7 | 60.0 | 68.3 |
| 688E2M | 18.3 | 43.3 | 51.7 | 73.3 |
| 688F9D | 10.0 | 31.7 | 49.2 | 76.7 |
| 754 | 58.3 | 61.7 | 83.3 | 89.3 |

TABLE 3c

ECHCF % Control

| Composition | 75 g a.e./ha | 100 g a.e./ha | 150 g a.e./ha | 200 g a.e./ha |
|---|---|---|---|---|
| 139 | 12.5 | 43.3 | 44.2 | 65.8 |
| 554 | 6.7 | 26.7 | 50.0 | 53.3 |
| 360 | 79.2 | 90.0 | 99.2 | 99.2 |
| 664A5A | 65.0 | 83.3 | 97.0 | 98.3 |
| 687A1J | 60.0 | 81.7 | 88.2 | 99.2 |
| 687B8S | 53.3 | 75.0 | 90.7 | 97.8 |
| 687C8L | 55.8 | 70.0 | 87.5 | 97.7 |
| 688D3F | 63.3 | 81.7 | 96.2 | 98.7 |
| 688E2M | 60.0 | 80.8 | 96.2 | 93.3 |
| 688F9D | 61.7 | 75.0 | 93.8 | 98.7 |
| 754 | 61.7 | 86.7 | 92.3 | 100.0 |

Example 4

Aqueous concentrate compositions were prepared containing glyphosate salt and excipient ingredients as shown in Table 4a.

TABLE 4a

| Comp. | Salt | g/l | Component 1 | g/l | Component 2 | g/l |
|---|---|---|---|---|---|---|
| 735A18H | K | 4.3 | S16 | 0.5 | S19 | 6.7 |
| 738A9J | K | 30 | S17 | 4.0 | S19 | 6.0 |
| 738B4H | K | 30 | S18 | 4.2 | S19 | 5.8 |
| 735D16X | K | 4.3 | | | S19 | 1.4 |
| 734E19H | K | 4.3 | S16 | 1.4 | | |
| 737C13A | K | 4.3 | S17 | 1.4 | | |
| 737D6G | K | 30 | S18 | 10.0 | | |

Velvetleaf (ABUTH) and Japanese millet (ECHCF) plants were grown and treated by the standard procedures above. The compositions of Table 4a and comparative compositions 554, 360 and 553 were applied. Results, averaged for all replicates of each treatment, are shown in Table 4b and 4c.

TABLE 4b

ABUTH % Control

| Composition | 75 g a.e/ha | 150 g a.e./ha | 225 g a.e./ha | 300 g a.e./ha |
|---|---|---|---|---|
| 554 | 0 | 13.3 | 30.8 | 58.3 |
| 360 | 10.0 | 78.3 | 85.0 | 92.5 |
| 553 | 64.2 | 82.5 | 95.0 | 97.2 |
| 735A18H | 25.8 | 57.5 | 78.3 | 87.5 |
| 738A9J | 16.7 | 63.3 | 80.0 | 86.7 |
| 738B4H | 25.8 | 68.3 | 81.7 | 87.5 |
| 735D16X | 17.5 | 74.2 | 85.0 | 86.7 |
| 734E19H | 15.0 | 42.5 | 70.8 | 81.7 |
| 737C13A | 16.7 | 38.3 | 68.3 | 77.5 |
| 737D6G | 10.0 | 53.3 | 77.5 | 83.3 |

TABLE 4c

ECHCF % Control

| Composition | 75 g a.e./ha | 150 g a.e./ha | 225 g a.e./ha | 300 g a.e./ha |
|---|---|---|---|---|
| 554 | 0 | 0 | 19.2 | 28.3 |
| 360 | 20.8 | 71.7 | 81.7 | 89.2 |
| 553 | 65.8 | 75.0 | 84.2 | 90.5 |
| 735A18H | 61.7 | 64.2 | 69.2 | 75.0 |
| 738A9J | 30.0 | 65.0 | 72.5 | 78.3 |
| 738B4H | 53.3 | 69.2 | 73.3 | 81.3 |
| 735D16X | 38.3 | 40.0 | 65.0 | 70.8 |
| 734E19H | 13.3 | 55.8 | 65.0 | 69.2 |
| 737C13A | 69.2 | 30.0 | 69.2 | 59.2 |
| 737D6G | 15.0 | 66.7 | 73.3 | 70.8 |

Example 5

Aqueous concentrate compositions were prepared containing glyphosate salt and excipient ingredients as shown in Table 5a.

TABLE 5a

| Comp. | Salt | g/l | Component 1 | g/l | Component 2 | g/l |
|---|---|---|---|---|---|---|
| 734A9D | K | 30 | S16 | 4.5 | PG069 | 5.5 |
| 734B7Y | K | 30 | S09 | 4.7 | PG069 | 5.3 |
| 734C9X | K | 30 | S18 | 5.0 | PG069 | 5.0 |
| 734D3J | K | 30 | | | PG069 | 10.0 |
| 734E5G | K | 4.3 | S16 | 1.4 | | |
| 734F8D | K | 30 | S09 | 10.0 | | |
| 734G3H | K | 30 | S18 | 10.0 | | |

Velvetleaf (ABUTH) and Japanese millet (ECHCF) plants were grown and treated by the standard procedures above. The compositions of Table 5a and comparative compositions 139, 360 and 553 were applied. Results, averaged for all replicates of each treatment, are shown in Table 5b and 5c.

TABLE 5b

ABUTH % Control

| Composition | 75 g a.e./ha | 150 g a.e./ha | 225 g a.e./ha | 300 g a.e./ha |
|---|---|---|---|---|
| 139 | 0 | 62.5 | 75.8 | 80.8 |
| 360 | 45.0 | 81.7 | 85.0 | 91.7 |
| 553 | 64.2 | 85.0 | 85.8 | 90.0 |
| 734A9D | 0 | 60.8 | 77.5 | 84.2 |
| 734B7Y | 0 | 63.3 | 80.8 | 83.3 |

TABLE 5b-continued

ABUTH % Control

| Composition | 75 g a.e./ha | 150 g a.e./ha | 225 g a.e./ha | 300 g a.e./ha |
|---|---|---|---|---|
| 734C9X | 17.5 | 74.2 | 80.8 | 84.2 |
| 734D3J | 10.0 | 61.7 | 78.3 | 71.7 |
| 734E5G | 30.8 | 68.3 | 81.7 | 83.3 |
| 734F8D | 41.7 | 75.8 | 83.3 | 85.8 |
| 734G3H | 30.0 | 79.2 | 84.2 | 87.5 |

TABLE 5c

ECHCF % Control

| Composition | 75 g a.e./ha | 150 g a.e./ha | 225 g a.e./ha | 300 g a.e./ha |
|---|---|---|---|---|
| 139 | 0 | 40.8 | 45.8 | 62.5 |
| 360 | 56.7 | 77.5 | 80.0 | 90.8 |
| 553 | 64.2 | 79.2 | 87.5 | 89.2 |
| 734A9D | 53.3 | 71.7 | 83.3 | 87.5 |
| 734B7Y | 35.8 | 70.8 | 85.5 | 89.2 |
| 734C9X | 23.3 | 73.3 | 78.3 | 86.5 |
| 734D3J | 44.2 | 74.2 | 75.8 | 47.5 |
| 734E5G | 24.2 | 66.7 | 68.3 | 73.3 |
| 734F8D | 16.7 | 54.2 | 68.3 | 73.3 |
| 734G3H | 12.5 | 59.2 | 67.5 | 71.7 |

Results for ABUTH and ECHCF: Compositions 743F8D and 743G3H exhibited similar herbicidal effectiveness for ABUTH to comparative composition 360.

Example 6

Aqueous concentrate compositions were prepared containing glyphosate salt and excipient ingredients as shown in Table 6a.

TABLE 6a

| Comp. | Salt | g/l | Component 1 | g/l |
|---|---|---|---|---|
| 627A5F | K | 30 | S42 | 10.0 |
| 627B8U | K | 30 | S43 | 10.0 |
| 627C9Z | K | 30 | S44 | 10.0 |
| 627D4W | K | 30 | S45 | 10.0 |
| 627E7V | K | 30 | S46 | 10.0 |
| 627F3K | K | 30 | S47 | 10.0 |
| 627G8M | K | 30 | S48 | 10.0 |
| 627H2X | K | 30 | S49 | 10.0 |
| 627I3E | K | 30 | S50 | 10.0 |

Velvetleaf (ABUTH) and Japanese millet (ECHCF) plants were grown and treated by the standard procedures above. The compositions of Table 6a and comparative compositions 554, 754 and 553 were applied. Results, averaged for all replicates of each treatment, are shown in Table 6b and 6c.

TABLE 6b

ABUTH % Control

| Composition | 75 g a.e./ha | 150 g a.e./ha | 225 g a.e./ha | 300 g a.e./ha |
|---|---|---|---|---|
| 554 | 0 | 12.5 | 26.7 | 60.0 |
| 754 | 0 | 76.7 | 85.8 | 90.8 |
| 553 | 55.8 | 84.2 | 91.7 | 95.7 |
| 627A5F | 8.3 | 45.8 | 55.0 | 74.2 |
| 627B8U | 3.3 | 54.2 | 77.5 | 87.5 |
| 627C9Z | 0 | 21.7 | 52.5 | 81.7 |
| 627D4W | 22.5 | 66.7 | 87.5 | 89.2 |
| 627E7V | 28.3 | 62.5 | 80.0 | 89.2 |
| 627F3K | 5.8 | 70.8 | 87.5 | 90.8 |
| 627G8M | 10.0 | 75.0 | 81.7 | 90.8 |
| 627H2X | 5.0 | 60.8 | 84.2 | 84.5 |
| 627I3E | 18.3 | 71.7 | 86.7 | 91.7 |

TABLE 6c

ECHCF % Control

| Composition | 75 g a.e./ha | 150 g a.e./ha | 225 g a.e./ha | 300 g a.e./ha |
|---|---|---|---|---|
| 554 | 0 | 0 | 3.3 | 4.2 |
| 754 | 0 | 66.7 | 70.8 | 77.5 |
| 553 | 29.2 | 72.5 | 82.5 | 87.5 |
| 627A5F | 5.0 | 39.2 | 49.2 | 52.5 |
| 627B8U | 1.7 | 30.8 | 54.2 | 67.5 |
| 627C9Z | 1.7 | 60.0 | 66.7 | 74.2 |
| 627D4W | 37.5 | 65.8 | 66.7 | 74.2 |
| 627E7V | 22.5 | 59.2 | 71.7 | 73.3 |
| 627F3K | 42.5 | 70.0 | 73.3 | 78.3 |
| 627G8M | 47.5 | 69.2 | 70.8 | 72.5 |
| 627H2X | 34.2 | 65.8 | 73.3 | 80.0 |
| 627I3E | 36.7 | 68.3 | 73.3 | 76.7 |

Results for ABUTH and ECHCF: Compositions 627D4W and 627I3E exhibited similar herbicidal effectiveness overall to comparative composition 754.

Example 7

Aqueous concentrate compositions were prepared containing glyphosate salt and excipient ingredients as shown in Table 7a.

TABLE 7a

| Comp. | Salt | g/l | Component 1 | g/l | Component 2 | g/l | Component 3 | g/l |
|---|---|---|---|---|---|---|---|---|
| 449A2Q | K | 540 | ETH12 | 45.00 | WIT60 | 45.00 | TAM12 | 45.00 |
| 449B8W | K | 540 | ETH12 | 33.75 | WIT60 | 50.63 | TAM12 | 50.63 |
| 450C7U | K | 540 | ETH12 | 33.75 | WIT60 | 45.00 | TAM12 | 56.25 |
| 450D4C | K | 540 | ETH12 | 33.75 | WIT60 | 56.25 | TAM12 | 45.00 |
| 451E6H | K | 540 | ETH12 | 33.75 | WIT60 | 61.25 | TAM12 | 45.00 |
| 456A3B | K | 480 | ETH12 | 53.33 | ETH15 | 53.33 | TAM12 | 53.33 |
| 456B2O | K | 480 | ETH12 | 40.00 | ETH15 | 60.00 | TAM12 | 60.00 |
| 457C9S | K | 480 | ETH12 | 40.00 | ETH15 | 53.33 | TAM12 | 66.67 |
| 457D1A | K | 480 | ETH12 | 40.00 | ETH15 | 66.67 | TAM12 | 53.33 |

TABLE 7a-continued

| Comp. | Salt | g/l | Component 1 | g/l | Component 2 | g/l | Component 3 | g/l |
|---|---|---|---|---|---|---|---|---|
| 360 | IPA | 360 | | | | | | |
| 754 | IPA | 445 | TAM105 | 509 | INT00 | 2.24 | | |
| 554 | K | 725 | | | | | | |

Velvetleaf (ABUTH) and Japanese millet (ECHCF) plants were grown and treated by the standard procedures above. The compositions of Table 7a and comparative compositions 554, 754 and 360 were applied. Results, averaged for all replicates of each treatment, are shown in Table 7b and 7c.

TABLE 7b

ABUTH % Control

| Composition | 150 g a.e./ha | 200 g a.e./ha | 300 g a.e./ha | 400 g a.e./ha |
|---|---|---|---|---|
| 554 | 40.0 | 67.0 | 80.0 | 80.4 |
| 360 | 81.0 | 89.0 | 97.0 | 98.0 |
| 754 | 83.0 | 90.0 | 96.2 | 98.2 |
| 449A2Q | 78.0 | 83.0 | 90.0 | 95.6 |
| 449B8W | 78.0 | 84.0 | 91.0 | 98.2 |
| 450C7U | 79.0 | 85.0 | 92.0 | 96.2 |
| 450D4C | 77.0 | 82.0 | 92.0 | 96.2 |
| 451E6H | 74.0 | 79.0 | 91.0 | 95.0 |
| 456A3B | 77.0 | 81.0 | 93.0 | 96.2 |
| 456B2O | 77.0 | 88.0 | 94.0 | 96.4 |
| 457C9S | 76.0 | 84.0 | 93.0 | 97.4 |
| 457D1A | 74.0 | 81.0 | 89.0 | 97.0 |

TABLE 7c

ECHCF % Control

| Composition | 150 g a.e./ha | 200 g a.e./ha | 300 g a.e./ha | 400 g a.e./ha |
|---|---|---|---|---|
| 554 | 44.0 | 54.0 | 57.0 | 62.0 |
| 360 | 85.0 | 97.0 | 99.6 | 99.8 |
| 754 | 83.0 | 95.0 | 99.8 | 99.0 |
| 449A2Q | 85.0 | 93.0 | 95.2 | 98.2 |
| 449B8W | 90.6 | 97.4 | 98.0 | 99.6 |
| 450C7U | 83.0 | 91.2 | 96.6 | 98.4 |
| 450D4C | 85.0 | 94.0 | 99.0 | 99.2 |
| 451E6H | 89.0 | 89.0 | 95.8 | 99.6 |
| 456A3B | 87.0 | 98.4 | 97.8 | 99.4 |
| 456B2O | 84.0 | 95.0 | 98.2 | 99.6 |
| 457C9S | 84.0 | 94.6 | 97.2 | 98.2 |
| 457D1A | 83.0 | 94.6 | 95.4 | 99.4 |

Results for ABUTH and ECHCF: Overall, the formulations of this example were slightly less efficacious than the 754 and 360 standards.

Example 8

Aqueous concentrate compositions were prepared containing glyphosate salt and excipient ingredients as shown in Table 8a.

TABLE 8a

| Comp. | Salt | g/l | Component 1 | g/l | Component 2 | g/l |
|---|---|---|---|---|---|---|
| 721L9G | K | 30 | S51 | 3.0 | RH010 | 7.0 |
| 721M7M | K | 30 | S51 | 5.0 | INT00 | 5.0 |
| 721N3W | K | 30 | S52 | 2.2 | RH010 | 7.8 |
| 721O9U | K | 30 | S52 | 3.8 | INT00 | 6.2 |
| 721E2V | K | 30 | S51 | 10.0 | | |
| 721F5C | K | 30 | S52 | 10.0 | | |

TABLE 8a-continued

| Comp. | Salt | g/l | Component 1 | g/l | Component 2 | g/l |
|---|---|---|---|---|---|---|
| 721A8K | K | 30 | | | RH010 | 10.0 |
| 721B3N | K | 30 | | | INT00 | 10.0 |

Velvetleaf (ABUTH) and Japanese millet (ECHCF) plants were grown and treated by the standard procedures above. The compositions of Table 8a and comparative compositions 553, 139 and 360 were applied. Results, averaged for all replicates of each treatment, are shown in Table 8b and 8c.

TABLE 8b

ABUTH % Control

| Composition | 75 g a.e./ha | 150 g a.e./ha | 225 g a.e./ha | 300 g a.e./ha |
|---|---|---|---|---|
| 139 | 0 | 30.8 | 71.7 | 84.2 |
| 360 | 13.3 | 82.5 | 88.3 | 92.3 |
| 553 | 57.5 | 85.8 | 90.8 | 94.7 |
| 721L9G | 5.8 | 47.5 | 71.7 | 81.7 |
| 721M7M | 13.3 | 43.3 | 75 | 83.3 |
| 721N3W | 1.7 | 57.5 | 80.8 | 85 |
| 721O9U | 6.7 | 48.3 | 76.7 | 80.8 |
| 721E2V | 12.5 | 56.7 | 80 | 88.3 |
| 721F5C | 5.8 | 62.5 | 73.3 | 85 |
| 721A8K | 10.8 | 31.7 | 64.2 | 84.2 |
| 721B3N | 0 | 28.3 | 58.3 | 80 |

TABLE 8c

ECHCF % Control

| Composition | 75 g a.e./ha | 150 g a.e./ha | 225 g a.e./ha | 300 g a.e./ha |
|---|---|---|---|---|
| 139 | 0 | 45.8 | 64.2 | 67.5 |
| 360 | 70 | 87.5 | 94.2 | 98.7 |
| 553 | 71.7 | 84 | 94.5 | 95.8 |
| 721L9G | 61.7 | 68.3 | 79.8 | 92.8 |
| 721M7M | 35.8 | 70 | 71.7 | 76.7 |
| 721N3W | 43.3 | 66.7 | 74.2 | 80.8 |
| 721O9U | 18.3 | 67.5 | 72.5 | 81.7 |
| 721E2V | 66.7 | 80 | 92.3 | 99.8 |
| 721F5C | 50 | 70 | 81.7 | 93.3 |
| 721A8K | 35.8 | 70 | 74.2 | 82.5 |
| 721B3N | 0 | 60.8 | 75.8 | 73.3 |

Results for ABUTH and ECHCF: Overall, the formulations of this example were not as efficacious as the 360 standard.

Example 9

Aqueous concentrate compositions were prepared containing glyphosate salt and excipient ingredients as shown in Table 9a.

TABLE 9a

| Comp. | Salt | g/l | Component 1 | g/l | Component 2 | g/l | Component 3 | g/l |
|---|---|---|---|---|---|---|---|---|
| 6226D | K | 480 | M121 | 160.0 | | | | |
| 5603F | K | 540 | M121 | 135.0 | | | | |
| 2398A | K | 480 | M121 | 120.0 | | | | |
| 6761A | K | 480 | ETH12 | 64.0 | WIT80 | 64.0 | INT00 | 32.0 |
| 6773B | K | 480 | ETH12 | 48.0 | WIT80 | 48.0 | INT00 | 24.0 |
| 7679V | K | 510 | 1816E | 5.0 | ARQ37 | 1.5 | | |
| 7678V | K | 510 | 1816E | 5.0 | ARQ37 | 1.5 | | |
| 360 | IPA | 360 | | | | | | |
| 754 | IPA | 445 | | | | | | |
| 554 | K | 725 | | | | | | |

Velvetleaf (ABUTH) and Japanese millet (ECHCF) plants were grown and treated by the standard procedures above. The compositions of Table 9a and comparative compositions 554, 139 and 360 were applied. Results, averaged for all replicates of each treatment, are shown in Table 9b and Table 9c.

TABLE 9b

ABUTH % Control

| Composition | 100 g a.e./ha | 150 g a.e./ha | 200 g a.e./ha | 300 g a.e./ha |
|---|---|---|---|---|
| 139 | 0 | 17.5 | 50.0 | 68.3 |
| 554 | 0 | 0.8 | 37.5 | 55.0 |
| 360 | 23.3 | 65.0 | 80.0 | 90.0 |
| 754 | 30.0 | 68.3 | 80.0 | 90.8 |
| 6226D | 16.7 | 57.5 | 78.3 | 85.0 |
| 5603F | 8.3 | 45.0 | 66.7 | 77.5 |
| 2398A | 11.7 | 50.0 | 65.8 | 73.3 |
| 6761A | 12.5 | 60.0 | 71.7 | 76.7 |
| 6773B | 5.0 | 56.7 | 65.0 | 73.3 |
| 7679V | 18.3 | 65.3 | 80.0 | 83.3 |
| 7678V | 25.0 | 72.5 | 77.5 | 80.8 |

TABLE 9c

ECHCF % Control

| Composition | 100 g a.e./ha | 150 a.e./ha | 200 g a.e./ha | 300 g a.e./ha |
|---|---|---|---|---|
| 139 | 35.0 | 45.0 | 55.8 | 65.0 |
| 554 | 20.0 | 39.2 | 49.2 | 60.8 |
| 360 | 66.7 | 76.7 | 92. | 93.0 |
| 754 | 63.3 | 77.5 | 86.7 | 92.5 |
| 6226D | 64.2 | 79.2 | 90.0 | 92.8 |
| 5603F | 65.8 | 73.3 | 84.2 | 85.0 |
| 2398A | 61.7 | 62.5 | 80.0 | 84.2 |
| 6761A | 65.0 | 75.0 | 87.5 | 93.0 |
| 6773B | 63.3 | 68.3 | 88.2 | 88.8 |
| 7679V | 61.7 | 66.7 | 67.5 | 74.2 |
| 7678V | 55.0 | 62.5 | 70.8 | 85.0 |

Results for ABUTH and ECHCF: Overall, the formulations of this example were not as efficacious as the 360 and 754 standards. However, the 622 and 676 formulations were close in performance to the 360 and 754standards.

Example 10

Aqueous concentrate compositions were prepared containing glyphosate salt and excipient ingredients as shown in Table 10a.

TABLE 10a

| Comp. | Salt | g/l | Component 1 | g/l | Component 2 | g/l |
|---|---|---|---|---|---|---|
| 761A4S | K | 4.3 | S10 | 0.0 | S61 | 1.4 |
| 761B2X | K | 4.3 | S10 | 0.3 | S61 | 1.1 |
| 761C6Q | K | 30 | S10 | 4.0 | S61 | 6.0 |
| 765L1D | K | 30 | S10 | 5.0 | S61 | 5.0 |
| 761E9N | K | 30 | S10 | 6.0 | S61 | 4.0 |
| 761F4D | K | 30 | S10 | 8.0 | S61 | 2.0 |
| 761G8S | K | 30 | S10 | 10.0 | S61 | 0.0 |

Velvetleaf (ABUTH) and Japanese millet (ECHCF) plants were grown and treated by the standard procedures above. The compositions of Table 10a and comparative compositions 554, 553 and 360 were applied. Results, averaged for all replicates of each treatment, are shown in Table 10b and 10c.

TABLE 10b

ABUTH % Control

| Composition | 75 g a.e./ha | 150 g a.e./ha | 225 g a.e./ha | 300 g a.e./ha |
|---|---|---|---|---|
| 554 | 0.0 | 11.7 | 62.5 | 69.2 |
| 360 | 17.5 | 78.3 | 85.8 | 91.3 |
| 553 | 65.8 | 88.3 | 93.2 | 98.2 |
| 761A4S | 39.2 | 73.3 | 83.3 | 90.0 |
| 761B2X | 51.7 | 80.0 | 89.2 | 94.5 |
| 761C6Q | 62.5 | 85.8 | 92.5 | 95.8 |
| 765L1D | 70.8 | 85.8 | 89.7 | 95.3 |
| 761E9N | 69.2 | 85.8 | 90.0 | 94.5 |
| 761F4D | 77.5 | 89.2 | 92.2 | 94.8 |
| 761G8S | 74.2 | 86.7 | 91.5 | 96.0 |

TABLE 10c

ECHCF % Control

| Composition | 75 g a.e./ha | 150 g a.e./ha | 225 g a.e./ha | 300 g a.e./ha |
|---|---|---|---|---|
| 554 | 0.0 | 0.0 | 5.0 | 33.3 |
| 360 | 25.0 | 70.8 | 80.8 | 84.2 |
| 553 | 64.2 | 78.3 | 85.0 | 83.3 |
| 761A4S | 0.0 | 57.5 | 68.3 | 72.5 |
| 761B2X | 3.3 | 65.8 | 71.7 | 74.2 |
| 761C6Q | 29.2 | 71.7 | 76.7 | 78.3 |
| 765L1D | 23.3 | 75.0 | 75.0 | 82.5 |
| 761E9N | 37.5 | 74.2 | 77.5 | 81.7 |
| 761F4D | 51.7 | 75.8 | 80.0 | 83.3 |
| 761G8S | 60.0 | 75.0 | 82.5 | 85.0 |

Example 11

Aqueous concentrate compositions were prepared containing glyphosate salt and excipient ingredients as shown in Table 11a.

TABLE 11a

| Comp. | Salt | g/l | Component 1 | g/l | Component 2 | g/l |
|---|---|---|---|---|---|---|
| 105A3S | K | 30 | NEO25 | 5 | SUR50 | 5 |
| 105B7N | K | 30 | NEO25 | 5 | SUR50 | 5 |
| 106A8X | K | 30 | TER9 | 5 | SUR50 | 5 |
| 106B6N | K | 30 | SUR9 | 5 | SUR50 | 5 |
| 106C6Y | K | 30 | SUR6 | 5 | SUR50 | 5 |
| 106D8E | K | 30 | SUR10 | 5 | SUR50 | 5 |
| 106E9R | K | 30 | SUR12 | 5 | SUR50 | 5 |
| 767 | K | 510 | | | | |
| 360 | IPA | 360 | | | | |

TABLE 11a-continued

| Comp. | Salt | g/l | Component 1 | g/l | Component 2 | g/l |
|---|---|---|---|---|---|---|
| 754 | IPA | 445 | TAM105 | 5.9 | INT00 | 2.24 |
| 554 | K | 725 | | | | |

Velvetleaf (ABUTH) and Japanese millet (ECHCF) plants were grown and treated by the standard procedures above.

The compositions of Table 11a and comparative compositions 554, 139, 754 and 360 were applied. Results, averaged for all replicates of each treatment, are shown in Table 11b and 11c.

TABLE 11b

ABUTH % Control

| Composition | 100 g a.e./ha | 150 g a.e./ha | 200 g a.e./ha | 300 g a.e./ha |
|---|---|---|---|---|
| 139 | 10.0 | 75.0 | 80.0 | 85.0 |
| 554 | 5.0 | 65.8 | 75.0 | 84.2 |
| 360 | 70.0 | 82.5 | 89.2 | 90.0 |
| 754 | 67.5 | 84.2 | 87.5 | 92.5 |
| 105A3S | 77.5 | 86.7 | 91.3 | 93.0 |
| 105B7N | 68.3 | 84.2 | 86.7 | 92.7 |
| 106A8X | 75.8 | 82.5 | 89.2 | 91.7 |
| 106B6N | 75.8 | 86.7 | 87.5 | 94.7 |
| 106C6Y | 68.3 | 80.8 | 85.0 | 90.8 |
| 106D8E | 73.3 | 84.2 | 84.2 | 87.5 |
| 106E9R | 71.7 | 82.5 | 89.2 | 90.0 |
| 767 | 75.0 | 82.5 | 85.0 | 90.0 |

TABLE 11c

ECHCF % Control

| Composition | 100 g a.e./ha | 150 g a.e./ha | 200 g a.e./ha | 300 g a.e./ha |
|---|---|---|---|---|
| 139 | 47.5 | 50.8 | 55.8 | 69.2 |
| 554 | 43.3 | 50.0 | 57.5 | 67.5 |
| 360 | 65.0 | 79.7 | 91.5 | 97.7 |
| 754 | 58.3 | 75.0 | 81.5 | 97.0 |
| 105A3S | 60.0 | 82.5 | 89.7 | 97.0 |
| 105B7N | 59.2 | 81.7 | 82.5 | 98.0 |
| 106A8X | 57.5 | 88.0 | 93.7 | 93.7 |
| 106B6N | 64.2 | 82.3 | 87.5 | 89.2 |
| 106C6Y | 61.7 | 85.3 | 91.8 | 96.2 |
| 106D8E | 63.3 | 71.7 | 88.2 | 98.0 |
| 106E9R | 65.0 | 80.8 | 96.8 | 99.2 |
| 767 | 59.2 | 63.3 | 74.2 | 92.7 |

Results for ABUTH and ECHCF: All of the formulations of the example were determined to be as efficacious as the standards 754 and 360.

Example 12

Aqueous concentrate compositions were prepared containing glyphosate salt and excipient ingredients as shown in Table 12a.

TABLE 12a

| Comp. | Salt | g/l | Component 1 | g/l | Component 2 | g/l | Component 3 | g/l |
|---|---|---|---|---|---|---|---|---|
| 476A4H | K | 480 | ETH12 | 40.0 | ETH15 | 60.0 | SUR9 | 60.0 |
| 476B6V | K | 480 | ETH12 | 40.0 | ETH15 | 53.3 | SUR9 | 53.3 |
| 477C9S | K | 540 | ETH12 | 33.8 | ETH15 | 50.6 | SUR9 | 50.6 |
| 477D2M | K | 480 | ETH12 | 64.0 | WIT60 | 32.0 | INT00 | 32.0 |
| 478E6Y | K | 480 | ETH12 | 48.0 | WIT60 | 24.0 | INT00 | 24.0 |
| 478F1H | K | 540 | ETH12 | 60.75 | WIT05 | | | |
| 360 | IPA | 360 | | | | | | |
| 754 | IPA | 445 | TAM105 | 5.9 | INT00 | 2.24 | | |
| 554 | K | 725 | | | | | | |

Velvetleaf (ABUTH) and Japanese millet (ECHCF) plants were grown and treated by the standard procedures above. The compositions of Table 12a and comparative compositions 554, 139, 754 and 360 were applied. Results, averaged for all replicates of each treatment, are shown in Table 12b and 12c.

TABLE 12b

ABUTH % Control

| Composition | 150 g a.e./ha | 200 g a.e./ha | 300 g a.e./ha | 400 g a.e./ha |
|---|---|---|---|---|
| 139 | 0.0 | 1.7 | 65.0 | 81.7 |
| 554 | 0.0 | 6.7 | 665.0 | 68.3 |
| 360 | 73.3 | 81.7 | 83.3 | 91.7 |
| 754 | 50.0 | 71.7 | 83.3 | 90.0 |
| 476A4H | 21.7 | 63.3 | 80.0 | 83.3 |
| 476B6V | 60.0 | 65.0 | 75.0 | 86.7 |
| 477C9S | 53.3 | 66.7 | 78.3 | 85.0 |
| 477D2M | 56.7 | 60.0 | 85.0 | 85.0 |
| 478E6Y | 53.3 | 66.7 | 81.7 | 85.0 |
| 478F1H | 36.7 | 68.3 | 81.7 | 83.3 |

TABLE 12c

ECHCF % Control

| Composition | 150 g a.e./ha | 200 g a.e./ha | 300 g a.e./ha | 400 g a.e./ha |
|---|---|---|---|---|
| 139 | 16.7 | 33.3 | 55.0 | 65.0 |
| 554 | 5.0 | 11.7 | 45.0 | 56.7 |
| 360 | 65.0 | 71.7 | 88.3 | 91.0 |
| 754 | 63.3 | 65.0 | 85.0 | 90.0 |
| 476A4H | 61.7 | 66.7 | 75.0 | 83.3 |
| 476B6V | 65.0 | 70.0 | 76.7 | 94.3 |
| 477C9S | 46.7 | 66.7 | 81.7 | 88.3 |
| 477D2M | 53.3 | 63.3 | 70.0 | 75.0 |
| 478E6Y | 58.3 | 68.3 | 76.7 | 81.7 |
| 478F1H | 61.7 | 78.3 | 90.0 | 95.0 |

Results for ABUTH and ECHCF: All of the formulations of this example were determined to be similar to each other for overall efficacy. No formulation was as efficacious as the standards of 360 and 754 for ABUTH. The formulations of 476F1H and 476B6V were similar to the standards of 360 and 754 for ECHCF.

Example 13

Aqueous concentrate compositions were prepared containing glyphosate salt and excipient ingredients as shown in Table 13a.

TABLE 13a

| Comp. | Salt | g/l | Component 1 | g/l |
|---|---|---|---|---|
| 649A7J | K | 30 | S71 | 10.0 |
| 649B4B | K | 30 | S72 | 10.0 |
| 649C9X | K | 30 | S56 | 10.0 |
| 649D2W | K | 4.3 | S97 | 1.4 |
| 649E7A | K | 30 | S71 | 5.0 |
| 649F8C | K | 30 | S72 | 5.0 |
| 649G6M | K | 30 | S56 | 5.0 |
| 649H2V | K | 30 | S71 | 5.0 |

Velvetleaf (ABUTH) and Japanese millet (ECHCF) plants were grown and treated by the standard procedures above. The compositions of Table 13a and comparative compositions 554, 553, and 754 were applied. Results, averaged for all replicates of each treatment, are shown in Table 13b and 13c.

TABLE 13b

ABUTH % Control

| Composition | 75 g a.e./ha | 150 g a.e./ha | 225 g a.e./ha | 300 g a.e./ha |
|---|---|---|---|---|
| 554 | 0.0 | 0.0 | 9.2 | 28.3 |
| 754 | 0.0 | 0.0 | 80.0 | 80.8 |
| 553 | 10.0 | 55.0 | 87.5 | 91.7 |
| 649A7J | 35.8 | 57.5 | 80.8 | 90.0 |
| 649B4B | 50.0 | 70.8 | 89.2 | 94.2 |
| 649C9X | 34.2 | 60.8 | 81.7 | 85.0 |
| 649D2W | 29.2 | 71.7 | 82.5 | 88.3 |
| 649E7A | 48.3 | 49.2 | 78.3 | 89.2 |
| 649F8C | 48.2 | 63.3 | 88.3 | 88.3 |
| 649G6M | 59.2 | 44.2 | 80.0 | 84.2 |
| 649H2V | 71.7 | 60.8 | 90.0 | 86.7 |

TABLE 13c

ECHCF % Control

| Composition | 75 g a.e./ha | 150 g a.e./ha | 225 g a.e./ha | 300 g a.e./ha |
|---|---|---|---|---|
| 554 | 0.0 | 0.0 | 16.7 | 6.7 |
| 754 | 0.0 | 42.5 | 80.0 | 81.7 |
| 553 | 57.5 | 65.8 | 81.7 | 86.7 |
| 649A7J | 15.0 | 52.5 | 75.0 | 85.8 |
| 649B4B | 47.5 | 61.5 | 79.2 | 79.2 |
| 649C9X | 8.3 | 23.3 | 70.0 | 75.0 |
| 649D2W | 6.7 | 64.2 | 77.5 | 79.2 |
| 649E7A | 0.0 | 16.7 | 62.5 | 75.8 |
| 649F8C | 23.3 | 32.5 | 78.3 | 80.0 |
| 649G6M | 5.0 | 20.0 | 53.3 | 72.5 |
| 649H2V | 16.7 | 31.7 | 73.3 | 81.7 |

Results for ABUTH and ECHCF: The most active formulation for ABUTH was 649B4B and the most active for ECHCF was the standard 553.

Example 14

Aqueous concentrate compositions were prepared containing glyphosate salt and excipient ingredients as shown in Table 14a.

TABLE 14a

| Comp | Salt | Active | g/l |
|---|---|---|---|
| M121 | | surfactant (Etheramine Surfactant system) | 100 |
| 139 | IPA | | 570 |
| 554 | K | | 725 |

Velvetleaf (ABUTH) and Japanese millet (ECHCF) plants were grown and treated by the standard procedures above. The compositions of Table 14a and comparative compositions 139 and 554 alone were applied. Results, averaged for all replicates of each treatment, are shown in Table 14b and 14c.

TABLE 14b

ABUTH % Control

| Glyphosate Composition | Surfactant M121 (wt. %) | 75 g a.e./ha | 100 g a.e./ha | 150 g a.e./ha |
|---|---|---|---|---|
| 139 | 0 | 10.8 | 12.5 | 57.5 |
| 554 | 0 | 0 | 0 | 21.7 |
| 139 | 0.05% | 51.7 | 69.2 | 79.2 |
| 139 | 0.1% | 62.5 | 75.0 | 83.3 |
| 139 | 0.2% | 50.0 | 62.5 | 79.2 |
| 139 | 0.5% | 57.5 | 75.8 | 79.2 |
| 139 | 1.0% | 56.7 | 77.5 | 79.2 |
| 139 | 5.0% | 23.3 | 30.0 | 31.7 |
| 554 | 0.05% | 45.0 | 59.2 | 75.8 |
| 554 | 0.1% | 45.8 | 63.3 | 72.5 |
| 554 | 0.2% | 56.7 | 64.2 | 75.0 |
| 554 | 0.5% | 45.8 | 73.3 | 77.5 |
| 554 | 1.0% | 37.5 | 62.5 | 77.5 |
| 554 | 5.0% | 4.2 | 9.2 | 10.0 |

TABLE 14c

ECHCF % Control

| Glyphosate Composition | Surfactant M121 (wt. %) | 75 g a.e./ha | 100 g a.e./ha | 150 g a.e./ha |
|---|---|---|---|---|
| 139 | 0 | 5.0 | 7.5 | 31.7 |
| 554 | 0 | 0.0 | 5.8 | 13.3 |
| 139 | 0.05% | 60.0 | 69.2 | 85.0 |
| 139 | 0.1% | 65.0 | 68.3 | 84.2 |
| 139 | 0.2% | 70.8 | 87.0 | 98.5 |
| 139 | 0.5% | 70.8 | 90.7 | 89.7 |
| 139 | 1.0% | 60.8 | 65.0 | 83.3 |
| 139 | 5.0% | 30.0 | 31.7 | 35.0 |
| 554 | 0.05% | 33.3 | 55.0 | 65.8 |
| 554 | 0.1% | 40.8 | 42.5 | 63.3 |
| 554 | 0.2% | 40.0 | 64.2 | 73.3 |
| 554 | 0.5% | 33.3 | 56.7 | 70.0 |
| 554 | 1.0% | 7.5 | 40.8 | 63.3 |
| 554 | 5.0% | 1.7 | 2.5 | 5.8 |

Results for ABUTH and ECHCF: Comparison of M121 as a surfactant for each of the IPA and K salts of glyphosate showed this surfactant system to be more fective for potentiating the IPA. Overall higher efficacy was noted at each test rate for the IPA versus the K salt. The M121 surfactant system appeared to reach its maximum effectiveness in a range of about 0.1% to 0.5% of spray volume for each glyphosate salt, after which efficacy did not change or decreased when increasing surfactant levels to 1% or 5% with both salts.

Example 15

Aqueous concentrate compositions were prepared containing glyphosate salt and excipient ingredients as shown in Table 15a.

TABLE 15a

| Comp. | Salt | g/l | Component 1 | g/l | Component 2 | g/l | Component 3 | g/l |
|---|---|---|---|---|---|---|---|---|
| 387-15G | K | 410 | VAR05 | 132.2 | | | | |
| 387-24N | K | 476 | VAR05 | 66.2 | 117 | 66.2 | | |
| 387-32C | K | 488 | VAR05 | 66.7 | APG67 | 66.7 | | |
| 387-48N | K | 490 | VAR05 | 33.5 | 117 | 13.4 | APG67 | 100.4 |
| 387-59A | K | 484 | VAR05 | 33.5 | 117 | 40.2 | APG67 | 100.4 |
| 387-67X | K | 487 | VAR02 | 49.6 | 117 | 66.1 | APG67 | 16.5 |
| 387-75G | K | 544 | VAR02 | 16.6 | 117 | 66.5 | APG67 | 49.9 |
| 387-98C | K | | VAR02 | 40.8 | 117 | 81.6 | APG67 | 13.6 |

Velvetleaf (ABUTH) and Japanese millet (ECHCF) plants were grown and treated by the standard procedures above. The compositions of Table 15a and comparative compositions 554, 360, 139 and 754 were applied. Results, averaged for all replicates of each treatment, are shown in Table 15b and Table 15c.

TABLE 15b

ABUTH % Control

| Composition | 150 g a.e./ha | 200 g a.e./ha | 300 g a.e./ha | 400 g a.e./ha |
|---|---|---|---|---|
| 139 | 39.0 | 59.0 | 79.0 | 85.0 |
| 554 | 27.0 | 30.0 | 72.0 | 78.0 |
| 360 | 80.0 | 80.0 | 88.0 | 91.0 |
| 754 | 79.0 | 81.0 | 88.0 | 90.0 |
| 387-15G | 78.0 | 78.0 | 88.0 | 91.0 |
| 387-24N | 77.0 | 80.0 | 84.0 | 89.0 |
| 387-32C | 74.0 | 79.0 | 83.0 | 88.0 |
| 387-48N | 76.0 | 78.0 | 84.0 | 87.0 |
| 387-59A | 66.0 | 80.0 | 85.0 | 87.0 |
| 387-67X | 69.0 | 74.0 | 83.0 | 86.0 |
| 387-75G | 67.0 | 78.0 | 87.0 | 87.0 |
| 387-98C | 67.0 | 80.0 | 85.0 | 86.0 |

TABLE 15c

ECHCF % Control

| Composition | 150 g a.e./ha | 200 g a.e./ha | 300 g a.e./ha | 400 g a.e./ha |
|---|---|---|---|---|
| 139 | 10.0 | 25.0 | 42.0 | 62.0 |
| 554 | 10.0 | 11.0 | 30.0 | 44.0 |
| 360 | 72.0 | 82.0 | 89.6 | 91.0 |
| 754 | 71.0 | 74.0 | 91.8 | 90.6 |
| 387-15G | 68.0 | 78.0 | 93.6 | 96.0 |
| 387-24N | 68.0 | 81.0 | 89.8 | 93.0 |
| 387-32C | 68.0 | 72.0 | 74.0 | 96.8 |
| 387-48N | 64.0 | 70.0 | 83.0 | 87.6 |
| 387-59A | 69.0 | 70.0 | 78.0 | 91.2 |
| 387-67X | 70.0 | 74.0 | 79.0 | 82.8 |
| 387-75G | 68.0 | 74.0 | 80.8 | 87.8 |
| 387-98C | 66.0 | 72.0 | no data | no data |

Results for ABUTH and ECHCF: The formulation of 387-15G was similar in efficacy to the standards of 360 and 754 for both ABUTH and ECHCF. The formulation of 387-24N was the next most efficacious formulation for ABUTH and ECHCF. The treatments were mis-sprayed for 387-98C at 300 and 400 g/ha and therefore no data was collected.

Example 16

Aqueous concentrate compositions were prepared containing glyphosate salt and excipient ingredients as shown in Table 16a.

TABLE 16a

| Comp. | Salt | g/l | Component 1 | g/l | Component 2 | g/l | Component 3 | g/l |
|---|---|---|---|---|---|---|---|---|
| 387-13M | K | 410 | VAR05 | 132.2 | | | | |
| 387-25F | K | 476 | VAR05 | 66.2 | 117 | 66.2 | | |
| 387-38C | K | 488 | VAR05 | 66.7 | APG67 | 66.7 | | |
| 387-63J | K | 484 | VAR02 | 49.6 | 117 | 66.1 | APG67 | 16.5 |
| 387-96F | K | 544 | VAR02 | 40.8 | 117 | 81.6 | APG67 | 13.6 |
| 387-89D | K | 483 | ETH12 | 66.0 | 117 | 66 | | |
| 387-108U | K | 544 | ETH12 | 40.8 | 117 | 81.6 | APG67 | 13.6 |
| 387-116Y | K | 543 | ETH12 | 54.3 | 117 | 81.4 | | |
| 360 | IPA | 360 | | | | | | |
| 754 | IPA | 445 | WIT05 | 5.9 | INT00 | 2.24 | | |
| 554 | K | 725 | | | | | | |

Velvetleaf (ABUTH) and Japanese millet ECHCF) plants were grown and (Et:t6 treated by the standard procedures above. The compositions of Table 16a and comparative compositions 554, 139, 360 and 754 were applied. Results, averaged for all replicates of each treatment, are shown in Table 16b and 16c.

TABLE 16b

ABUTH % Control

| Composition | 150 g a.e./ha | 200 g a.e./ha | 300 g a.e./ha | 400 g a.e./ha |
|---|---|---|---|---|
| 139 | 5.0 | 70.0 | 79.0 | 82.0 |
| 554 | 8.0 | 65.0 | 77.0 | 80.0 |
| 360 | 78.0 | 84.0 | 88.0 | 92.0 |
| 754 | 80.0 | 84.0 | 87.0 | 91.0 |
| 387-13M | 60.0 | 83.0 | 84.0 | 88.0 |
| 387-25F | 54.0 | 75.0 | 82.0 | 86.0 |
| 387-38C | 22.0 | 69.0 | 80.0 | 83.0 |
| 387-63J | 65.0 | 68.0 | 80.0 | 81.0 |
| 387-96F | 26.0 | 40.0 | 80.0 | 81.0 |
| 387-89D | 13.0 | 54.0 | 81.0 | 81.0 |
| 387-108U | 50.0 | 64.0 | 79.0 | 82.0 |
| 387-116Y | 55.0 | 65.0 | 81.0 | 82.0 |

TABLE 16c

ECHCF % Control

| Composition | 150 g a.e./ha | 200 g a.e./ha | 300 g a.e./ha | 400 g a.e./ha |
|---|---|---|---|---|
| 139 | 14.0 | 38.0 | 55.0 | 61.0 |
| 554 | 14.0 | 36.0 | 55.0 | 65.0 |
| 360 | 64.0 | 71.0 | 91.8 | 93.8 |
| 754 | 62.0 | 69.0 | 82.0 | 93.0 |
| 387-13M | 66.0 | 81.6 | 89.0 | 87.8 |
| 387-25F | 66.0 | 72.0 | 83.8 | 85.8 |
| 387-38C | 64.0 | 67.0 | 81.0 | 80.6 |
| 387-63J | 63.0 | 67.0 | 75.6 | 86.2 |
| 387-96F | 62.0 | 63.0 | 76.0 | 81.0 |
| 387-89D | 61.0 | 66.0 | 76.0 | 82.2 |
| 387-108U | 62.0 | 63.0 | 73.0 | 85.0 |
| 387-116Y | 65.0 | 65.0 | 78.0 | 85.0 |

Results for ABUTH and ECHCF: The formulation of 387-13M was similar equal in efficacy to the standards of 360 and 754 for ECHCF. The formulation of 387-25F was the next most efficacious. No formulation of this experiment was as efficacious as the standards 360 and 754 for ABUTH.

Example 17

Aqueous concentrate compositions were prepared containing glyphosate salt and excipient ingredients as shown in Table 17a.

TABLE 17a

| Comp. | Salt | g/l | Component 1 | g/l |
|---|---|---|---|---|
| 488A6Y | K | 4.3 | 855 | 1.4 |
| 488B5G | K | 30 | 855 | 10.0 |
| 488C7U | K | 30 | 855 | 10.0 |
| 488D5H | K | 30 | 855 | 10.0 |
| 488E4J | K | 30 | 855 | 10.0 |
| 488F2Z | K | 30 | 855 | 10.0 |
| 488G8Q | K | 4.3 | 855 | 1.4 |
| 488H7M | K | 30 | 855 | 10.0 |
| 488I5T | K | 30 | 855 | 12.0 |
| 488J3T | IPA | 4.3 | 139 | 1.4 |
| 488K9S | IPA | 30 | 139 | 10.0 |
| 488L3A | IPA | 30 | 139 | 10.0 |

TABLE 17a-continued

| Comp. | Salt | g/l | Component 1 | g/l |
|---|---|---|---|---|
| 488M5S | IPA | 30 | 139 | 10.0 |
| 488N7Z | IPA | 30 | 139 | 10.0 |
| 488O8T | IPA | 30 | 139 | 10.0 |
| 488P9H | IPA | 4.3 | 139 | 1.4 |
| 488Q7G | IPA | 30 | 139 | 10.0 |
| 488R3E | IPA | 30 | 139 | 12.0 |

Velvetleaf (ABUTH) and Japanese millet (ECHCF) plants were grown and treated by the standard procedures above. The compositions of Table 17a and comparative compositions 139, 553, and 360 were applied. Results, averaged for all replicates of each treatment, are shown in Table 18b and 18c.

TABLE 17b

ABUTH % Control

| Composition | 50 g a.e./ha | 100 g a.e./ha | 200 g a.e./ha | 400 g a.e./ha |
|---|---|---|---|---|
| 139 | 0.0 | 14.2 | 50.0 | 85.8 |
| 360 | 0.0 | 55.0 | 90.8 | 99.5 |
| 553 | 42.5 | 82.5 | 95.3 | 99.7 |
| 488A6Y | 1.7 | 72.5 | 85.8 | 90.8 |
| 488B5G | 0.0 | 63.3 | 70.0 | 93.0 |
| 488C7U | 5.8 | 29.2 | 66.7 | 92.7 |
| 488D5H | 6.7 | 56.7 | 52.5 | 94.5 |
| 488E4J | 5.0 | 51.7 | 80.8 | 93.0 |
| 488F2Z | 16.7 | 55.0 | 87.0 | 88.2 |
| 488G8Q | 16.7 | 72.5 | 91.7 | 99.2 |
| 488H7M | 15.0 | 42.5 | 85.0 | 95.8 |
| 488I5T | 17.5 | 62.5 | 82.5 | 97.8 |
| 488J3T | 11.7 | 59.2 | 85.8 | 99.2 |
| 488K9S | 37.5 | 27.5 | 81.7 | 92.7 |
| 488L3A | 0.0 | 30.8 | 75.0 | 91.3 |
| 488M5S | 8.3 | 13.3 | 55.8 | 88.3 |
| 488N7Z | 6.7 | 26.7 | 80.8 | 89.8 |
| 488O8T | 1.7 | 50.0 | 89.2 | 95.0 |
| 488P9H | 16.7 | 39.2 | 84.2 | 99.0 |
| 488Q7G | 10.8 | 29.2 | 89.2 | 95.3 |
| 488R3E | 8.3 | 45.0 | 87.5 | 97.0 |

TABLE 17c

ECHCF % Control

| Composition | 50 g a.e./ha | 100 g a.e./ha | 200 g a.e./ha | 400 g a.e./ha |
|---|---|---|---|---|
| 130 | 0.0 | 6.7 | 51.7 | 71.7 |
| 360 | 52.5 | 69.2 | 83.3 | 95.8 |
| 553 | 60.8 | 73.3 | 90.0 | 96.7 |
| 488A6Y | 48.3 | 67.5 | 79.2 | 95.5 |
| 488B5G | 18.3 | 54.2 | 70.8 | 81.7 |
| 488C7U | 0.0 | 30.0 | 65.0 | 75.0 |
| 488D5H | 0.0 | 31.7 | 63.3 | 75.8 |
| 488E4J | 19.2 | 60.0 | 70.0 | 80.8 |
| 488F2Z | 13.3 | 55.0 | 74.2 | 88.3 |
| 488G8Q | 38.3 | 64.2 | 85.8 | 98.3 |
| 488H7M | 44.2 | 72.5 | 93.2 | 97.3 |
| 488I5T | 34.2 | 62.5 | 73.3 | 92.5 |
| 488J3T | 25.0 | 50.0 | 83.3 | 98.2 |
| 488K9S | 37.5 | 60.8 | 73.3 | 87.5 |
| 488L3A | 3.3 | 19.2 | 66.7 | 75.8 |
| 488M5S | 3.3 | 44.2 | 65.0 | 75.0 |
| 488N7Z | 5.0 | 55.0 | 72.5 | 91.7 |
| 488O8T | 5.0 | 56.7 | 68.3 | 90.7 |
| 488P9H | 50.8 | 68.3 | 87.5 | 100.0 |
| 488Q7G | 54.2 | 71.7 | 79.2 | 98.3 |
| 488R3E | 36.7 | 44.2 | 70.8 | 93.2 |

Results for ABUTH and ECHCF: The best formulation overall was the 553 standard as it was more active than all of the test formulations. The formulations containing the potassium salt tended to have more activity than the corresponding IPA salts.

Example 18

Aqueous concentrate compositions were prepared containing glyphosate salt and excipient ingredients as shown in Table 18a.

TABLE 18a

| Comp. | Salt | g/l | Component 1 | wt. % | Component 2 | wt. % |
|---|---|---|---|---|---|---|
| 863A9W | IPA | 62 | MS10 | 2.00% | | |
| 863B8M | IPA | 62 | MS10 | 1.00% | HET20 | 1.00% |
| 863C4G | IPA | 62 | DUO50 | 1.00% | | |
| 863D6S | IPA | 62 | DUO50 | 0.50% | HET20 | 1.00% |
| 863E2N | IPA | 62 | ARQ50 | 1.00% | | |
| 863F7X | IPA | 62 | ARQ50 | 0.50% | HET20 | 1.00% |
| 863G3B | IPA | 62 | | | HET20 | 2.00% |

Velvetleaf (ABUTH) plants were grown and treated by the standard procedures above. The compositions of Table 18a and comparative compositions 139 and 360 were applied. Results are shown in Table 18b for two tests.

TABLE 18b

ABUTH % Control

| Composition | 100 a.e. g/ha | 200 a.e. g/ha | 300 a.e. g/ha | 400 a.e. g/ha | 100 a.e. g/ha | 200 a.e. g/ha | 300 a.e. g/ha | 400 a.e. g/ha |
|---|---|---|---|---|---|---|---|---|
| 139 | 0 | 3.3 | 60 | 75 | 0 | 5 | 51.7 | 76.7 |
| 360 | 1 | 53.3 | 86.3 | 98.3 | 1.7 | 48.3 | 91.7 | 95.3 |
| 863A9W | 3.3 | 60 | 81.7 | 87.7 | 1.7 | 60 | 83.7 | 87.7 |
| 863B8M | 3.3 | 61.7 | 93 | 98.7 | 1.7 | 65 | 93 | 97.7 |
| 863C4G | 3.3 | 5 | 73.3 | 82.7 | 0 | 23.3 | 71.7 | 82.7 |
| 863D6S | 1.7 | 58.3 | 88.3 | 94.3 | 0 | 61.7 | 92.3 | 98.3 |
| 863E2N | 45 | 33.3 | 75 | 85.7 | 36.7 | 33.3 | 73.3 | 88 |
| 863F7X | 0 | 61.7 | 86.7 | 97.3 | 1.7 | 66.7 | 87.3 | 98.3 |
| 863G3B | 1.7 | 61.7 | 85 | 90 | 5 | 63.3 | 79.3 | 95 |

Results for ABUTH: The formulation of 863E2N showed the best efficacy and was more efficacious than the standard of 360 at the rate of 100 ae g/ha. At 200 ae g/ha 863B8M, 863F7X, and 863G3B were more effective than the standard of 360 for ABUTH.

Example 19

Aqueous concentrate compositions were prepared containing glyphosate salt and excipient ingredients as shown in Table 19a.

TABLE 19a

| Comp. | Salt | g/l | Component 1 | wt. % | Component 2 | wt. % |
|---|---|---|---|---|---|---|
| 348A2W | IPA | 62 | HET20 | 2.00% | | |
| 348B6M | IPA | 62 | | | S89 | 2.00% |
| 348C9X | IPA | 62 | HET20 | 1.75% | S89 | 0.25% |
| 863D6V | IPA | 62 | | | S88 | 2.00% |
| 348E2N | IPA | 62 | HET20 | 1.70% | S88 | 0.30% |
| 348F2S | IPA | 62 | | | S90 | 2.00% |
| 348G4K | IPA | 62 | HET20 | 1.40% | S90 | 0.60% |

Velvetleaf (ABUTH) and Japanese millet (ECHCF) plants were grown and treated by the standard procedures above. The compositions of Table 19a and comparative compositions 139 and 360 were applied. Results are shown in Table 19b and Table 19c for two tests.

TABLE 19b

ABUTH % Control

| Composition | 100 a.e. g/ha | 200 a.e. g/ha | 300 a.e. g/ha | 400 a.e. g/ha | 100 a.e. g/ha | 200 a.e. g/ha | 300 a.e. g/ha | 400 a.e. g/ha |
|---|---|---|---|---|---|---|---|---|
| 139 | 5 | 28.3 | 56.7 | 60 | 50 | 45 | 65 | 66.7 |
| 360 | 60 | 81 | 87.7 | 95 | 56.7 | 83.3 | 93.7 | 94.3 |
| 348A2W | 70 | 85 | 93 | 95 | 71.7 | 81.7 | 95 | 93.7 |
| 348B6M | 0 | 45 | 68.3 | 65 | 5 | 38.3 | 68.3 | 66.7 |
| 348C9X | 68.3 | 90 | 93.3 | 94.3 | 70 | 84 | 92 | 94.3 |
| 863D6V | 5 | 46.7 | 66.7 | 70 | 6.7 | 51.7 | 68.3 | 70 |
| 348E2N | 71.7 | 85 | 92 | 96.3 | 73.3 | 85 | 95.7 | 95.7 |
| 348F2S | 5 | 41.7 | 65 | 63.3 | 46.7 | 61.7 | 78.3 | 80 |
| 348G4K | 70 | 81.7 | 93.7 | 95.7 | 58.3 | 81.7 | 83.3 | 93.7 |

TABLE 19c

ECHCF % Control

| Composition | 100 a.e. g/ha | 200 a.e. g/ha | 300 a.e. g/ha | 400 a.e. g/ha | 100 a.e. g/ha | 200 a.e. g/ha | 300 a.e. g/ha | 400 a.e. g/ha |
|---|---|---|---|---|---|---|---|---|
| 139 | 16.7 | 36.7 | 36.7 | 43.3 | 23.3 | 35 | 40 | 41.7 |
| 360 | 38.3 | 45 | 81.7 | 83.3 | 40 | 65 | 83.3 | 86.7 |
| 348A2W | 36.7 | 40 | 75 | 80 | 46.7 | 48.3 | 63.3 | 81.7 |
| 348B6M | 26.7 | 30 | 41.7 | 53.3 | 15 | 43.3 | 41.7 | 48.3 |
| 348C9X | 28.3 | 53.3 | 71.7 | 78.3 | 31.7 | 50 | 73.3 | 86.7 |
| 863D6V | 25 | 36.7 | 38.3 | 48.3 | 23.3 | 40 | 41.7 | 46.7 |
| 348E2N | 45 | 38.3 | 81.7 | 83.3 | 30 | 63.3 | 78.3 | 88.3 |
| 348F2S | 33.3 | 36.7 | 43.3 | 43.3 | 33.3 | 38.3 | 43.3 | 48.3 |
| 348G4K | 38.3 | 43.3 | 78.3 | 86.7 | 30 | 50 | 60 | 86.7 |

Results for ABUTH and ECHCF: The formulations of 348A2W, 348C9X, 348E2N and 348G4K and the standard 360 provided higher levels of control for ABUTH at all test rates and for ECHCF at test rates of 300 and 400 ae g/ha.

Example 20

Aqueous concentrate compositions were prepared containing glyphosate salt and excipient ingredients as shown in Table 20a.

TABLE 20a

| Comp. | Salt | g/l | Component 1 | g/l | Component 2 | g/l |
|---|---|---|---|---|---|---|
| 471A5W | IPA | 30 | S40 | 2.3 | BRI35 | 7.7 |
| 471B9X | IPA | 30 | S41 | 2.6 | BRI35 | 7.4 |
| 471C3N | IPA | 30 | S39 | 2.9 | BRI35 | 7.1 |
| 471D7S | IPA | 30 | S40 | 2.3 | BRI35 | 7.7 |
| 471E8C | IPA | 30 | S41 | 2.6 | BRI35 | 7.4 |
| 471F4A | IPA | 30 | S39 | 2.9 | BRI35 | 7.1 |

Velvetleaf (ABUTH) and Japanese millet (ECHCF) plants were grown and treated by the standard procedures above. The compositions of Table 20a and comparative compositions 139 and 360 were applied. Results, averaged for all replicates of each treatment, are shown in Table 20b and 20c.

TABLE 20b

ABUTH % Control

| Composition | 50 g a.e./ha | 100 g a.e./ha | 200 g a.e./ha | 400 g a.e./ha |
|---|---|---|---|---|
| 139 | 5.0 | 58.3 | 85.0 | 90.8 |
| 360 | 10.0 | 74.2 | 91.5 | 99.5 |
| 471A5W | 16.7 | 67.5 | 90.0 | 97.3 |
| 471B9X | 20.0 | 40.8 | 85.8 | 98.7 |
| 471C3N | 11.7 | 72.5 | 90.8 | 99.0 |
| 471D7S | 51.7 | 85.8 | 94.7 | 99.7 |
| 471E8C | 46.7 | 83.3 | 92.2 | 99.2 |
| 471F4A | 65.0 | 86.7 | 95.2 | 100.0 |

TABLE 20c

ECHCF % Control

| Composition | 50 g a.e./ha | 100 g a.e./ha | 200 g a.e./ha | 400 g a.e./ha |
|---|---|---|---|---|
| 139 | 33.3 | 55.8 | 66.7 | 75.0 |
| 360 | 68.3 | 74.2 | 83.3 | 99.5 |
| 471A5W | 67.5 | 73.3 | 89.2 | 99.8 |
| 471B9X | 60.0 | 70.0 | 80.0 | 95.0 |
| 471C3N | 65.0 | 42.5 | 88.3 | 99.2 |
| 471D7S | 60.8 | 76.7 | 79.2 | 93.2 |
| 471E8C | 56.7 | 73.3 | 88.8 | 100.0 |
| 471F4A | 67.5 | 73.3 | 80.0 | 99.0 |

Results for ABUTH and ECHCF: The best formulations overall were 471D7S and 471F4A. Both 471D7S and 471F4A provided greater activity on ABUTH than the standard of 360, and provided similar activity on ECHCF to the standard 360. The formulation of 471E8C also provided better activity on ABUTH than did the standard 360.

Example 21

Aqueous concentrate compositions were prepared containing glyphosate salt and excipient ingredients as shown in Table 21a.

TABLE 21a

| Comp. | Salt | g/l | Component 1 | g/l | Component 2 | g/l |
|---|---|---|---|---|---|---|
| 471C3Q | IPA | 30 | S39 | 7.1 | BRI35 | 2.9 |
| 471F6W | IPA | 30 | S39 | 7.1 | BRI78 | 2.9 |
| 457C2M | IPA | 30 | S39 | 7.0 | BRI58 | 3.0 |
| 471A8C | IPA | 30 | S40 | 7.7 | BRI35 | 2.3 |
| 471D7A | IPA | 30 | S40 | 7.7 | BRI78 | 2.3 |
| 457A9J | IPA | 30 | S40 | 7.5 | BRI58 | 2.5 |
| 480A2K | IPA | 30 | | | BRI35 | 10.0 |
| 480B3V | IPA | 30 | | | BRI78 | 10.0 |
| 480C6N | IPA | 30 | | | BRI58 | 10.0 |

Velvetleaf (ABUTH) and Japanese millet (ECHCF) plants were grown and treated by the standard procedures above. The compositions of Table 21a and comparative compositions 139 and 360 were applied. Results, averaged for all replicates of each treatment, are shown in Table 21b and 21c.

TABLE 21b

ABUTH % Control

| Composition | 50 g a.e./ha | 100 g a.e./ha | 200 g a.e./ha | 400 g a.e./ha |
|---|---|---|---|---|
| 139 | 3.3 | 69.2 | 81.7 | 92.7 |
| 360 | 42.5 | 86.7 | 94.3 | 99.0 |
| 457A9J | 55.8 | 85.8 | 91.3 | 99.2 |

TABLE 21b-continued

ABUTH % Control

| Composition | 50 g a.e./ha | 100 g a.e./ha | 200 g a.e./ha | 400 g a.e./ha |
|---|---|---|---|---|
| 457C2M | 68.3 | 87.5 | 94.2 | 99.2 |
| 471A8C | 62.5 | 83.3 | 90.0 | 98.5 |
| 471C3Q | 46.7 | 79.2 | 92.5 | 96.2 |
| 471D7A | 63.3 | 88.3 | 96.5 | 99.2 |
| 471F6W | 75.8 | 88.3 | 94.3 | 100.0 |
| 480A2K | 50.8 | 82.5 | 89.7 | 97.0 |
| 480B3V | 58.3 | 88.3 | 94.7 | 99.2 |
| 480C6N | 54.2 | 83.3 | 92.8 | 98.0 |

TABLE 21c

ECHCF % Control

| Composition | 50 g a.e./ha | 100 g a.e./ha | 200 g a.e./ha | 400 g a.e./ha |
|---|---|---|---|---|
| 139 | 12.5 | 65.0 | 56.7 | 73.3 |
| 360 | 65.0 | 77.5 | 85.5 | 98.2 |
| 457A95 | 65.8 | 75.0 | 77.5 | 96.7 |
| 457C2M | 68.3 | 78.3 | 80.8 | 99.0 |
| 471A8C | 57.5 | 73.3 | 80.8 | 95.8 |
| 471C3Q | 59.2 | 72.5 | 84.2 | 93.3 |
| 471D7A | 66.7 | 71.7 | 78.3 | 94.2 |
| 471F6W | 60.0 | 72.5 | 90.0 | 96.7 |
| 480A2K | 65.8 | 75.0 | 86.7 | 99.8 |
| 480B3V | 62.5 | 72.5 | 84.2 | 97.3 |
| 480C6N | 48.3 | 71.7 | 89.2 | 100.0 |

Example 22

Aqueous concentrate compositions were prepared containing glyphosate salt and excipient ingredients as shown in Table 22a.

TABLE 22a

| Comp. | Salt | g/l | Component 1 | g/l |
|---|---|---|---|---|
| 623A8W | K | 30 | S10 | 10.0 |
| 623B3M | K | 30 | S11 | 10.0 |
| 623C6J | K | 4.3 | S91 | 1.4 |
| 623D2S | K | 30 | S07 | 10.0 |
| 623E9J | K | 30 | S92 | 10.0 |
| 623F7G | K | 30 | S93 | 10.0 |
| 623G3E | K | 30 | S94 | 10.0 |
| 623H9R | K | 30 | S95 | 10.0 |

Velvetleaf (ABUTH) and Japanese millet (ECHCF) plants were grown and treated by the standard procedures above. The compositions of Table 22a and comparative compositions 554, 754 and 553 were applied. Results, averaged for all replicates of each treatment, are shown in Table 22b and 22c.

TABLE 22b

ABUTH % Control

| Composition | 75 g a.e./ha | 150 g a.e./ha | 225 g a.e./ha | 300 g a.e./ha |
|---|---|---|---|---|
| 554 | 0.0 | 4.2 | 22.5 | 55.8 |
| 754 | 0.0 | 56.7 | 79.2 | 85.8 |
| 553 | 31.7 | 79.2 | 90.8 | 94.5 |
| 623A8W | 57.5 | 85.8 | 90.8 | 95.5 |
| 623B3M | 31.7 | 73.3 | 90.0 | 90.8 |
| 623C6J | 25.8 | 29.2 | 66.7 | 75.8 |
| 623D2S | 36.7 | 82.5 | 90.0 | 96.5 |

TABLE 22b-continued

ABUTH % Control

| Composition | 75 g a.e./ha | 150 g a.e./ha | 225 g a.e./ha | 300 g a.e./ha |
|---|---|---|---|---|
| 623E9J | 65.0 | 87.5 | 91.7 | 95.0 |
| 623F7G | 72.5 | 90.0 | 93.3 | 96.8 |
| 623G3E | 55.2 | 80.8 | 87.5 | 93.2 |
| 623H9R | 62.5 | 83.3 | 92.5 | 93.3 |

TABLE 22c

ECHCF % Control

| Composition | 75 g a.e./ha | 150 g a.e./ha | 225 g a.e./ha | 300 g a.e./ha |
|---|---|---|---|---|
| 554 | 0.0 | 0.0 | 47.5 | 48.3 |
| 754 | 8.3 | 65.0 | 71.7 | 76.7 |
| 553 | 45.8 | 71.7 | 74.2 | 76.7 |
| 623A8W | 46.7 | 67.5 | 72.5 | 71.7 |
| 623B3M | 40.8 | 69.2 | 72.5 | 74.2 |
| 623C6J | 1.7 | 54.2 | 66.7 | 71.7 |
| 623D2S | 36.7 | 65.0 | 72.5 | 75.8 |
| 623E9J | 50.0 | 70.8 | 75.0 | 75.8 |
| 623F7G | 25.8 | 64.2 | 73.3 | 75.8 |
| 623G3E | 42.5 | 68.3 | 70.8 | 75.0 |
| 623H9R | 34.2 | 70.0 | 74.2 | 76.7 |

Results for ABUTH and ECHCF: The most active formulation tested for ABUTH was 623F7G. Several formulations showed comparable activity for ECHF.

Example 23

Aqueous concentrate compositions were prepared containing glyphosate salt and excipient ingredients as shown in Table 23a.

TABLE 23a

| Comp. | Salt | g/l | Component 1 | g/l | Component 2 | g/l |
|---|---|---|---|---|---|---|
| 755A8W | K | 4.3 | S96 | 1.4 | | |
| 755B7V | K | 4.3 | S91 | 1.4 | | |
| 757A3R | K | 4.3 | S97 | 1.4 | | |
| 755D9Z | K | 4.3 | S96 | 0.7 | S19 | 0.7 |
| 755E1H | K | 4.3 | S91 | 0.7 | S19 | 0.7 |
| 755F6S | K | 4.3 | S97 | 0.9 | S19 | 0.5 |
| 755G8E | K | 4.3 | | | S19 | 1.4 |

Velvetleaf (ABUTH) and Japanese millet (ECHCF) plants were grown and treated by the standard procedures above. The compositions of Table 23a and comparative compositions 554, 360 and 553 were applied. Results, averaged for all replicates of each treatment, are shown in Table 23b and 23c.

TABLE 23b

ABUTH % Control

| Composition | 75 g a.e./ha | 150 g a.e./ha | 225 g a.e./ha | 300 g a.e./ha |
|---|---|---|---|---|
| 554 | 0.0 | 49.2 | 70.0 | 80.8 |
| 360 | 40.0 | 81.7 | 89.2 | 90.0 |
| 553 | 72.5 | 87.5 | 90.0 | 92.0 |
| 755A8W | 23.3 | 66.7 | 79.2 | 84.2 |
| 755B7V | 3.3 | 62.5 | 78.3 | 85.0 |
| 757A3R | 39.2 | 76.7 | 83.3 | 85.8 |
| 755D9Z | 38.3 | 81.7 | 85.0 | 87.5 |
| 755E1H | 58.3 | 80.0 | 85.0 | 85.0 |

TABLE 23b-continued

ABUTH % Control

| Composition | 75 g a.e./ha | 150 g a.e./ha | 225 g a.e./ha | 300 g a.e./ha |
|---|---|---|---|---|
| 755F6S | 54.2 | 75.8 | 85.8 | 86.7 |
| 755G8E | 7.5 | 10.0 | 3.3 | 1.7 |

TABLE 23c

ECHCF % Control

| Composition | 75 g a.e./ha | 150 g a.e./ha | 225 g a.e./ha | 300 g a.e./ha |
|---|---|---|---|---|
| 554 | 0.0 | 6.7 | 37.5 | 43.3 |
| 360 | 35.8 | 69.2 | 75.8 | 80.8 |
| 553 | 65.8 | 72.5 | 81.7 | 85.8 |
| 755A8W | 0.0 | 58.3 | 69.2 | 72.5 |
| 755B7V | 5.0 | 52.5 | 71.7 | 74.2 |
| 757A3R | 6.7 | 42.5 | 67.5 | 70.0 |
| 755D9Z | 0.0 | 62.5 | 71.7 | 74.2 |
| 755E1H | 11.7 | 54.2 | 70.8 | 72.5 |
| 755F6S | 1.7 | 57.5 | 70.8 | 76.7 |
| 755G8E | 0.0 | 0.0 | 0.0 | 0.0 |

Results for ABUTH and ECHCF: The most active and efficacious formulations tested for ABUTH and ECHCF were the standards 360 and 553.

Example 24

Aqueous concentrate compositions were prepared containing glyphosate salt and excipient ingredients as shown in Table 24a.

TABLE 24a

| Comp. | Salt | g/l | Component 1 | g/l |
|---|---|---|---|---|
| 469A7S | K | 30 | S65 | 10.0 |
| 469B3M | K | 30 | S98 | 10.0 |
| 469A8A | K | 30 | S20 | 10.0 |
| 469D2N | K | 30 | S09 | 10.0 |

Velvetleaf (ABUTH) and Japanese millet (ECHCF) plants were grown and treated by the standard procedures above. The compositions of Table 24a and comparative compositions 139, and 360 were applied. Results, averaged for all replicates of each treatment, are shown in Table 24b and 24c.

TABLE 24b

ABUTH % Control

| Composition | 50 g a.e./ha | 100 g a.e./ha | 200 g a.e./ha | 400 g a.e./ha |
|---|---|---|---|---|
| 139 | 0.0 | 50.0 | 71.7 | 90.8 |
| 360 | 33.3 | 70.0 | 88.0 | 99.0 |
| 469A7S | 2.5 | 48.3 | 73.3 | 93.2 |
| 469B3M | 4.2 | 49.2 | 78.3 | 93.3 |
| 469A8A | 10.0 | 67.5 | 84.2 | 97.7 |
| 469D2N | 10.8 | 70.8 | 88. | 97.5 |

TABLE 24c

| | ECHCF % Control | | | |
|---|---|---|---|---|
| Composition | 50 g a.e./ha | 100 g a.e./ha | 200 g a.e./ha | 400 g a.e./ha |
| 139 | 10.0 | 46.7 | 55.8 | 70.8 |
| 360 | 49.2 | 77.5 | 98.3 | 97.5 |
| 469A7S | 25.8 | 50.8 | 66.7 | 75.8 |
| 469B3M | 24.2 | 57.5 | 62.5 | 75.8 |
| 469A8A | 27.5 | 51.7 | 72.5 | 79.2 |
| 469D2N | 49.2 | 65.8 | 75.8 | 92.8 |

Results for ABUTH and ECHCF: All of the test formulations outperformed the standard of 139 for ECHCF. Also three of the four tested formulations outperformed the standard of 139 for ABUTH. The standard of 360 was the most active formulation on both ABUTH and ECHCF.

Example 25

Aqueous concentrate compositions were prepared containing glyphosate salt and excipient ingredients as shown in Table 25a.

TABLE 25a

| Comp. | Salt | g/l | Component 1 | g/l | Component 2 | g/l |
|---|---|---|---|---|---|---|
| 659B6S | K | 480.00 | MPE01 | 120.0 | | |
| 659C8Q | K | 480.00 | EA175 | 120.0 | | |
| 659D4B | K | 480.00 | ED175 | 120.0 | | |
| 664B7E | K | 480.00 | EA175 | 108.0 | ED175 | 12.0 |
| 664A3G | K | 480.00 | EA175 | 96.0 | ED175 | 24.0 |
| 662C1R | K | 480.00 | EA175 | 90.0 | ED175 | 30.0 |
| 662D9S | K | 480.00 | EA175 | 60.0 | ED175 | 60.0 |
| 360 | K | 480.00 | EA175 | | | |
| 754 | K | 480.00 | EA175 | | | |
| 560 | K | 480.00 | EA175 | 121 | | 135 |

Velvetleaf (ABUTH) and Japanese millet (ECHCF) plants were grown and treated by the standard procedures above. The compositions of Table 25a and comparative compositions 754, 560 and 360 were applied. Results, averaged for all replicates of each treatment, are shown in Table 25b and 25c.

TABLE 25b

| | ABUTH % Control | | | |
|---|---|---|---|---|
| Composition | 100 g a.e./ha | 200 g a.e./ha | 300 g a.e./ha | 400 g a.e./ha |
| 754 | 14.2 | 81.7 | 85.8 | 90.8 |
| 360 | 48.3 | 80.0 | 88.3 | 90.0 |
| 560 | 40.0 | 74.2 | 85.0 | 89.2 |
| 659B6S | 24.2 | 72.5 | 81.7 | 85.8 |
| 659C8Q | 10.0 | 73.3 | 80.8 | 85.0 |
| 659D4B | 23.3 | 69.2 | 82.5 | 84.2 |

TABLE 25b-continued

| | ABUTH % Control | | | |
|---|---|---|---|---|
| Composition | 100 g a.e./ha | 200 g a.e./ha | 300 g a.e./ha | 400 g a.e./ha |
| 664B7E | 12.5 | 75.0 | 82.5 | 85.8 |
| 664A3G | 61.7 | 76.7 | 82.5 | 86.7 |
| 662C1R | 43.3 | 79.2 | 82.5 | 85.0 |
| 662D9S | 74.2 | 79.2 | 81.7 | 85.0 |

TABLE 25c

| | ECHCF % Control | | | |
|---|---|---|---|---|
| Composition | 100 g a.e./ha | 200 g a.e./ha | 300 g a.e./ha | 400 g a.e./ha |
| 754 | 5.0 | 58.3 | 72.5 | 79.2 |
| 360 | 13.3 | 58.3 | 72.5 | 80.0 |
| 560 | 15.0 | 55.8 | 64.2 | 68.3 |
| 659B6S | 15.0 | 51.7 | 60.0 | 64.2 |
| 659C8Q | 22.5 | 53.3 | 65.0 | 67.5 |
| 659D4B | 27.5 | 60.0 | 59.2 | 66.7 |
| 664B7E | 26.7 | 55.0 | 62.5 | 70.0 |
| 664A3G | 34.2 | 52.5 | 60.0 | 67.5 |
| 662C1R | 32.5 | 55.0 | 66.7 | 70.8 |
| 662D9S | 35.0 | 55.0 | 66.7 | 72.5 |

Results for ABUTH and ECHCF: The formulation of 662D9S was nearly equal in efficacy to the standard of 360 for overall performance.

Example 26

Aqueous concentrate compositions were prepared containing glyphosate salt and excipient ingredients as shown in Table 26a.

TABLE 26a

| Comp. | Salt | g/l | Component 1 | g/l |
|---|---|---|---|---|
| 206A2W | IPA | 480.00 | T003A | 120.0 |
| 206B4G | MEA | 480.00 | T003A | 120.0 |
| 206C8S | K | 480.00 | T003A | 120.0 |
| 206D3N | IPA | 480.00 | T003B | 120.0 |
| 206E7X | MEA | 480.00 | T003B | 120.0 |
| 206F1A | IPA | 480.00 | T003C | 120.0 |
| 206G9A | MEA | 480.00 | T003C | 120.0 |
| 206H6N | IPA | 480.00 | T003D | 120.0 |
| 206I2D | IPA | 480.00 | T003E | 120.0 |
| 360 | IPA | 360 | | |
| 754 | IPA | 445 | WIT05 | 5.9 |
| 280 | IPA | 480 | M121 | 120 |
| 128 | MEA | 480 | M121 | 120 |

Velvetleaf (ABUTH) and Japanese millet (ECHCF) plants were grown and treated by the standard procedures above. The compositions of Table 26a and comparative compositions 754, 128 and 280 were applied. Results, averaged for all replicates of each treatment, are shown in Table 26b and 26c.

TABLE 26b

ABUTH % Control

| Composition | 100 g a.e./ha | 200 g a.e./ha | 300 g a.e./ha | 400 g a.e./ha |
|---|---|---|---|---|
| 754 | 30.0 | 80.0 | 86.0 | 96.0 |
| 206A2W | 0.0 | 67.0 | 81.0 | 84.0 |
| 206B4G | 1.0 | 70.0 | 81.0 | 84.0 |
| 206C8S | 60. | 68.0 | 82.0 | 84.0 |
| 206D3N | 8.0 | 60.0 | 82.0 | 84.0 |
| 206E7X | 17.0 | 73.0 | 82.0 | 84.0 |
| 206F1A | 22.0 | 71.0 | 81.0 | 85.0 |
| 206G9A | 33.0 | 76.0 | 82.0 | 85.0 |
| 206H6N | 21.0 | 75.0 | 83.0 | 87.0 |
| 206I2D | 26.0 | 66.0 | 83.0 | 86.0 |
| 128 | 42.0 | 82.0 | 86.0 | 93.0 |
| 280 | 38.0 | 80.0 | 86.0 | 92.0 |

TABLE 26c

ECHCF % Control

| Composition | 100 g a.e./ha | 200 g a.e./ha | 300 g a.e./ha | 400 g a.e./ha |
|---|---|---|---|---|
| 754 | 52.0 | 84.0 | 91.4 | 97.2 |
| 206A2W | 26.0 | 63.0 | 71.0 | 80.0 |
| 206B4G | 29.0 | 60.0 | 73.0 | 85.0 |
| 206C8S | 48.0 | 68.0 | 70.0 | 82.0 |
| 206D3N | 26.0 | 55.0 | 70.0 | 88.0 |
| 206E7X | 55.0 | 63.0 | 73.0 | 86.0 |
| 206F1A | 46.0 | 61.0 | 79.0 | 86.0 |
| 206G9A | 57.0 | 66.0 | 75.0 | 83.0 |
| 206H6N | 38.0 | 63.0 | 78.0 | 89.6 |
| 206I2D | 51.0 | 62.0 | 71.0 | 85.0 |
| 128 | 59.0 | 88.0 | 97.4 | 99.8 |
| 280 | 60.0 | 85.0 | 97.8 | 97.6 |

Results for ABUTH and ECHCF: No test formulation was as effective as the standards 754, 128, and 280 on both weeds tested.

Example 27

Aqueous concentrate compositions were prepared containing glyphosate salt and excipient ingredients as shown in Table 27a.

Velvetleaf (ABUTH) and Japanese millet (ECHCF) plants were grown and treated by the standard procedures above. The compositions of Table 27a and comparative compositions 360, 754, 139 and 554 were applied. Results, averaged for all replicates of each treatment, are shown in Table 27b and 27c.

TABLE 27b

ABUTH % Control

| Composition | 75 g a.e./ha | 100 g a.e./ha | 150 g a.e./ha | 200 g a.e./ha |
|---|---|---|---|---|
| 139 | 5.8 | 30.8 | 60.0 | 74.2 |
| 554 | 11.7 | 19.2 | 46.7 | 60.0 |
| 360 | 43.3 | 64.2 | 89.7 | 90.8 |
| 616A5F | 30.0 | 36.7 | 65.0 | 65.0 |
| 664A6H | 25.0 | 50.0 | 70.0 | 75.8 |
| 615C3M | 48.3 | 50.0 | 76.7 | 81.7 |
| 615D2M | 29.2 | 55.0 | 78.3 | 81.7 |
| 615E1F | 16.7 | 45.0 | 70.0 | 70.8 |
| 615F8C | 23.3 | 43.3 | 66.7 | 81.7 |
| 616G3S | 16.7 | 36.7 | 72.5 | 76.7 |
| 754 | 30.0 | 65.0 | 84.2 | 90.5 |

TABLE 27c

ECHCF % Control

| Composition | 75 g a.e./ha | 100 g a.e./ha | 150 g a.e./ha | 200 g a.e./ha |
|---|---|---|---|---|
| 139 | 30.8 | 33.3 | 39.2 | 56.7 |
| 554 | 15.0 | 33.3 | 37.5 | 55.0 |
| 360 | 81.7 | 95.5 | 98.8 | 99.2 |
| 616A5F | 40.0 | 45.0 | 62.5 | 69.2 |
| 664A6H | 65.0 | 75.8 | 93.8 | 95.2 |
| 615C3M | 73.3 | 77.5 | 86.7 | 93.5 |
| 615D2M | 62.5 | 86.7 | 98.0 | 98.0 |
| 615E1F | 75.0 | 91.2 | 93.2 | 99.0 |
| 615F8C | 75.8 | 85.0 | 97.3 | 98.8 |
| 616G3S | 77.5 | 91.5 | 96.3 | 99.2 |
| 754 | 72.5 | 87.5 | 98.0 | 99.0 |

Results for ABUTH and ECHCF: No formulation of this test was as efficacious on ABUTH as the standards of 360 and 754. The test formulations of 615C3M and 615D2M were the best for efficacy on ABUTH.

TABLE 27a

| Comp. | Salt | g/l | Compt. 1 | g/l | Compt. 2 | g/l | Compt. 3 | g/l |
|---|---|---|---|---|---|---|---|---|
| 616A5F | K | 540 | NDPA | 135.0 | | | | |
| 664A6H | K | 540 | M121 | 135.0 | | | | |
| 615C3M | K | 540 | ETH12 | 45.1 | WIT60 | 45.1 | SUR12 | 45.1 |
| 615D2M | K | 540 | ETH12 | 54.0 | WIT60 | 54.0 | SUR12 | 54.0 |
| 615E1F | K | 540 | ETH12 | 67.5 | WIT60 | 67.5 | SUR12 | 27.0 |
| 615F8C | K | 540 | ETH12 | 54.0 | WIT60 | 54.0 | SUR12 | 27.0 |
| 616G3S | K | 540 | ETH12 | 67.5 | WIT05 | 67.5 | | |
| 360 | | 360 | ETH12 | | | | | |
| 754 | | 445 | ETH12 | | | | | |

Example 28

Aqueous concentrate compositions were prepared containing glyphosate salt and excipient ingredients as shown in Table 28a.

TABLE 28a

| Comp. | Salt | g/l | Compt. 1 | g/l | Compt. 2 | g/l | Compt. 3 | g/l | Compt.4 | g/l |
|---|---|---|---|---|---|---|---|---|---|---|
| 5606H | K | 540 | M121 | 135 | | | | | | |
| 1289M | MEA | 480 | M121 | 120 | | | | | | |
| 2687J | K | 540 | ETH12 | 54 | WIT05 | 81 | AGN68 | 0.27 | | |
| 2693C | K | 540 | ETH12 | 81 | WIT05 | 54 | AGN68 | 0.27 | | |
| 2704X | K | 540 | ETH12 | 61 | WIT05 | 74 | AGN68 | 0.27 | CIT1 | 3.7 |
| 2716B | K | 480 | ETH12 | 48 | WIT80 | 48 | AGN68 | 0.27 | INT00 | 24 |
| 2724C | K | 540 | ETH12 | 61 | WIT05 | 74 | AGN68 | 0.27 | | |
| 4598H | K | 480 | M121 | 121 | | | GLYC | 51 | CIT01 | 3.5 |
| 4603D | K | 540 | M121 | 135 | | | | | CIT01 | 4 |
| 5633S | K | 540 | ETH12 | 60.8 | WIT05 | 74.3 | ARO66 | | GLYC | 102 |
| 7655R | K | 472 | ARMC | | WIT305 | | | | | |
| 360 | | 360 | | | | | | | | |
| 754 | | 445 | WIT05 | 5.9 | INT00 | 2.24 | | | | |

Velvetleaf (ABUTH) and Japanese millet (ECHCF) plants were grown and treated by the standard procedures above. The compositions of Table 28a and comparative compositions 360, and 754 were applied. Results, averaged for all replicates of each treatment, are shown in Table 28b and 28c.

TABLE 28b

ABUTH % Control

| Composition | 100 g a.e./ha | 200 g a.e./ha | 300 g a.e./ha | 400 g a.e./ha |
|---|---|---|---|---|
| 754 | 41.7 | 80.0 | 85.0 | 88.3 |
| 360 | 36.7 | 80.0 | 88.3 | 94.3 |
| 5606H | 5.0 | 78.3 | 81.7 | 86.7 |
| 1289M | 26.7 | 81.7 | 85.0 | 88.3 |
| 2687J | 0.0 | 76.7 | 81.7 | 83.3 |
| 2693C | 0.0 | 73.3 | 81.7 | 81.7 |
| 2704X | 0.0 | 75.0 | 76.7 | 80.0 |
| 2716B | 0.0 | 60.0 | 76.7 | 81.7 |
| 2724C | 3.3 | 60.0 | 78.3 | 81.7 |
| 4598H | 20.0 | 78.3 | 81.7 | 88.3 |
| 4603D | 1.7 | 73.3 | 80.0 | 88.3 |
| 5633S | 1.7 | 66.7 | 80.0 | 83.3 |
| 7655R | 1.7 | 71.7 | 80.0 | 88.3 |

TABLE 28c

ECHCF % Control

| Composition | 100 g a.e./ha | 200 g a.e./ha | 300 g a.e./ha | 400 g a.e./ha |
|---|---|---|---|---|
| 754 | 31.7 | 68.3 | 73.3 | 75.0 |
| 360 | 43.3 | 66.7 | 75.0 | 76.7 |
| 5606H | 26.7 | 70.0 | 71.7 | 71.7 |
| 1289M | 48.3 | 70.0 | 71.7 | 75.0 |
| 2687J | 20.0 | 65.0 | 68.3 | 70.0 |
| 2693C | 20.0 | 63.3 | 66.7 | 70.0 |
| 2704X | 16.7 | 63.3 | 66.7 | 70.0 |
| 2716B | 26.7 | 58.3 | 65.0 | 70.0 |
| 2724C | 30.0 | 65.0 | 68.3 | 70.0 |
| 4598H | 23.3 | 70.0 | 73.3 | 71.7 |
| 4603D | 30.0 | 66.7 | 70.0 | 71.7 |
| 5633S | 25.0 | 60.0 | 65.0 | 70.0 |
| 7655R | 26.7 | 70.0 | 71.7 | 75.0 |

Results for ABUTH and ECHCF: No formulations in this trial were as efficacious as standards 360 and 754 for ABUTH. However, most formulations were similar to the standard 754 for ECHCF.

Example 29

Aqueous concentrate compositions were prepared containing glyphosate salt and excipient ingredients as shown in Table 29a.

TABLE 29a

| Comp. | Salt | g/l | Component 1 | g/l | Component 2 | g/l |
|---|---|---|---|---|---|---|
| 553 | IPA | 360 | BRI56 | 6.4 | ETH25 | 9.6 |
| M368 | IPA | 31 | EUMU | 4.9 | TAM05 | 7.4 |
| M318 | K | 37 | EUMU | 4.9 | TAM80 | 7.4 |
| 992A6H | K | 480 | EUMU | 4.9 | TAM80 | 7.4 |
| 992B3D | K | 480 | B1A | 4.9 | TAM80 | 7.4 |
| 992C7X | K | 480 | B1B | 4.9 | TAM80 | 7.4 |
| 992D1G | K | 480 | B1C | 4.9 | TAM80 | 7.4 |
| 992E5R | K | 480 | B1F | 4.9 | TAM80 | 7.4 |
| 992F3E | K | 480 | EXP86 | 4.9 | TAM80 | 7.4 |

Velvetleaf (ABUTH) plants were grown and treated by the standard procedures above. The compositions of Table 29a and comparative compositions 553, 554 and 754 were applied. Results, averaged for all replicates of each treatment, are shown in Table 29b.

TABLE 29b

ABUTH % Control

| Composition | 75 g a.e./ha | 125 g a.e./ha | 175 g a.e./ha | 250 g a.e./ha |
|---|---|---|---|---|
| 553 | 13.3 | 65 | 82.5 | 88.3 |
| 754 | 0 | 26.7 | 51.7 | 80 |
| M318 | 6.7 | 48.3 | 70 | 79.2 |
| 554 | 0 | 0 | 0 | 1.7 |
| M368 | 0 | 14.2 | 65 | 77.5 |
| 992A6H | 19.2 | 35.8 | 64.2 | 75 |
| 992B3D | 8.3 | 55 | 65 | 84.2 |
| 992C7X | 20 | 56.7 | 70.8 | 81.7 |
| 992D1G | 0 | 38.3 | 69.2 | 79.2 |
| 992E5R | 19.2 | 52.5 | 77.5 | 83.3 |
| 992F3E | 1.7 | 55.8 | 70 | 84.2 |

Results for ABUTH: The 553 standard was the best formulation for efficacy in the test. M318 was less active than the 553 standard and more active than M368 and 754. M368 and 754 were similar in performance.

Example 30

Aqueous concentrate compositions were prepared containing glyphosate salt and excipient ingredients as shown in Table 30a.

TABLE 30a

| Comp. | Salt | g/l | Component 1 | wt. % | Component 2 | wt. % |
|---|---|---|---|---|---|---|
| 553 | IPA | 360 | BRI56 | 6.4 | ETH25 | 9.6 |
| M620 | IPA | 360 | BRI56 | 4.8 | ETH25 | 7.2 |
| M619 | IPA | 360 | BRI56 | 4 | ETH25 | 6 |
| 968A7F | K | 480 | EMUL | 4.8 | WIT80 | 7.2 |
| 968B4R | K | 480 | EXP86 | 4.8 | WIT80 | 7.2 |
| 968C9S | K | 480 | EMUL | 4.8 | WIT05 | 7.2 |
| 968D3E | K | 480 | EXP86 | 4.8 | WIT05 | 7.2 |
| 968E6V | K | 480 | EMUL | 4.8 | EMC42 | 7.2 |
| 968F2A | K | 480 | EXP86 | 4.8 | EMC42 | 7.2 |
| 968G5J | K | 480 |  | 12 | EMC42 | 6 |

Velvetleaf (ABUTH) and Japanese millet (ECHCF) plants were grown and treated by the standard procedures above. The compositions of Table 30a and comparative compositions 553, 554, and 360 were applied. Results, averaged for all replicates of each treatment, are shown in Table 30b and 30c.

TABLE 30b

ABUTH % Control

| Composition | 100 g a.e./ha | 150 g a.e./ha | 200 g a.e./ha | 300 g a.e./ha |
|---|---|---|---|---|
| 554 | 0 | 16 | 63 | 70 |
| 360 | 70 | 79 | 85 | 90 |
| 553 | 78 | 83 | 90 | 94 |
| M620 | 73 | 82 | 88 | 90 |
| M619 | 73 | 80 | 89 | 94 |
| 968A7F | 69 | 70 | 78 | 84 |
| 968B4R | 69 | 78 | 82 | 93 |
| 968C9S | 58 | 75 | 81 | 88 |
| 968D3E | 73 | 79 | 88 | 94 |
| 968E6V | 60 | 69 | 80 | 81 |
| 968F2A | 63 | 76 | 83 | 88 |
| 968G5J | 37 | 53 | 76 | 79 |

TABLE 30c

ECHCF % Control

| Composition | 100 g a.e./ha | 150 g a.e./ha | 200 g a.e./ha | 300 g a.e./ha |
|---|---|---|---|---|
| 554 | 0 | 6 | 15 | 24 |
| 360 | 44 | 56 | 73 | 81.6 |
| 553 | 54 | 70 | 77 | 82.8 |
| M620 | 50 | 62 | 73 | 85.8 |
| M619 | 51 | 67 | 79 | 91.6 |
| 968A7F | 36 | 57 | 59 | 62 |
| 968B4R | 39 | 55 | 63 | 75 |
| 968C9S | 40 | 56 | 55 | 68 |
| 968D3E | 34 | 56 | 64 | 71 |
| 968E6V | 20 | 47 | 58 | 66 |
| 968F2A | 22 | 46 | 56 | 58 |
| 968G5J | 14 | 41 | 55 | 58 |

Results for ABUTH and ECHCF: The best performing test formulation in this test overall was 968B4R.

Example 31

Aqueous concentrate compositions were prepared containing glyphosate salt and excipient ingredients as shown in Table 31a.

TABLE 31a

| Comp. | Salt | g/l | Component 1 | g/l | Component 2 | g/l |
|---|---|---|---|---|---|---|
| 730A0A | K | 30 | S2 | 10 |  |  |
| 730C7U | K | 30 | S1 | 10 |  |  |
| 730D7C | K | 30 | 1816E | 10 |  |  |
| 487H3K | K | 4.3 | S2 | 0.7 | BRI 56 | 0.7 |
| 487I2W | K | 4.3 | S1 | 0.9 | BRI 56 | 0.5 |
| 487L99I | K | 4.3 | 1816E | 0.8 | BRI 56 | 0.6 |
| 496C7Y | K | 30 | Eth25 | 5.8 | BRI 56 | 4.2 |
| 730E8J | K | 30 | Eth25 | 10 |  |  |
| 731A9T | K | 4.3 |  |  | BRI 56 | 1.4 |

Velvetleaf (ABUTH) and Japanese millet (ECHCF) plants were grown and treated by the standard procedures above. The compositions of Table 31a and comparative compositions 139, 553 and 360 were applied. Results, averaged for all replicates of each treatment, are shown in Table 31b and 31c.

TABLE 31b

ABUTH % Control

| Composition | 75 g a.e./ha | 150 g a.e./ha | 225 g a.e./ha | 300 g a.e./ha |
|---|---|---|---|---|
| 139 | 0 | 60 | 73.8 | 80 |
| 360 | 40 | 80 | 92 | 91.3 |
| 553 | 50 | 82.5 | 93.3 | 90 |
| 730A0A | 62.5 | 81.3 | 91.3 | 94.8 |
| 730C7U | 78.8 | 90 | 97.8 | 96 |
| 730D7C | 72.5 | 87.5 | 97.8 | 96 |
| 487H3K | 52.5 | 77.5 | 90 | 92.5 |
| 487I2W | 60 | 80 | 95.8 | 95.8 |
| 487L9I | 68.8 | 80 | 92.5 | 88.8 |
| 496C7Y | 66.3 | 82.5 | 92.5 | 88.8 |
| 730E8J | 53.8 | 80 | 91.3 | 91.3 |
| 731A9T | 5 | 73.8 | 86.3 | 90 |

TABLE 31c

ECHCF % Control

| Composition | 75 g a.e./ha | 150 g a.e./ha | 225 g a.e./ha | 300 g a.e./ha |
|---|---|---|---|---|
| 139 | 26.3 | 62.5 | 63.8 | 71.3 |
| 360 | 63.8 | 81.3 | 85 | 97.5 |
| 553 | 66.3 | 78.8 | 86.3 | 94.8 |
| 730A0A | 65 | 81.3 | 80 | 93.5 |
| 730C7U | 68.8 | 80 | 93.8 | 92.5 |
| 730D7C | 67.5 | 77.5 | 88.8 | 92.3 |
| 487H3K | 62.5 | 77.5 | 80 | 87.3 |
| 487I2W | 61.3 | 88.3 | 85 | 94.8 |
| 487L9I | 62.5 | 76.3 | 91.3 | 87.5 |
| 496C7Y | 62.5 | 78.8 | 82.5 | 95 |
| 730E8J | 62.5 | 78.8 | 84.8 | 87.5 |
| 731A9T | 21.3 | 73.8 | 76.3 | 76.3 |

Results for ABUTH and ECHCF: Composition 730C7U was the most active formulation in this experiment and exhibited enhanced herbicidal effectiveness to comparative composition 360 across all rates for velvetleaf (ABUTH) and similar herbicidal effectiveness to comparative composition 360 for grass (ECHCF). Composition 730AOA exhibited similar herbicidal effectiveness to comparative composition 360 for grass (ECHCF) but exhibited enhanced herbicidal effectiveness to comparative compositions for velvetleaf (ABUTH) at the high and low rates.

Example 32

Aqueous concentrate compositions were prepared containing glyphosate salt and excipient ingredients as shown in Table 32a.

TABLE 32a

| Comp. | Salt | % | Component 1 | % | Component 2 | % |
|---|---|---|---|---|---|---|
| 553 | K | 31 | BRI 56 | 6.4 | Eth25 | 9.6 |
| 966A7A | K | 39 | | 12 | WIT80 | 6 |
| 966B2W | K | 36.9 | | 12 | WIT80 | 5 |
| 966C5T | K | 36.9 | | 12 | WIT80 | 5 |
| 966D8J | K | 36.9 | | 12 | WIT80 | 5 |

Velvetleaf (ABUTH) and Japanese millet (ECHCF) plants were grown and treated by the standard procedures above. The compositions of Table 32a and comparative compositions 360, 553, 554, 560, 754 and 765 were applied. Results, averaged for all replicates of each treatment, are shown in Table 32b and 32c.

TABLE 32b

ABUTH % Control

| Composition | 100 g a.e./ha | 150 g a.e./ha | 200 g a.e./ha | 300 g a.e./ha |
|---|---|---|---|---|
| 554 | 21.7 | 10 | 67.5 | 66.7 |
| 360 | 60.8 | 75 | 81.7 | 88.3 |
| 754 | 29.2 | 72.5 | 81.7 | 84.2 |
| 553 | 67.5 | 76.7 | 88.3 | 90 |
| 560 | 29.2 | 64.2 | 78.3 | 81.7 |
| 765 | 30.8 | 69.2 | 79.2 | 86.7 |
| 966A7A | 3.3 | 50.8 | 76.7 | 80 |
| 966B2W | 47.5 | 73.3 | 80 | 83.3 |
| 966C5T | 14.2 | 64.2 | 75 | 80 |
| 966D8J | 35 | 65.8 | 79.2 | 80.8 |

TABLE 32c

ECHCF % Control

| Composition | 100 g a.e./ha | 150 g a.e./ha | 200 g a.e./ha | 300 g a.e./ha |
|---|---|---|---|---|
| 554 | 5 | 5 | 20 | 35 |
| 360 | 37.5 | 54.2 | 59.2 | 75.8 |
| 754 | 20 | 55 | 59.2 | 72.5 |
| 553 | 50 | 65 | 74.2 | 78.3 |
| 560 | 30 | 51.7 | 55.8 | 65 |
| 765 | 36.7 | 54.2 | 60 | 66.7 |
| 966A7A | 8.3 | 52.5 | 55.8 | 66.7 |
| 966B2W | 34.2 | 58.3 | 59.2 | 65 |
| 966C5T | 8.3 | 53.3 | 54.2 | 64.2 |
| 966D8J | 34.2 | 52.5 | 57.5 | 70.8 |

Example 33

Aqueous concentrate compositions were prepared containing glyphosate salt and excipient ingredients as shown in Table 33a.

TABLE 33a

| Comp. | Salt | g/l | Component 1 | g/l |
|---|---|---|---|---|
| 487A2Q | K | 30 | S53 | 10 |
| 487B4R | K | 30 | S54 | 10 |
| 487C7U | K | 30 | S10 | 10 |
| 487D9I | K | 30 | S55 | 10 |
| 487E8Y | K | 30 | S56 | 10 |
| 487F0P | K | 30 | S57 | 10 |
| 487G4E | K | 30 | 1816E | 10 |
| 496A5T | K | 30 | ETH25 | 10 |

Velvetleaf (ABUTH) and Japanese millet (ECHCF) plants were grown and treated by the standard procedures above. The compositions of Table 33a and comparative compositions 139, 553 and 360 were applied. Results, averaged for all replicates of each treatment, are shown in Tables 33b and 33c.

TABLE 33b

ABUTH % Control

| Composition | 50 g a.e./ha | 100 g a.e./ha | 150 g a.e./ha | 200 g a.e./ha |
|---|---|---|---|---|
| 139 | 0 | 9.2 | 50.8 | 61.7 |
| 360 | 0 | 54.2 | 80 | 82.5 |
| 553 | 8.3 | 75 | 84.2 | 85.8 |
| 487A2Q | 0 | 39.2 | 68.3 | 73.3 |
| 487B4R | 27.5 | 75 | 82.5 | 85 |
| 487C7U | 25.8 | 70.8 | 79.2 | 80 |
| 487D9I | 0 | 54.2 | 77.5 | 80.8 |
| 487E8Y | 11.7 | 69.2 | 76.7 | 80.8 |
| 487F0P | 0 | 71.7 | 80.8 | 85.8 |
| 487G4E | 15.8 | 63.3 | 80 | 82.5 |
| 496A5T | 0 | 32.5 | 73.3 | 76.7 |

TABLE 33c

ECHCF % Control

| Composition | 50 g a.e./ha | 100 g a.e./ha | 150 g a.e./ha | 200 g a.e./ha |
|---|---|---|---|---|
| 139 | 0 | 44.2 | 65 | 64.2 |
| 360 | 48.3 | 68.3 | 72.5 | 77.5 |
| 553 | 64.2 | 68.3 | 78.3 | 80 |
| 487A2Q | 65.8 | 70.8 | 74.2 | 79.2 |
| 487B4R | 64.2 | 70 | 74.2 | 75.8 |
| 487C7U | 64.2 | 69.2 | 73.3 | 75 |
| 487D9I | 65.8 | 66.7 | 75.8 | 85 |
| 487E8Y | 63.3 | 69.2 | 73.3 | 79.2 |
| 487F0P | 64.2 | 66.7 | 72.5 | 76.7 |
| 487G4E | 64.2 | 66.7 | 69.2 | 74.2 |
| 496A5T | 49.2 | 65.8 | 73.3 | 76.7 |

Results for ABUTH and ECHCF: Composition 487B4R exhibited herbicidal effectiveness similar to comparative composition 553; both composition 487B4R and comparative composition 553 were the most active compositions in the experiment on ABUTH.

Example 34

Aqueous concentrate compositions were prepared containing glyphosate salt and excipient ingredients as shown in Table 34a.

TABLE 34a

| Comp. | Salt | g/l | Component 1 | g/l |
|---|---|---|---|---|
| 732A3Q | K | 30 | S66 | 10 |
| 732B3R | K | 30 | S67 | 10 |
| 732C9T | K | 30 | S68 | 10 |
| 730A5R | K | 30 | S10 | 10 |
| 730B5X | K | 30 | S54 | 10 |

TABLE 34a-continued

| Comp. | Salt | g/l | Component 1 | g/l |
|---|---|---|---|---|
| 730C1P | K | 30 | S53 | 10 |
| 487E2I | K | 30 | S56 | 10 |
| 487F7S | K | 30 | S57 | 10 |

Velvetleaf (ABUTH) and Japanese millet (ECHCF) plants were grown and treated by the standard procedures above. The compositions of Table 34a and comparative compositions 139, 553 and 360 were applied. Results, averaged for all replicates of each treatment, are shown in Tables 34b and 34c.

TABLE 34b

ABUTH % Control

| Composition | 75 g a.e./ha | 150 g a.e./ha | 225 g a.e./ha | 300 g a.e./ha |
|---|---|---|---|---|
| 139 | 8.3 | 53.3 | 62.5 | 73.3 |
| 360 | 31.7 | 74.2 | 85.8 | 90.3 |
| 553 | 44.2 | 74.2 | 84.2 | 92.7 |
| 732A3Q | 24.2 | 61.7 | 76.7 | 84.2 |
| 732B3R | 50.8 | 75 | 86.7 | 91.7 |
| 732C9T | 53.3 | 81.7 | 88.3 | 92.5 |
| 730A5R | 13.3 | 64.2 | 78.3 | 85 |
| 730B5X | 57.5 | 77.5 | 89.2 | 93.8 |
| 730C1P | 70.8 | 83.3 | 91.7 | 92.5 |
| 487E2I | 61.7 | 74.2 | 87.5 | 91.3 |
| 487F7S | 65 | 81.7 | 90.8 | 94.7 |

TABLE 34c

ECHCF % Control

| Composition | 75 g a.e./ha | 150 g a.e./ha | 225 g a.e./ha | 300 g a.e./ha |
|---|---|---|---|---|
| 139 | 0 | 42.5 | 50.8 | 60 |
| 360 | 50.8 | 80.8 | 82.5 | 89.2 |
| 553 | 60 | 75.8 | 80.8 | 88.3 |
| 732A3Q | 61.7 | 81.7 | 85 | 92.2 |
| 732B3R | 58.3 | 77.5 | 83.3 | 93.3 |
| 732C9T | 65 | 82.5 | 86.7 | 95.7 |
| 730A5R | 64.2 | 79.2 | 82.5 | 93 |
| 730B5X | 58.3 | 75 | 80 | 89.2 |
| 730C1P | 59.2 | 75.8 | 84.2 | 90.8 |
| 487E2I | 57.5 | 80 | 80 | 86.7 |
| 487F7S | 66.7 | 78.3 | 85 | 85.8 |

Results for ABUTH and ECHCF: Composition 730C1P was the most active composition on velvetleaf (ABUTH) in the experiment; composition 730C9T exhibited superior herbicidal effectiveness to comparative composition 360 and comparative composition 553 at the two lowest rates. Composition 732C9T was the most active composition on barnyardgrass (ECHCF); composition 732C9T exhibited superior herbicidal effectiveness to comparative composition 360.

Example 35

Aqueous concentrate compositions were prepared containing glyphosate salt and excipient ingredients as shown in Table 35a.

TABLE 35a

| Comp. | Salt | % | Component 1 | % | Component 2 | % | Component 3 | % |
|---|---|---|---|---|---|---|---|---|
| 554 | IPA | 0 | BRI56 | 6.4 | ETH25 | 9.6 | SC85 | 1.0 |
| 368 | IPA | 0 | EMUL | 4.9 | WIT05 | 6 | OA | 6.5 |
| 318 | K | 0 | EMUL | 4.9 | WIT05 | 5 | OA | 6.5 |
| 905A3Z | K | 36.9 | LF700 | 4.0 | WIT05 | 5 | OA | 6.5 |
| 905B6N | K | 36.9 | LF700 | 5.0 | WIT05 | 5 | OA | 6.5 |
| 905C5B | K | 36.9 | LF700 | 4.0 | EXPB2 | 6 | OA | 6.5 |
| 905D3D | K | 36.9 | LF700 | 5.0 | EXPB2 | 5 | OA | 6.5 |
| 905E0L | K | 36.9 | EXPB2 | 4.0 | WIT05 | 6 | OA | 6.5 |
| 905F8M | K | 36.9 | EXPB2 | 4.0 | EXPB2 | 6 | OA | 6.5 |

Velvetleaf (ABUTH) plants were grown and treated by the standard procedures above. The compositions of Table 35a and comparative compositions 368, 318, 553, 754, 554 and 765 were applied. Results, averaged for all replicates of each treatment, are shown in Table 35b.

TABLE 35b

ABUTH % Control

| Composition | 75 g a.e./ha | 125 g a.e./ha | 175 g a.e./ha | 250 g a.e./ha |
|---|---|---|---|---|
| 554 | 3.3 | 9.2 | 25.8 | 45.8 |
| 754 | 11.7 | 60 | 68.3 | 67.5 |
| 553 | 50.8 | 66.7 | 70.8 | 66.7 |
| 368 | 15 | 45 | 67.5 | 60 |
| 318 | 21.7 | 59.2 | 70 | 64.2 |
| 905A3Z | 12.5 | 40.8 | 60 | 55 |
| 905B6N | 15.8 | 25.8 | 55 | 64.2 |
| 905C5B | 23.3 | 20.8 | 60 | 60 |
| 905D3D | 19.2 | 25 | 59.2 | 61.7 |
| 905E0L | 41.7 | 48.3 | 60 | 58.3 |
| 905F8M | 5 | 39.2 | 57.5 | 67.5 |

Results for ABUTH: Comparative composition 553 exhibited the best herbicidal effectiveness in the experiment.

Example 36

Aqueous concentrate compositions were prepared containing glyphosate salt and excipient ingredients as shown in Table 36a.

TABLE 36a

| Comp. | Salt | g/l | Component 1 | g/l |
|---|---|---|---|---|
| 767H2R | K | 30 | S1 | 10 |
| 610B4S | K | 30 | S62 | 10 |
| 610C7V | K | 30 | S13 | 10 |

TABLE 36a-continued

| Comp. | Salt | g/l | Component 1 | g/l |
|---|---|---|---|---|
| 610D9J | K | 30 | S2 | 10 |
| 610E8Z | K | 30 | S81 | 10 |
| 610F0Q | K | 30 | S82 | 10 |
| 610G4F | K | 30 | S83 | 10 |
| 610H5U | K | 30 | S84 | 10 |

Velvetleaf (ABUTH) and Japanese millet (ECHCF) plants were grown and treated by the standard procedures above. The compositions of Table 36a and comparative compositions 553, 554, and 754 were applied. Results, averaged for all replicates of each treatment, are shown in Table 36b and 36c.

TABLE 36b

ABUTH % Control

| Composition | 75 g a.e./ha | 150 g a.e./ha | 225 g a.e./ha | 300 g a.e./ha |
|---|---|---|---|---|
| 554 | 0 | 6.7 | 60.8 | 61.7 |
| 754 | 8.3 | 68.3 | 86.7 | 91.7 |
| 553 | 63.3 | 83.3 | 90.8 | 94.5 |
| 767H2R | 70.8 | 86.7 | 92.5 | 95.7 |
| 610B4S | 26.7 | 70.8 | 87.5 | 88.3 |
| 610C7V | 42.5 | 64.2 | 83.3 | 84.2 |
| 610D9J | 9.2 | 62.5 | 79.2 | 85 |
| 610E8Z | 42.5 | 77.5 | 87.5 | 90.8 |
| 610F0Q | 21.7 | 73.3 | 84.2 | 86.7 |
| 610G4F | 61.7 | 74.2 | 88.3 | 90 |
| 610H5U | 11.7 | 59.2 | 78.3 | 89.2 |

TABLE 36c

ECHCF % Control

| Composition | 75 g a.e./ha | 150 g a.e./ha | 225 g a.e./ha | 300 g a.e./ha |
|---|---|---|---|---|
| 554 | 0 | 6.7 | 28.3 | 46.7 |
| 754 | 5.0 | 70 | 71.7 | 75.8 |
| 553 | 54.2 | 71.7 | 77.5 | 85.8 |
| 767H2R | 51.7 | 69.2 | 73.3 | 77.5 |
| 610B4S | 40.0 | 70 | 75.8 | 75.8 |
| 610C7V | 25.0 | 68.3 | 73.3 | 75.8 |
| 610D9J | 28.3 | 67.5 | 74.2 | 75.8 |
| 610E8Z | 54.2 | 72.5 | 75 | 83.3 |
| 610F0Q | 53.3 | 71.7 | 75 | 80 |
| 610G4F | 59.2 | 74.2 | 76.7 | 75 |
| 610H5U | 21.7 | 70.8 | 75.8 | 74.2 |

Results for ABUTH and ECHCF: Composition 767H2R and composition 553 were the most active compositions on velvetleaf (ABUTH) in the experiment. Composition 553 was the most active composition on barnyardgrass (ECHCF). Composition 610E8Z and composition 610G4F exhibited superior activity to comparative composition 754 on both velvetleaf (ABUTH) and barnyardgrass (ECHCF) at lower rates.

Example 37

Aqueous concentrate compositions were prepared containing glyphosate salt and excipient ingredients as shown in Table 37a.

TABLE 37a

| Comp. | Salt | g/l | Component 1 | g/l |
|---|---|---|---|---|
| 760A3G | K | 30 | S73 | 10 |
| 760B7I | K | 30 | S74 | 10 |
| 760C4J | K | 30 | S75 | 10 |
| 760D4R | K | 30 | S76 | 10 |
| 761G5H | K | 30 | S01 | 10 |
| 741A6P | K | 30 | S77 | 10 |

Velvetleaf (ABUTH) and Japanese millet (ECHCF) plants were grown and treated by the standard procedures above. The compositions of Table 37a and comparative compositions 553, 554, and 360 were applied. Results, averaged for all replicates of each treatment, are shown in Table 37b and 37c.

TABLE 37b

ABUTH % Control

| Composition | 75 g a.e./ha | 150 g a.e./ha | 225 g a.e./ha | 300 g a.e./ha |
|---|---|---|---|---|
| 554 | 0 | 14.2 | 54.2 | 65.8 |
| 360 | 3.3 | 78.3 | 87.5 | 90 |
| 553 | 55.8 | 85 | 89.2 | 96.3 |
| 760A3G | 34.2 | 59.2 | 74.2 | 81.7 |
| 760B7I | 23.3 | 60 | 74.2 | 79.2 |
| 760C4J | 50.8 | 65.8 | 80.8 | 82.5 |
| 760D4R | 40 | 72.5 | 83.3 | 85.8 |
| 761G5H | 80.8 | 89.2 | 92.5 | 94.2 |
| 741A6P | 41.7 | 75.8 | 84.2 | 87.5 |

TABLE 37c

ECHCF % Control

| Composition | 75 g a.e./ha | 150 g a.e./ha | 225 g a.e./ha | 300 g a.e./ha |
|---|---|---|---|---|
| 554 | 0 | 3.3 | 18.3 | 45.8 |
| 360 | 16.7 | 70.8 | 70.8 | 75 |
| 553 | 36.7 | 75 | 79.2 | 84.2 |
| 760A3G | 15.8 | 67.5 | 67.5 | 75.8 |
| 760B7I | 11.7 | 62.5 | 70 | 75 |
| 760C4J | 20 | 77.5 | 77.5 | 78.3 |
| 760D4R | 13.3 | 73.3 | 72.5 | 74.2 |
| 761G5H | 55.8 | 73.3 | 75.8 | 76.7 |
| 741A6P | 50 | 75.8 | 75.8 | 77.5 |

Composition 553 was the most active composition on barnyardgrass (ECHCF) at higher rates.

Example 38

Aqueous concentrate compositions were prepared containing glyphosate salt and excipient ingredients as shown in Table 38a.

TABLE 38a

| Comp. | Salt | g/l | Component 1 | g/l |
|---|---|---|---|---|
| 603A7A | K | 30 | S74 | 10 |
| 603B 2W | K | 30 | S75 | 10 |
| 603C5T | K | 30 | S76 | 10 |
| 603D8J | K | 30 | S77 | 10 |
| 603E8I | K | 30 | S78 | 10 |
| 603F6Y | K | 30 | S79 | 10 |
| 603G0P | K | 30 | S80 | 10 |

Velvetleaf (ABUTH) and Japanese millet (ECHCF) plants were grown and treated by the standard procedures above.

The compositions of Table 38a and comparative compositions 553, 554, and 360 were applied. Results, averaged for all replicates of each treatment, are shown in Table 38b and 38c.

TABLE 38b

ABUTH % Control

| Composition | 75 g a.e./ha | 150 g a.e./ha | 225 g a.e./ha | 300 g a.e./ha |
|---|---|---|---|---|
| 554 | 0 | 21.7 | 43.3 | 58.3 |
| 754 | 0 | 61.7 | 85.8 | 80.0 |
| 553 | 30 | 78.3 | 87.5 | 92.0 |
| 603A7A | 3.3 | 35.0 | 70.8 | 80.8 |
| 603B2W | 8.3 | 18.3 | 62.5 | 70.8 |
| 603C5T | 5.0 | 47.5 | 68.3 | 70.8 |
| 603D8J | 28.3 | 50.8 | 76.7 | 88.3 |
| 603E8I | 44.2 | 50.0 | 65.8 | 82.5 |
| 603F6Y | 45.0 | 68.3 | 76.7 | 85.0 |
| 603G9O | 40.8 | 45.8 | 66.7 | 75.0 |

TABLE 38c

ECHCF % Control

| Composition | 75 g a.e./ha | 150 g a.e./ha | 225 g a.e./ha | 300 g a.e./ha |
|---|---|---|---|---|
| 554 | 0 | 0 | 13.3 | 19.2 |
| 754 | 3.3 | 68.3 | 72.5 | 83.8 |
| 553 | 56.7 | 74.2 | 80.0 | 99.0 |
| 603A7A | 20.8 | 63.3 | 67.5 | 74.2 |
| 603B2W | 27.5 | 60.8 | 70.8 | 75.0 |
| 603C5T | 45.0 | 70.8 | 75.0 | 80.8 |
| 603D8J | 47.5 | 70.8 | 81.7 | 95.8 |
| 603E8I | 41.7 | 72.5 | 81.7 | 95.5 |
| 603F6Y | 30.0 | 70.8 | 78.3 | 90.5 |
| 603G9O | 11.7 | 65.0 | 70.0 | 77.5 |

Results for ABUTH and ECHCF: Composition 553 was the most active composition for both velvetleaf (ABUTH) and barnyardgrass (ECHCF).

Example 39

Aqueous concentrate compositions were prepared containing glyphosate salt and excipient ingredients as shown in Table 39a.

TABLE 39a

| Comp. | Salt | g/l | Component 1 | g/l | Component 2 | g/l |
|---|---|---|---|---|---|---|
| 721H0A | K | 30 | S54 | 4.2 | RH010 | 5.8 |
| 721I7U | K | 30 | S54 | 6.2 | INT00 | 3.8 |
| 721J7C | K | 30 | S56 | 4.4 | RH010 | 5.6 |
| 721K3K | K | 30 | S56 | 6.2 | INT00 | 3.8 |
| 721C2W | K | 30 | S54 | 10 | | |
| 721D9I | K | 30 | S56 | 10 | | |
| 721A7Y | K | 30 | | | RH010 | 10 |
| 721B8J | K | 30 | | | INT00 | 10 |

Velvetleaf (ABUTH) and Japanese millet (ECHCF) plants were grown and treated by the standard procedures above. The compositions of Table 39a and comparative compositions 139, 360 and 553 were applied. Results, averaged for all replicates of each treatment, are shown in Table 39b and 39c.

TABLE 39b

ABUTH % Control

| Composition | 75 g a.e./ha | 150 g a.e./ha | 225 g a.e./ha | 300 g a.e./ha |
|---|---|---|---|---|
| 139 | 50.8 | 56.7 | 70 | 75.8 |
| 360 | 29.2 | 70 | 85 | 90 |
| 553 | 41.7 | 78.3 | 86.7 | 94.7 |
| 721H0A | 27.5 | 67.5 | 80.8 | 86.7 |
| 721I7U | 32.5 | 73.3 | 80 | 85.8 |
| 721J7C | 22.5 | 68.3 | 80 | 85 |
| 721K3K | 16.7 | 73.3 | 84.2 | 86.7 |
| 721C2W | 50.8 | 75 | 87.5 | 88.3 |
| 721D9I | 35.8 | 75 | 85.8 | 88.3 |
| 721A7Y | 19.2 | 65 | 75.8 | 75.8 |
| 721B8J | 0 | 53.3 | 75.8 | 73.3 |

TABLE 39c

ECHCF % Control

| Composition | 75 g a.e./ha | 150 g a.e./ha | 225 g a.e./ha | 300 g a.e./ha |
|---|---|---|---|---|
| 139 | 30 | 48.3 | 64.2 | 62.5 |
| 360 | 58.3 | 73.3 | 81.7 | 84.2 |
| 553 | 69.2 | 75 | 80 | 84.2 |
| 721H0A | 63.3 | 70.8 | 77.5 | 80 |
| 721I7U | 62.5 | 73.3 | 76.7 | 83.3 |
| 721J7C | 63.3 | 73.3 | 78.3 | 78.3 |
| 721K3K | 62.5 | 72.5 | 80 | 83.3 |
| 721C2W | 65 | 75 | 78.3 | 79.2 |
| 721D9I | 64.2 | 74.2 | 75.8 | 80 |
| 721A7Y | 29.2 | 62.5 | 70 | 70 |
| 721B8J | 10 | 63.3 | 65.8 | 70 |

Results for ABUTH and ECHCF: Composition 553 was the most active composition in this experiment for both velvetleaf (ABUTH) and barnyardgrass (ECHCF). Compositions 721C2W and 721D9I demonstrated comparable herbicidal effectiveness to comparative composition 360.

Example 40

Aqueous concentrate compositions were prepared containing glyphosate salt and excipient ingredients as shown in Table 40a.

TABLE 40a

| Comp. | Salt | g/l | Component 1 | g/l | Component 2 | g/l |
|---|---|---|---|---|---|---|
| 721H7S | K | 30 | S54 | 4.2 | RH010 | 5.8 |
| 721I2I | K | 30 | S54 | 6.2 | INT00 | 3.8 |
| 721J1P | K | 30 | S56 | 4.4 | RH010 | 5.6 |
| 721K5X | K | 30 | S56 | 6.2 | INT00 | 3.8 |
| 721C5R | K | 30 | S54 | 10 | | |
| 721D9T | K | 30 | S56 | 10 | | |
| 721A3R | K | 30 | | | RH010 | 10 |
| 721B3Q | K | 30 | | | INT00 | 10 |

Velvetleaf (ABUTH) and Japanese millet (ECHCF) plants were grown and treated by the standard procedures above. The compositions of Table 40a and comparative compositions 139, 360 and 553 were applied. Results, averaged for all replicates of each treatment, are shown in Table 40b and 40c.

TABLE 40b

ABUTH % Control

| Composition | 75 g a.e./ha | 150 g a.e./ha | 225 g a.e./ha | 300 g a.e./ha |
|---|---|---|---|---|
| 139 | 0 | 14.2 | 60.8 | 68.3 |
| 360 | 48.3 | 79.2 | 88.3 | 93.7 |
| 553 | 60.8 | 89.7 | 92.5 | 95.5 |
| 721P7S | 26.7 | 66.7 | 79.2 | 84.2 |
| 721Q2I | 4.2 | 65.8 | 80 | 82.5 |
| 721H1P | 19.5 | 70 | 79.2 | 84.2 |
| 721I5X | 11.7 | 68.3 | 80.8 | 85 |
| 721G5R | 46.7 | 69.2 | 83.3 | 90 |
| 721C9T | 63.3 | 86.7 | 90 | 94.8 |
| 721A3R | 5 | 32.5 | 61.7 | 74.2 |
| 721B3Q | 0 | 8.3 | 44.2 | 59.2 |

TABLE 40c

ECHCF % Control

| Composition | 75 g a.e./ha | 150 g a.e./ha | 225 g a.e./ha | 300 g a.e./ha |
|---|---|---|---|---|
| 139 | 0 | 31.7 | 31.7 | 35.8 |
| 360 | 33.3 | 79.2 | 92.5 | 97.3 |
| 553 | 60.8 | 93.3 | 96.7 | 98.7 |
| 721P7S | 20 | 59.2 | 81.7 | 88 |
| 721Q2I | 39.2 | 70.8 | 82.3 | 90.8 |
| 721H1P | 1.7 | 55 | 70 | 80.8 |
| 721I5X | 5.8 | 50.8 | 69.2 | 78.3 |
| 721G5R | 28.3 | 72.5 | 83.2 | 88.3 |
| 721C9T | 40.8 | 61.7 | 84.2 | 95.8 |
| 721A3R | 0 | 41.7 | 59.2 | 69.2 |
| 721B3Q | 0 | 10.8 | 30 | 37.5 |

Results for ABUTH and ECHCF: Composition 721C9T and composition 553 were the most active compositions on velvetleaf (ABUTH) in the experiment. Composition 553 was the most active composition on barnyardgrass (ECHCF).

Example 41

Aqueous concentrate compositions were prepared containing glyphosate salt and excipient ingredients as shown in Table 41a.

TABLE 41a

| Comp. | Salt | g/l | Component 1 | g/l | Component 2 | g/l |
|---|---|---|---|---|---|---|
| 721H2Q | K | 30 | S54 | 4.2 | RH010 | 5.8 |
| 721I4R | K | 30 | S54 | 6.2 | INT00 | 3.8 |
| 721J7U | K | 30 | S56 | 4.4 | RH010 | 5.6 |
| 721K9I | K | 30 | S56 | 6.2 | INT00 | 3.8 |
| 721C8Y | K | 30 | S54 | 10 | | |
| 721D0P | K | 30 | S56 | 10 | | |
| 721A4E | K | 30 | | | RH010 | 10 |
| 721B5T | K | 30 | | | INT00 | 10 |

Velvetleaf (ABUTH) and Japanese millet (ECHCF) plants were grown and treated by the standard procedures above. The compositions of Table 41a and comparative compositions 754, 360, 554 and 139 were applied. Results, averaged for all replicates of each treatment, are shown in Table 41b and 41c.

TABLE 41b

ABUTH % Control

| Composition | 150 g a.e./ha | 200 g a.e./ha | 300 g a.e./ha | 400 g a.e./ha |
|---|---|---|---|---|
| | 0 | 14.2 | 60.8 | 68.3 |
| 360 | 48.3 | 79.2 | 88.3 | 93.7 |
| 553 | 60.8 | 89.7 | 92.5 | 95.5 |
| 721P2Q | 26.7 | 66.7 | 79.2 | 84.2 |
| 721Q4R | 4.2 | 65.8 | 80 | 82.5 |
| 721H7U | 19.5 | 70 | 79.2 | 84.2 |
| 721I9I | 11.7 | 68.3 | 80.8 | 85 |
| 721G8Y | 46.7 | 69.2 | 83.3 | 90 |
| 721C0P | 63.3 | 86.7 | 90 | 94.8 |
| 721A4E | 5 | 32.5 | 61.7 | 74.2 |
| 721B5T | 0 | 8.3 | 44.2 | 59.2 |

TABLE 41c

ECHCF % Control

| Composition | 75 g a.e./ha | 150 g a.e./ha | 225 g a.e./ha | 300 g a.e./ha |
|---|---|---|---|---|
| 139 | 0 | 31.7 | 31.7 | 35.8 |
| 360 | 33.3 | 79.2 | 92.5 | 97.3 |
| 553 | 60.8 | 93.3 | 96.7 | 98.7 |
| 721P2Q | 20 | 59.2 | 81.7 | 88 |
| 721Q4R | 39.2 | 70.8 | 82.3 | 90.8 |
| 721H7U | 1.7 | 55 | 70 | 80.8 |
| 721I9I | 5.8 | 50.8 | 69.2 | 78.3 |
| 721G8Y | 28.3 | 72.5 | 83.2 | 88.3 |
| 721C0P | 40.8 | 61.7 | 84.2 | 95.8 |
| 721A4E | 0 | 41.7 | 59.2 | 69.2 |
| 721B5T | 0 | 10.8 | 30 | 37.5 |

Results for ABUTH and ECHCF: Composition 721C0P and composition 553 were the most active compositions on velvetleaf (ABUTH) in the experiment. Composition 553 was the most active composition on barnyardgrass (ECHCF).

Example 42

Aqueous concentrate compositions were prepared containing glyphosate salt and excipient ingredients as shown in Table 42a.

TABLE 42a

| Comp. | Salt | g/l | Component 1 | g/l | Component 2 | g/l | Component 3 | g/l |
|---|---|---|---|---|---|---|---|---|
| 643G5J | K | 540 | M121 | 111.4 | EA | 23.6 | | |
| 652A9K | K | 540 | ETH12 | 54.0 | WIT60 | 54.0 | INT00 | 27.0 |
| 652B8S | K | 540 | ETH12 | 54.0 | WIT80 | 54.0 | INT00 | 27.0 |
| 651E2D | K | 540 | ETH12 | 54.0 | WIT60 | 54.0 | INT00 | 30.0 |
| 650C7S | K | 540 | ETH12 | 54.0 | WIT60 | 54.0 | AR41 | 32.0 |
| 651H9E | K | 540 | ETH12 | 54.0 | WIT60 | 54.0 | AR41 | 24.0 |

TABLE 42a-continued

| Comp. | Salt | g/l | Component 1 | g/l | Component 2 | g/l | Component 3 | g/l |
|---|---|---|---|---|---|---|---|---|
| 649G2S | K | 540 | ETH12 | 54.0 | WIT80 | 54.0 | AR41 | 27.0 |
| 360 | | 360 | | | | | | |
| 754 | | 445 | | | | | | |

Velvetleaf (ABUTH) and Japanese millet (ECHCF) plants were grown and treated by the standard procedures above. The compositions of Table 42a and comparative compositions 139, 553, 360 and 754 were applied. Results, averaged for all replicates of each treatment, are shown in Table 42b and 42c.

TABLE 42b

ABUTH % Control

| Composition | 100 g a.e./ha | 150 g a.e./ha | 200 g a.e./ha | 300 g a.e./ha |
|---|---|---|---|---|
| 643G5J | 50.8 | 69.2 | 82.5 | 96.7 |
| 652A9K | 48.3 | 76.7 | 84.2 | 97.7 |
| 652B8S | 50.0 | 71.7 | 83.3 | 97.7 |
| 651E2D | 65.8 | 78.3 | 88.3 | 94.2 |
| 650C7S | 39.2 | 72.5 | 75.0 | 89.2 |
| 651H9E | 52.5 | 69.2 | 80.8 | 92.8 |
| 649G2S | 55.8 | 63.3 | 80.0 | 89.7 |
| 139 | 18.3 | 46.7 | 65.0 | 86.7 |
| 554 | 5.8 | 38.3 | 47.5 | 71.7 |
| 360 | 60.8 | 85.0 | 88.8 | 98.8 |
| 754 | 55.8 | 79.7 | 91.0 | 96.7 |

TABLE 42c

ECHCF % Control

| Composition | 100 g a.e./ha | 150 g a.e./ha | 200 g a.e./ha | 300 g a.e./ha |
|---|---|---|---|---|
| 643G5J | 96.0 | 99.7 | 99.8 | 99.8 |
| 652A9K | 89.5 | 99.5 | 99.8 | 99.8 |
| 652B8S | 87.8 | 96.2 | 97.8 | 100.0 |
| 651E2D | 80.8 | 96.5 | 99.5 | 100.0 |
| 650C7S | 84.0 | 99.5 | 96.0 | 100.0 |
| 651H9E | 93.0 | 98.3 | 97.5 | 99.8 |
| 649G2S | 92.8 | 95.2 | 98.0 | 100.0 |
| 139 | 21.7 | 47.5 | 60.0 | 85.5 |
| 554 | 26.7 | 52.5 | 65.8 | 70.0 |
| 360 | 98.3 | 99.7 | 100.0 | 100.0 |
| 754 | 89.5 | 98.8 | 99.7 | 100.0 |

Results for ABUTH and ECHCF: Compositions 652A9K, 652B8S and 651E2D were slightly superior over compositions 650C7S, 651H9E and 649G2S on ABUTH. Performance of the compositions were slightly less performing than composition 360.

Example 43

Aqueous concentrate compositions were prepared containing glyphosate salt and excipient ingredients as shown in Table 43a.

TABLE 43a

| Comp. | Salt | g/l | Component 1 | g/l |
|---|---|---|---|---|
| 127A3K | K | 540 | TPAE6 | 9.9 |
| 127B4S | K | 540 | TPAE6 | 9.91 |
| 129A8D | K | 540 | TPAE6 | 13.23 |
| 129B7W | K | 540 | TPAE6 | 13.20 |
| 129D2D | K | 540 | TED5 | 12.51 |
| 140A3G | K | 540 | TPA0E | 9.97 |
| 140C5L | K | 540 | T23E5 | 9.89 |
| 560 | | 540 | | |
| 754 | | 445 | | |
| 360 | | 360 | | |

Velvetleaf (ABUTH) and Japanese millet (ECHCF) plants were grown and treated by the standard procedures above. The compositions of Table 43a and comparative compositions 560, 754 and 350 were applied. Results, averaged for all replicates of each treatment, are shown in Table 43b and 43c.

TABLE 43b

ABUTH % Control

| Composition | 100 g a.e./ha | 150 g a.e./ha | 200 g a.e./ha | 300 g a.e./ha |
|---|---|---|---|---|
| 127A3K | 15 | 55 | 78.3 | 82.5 |
| 127B4S | 15 | 68.3 | 74.2 | 80 |
| 129A8D | 8.3 | 55.8 | 70 | 82.5 |
| 129B7W | 20.8 | 56.7 | 75.8 | 81.7 |
| 129D2D | 0.8 | 43.3 | 78.3 | 86.7 |
| 140A3G | 2.5 | 55 | 69.2 | 80.8 |
| 140C5L | 35 | 69.2 | 82.5 | 82.5 |
| 560 | 33.3 | 70 | 80 | 85.8 |
| 754 | 55 | 77.5 | 84.2 | 91.7 |
| 360 | 35 | 79.2 | 84.2 | 90 |

TABLE 43c

ECHCF % Control

| Composition | 100 g a.e./ha | 150 g a.e./ha | 200 g a.e./ha | 300 g a.e./ha |
|---|---|---|---|---|
| 127A3K | 51.7 | 50 | 57.5 | 57.5 |
| 127B4S | 43.3 | 50 | 53.3 | 57.5 |
| 129A8D | 17.5 | 51.7 | 50.8 | 60 |
| 129B7W | 39.2 | 51.7 | 59.2 | 48.3 |
| 129D2D | 51.7 | 58.3 | 60.8 | 67.5 |
| 140A3G | 45 | 51.7 | 57.5 | 59.2 |
| 140C5L | 58.3 | 61.7 | 65.8 | 78.3 |
| 560 | 52.5 | 60 | 61.7 | 69.2 |
| 754 | 60 | 62.5 | 69.2 | 85.8 |
| 360 | 57.5 | 68.3 | 80 | 94.7 |

Results for ABUTH and ECHCF: Composition 140C5L exhibited similar herbicidal effectiveness over comparative composition 560 on velvetleaf (ABUTH) and demonstrated higher herbicidal effectiveness over comparative composition 560 on barnyard grass (ECHCF). Composition 129D2D was one of th weakest performers on velvetleaf but was similar to composition 560 on barnyardgrass. Increasing surfactant from 9.9% (composition 127A3K and 127B4S) to 13.2% (compositions 129A8D and 129B7W) did not substantially affect performance.

Example 44

Aqueous concentrate compositions were prepared containing glyphosate salt and excipient ingredients as shown in Table 44a.

TABLE 44a

| Comp. | Salt | g/l | Component 1 | g/l |
|---|---|---|---|---|
| 572A7S | K | 475 | TQ14 | 8.99 |
| 572B3L | K | 437 | TQ17 | 8.42 |
| 572C2J | K | 434 | WIT05 | 3.28 |
| 574A3B | K | 479 | WEX7 | 8.95 |
| 574B6C | K | 479 | WEX6 | 9.07 |
| 574C1U | K | 479 | WEX5 | 9.09 |
| 360AD | K | 360 | L770 | 100 |
| 139 | | 570 | | |
| 360 | | 360 | | |

Velvetleaf (ABUTH) and Japanese millet (ECHCF) plants were grown and treated by the standard procedures above. The compositions of Table 44a and comparative compositions 139 and 360 were applied. Results, averaged for all replicates of each treatment, are shown in Table 44b and 44c.

TABLE 44b

ABUTH % Control

| Composition | 100 g a.e./ha | 150 g a.e./ha | 200 g a.e./ha | 300 g a.e./ha |
|---|---|---|---|---|
| 572A7S | 2 | 19 | 43 | 72 |
| 572B3L | 6 | 31 | 51 | 79 |
| 572C2J | 2 | 18 | 59 | 78 |
| 574A3B | 3 | 13 | 40 | 60 |
| 574B6C | 0 | 12 | 38 | 62 |
| 574C1U | 8 | 38 | 51 | 73 |
| 360AD | 85 | 88 | 90 | 93 |
| 139 | 0 | 9 | 11 | 39 |
| 360 | 11 | 68 | 79 | 86 |

TABLE 44c

ECHCF % Control

| Composition | 100 g a.e./ha | 150 g a.e./ha | 200 g a.e./ha | 300 g a.e./ha |
|---|---|---|---|---|
| 572A7S | 17 | 36 | 48 | 56 |
| 572B3L | 18 | 43 | 49 | 64 |
| 572C2J | 43 | 60 | 64 | 71 |
| 574A3B | 22 | 45 | 53 | 68 |
| 574B6C | 28 | 44 | 55 | 63 |
| 574C1U | 23 | 43 | 48 | 65 |
| 360AD | 76 | 82 | 80 | 85 |
| 139 | 10 | 28 | 35 | 43 |
| 360 | 31 | 57 | 67 | 77 |

Results for ABUTH and ECHCF: Composition 360AD provided the highest level herbicidal effectiveness for barnyardgrass control. Compositions 572A7S, 572B3L, 572C2J, 574A3B, 574B6C, 574C1U and 360 demonstrated less control of velvetleaf than composition 360AD.

Example 45

Aqueous concentrate compositions were prepared containing glyphosate salt and excipient ingredients as shown in Table 45a.

TABLE 45a

| Comp. | Salt | g/l | Component 1 | g/l |
|---|---|---|---|---|
| 612A1S | K | 30 | S01 | 10.0 |
| 612B8I | K | 30 | S02 | 10.0 |
| 612C7Y | K | 30 | S03 | 10.0 |
| 612D4P | K | 30 | S04 | 10.0 |
| 612E3X | K | 30 | S05 | 10.0 |
| 612F0P | K | 30 | S06 | 10.0 |
| 612G5G | K | 30 | S07 | 10.0 |
| 612H5T | K | 30 | S08 | 10.0 |

Velvetleaf (ABUTH) and barnyard grass (ECHCF) plants were grown and treated by the standard procedures above. The compositions of Table 45a and comparative compositions 554, 754 and 553 were applied. Results, averaged for all replicates of each treatment, are shown in Table 45b and 45c.

TABLE 45b

ABUTH % Control

| Composition | 75 g a.e./ha | 150 g a.e./ha | 225 a.e./ha | 300 g a.e./ha |
|---|---|---|---|---|
| 554 | 0.0 | 0.0 | 10.0 | 30.8 |
| 754 | 0.0 | 67.5 | 85.0 | 89.2 |
| 553 | 25.8 | 85.0 | 90.0 | 92.5 |
| 612A1S | 74.2 | 88.3 | 90.0 | 90.8 |
| 612B8I | 0.0 | 26.7 | 81.7 | 84.2 |
| 612C7Y | 8.3 | 76.7 | 86.7 | 90.0 |
| 612D4P | 27.5 | 80.0 | 88.3 | 90.8 |
| 612E3X | 16.7 | 63.3 | 85.8 | 87.5 |
| 612F0P | 17.5 | 81.7 | 88.3 | 89.2 |
| 612G5G | 65.0 | 85.0 | 91.7 | 90.8 |
| 612H5T | 0.0 | 5.8 | 61.7 | 54.2 |

TABLE 45c

ECHCF % Control

| Composition | 75 g a.e./ha | 150 g a.e./ha | 225 a.e./ha | 300 g a.e./ha |
|---|---|---|---|---|
| 554 | 0.0 | 1.7 | 13.3 | 24.2 |
| 754 | 0.0 | 57.5 | 69.2 | 72.5 |
| 553 | 25.8 | 70.8 | 76.7 | 88.8 |
| 612A1S | 52.5 | 70.0 | 70.0 | 76.7 |
| 612B8I | 21.7 | 65.0 | 69.2 | 71.7 |
| 612C7Y | 34.2 | 70.8 | 71.7 | 72.5 |
| 612D4P | 22.5 | 66.7 | 70.8 | 70.8 |
| 612E3X | 13.3 | 67.5 | 69.2 | 73.3 |
| 612F0P | 28.3 | 69.2 | 70.0 | 70.8 |
| 612G5G | 15.0 | 66.7 | 70.0 | 70.8 |
| 612H5T | 0.0 | 8.3 | 5.0 | 35.0 |

Results for ABUTH and ECHCF: The most active formulation on velvetleaf was 612A1S. The most active formulation on barnyardgrass was 553.

Example 46

Aqueous concentrate compositions were prepared containing glyphosate salt and excipient ingredients as shown in Table 46a.

TABLE 46a

| Comp. | Salt | g/l | Component 1 | g/l |
|---|---|---|---|---|
| 607A3G | K | 30 | S09 | 10.0 |
| 607B7I | K | 30 | S10 | 10.0 |

TABLE 46a-continued

| Comp. | Salt | g/l | Component 1 | g/l |
|---|---|---|---|---|
| 607C4J | K | 30 | S11 | 10.0 |
| 607D4R | K | 30 | S12 | 10.0 |
| 607E5H | K | 30 | S13 | 10.0 |
| 607F6P | K | 4.3 | S14 | 1.4 |
| 607G7O | K | 30 | S15 | 10.0 |

Velvetleaf (ABUTH) and barnyard grass (ECHCF) plants were grown and treated by the standard procedures above. The compositions of Table 46a and comparative compositions 554, 754 and 553 were applied. Results, averaged for all replicates of each treatment, are shown in Table 46b and 46c.

TABLE 46b

| | ABUTH % Control | | | |
|---|---|---|---|---|
| Composition | 75 g a.e./ha | 150 g a.e./ha | 225 a.e./ha | 300 g a.e./ha |
| 554 | 0.0 | 0.0 | 0.0 | 12.5 |
| 754 | 0.0 | 32.5 | 80.8 | 84.2 |
| 553 | 0.0 | 74.2 | 89.2 | 93.3 |
| 607A3G | 0.0 | 0.0 | 30.8 | 64.2 |
| 607B7I | 64.2 | 81.7 | 89.2 | 90.0 |
| 607E5H | 24.2 | 22.5 | 56.7 | 70.0 |
| 607F6P | 10.0 | 1.7 | 30.8 | 40.8 |
| 607G7O | 44.2 | 30.0 | 62.5 | 78.3 |

TABLE 46c

| | ECHCF % Control | | | |
|---|---|---|---|---|
| Composition | 75 g a.e./ha | 150 g a.e./ha | 225 a.e./ha | 300 g a.e./ha |
| 554 | 0.0 | 0.0 | 15.0 | 27.5 |
| 754 | 0.0 | 28.3 | 70.0 | 72.5 |
| 553 | 1.7 | 66.7 | 80.0 | 83.3 |
| 607A3G | 0.0 | 10.8 | 55.0 | 67.5 |
| 607B7I | 5.0 | 67.5 | 73.3 | 74.2 |
| 607E5H | 8.3 | 61.7 | 70.8 | 74.2 |
| 607F6P | 0.0 | 0.0 | 29.2 | 54.2 |
| 607G7O | 0.0 | 65.0 | 72.5 | 73.3 |

Results for ABUTH and ECHCF: Composition 607B7I was the most active on velvetleaf and Composition 607A3G was more effective than 607F6P on both velvetleaf and barnyardgrass.

Example 47

Aqueous concentrate compositions were prepared containing glyphosate salt and excipient ingredients as shown in Table 47a.

TABLE 47a

| Comp. | Salt | g/l | Component 1 | g/l |
|---|---|---|---|---|
| 487A7S | K | 30 | S53 | 10.0 |
| 487B2I | K | 30 | S54 | 10.0 |
| 487C1P | K | 30 | 501 | 10.0 |
| 487D5X | K | 30 | 555 | 10.0 |
| 487E5R | K | 30 | 556 | 10.0 |
| 487F9T | K | 30 | 557 | 10.0 |
| 487G3R | K | 30 | 1816E | 10.0 |
| 496A3Q | K | 30 | ETH25 | 10.0 |

Velvetleaf (ABUTH) and barnyard grass (ECHCF) plants were grown and treated by the standard procedures above. The compositions of Table 47a and comparative compositions 139, 360 and 553 were applied. Results, averaged for all replicates of each treatment, are shown in Table 47b and 47c.

TABLE 47b

| | ABUTH % Control | | | |
|---|---|---|---|---|
| Composition | 50 g a.e./ha | 100 g a.e./ha | 200 g a.e./ha | 400 g a.e./ha |
| 139 | 0.0 | 22.5 | 80.8 | 91.7 |
| 360 | 51.7 | 88.3 | 95.0 | 99.5 |
| 553 | 71.7 | 93.3 | 96.8 | 98.7 |
| 487A7S | 42.5 | 70.0 | 91.7 | 97.3 |
| 487B2I | 80.0 | 94.2 | 96.3 | 97.8 |
| 487C1P | 87.5 | 92.5 | 97.8 | 98.7 |
| 487D5X | 80.0 | 90.8 | 96.2 | 98.0 |
| 487E5R | 84.2 | 90.0 | 97.5 | 98.3 |
| 487F9T | 85.0 | 90.0 | 96.7 | 99.7 |
| 487G3R | 84.2 | 94.2 | 97.7 | 99.3 |
| 496A3Q | 61.7 | 90.8 | 96.7 | 99.5 |

TABLE 47c

| | ECHCF % Control | | | |
|---|---|---|---|---|
| Composition | 50 g a.e./ha | 100 g a.e./ha | 200 g a.e./ha | 400 g a.e./ha |
| 139 | 0.0 | 56.7 | 68.3 | 88.3 |
| 360 | 64.2 | 89.2 | 98.3 | 100.0 |
| 553 | 75.0 | 88.3 | 99.3 | 100.0 |
| 487A7S | 68.3 | 86.7 | 100.0 | 100.0 |
| 487B2I | 67.5 | 84.2 | 97.5 | 100.0 |
| 487C1P | 67.5 | 81.7 | 100.0 | 100.0 |
| 487D5X | 67.5 | 87.5 | 98.3 | 100.0 |
| 487E5R | 67.5 | 82.5 | 98.2 | 100.0 |
| 487F9T | 72.5 | 91.7 | 97.5 | 100.0 |
| 487G3R | 63.3 | 85.0 | 99.7 | 100.0 |
| 496A3Q | 67.5 | 94.2 | 97.5 | 100.0 |

Results for ABUTH and ECHCF: All of the compositions except 487A7S exhibited more activity over comparative compositions 360, 553 and 139 on velvetleaf (ABUTH).

Example 48

Aqueous concentrate compositions were prepared containing glyphosate salt and excipient ingredients as shown in Table 48a.

TABLE 48a

| Comp. | Salt | g/l | Component 1 | g/l | Component 2 | g/l | Component 3 | g/l |
|---|---|---|---|---|---|---|---|---|
| 031F3Z | K | 485 | Gen2 | 9.0 | Eth12 | 7.0 | | |
| 031K6N | K | 485 | Gen2 | 5.0 | Eth12 | 6.0 | Gen4 | 3.0 |
| 031M5B | K | 485 | Gen2 | 5.0 | Eth12 | 6.0 | Gen3 | 3.0 |
| 031N3D | K | 485 | Gen2 | 10.0 | Eth12 | 7.0 | | |
| 031S0L | K | 485 | Gen2 | 4.0 | Eth12 | 6.0 | Gen4 | 2.0 |
| 265 | K | 391 | S58 | 10.0 | | | | |
| 769 | K | 490 | S59 | 7.5 | Eth12 | 6.5 | | |
| 754 | IPA | 445 | | | | | | |

Velvetleaf (ABUTH) and Japanese millet (ECHCF) plants were grown and treated by the standard procedures above. The compositions of Table 48a and comparative compositions 139, 554, and 754 were applied. Results, averaged for all replicates of each treatment, are shown in Table 48b and 48c.

TABLE 48b

ABUTH % Control

| Composition | 100 g a.e./ha | 150 g a.e./ha | 200 g a.e./ha | 400 g a.e./ha |
|---|---|---|---|---|
| 554 | 0.0 | 0.0 | 16.7 | 70.0 |
| 139 | 0.0 | 15.0 | 30.0 | 77.5 |
| 754 | 13.3 | 78.3 | 80.0 | 92.2 |
| 031F3Z | 8.3 | 69.2 | 75.0 | 85.0 |
| 031K6N | 4.2 | 64.2 | 75.0 | 85.0 |
| 031M5B | 29.2 | 65.0 | 73.3 | 85.0 |
| 031N3D | 12.5 | 67.5 | 75.0 | 85.0 |
| 031S0L | 16.7 | 51.7 | 74.2 | 84.2 |
| 265 | 36.7 | 76.7 | 80.0 | 90.8 |
| 769 | 50.8 | 74.2 | 75.0 | 85.8 |

TABLE 48c

ECHCF % Control

| Composition | 100 g a.e./ha | 150 g a.e./ha | 200 g a.e./ha | 400 g a.e./ha |
|---|---|---|---|---|
| 554 | 0.0 | 3.3 | 11.7 | 46.7 |
| 139 | 0.8 | 19.2 | 15.0 | 35.8 |
| 754 | 7.5 | 50.8 | 55.0 | 75.0 |
| 031F3Z | 25.0 | 54.2 | 57.5 | 73.3 |
| 031K6N | 33.3 | 52.5 | 55.8 | 67.5 |
| 031M5B | 24.2 | 50.8 | 55.8 | 73.3 |
| 031N3D | 31.7 | 55.0 | 60.8 | 82.5 |
| 031S0L | 33.3 | 55.0 | 55.8 | 72.5 |
| 265 | 35.0 | 55.0 | 57.5 | 74.2 |
| 769 | 36.7 | 54.2 | 57.5 | 76.7 |

Results for ABUTH and ECHCF: Compositions 265 and 769 exhibited similar herbicidal activity to composition 754 on velvetleaf (ABUTH) and barnyardgrass (ECHCF).

EXAMPLE 49

Aqueous concentrate compositions were prepared containing glyphosate salt and excipient ingredients as shown in Table 49a.

TABLE 49a

| Comp. | Salt | g/l | Comp. 1 | g/l | Comp. 2 | g/l | Comp. 3 | g/l |
|---|---|---|---|---|---|---|---|---|
| 015A6D | K | 391 | S85 | 131 | | | | |
| 024A5Q | K | 485 | S86 | 131 | ETH12 | 65 | | |
| 024B2L | K | 485 | S87 | 91 | ETH12 | 91 | | |
| 024C3M | K | 485 | S87 | 65 | ETH12 | 65 | S86 | 65 |
| 024D1X | K | 485 | S87 | 78 | ETH12 | 52 | S86 | 65 |
| 024E0P | K | 485 | S87 | 91 | ETH12 | 91 | Oxalic Acid | 13 |

Velvetleaf (ABUTH) and Japanese millet (ECHCF) plants were grown and treated by the standard procedures above. The compositions of Table 49a and comparative compositions 139, 554, 754 and 360 were applied. Results, averaged for all replicates of each treatment, are shown in Table 49b and Table 49c.

TABLE 49b

ABUTH % Control

| Composition | 100 g a.e./ha | 200 g a.e./ha | 300 g a.e./ha | 400 g a.e./ha |
|---|---|---|---|---|
| 015A6D | 55 | 80 | 86.7 | 89.2 |
| 024A5Q | 15.8 | 76.7 | 83.3 | 84.2 |
| 024B2L | 40 | 80.7 | 86.7 | 88.3 |
| 024C3M | 0 | 0 | 1.7 | 1.7 |
| 024D1X | 29.2 | 80.8 | 82.5 | 90 |
| 024E0P | 75 | 82.5 | 91.7 | 92.5 |
| 139 | 0 | 15 | 73.3 | 75.8 |
| 554 | 0.8 | 20 | 71.7 | 80.8 |
| 754 | 45.8 | 80.8 | 87.5 | 90 |
| 360 | 33.3 | 81.7 | 87.5 | 90.8 |

TABLE 49c

ECHCF % Control

| Composition | 100 g a.e./ha | 200 g a.e./ha | 300 g a.e./ha | 400 g a.e./ha |
|---|---|---|---|---|
| 015A6D | 48.3 | 54.2 | 59.2 | 68.3 |
| 024A5Q | 35 | 51.7 | 65 | 72.5 |
| 024B2L | 46.7 | 53.3 | 62.5 | 69.2 |
| 024C3M | 0 | 0 | 1.7 | 1.7 |
| 024D1X | 38.3 | 55.8 | 70 | 77.5 |
| 024E0P | 50 | 55 | 75.8 | 79.2 |
| 139 | 0 | 15 | 73.3 | 75.8 |
| 554 | 0.8 | 20 | 71.7 | 80.8 |
| 754 | 45.8 | 80.8 | 87.5 | 90 |
| 360 | 33.3 | 81.7 | 87.5 | 90.8 |

Results for ABUTH and ECHCF: Composition 024E0P exhibited enhanced herbicidal effectiveness over all of the comparative compositions on ABUTH. Composition 024D1X exhibited enhanced herbicidal effectiveness over comparative compositions 139 and 554. Compositions 015A6D, 024A5Q and 024B2L demonstrated enhanced herbicidal effectiveness over comparative compositions 139 and 554.

Example 50

Aqueous concentrate compositions were prepared containing glyphosate salt and excipient ingredients as shown in Table 50a.

TABLE 50a

| Composition | Salt | g ae/l | Comp. 1 | g ae/l | Comp. 2 | g ae/l |
|---|---|---|---|---|---|---|
| 015B2A | K | 391 | S85 | 126 | | |
| 019A7I | K | 501 | S86 | 156 | ETH12 | 65 |
| 019B2U | K | 481 | S85 | 130 | ETH12 | 65 |
| 019C9O | K | 481 | S87 | 104 | ETH12 | 91 |
| 019D1Y | K | 497 | S87 | 91 | ETH12 | 91 |
| 139 | | 570 | | | | |
| 554 | | 725 | | | | |
| 360 | | 360 | | | | |
| 754 | | 445 | | | | |

Velvetleaf (ABUTH) and Japanese millet (ECHCF) plants were grown and treated by the standard procedures above. The compositions of Table 50a and comparative compositions 139, 554, 754 and 360 were applied. Results, averaged for all replicates of each treatment, are shown in Table 50b and Table 50c.

TABLE 50b

ABUTH % Control

| Composition | 100 g a.e./ha | 200 g a.e./ha | 300 g a.e./ha | 400 g a.e./ha |
|---|---|---|---|---|
| 015B2A | 63.3 | 80.8 | 88.3 | 91.7 |
| 019A7I | 49.2 | 80.8 | 88.3 | 89.2 |
| 019B2U | 48.3 | 80.8 | 85 | 85.8 |
| 019C9O | 61.7 | 82.5 | 87.5 | 92.5 |
| 019D1Y | 61.7 | 80.8 | 87.5 | 90.8 |
| 139 | 0 | 7.5 | 61.7 | 75.8 |
| 554 | 0 | 18.3 | 74.2 | 79.2 |
| 754 | 61.7 | 82.5 | 87.5 | 88.3 |
| 360 | 60 | 82.5 | 87.5 | 94.2 |

TABLE 50c

ECHCF % Control

| Composition | 100 g a.e./ha | 200 g a.e./ha | 300 g a.e./ha | 400 g a.e./ha |
|---|---|---|---|---|
| 015B2A | 30 | 55.8 | 79.2 | 81.7 |
| 019A7I | 15.8 | 55 | 72.5 | 87.5 |
| 019B2U | 15.8 | 55.8 | 70.8 | 75 |

TABLE 50c-continued

ECHCF % Control

| Composition | 100 g a.e./ha | 200 g a.e./ha | 300 g a.e./ha | 400 g a.e./ha |
|---|---|---|---|---|
| 019C9O | 37.5 | 60.8 | 73.8 | 86.7 |
| 019D1Y | 31.7 | 58.3 | 71.7 | 75.8 |
| 139 | 0.8 | 6.7 | 35 | 52.5 |
| 554 | 0.8 | 28.3 | 48.3 | 55.8 |
| 754 | 6.7 | 55.8 | 69.2 | 70 |
| 360 | 10.8 | 55.8 | 76.7 | 80 |

Results for ABUTH and ECHCF: All compositions exhibited enhanced herbicidal effectiveness over compositions 139 and 554.

Example 51

Aqueous concentrate compositions were prepared containing glyphosate salt and excipient ingredients as shown in Table 51a.

TABLE 51a

| Comp. | Salt | g ae/l | Comp. 1 | w/w | Comp. 2 | w/w | Comp. 3 | w/w |
|---|---|---|---|---|---|---|---|---|
| 265C1 | K | 391 | S85 | 10% | | | | |
| 765T5 | K | 473 | ARO66 | 4% | VAR05 | 9.0% | ARMC | 1.0% |
| 677I9 | K | 480 | WIT80 | 48 g/l | ETH12 | 48 g/l | INT00 | 24 g/l |
| 769R5 | K | 490 | S87 | 7.5% | ETH12 | 6.5% | | |
| 767A2 | K | 510 | 1816E | 5.0% | ARQ37 | 1.5% | | |
| 560W3 | K | 540 | M121 | 9.9% | | | | |
| 563P5 | K | 540 | ETH12 | 60.8 g/l | | | | |

Compositions 677I9 and 563P5 additionally contain 102 g/l Ethylene Glycol.

The compositions of Table 51a and comparative composition 754 were sprayed in Fredericksburg, Tex. on 2–3 inch tall henbit (LAMAM), a common winter annual typically treated with ROUNDUP ULTRA® in preplant burndown applications. Results, averaged for all replicates of each treatment, are shown in Table 51b.

TABLE 51b

| Comp. | 315 g/ha | 420 g/ha | 526 g/ha | 631 g/ha | 736 g/ha |
|---|---|---|---|---|---|
| 265C1 | 62.3 | 59 | 65.3 | 69.8 | 73 |
| 765T5 | 58.5 | 64.8 | 69.8 | 74 | 76.8 |
| 677I9 | 61.3 | 59.3 | 69 | 74.8 | 76.8 |
| 769R5 | 55.3 | 67.3 | 70.3 | 77 | 76 |
| 767A2 | 57.3 | 57.3 | 65.8 | 71 | 73 |
| 560C6 | 60 | 62 | 72.3 | 73.8 | 82 |
| 563W3 | 60.8 | 61 | 65.3 | 68.5 | 75.8 |
| 754P5 | 54.5 | 62.8 | 66.3 | 67 | 72.8 |

Example 52

Aqueous concentrate compositions were prepared containing glyphosate salt and excipient ingredients as shown in Table 52a.

TABLE 52a

| Comp. | Salt | g/l | Comp. 1 | g/l | Comp. 2 | g/l | Comp. 3 | g/l | Comp. 4 | g/l |
|---|---|---|---|---|---|---|---|---|---|---|
| 560 | K | 540 | M121 | 135 | | | | | | |
| 968D1I | K | 480 | ETH12 | 48 | WIT80 | 48 | INT00 | 24 | No13 | 7 |
| 959C2J | K | 480 | ETH12 | 48 | WIT80 | 48 | INT00 | 24 | | |
| 959D4E | K | 480 | ETH12 | 48 | WIT05 | 48 | INT00 | 24 | glycol | 33 |
| 478E2U | K | 480 | ETH12 | 48 | WIT05 | 48 | INT00 | 24 | glycol | 120 |
| 960G9Z | K | 540 | ETH12 | 61 | WIT05 | 74 | | | | |
| 960H3C | K | 540 | ETH12 | 61 | WIT058 | 74 | | | glycol | 34 |
| 478F6K | K | 540 | ETH12 | 61 | WIT05 | 74 | | | glycol | 102 |
| 96O4X | K | 540 | ETH12 | 68 | WIT05 | 68 | | | | |
| 960J8J | K | 540 | ETH12 | 68 | WIT05 | 68 | | | glycol | 34 |
| 693N0L | K | 540 | ETH12 | 68 | WIT05 | 68 | | | glycol | 102 |
| 164B1H | K | 540 | SUR50 | 100 | Citric Acid | 4 | | | | |
| 187A7Y | K | 484 | SUR50 | 91 | Citric Acid | 3 | | | | |
| 360 | IPA | 360 | | | | | | | | |
| 754 | IPA | 445 | WIT05 | 5.9 | INT00 | 2 | | | | |

Velvetleaf (ABUTH) and Japanese millet (ECHCF) plants were grown and treated by the standard procedures above. The compositions of Table 52a and comparative compositions 554, 754 and 360 were applied. Results, averaged for all replicates of each treatment, are shown in Table 52b and Table 52c.

TABLE 52b

ABUTH % Control

| Comp. | 100 g a.e./ha | 200 g a.e./ha | 300 g a.e./ha | 400 g a.e./ha |
|---|---|---|---|---|
| 968D1I | 33.3 | 76.7 | 86.7 | 90 |
| 959C2J | 55 | 81.7 | 88.3 | 90 |
| 959D4E | 61.7 | 80 | 88.3 | 90 |
| 478E2U | 43.3 | 80 | 90 | 90 |
| 960G9Z | 36.7 | 83.3 | 88.3 | 90 |
| 960H3C | 46.7 | 80 | 90 | 93.3 |
| 478F6K | 36.7 | 80 | 90 | 95 |
| 96O4X | 65 | 80 | 90 | 91.7 |
| 960J8J | 28.3 | 83.3 | 85 | 90 |
| 693N0L | 5 | 76.7 | 85 | 90 |
| 164B1H | 26.7 | 78.3 | 86.7 | 93.3 |
| 187A7Y | 16.7 | 75 | 90 | 93 |
| 360 | 50 | 85 | 88.3 | 91.7 |
| 754 | 75 | 88.3 | 91.7 | 96 |
| 560 | 50 | 85 | 88.3 | 91.7 |

TABLE 52c

ECHCF % Control

| Composition | 100 g a.e./ha | 200 g a.e./ha | 300 g a.e./ha | 400 g a.e./ha |
|---|---|---|---|---|
| 968D1I | 30 | 56.7 | 75 | 78.3 |
| 959C2J | 48.3 | 61.7 | 68.3 | 75 |
| 959D4E | 16.7 | 63.3 | 70 | 73.3 |
| 478E2U | 30 | 60 | 78.3 | 81.7 |
| 960G9Z | 48.3 | 63.3 | 85 | 90 |
| 960H3C | 45 | 70 | 85 | 85 |
| 478F6K | 20 | 65 | 73.3 | 81.7 |
| 96O4X | 40 | 75 | 76.7 | 97 |
| 960J8J | 50 | 66.7 | 80 | 91 |
| 693N0L | 46.7 | 66.7 | 85.0 | 85.0 |
| 164B1H | 13.3 | 58.3 | 71.7 | 83.3 |
| 187A7Y | 43.3 | 66.7 | 78.3 | 90 |
| 360 | 53.3 | 81.7 | 91 | 97 |
| 754 | 43.3 | 75 | 95 | 97.7 |
| 560 | 41.7 | 65 | 71.7 | 89.3 |

The 360 and 754 standards outperformed the formulations in this trial. The addition of glycols and citric acid marginally affected efficacy.

Example 53

Aqueous concentrate compositions were prepared containing glyphosate salt and excipient ingredients as shown in Table 53a.

TABLE 53a

| Comp. | Salt | g a.e./l | Comp. 1 | g/l | Comp. 2 | g/l |
|---|---|---|---|---|---|---|
| 354A4E | K | 460 | MT13 | 0.8 | ETH15 | 0.5 |
| 354B5Y | K | 460 | MT13 | 0.9 | ETH12 | 0.4 |
| 354C2W | K | 460 | MT13 | 1 | ETH12 | 0.3 |
| 354D4E | K | 480 | MT13 | 1 | ETH12 | 0.3 |
| 354E9O | K | 480 | MT13 | 0.8 | ETH12 | 0.4 |
| 354F4R | K | 480 | MT13 | 0.7 | ETH12 | 0.2 |

Velvetleaf (ABUTH) plants were grown and treated by the standard procedures above. The compositions of Table 53a and comparative compositions 139, 554, 754 and 360 were applied. Results, averaged for all replicates of each treatment, are shown in Table 53b.

TABLE 53b

ABUTH % Control

| Composition | 100 g a.e./ha | 200 g a.e./ha | 300 g a.e./ha | 400 g a.e./ha |
|---|---|---|---|---|
| 354A4E | 2.5 | 46.7 | 62.5 | 77.5 |
| 354B5Y | 0.8 | 38.3 | 58.3 | 76.7 |
| 354C2W | 2.5 | 45 | 69.2 | 80 |
| 354D4E | 0.8 | 50 | 60 | 75 |
| 354E9O | 2.5 | 34.2 | 57.5 | 70.8 |
| 354F4R | 1.7 | 31.7 | 55 | 67.5 |
| 554 | 7.5 | 8.3 | 12.5 | 38.3 |
| 139 | 5.8 | 2.5 | 12.5 | 33.3 |
| 754 | 1.7 | 47.5 | 61.7 | 81.7 |
| 360 | 2.5 | 47.5 | 68.3 | 85 |

Four of the six formulations were similar in efficacy to 754 and 360 standards. The two remaining trials were only slightly less effective on velvetleaf than were the standards.

Example 54

Aqueous concentrate compositions were prepared containing glyphosate salt and excipient ingredients as shown in Table 54a.

TABLE 54a

| Comp. | Salt | g a.e./l | Comp. 1 | g/l |
|---|---|---|---|---|
| 131A | IPA | 570 | M818 | 0.5 |
| 131B | IPA | 570 | M818 | 1 |
| 131C | IPA | 570 | M818 | 2 |
| 131D | IPA | 570 | M818 | 5 |
| 131E | IPA | 570 | M818 | 10 |
| 131F | IPA | 570 | M818 | 50 |
| 554A | K | 725 | M818 | 0.5 |
| 554B | K | 725 | M818 | 1 |
| 554C | K | 725 | M818 | 2 |
| 554D | K | 725 | M818 | 5 |
| 554E | K | 725 | M818 | 10 |
| 554F | K | 725 | M818 | 50 |

Velvetleaf (ABUTH) and Japanese millet (ECHCF) plants were grown and treated by the standard procedures above. The compositions of Table 54a and comparative compositions 139 and 554 were applied. Results, averaged for all replicates of each treatment, are shown in Table 54b and 54c.

TABLE 54b

ABUTH % Control

| Composition | 75 g a.e./ha | 100 g a.e./ha | 150 g a.e./ha |
|---|---|---|---|
| 131A | 51.7 | 69.2 | 79.2 |
| 131B | 62.5 | 75 | 83.3 |
| 131C | 50 | 62.5 | 79.2 |
| 131D | 57.5 | 75.8 | 79.2 |
| 131E | 56.7 | 77.5 | 79.2 |
| 131F | 23.3 | 30 | 31.7 |
| 554A | 45 | 59.2 | 75.8 |
| 554B | 45.8 | 63.3 | 72.5 |
| 554C | 56.7 | 64.2 | 75 |
| 554D | 45.8 | 73.3 | 77.5 |
| 554E | 37.5 | 62.5 | 77.5 |
| 554F | 4.2 | 9.2 | 10.0 |
| 139 | 10.8 | 12.5 | 57.5 |
| 554 | 0 | 0 | 21.7 |

TABLE 54c

ECHCF % Control

| Composition | 75 g a.e./ha | 100 g a.e./ha | 150 g a.e./ha |
|---|---|---|---|
| 131A | 60 | 69.2 | 65 |
| 131B | 65 | 68.3 | 84.2 |
| 131C | 70.8 | 87 | 98.5 |
| 131D | 70.8 | 90.7 | 89.7 |
| 131E | 60.8 | 65 | 83.3 |
| 131F | 30 | 31.7 | 35 |
| 554A | 33.3 | 55 | 65.8 |
| 554B | 40.8 | 42.5 | 63.3 |
| 554C | 40 | 64.2 | 73.3 |
| 554D | 33.3 | 56.7 | 70 |
| 554E | 7.5 | 40.8 | 63.3 |
| 554F | 1.7 | 2.5 | 5.8 |
| 139 | 5 | 7.5 | 31.7 |
| 554 | 0 | 5.8 | 31.7 |

Example 55

Aqueous concentrate compositions were prepared containing glyphosate salt and excipient ingredients as shown in Table 55a.

TABLE 55a

| Comp. | Salt | g a.e./l | Comp. 1 | g/l | Comp. 2 | g/l |
|---|---|---|---|---|---|---|
| 434F4T | K | 480 | M121 | 90 | ARQ27 | 30 |
| 434G7U | K | 480 | M121 | 90 | ARQ27 | 60 |
| 434H8I | K | 480 | M121 | 90 | APG69 | 60 |
| 434I2Q | K | 480 | M121 | 90 | APG69 | 30 |
| 434J7Y | K | 480 | M121 | 120 | APG69 | 30 |
| 767E3 | K | 510 | 1816E | 50 | ARQ13 | 18.5 |
| 754 | IPA | 445 | | | | |
| 360 | IPA | 360 | WIT05 | 5.9 | | |
| 554 | K | 725 | | | INT00 | 2.2 |

Velvetleaf (ABUTH) and Japanese millet (ECHCF) plants were grown and treated by the standard procedures above. The compositions of Table 55a and comparative compositions 139, 554, 754 and 360 were applied. Results, averaged for all replicates of each treatment, are shown in Table 55b and 55c.

TABLE 55b

ABUTH % Control

| Composition | 100 g a.e./ha | 150 g a.e./ha | 200 g a.e./ha | 300 g a.e./ha |
|---|---|---|---|---|
| 434F4T | 55 | 60.8 | 79.2 | 85 |
| 434G7U | 45 | 72.5 | 82.5 | 86.7 |
| 434H8I | 46.7 | 66.7 | 82.5 | 86.7 |
| 434I2Q | 48.3 | 70 | 81.7 | 86.7 |
| 434J7Y | 56.7 | 66.7 | 81.7 | 90 |
| 767E3 | 69.2 | 80.8 | 85 | 97.7 |
| 754 | 75 | 80.8 | 84.2 | 95 |
| 360 | 72.5 | 80 | 85 | 94.2 |
| 554 | 33.3 | 41.7 | 68.3 | 77.5 |
| 139 | 37.5 | 50.8 | 75 | 81.7 |

TABLE 55c

ECHCF % Control

| Composition | 100 g a.e./ha | 150 g a.e./ha | 200 g a.e./ha | 300 g a.e./ha |
|---|---|---|---|---|
| 434F4T | 68.3 | 82.5 | 87.5 | 92.7 |
| 434G7U | 67.5 | 86.7 | 89.8 | 96.2 |
| 434H8I | 67.5 | 82.5 | 90.5 | 95.8 |
| 434I2Q | 66.7 | 85.8 | 92.8 | 99.2 |
| 434J7Y | 75 | 79.2 | 95.5 | 98.5 |
| 767E3 | 67.5 | 79.2 | 83.3 | 86.3 |
| 754 | 73.3 | 81.7 | 90 | 97.2 |
| 360 | 71.7 | 87.8 | 94.8 | 96.8 |
| 554 | 30 | 49.2 | 58.3 | 62.5 |
| 139 | 31.7 | 55.8 | 63.3 | 65.8 |

No K salt formulation outperformed the composition 360 or composition 754 for control of velvetleaf.

Example 56

Aqueous concentrate compositions were prepared containing glyphosate salt and excipient ingredients as shown in Table 56a.

TABLE 56a

| Comp. | Salt | g a.e./l | Comp. 1 | g/l | Comp. 2 | g/l |
|---|---|---|---|---|---|---|
| 734A2D | K | 30 | S16 | 4.5 | PG069 | 5.5 |
| 737A5Y | K | 30 | S20 | 5.2 | PG069 | 4.8 |
| 737B4X | K | 30 | S21 | 5.5 | PG069 | 4.5 |
| 734D6J | K | 30 | | | PG069 | 10.0 |

TABLE 56a-continued

| Comp. | Salt | g a.e./l | Comp. 1 | g/l | Comp. 2 | g/l |
|---|---|---|---|---|---|---|
| 734E1A | K | 4.3 | S16 | 1.4 | | |
| 737C9D | K | 4.3 | S20 | 1.4 | | |
| 737D6H | K | 30 | S21 | 10.0 | | |

Velvetleaf (ABUTH) and Japanese millet (ECHCF) plants were grown and treated by the standard procedures above. The compositions of Table 56a and comparative compositions 139, 554, 754 and 360 were applied. Results, averaged for all replicates of each treatment, are shown in Table 56b and Table 56c.

TABLE 56b

ABUTH % Control

| Composition | 75 g a.e./ha | 150 g a.e./ha | 225 g a.e./ha | 300 g a.e./ha |
|---|---|---|---|---|
| 734A2D | 0 | 35 | 57.5 | 70 |
| 737A5Y | 1.7 | 20 | 57.5 | 72.5 |
| 737B4X | 0 | 36.7 | 65 | 75.8 |
| 734D6J | 0 | 35.8 | 60.8 | 72.5 |
| 734E1A | 0 | 45 | 66.7 | 79.2 |
| 737C9D | 0 | 46.7 | 70.8 | 77.5 |
| 737D6H | 0 | 46.7 | 75.8 | 77.5 |
| 554 | 0 | 0 | 40.8 | 58.3 |
| 360 | 0 | 75.8 | 82.5 | 88.3 |
| 553 | 29.2 | 81.7 | 89.2 | 94.8 |

TABLE 56c

ECHCF % Control

| Composition | 75 g a.e./ha | 150 g a.e./ha | 225 g a.e./ha | 300 g a.e./ha |
|---|---|---|---|---|
| 734A2D | 10.8 | 70 | 75 | 80.8 |
| 737A5Y | 10 | 66.7 | 68.3 | 75 |
| 737B4X | 18.3 | 65 | 66.7 | 74.2 |
| 734D6J | 11.7 | 65 | 70 | 71.7 |
| 734E1A | 17.5 | 60 | 67.5 | 70 |
| 737C9D | 0 | 35 | 52.5 | 71.7 |
| 737D6H | 8.3 | 64.2 | 66.7 | 69.2 |
| 554 | 0 | 1.7 | 9.2 | 24.2 |
| 360 | 36.7 | 70 | 83.3 | 84.2 |
| 553 | 65 | 75.8 | 87.2 | 90.8 |

All formulations containing glucamine alone or in combination with PG069 were less active than composition 360 on velvetleaf and barnyardgrass.

Example 57

Aqueous concentrate compositions were prepared containing glyphosate salt and excipient ingredients as shown in Table 57a.

TABLE 57a

| Comp. | Salt | % (w/w) | Comp. 1 | g/l | Comp. 2 | g/l |
|---|---|---|---|---|---|---|
| 663B8K | K | 37.2 | PG069 | 12.8 | ETH12 | 3.5 |
| 663C3M | K | 34.2 | PG069 | 17.4 | ETH12 | 3.8 |
| 564A0B | K | 34.2 | PG069 | 11.9 | ETH12 | 7.7 |
| 568B7J | K | 34.2 | PG069 | 15 | ETH12[1] | 0.8 |
| 568C2V | K | 34 | PG069 | 14 | ETH15 | 3.8 |
| 568A4L | K | 34.2 | PG069 | 9.6 | ETH15 | 7.6 |

[1]Also contains 3% Eth25

Velvetleaf (ABUTH) and Japanese millet (ECHCF) plants were grown and treated by the standard procedures above. The compositions of Table 57a and comparative compositions 318, 765, 754 were applied. Results, averaged for all replicates of each treatment, are shown in Table 57b and Table 57c.

TABLE 57b

ABUTH % Control

| Composition | 75 g a.e./ha | 150 g a.e./ha | 225 g a.e./ha | 300 g a.e./ha |
|---|---|---|---|---|
| 663B8K | 0 | 0 | 0 | 0 |
| 663C3M | 0 | 0 | 0 | 0 |
| 564A0B | 0 | 0 | 0 | 0 |
| 568B7J | 0.8 | 0 | 0 | 0 |
| 568C2V | 0 | 0 | 0 | 0 |
| 568A4L | 0 | 0 | 0 | 0 |
| 754 | 2.5 | 80 | 86.7 | 89.8 |
| 765 | 0 | 70.8 | 80.8 | 85 |
| 318 | 37.5 | 80 | 90 | 89.2 |
| Touchdown IQ | 0 | 30.8 | 75.8 | 82.5 |

TABLE 57c

ECHCF % Control

| Composition | 75 g a.e./ha | 150 g a.e./ha | 225 g a.e./ha | 300 g a.e./ha |
|---|---|---|---|---|
| 663B8K | 4.2 | 0.8 | 0 | 2.5 |
| 663C3M | 0 | 0.8 | 0 | 5 |
| 564A0B | 3.3 | 1.7 | 1.7 | 2.5 |
| 568B7J | 0 | 0 | 7.5 | 0.8 |
| 568C2V | 0 | 0 | 0 | 0 |
| 568A4L | 0 | 0 | 0 | 0 |
| 754 | 1.7 | 55 | 62.5 | 73.3 |
| 765 | 13.3 | 55 | 60 | 65 |
| 318 | 40.8 | 55 | 65 | 67.5 |
| Touchdown IQ | 10 | 52.5 | 55.8 | 60 |

Compositions 754, 765, and 318 provided better control of both velvetleaf and barnyard grass than did Touchdown IQ.

Example 58

Aqueous concentrate compositions were prepared containing glyphosate salt and excipient ingredients as shown in Table 58a and Table 58b.

TABLE 58a

| Comp. | Salt | g/l | Comp. 1 | g/l | Comp. 2 | g/l | Comp. 3 | g/l |
|---|---|---|---|---|---|---|---|---|
| 676F3Z | K | 480 | ETH12 | 64 | WIT80 | 64 | INT00 | 32 |
| 677P9K | K | 480 | ETH12 | 48 | WIT80 | 48 | INT00 | 24 |
| 678J3C | K | 480 | ETH12 | 30 | WIT80 | 66 | INT00 | 24 |
| 562A1B | K | 480 | ETH12 | 30 | WIT05 | 90 | | |
| 56319W | K | 540 | ETH12 | 61 | WIT05 | 74 | | |
| 564N6L | K | 540 | ETH12 | 68 | WIT05 | 68 | | |
| 767A2S | K | 510 | | | 1816E | 5 | ARQ37 | 1.5 |
| 767B6U | K | 510 | | | 1816E | 5 | ARQ37 | 1.5 |
| 360 | IPA | 360 | | | | | | |
| 754 | IPA | 445 | | | | | | |

Velvetleaf (ABUTH) and Japanese millet (ECHCF) plants were grown and treated by the standard procedures above. The compositions of Table 58a and comparative compositions 139, 765, 754 were applied. Results, averaged for all replicates of each treatment, are shown in Table 58b and Table 58c.

TABLE 58b

ABUTH % Control

| Composition | 100 g a.e./ha | 150 g a.e./ha | 200 g a.e./ha | 300 g a.e./ha |
|---|---|---|---|---|
| 676F3Z | 68 | 80 | 82 | 88.6 |
| 677P9K | 38 | 83 | 81 | 87 |
| 678J3C | 32 | 73 | 80 | 87 |
| 562A1B | 22 | 63 | 84 | 84 |
| 563I9W | 14 | 64 | 75 | 82 |
| 564N6L | 16 | 75 | 82 | 85 |
| 767A2S | 49 | 83 | 86 | 89 |
| 767B6U | 70 | 79 | 83 | 89 |
| 360 | 73 | 86 | 90 | 95 |
| 754 | 76 | 84 | 87 | 92 |
| 139 | 4 | 38 | 65 | 82 |
| 554 | 2 | 20 | 57 | 77 |

TABLE 58c

ECHCF % Control

| Composition | 100 g a.e./ha | 150 g a.e./ha | 200 g a.e./ha | 300 g a.e./ha |
|---|---|---|---|---|
| 676F3Z | 66 | 89.6 | 98.4 | 99.2 |
| 677P9K | 65 | 85 | 94.2 | 99.4 |
| 678J3C | 64 | 78 | 96.4 | 98.8 |
| 562A1B | 66 | 92 | 94.6 | 99.4 |
| 563I9W | 64 | 89.6 | 96.2 | 97.2 |
| 564N6L | 62 | 90 | 96.8 | 98.6 |
| 767A2S | 52 | 71 | 76 | 87 |
| 767B6U | 54 | 74 | 83 | 94.8 |
| 360 | 74 | 95.8 | 99.2 | 99.8 |
| 754 | 65 | 92.4 | 97.2 | 99.6 |
| 139 | 15 | 55 | 61 | 69 |
| 554 | 7 | 43 | 53 | 61 |

All potassium salt formulations were less efficacious on velvetleaf versus composition 360 and composition 754. Efficacy of the amine and phosphate ester formulations on ECHCF was nearly equivalent to 360 and 754 compositions.

Example 59

Aqueous concentrate compositions were prepared containing glyphosate salt and excipient ingredients as shown in Table 59a.

TABLE 59a

| Comp. | Salt | g/l | Comp. 1 | g/l | Comp. 2 | g/l | Comp. 3 | g/l |
|---|---|---|---|---|---|---|---|---|
| 9831X3 | K | 30 | | | WIT80 | 6 | | |
| 989A2D | K | 30 | | | WIT80 | 6 | INT00 | 1.5 |
| 9833K9 | K | 30 | ETH12 | 3 | WIT80 | 3 | | |
| 9834X3 | K | 30 | ETH12 | 3 | WIT80 | 3 | INT00 | 1.5 |
| 989B7U | K | 30 | ETH12 | 6 | | | INT00 | 1.5 |
| 989C3R | K | 30 | ETH12 | | WIT80 | 6 | INT00 | 1.5 |
| 9835E2 | K | 30 | ETH12 | 3 | ETH15 | 3 | INT00 | 1.5 |
| 9836W9 | K | 30 | ETH12 | 3 | ETH15 | 3 | INT00 | 1.5 |
| 987A4G | K | 480 | ETH12 | 48 | ETH15 | 48 | INT00 | 24 |
| 987B3F | K | 480 | ETH12 | 48 | ETH15 | 48 | INT00 | 24 |
| 360 | IPA | 360 | | | | | | |
| 754 | IPA | 445 | WIT05 | 5.9 | INT00 | 2 | | |

Velvetleaf (ABUTH) and Japanese millet (ECHCF) plants were grown and treated by the standard procedures above. The compositions of Table 59a and comparative compositions 360 and 754 were applied. Results, averaged for all replicates of each treatment, are shown in Table 59b and Table 59c.

TABLE 59b

ABUTH % Control

| Composition | 100 g a.e./ha | 150 g a.e./ha | 200 g a.e./ha | 300 g a.e./ha |
|---|---|---|---|---|
| 9831X3 | 48 | 81 | 86 | 90 |
| 989A2D | 64 | 82 | 87 | 89 |
| 9833K9 | 27 | 77 | 83 | 85 |
| 9834X3 | 30 | 77 | 85 | 85 |
| 989B7U | 0 | 68 | 81 | 83 |
| 989C3R | 74 | 81 | 87 | 90 |
| 9835E2 | 24 | 75 | 82 | 82 |
| 9836W9 | 51 | 69 | 82 | 82 |
| 987A4G | 46 | 72 | 81 | 82 |
| 987B3F | 36 | 54 | 81 | 81 |
| 360 | 57 | 83 | 89 | 91 |
| 754 | 54 | 83 | 88 | 90 |

TABLE 59c

ECHCF % Control

| Composition | 100 g a.e./ha | 150 g a.e./ha | 200 g a.e./ha | 300 g a.e./ha |
|---|---|---|---|---|
| 9831X3 | 2 | 55 | 62 | 71 |
| 989A2D | 5 | 53 | 62 | 70 |
| 9833K9 | 11 | 54 | 59 | 66 |
| 9834X3 | 2 | 53 | 59 | 61 |
| 989B7U | 2 | 41 | 53 | 60 |
| 989C3R | 7 | 53 | 57 | 70 |
| 9835E2 | 3 | 44 | 58 | 63 |
| 9836W9 | 2 | 45 | 56 | 63 |
| 987A4G | 1 | 44 | 57 | 62 |
| 987B3F | 4 | 45 | 52 | 59 |
| 360 | 1 | 55 | 61 | 75 |
| 754 | 0 | 55 | 59 | 76 |

Example 60

Aqueous concentrate compositions were prepared containing glyphosate salt and excipient ingredients as shown in Table 60a.

TABLE 60a

| Comp. | Salt | g/l | Comp. 1 | g/l | Comp. 2 | g/l | Comp. 3 | g/l |
|---|---|---|---|---|---|---|---|---|
| 643G1A | K | 540 | M121 | 111 | T23E2 | 24 | | |
| 652A9I | K | 540 | ETH12 | 54 | WIT80 | 54 | INT00 | 27 |
| 652B4R | K | 540 | ETH12 | 54 | WIT80 | 54 | INT00 | 27 |
| 651E7H | K | 540 | ETH12 | 54 | WIT80 | 54 | INT00 | 30 |
| 650C5V | K | 540 | ETH12 | 54 | WIT80 | 54 | AR41 | 32 |
| 651H3X | K | 540 | ETH12 | 54 | WIT80 | 54 | AR41 | 24 |
| 649G6N | K | 540 | ETH12 | 54 | WIT80 | 54 | AR41 | 27 |

Velvetleaf (ABUTH) and Japanese millet (ECHCF) plants were grown and treated by the standard procedures above. The compositions of Table 60a and comparative compositions 139, 360, 554 and 754 were applied. Results, averaged for all replicates of each treatment, are shown in Table 60b and Table 60c.

TABLE 60b

ABUTH % Control

| Composition | 100 g a.e./ha | 150 g a.e./ha | 200 g a.e./ha | 300 g a.e./ha |
|---|---|---|---|---|
| 643G1A | 50.8 | 69.2 | 82.5 | 96.7 |
| 652A9I | 48.3 | 76.7 | 84.2 | 97.7 |

TABLE 60b-continued

ABUTH % Control

| Composition | 100 g a.e./ha | 150 g a.e./ha | 200 g a.e./ha | 300 g a.e./ha |
|---|---|---|---|---|
| 652B4R | 50 | 71.7 | 83.3 | 97.7 |
| 651E7H | 65.8 | 78.3 | 88.3 | 94.2 |
| 650C5V | 39.2 | 72.5 | 75 | 89.2 |
| 651H3X | 52.5 | 69.2 | 80.8 | 92.8 |
| 649G6N | 55.8 | 63.3 | 80 | 89.7 |
| 139 | 18.3 | 46.7 | 65 | 86.7 |
| 554 | 5.8 | 38.3 | 47.5 | 71.7 |
| 360 | 60.8 | 85 | 88.8 | 98.8 |
| 754 | 55.8 | 79.7 | 91 | 96.7 |

TABLE 60c

ECHCF % Control

| Composition | 100 g a.e./ha | 150 g a.e./ha | 200 g a.e./ha | 300 g a.e./ha |
|---|---|---|---|---|
| 643G1A | 96 | 99.7 | 99.8 | 99.8 |
| 652A9I | 89.5 | 99.5 | 99.8 | 99.8 |
| 652B4R | 87.8 | 96.2 | 97.8 | 100 |
| 651E7H | 80.8 | 96.5 | 99.5 | 100 |
| 650C5V | 84 | 99.5 | 96 | 100 |
| 651H3X | 93 | 98.3 | 97.5 | 99.8 |
| 649G6N | 92.8 | 95.2 | 98 | 100 |
| 139 | 21.7 | 47.5 | 60 | 85.5 |
| 554 | 26.7 | 52.5 | 65.8 | 70 |
| 360 | 98.3 | 99.7 | 100 | 100 |
| 754 | 89.5 | 98.8 | 99.7 | 100 |

Example 61

Aqueous concentrate compositions were prepared containing glyphosate salt and excipient ingredients as shown in Table 61a.

TABLE 61a

| Comp. | Salt | % (W/W) | Comp. 1 | % (W/W) | Comp. 2 | % (W/W) |
|---|---|---|---|---|---|---|
| 484A3G | K | 31 | AE10 | 3.6 | WIT05 | 8.4 |
| 484B7I | K | 36.9 | AE10 | 4.8 | WIT05 | 7.2 |
| 484C4J | K | 36.9 | AE10 | 6 | WIT05 | 6 |
| 484D4R | K | 36.9 | AE10 | 7.2 | WIT05 | 4.8 |
| 484E5H | K | 36.9 | AE10 | 8.4 | WIT05 | 3.6 |
| 484F6P | K | 36.9 | AE10 | 12 | | |
| 484G7O | K | 36.9 | | | WIT05 | 12 |

Velvetleaf (ABUTH) plants were grown and treated by the standard procedures above. The compositions of Table 61a and comparative compositions 553 and 554 were applied. Results, averaged for all replicates of each treatment, are shown in Table 61b.

TABLE 61b

ABUTH % Control

| Composition | 100 g a.e./ha | 150 g a.e./ha | 200 g a.e./ha | 300 g a.e./ha |
|---|---|---|---|---|
| 484A3G | 39.2 | 75 | 88.3 | 89.2 |
| 484B7I | 55.8 | 78.3 | 87.5 | 88.3 |
| 484C4J | 35 | 75.8 | 83.3 | 86.7 |
| 484D4R | 34.2 | 75 | 84.2 | 90.8 |
| 484E5H | 29.2 | 70.8 | 83.3 | 90.5 |
| 484F6P | 35.8 | 26.7 | 72.5 | 76.7 |
| 484G7O | 64.2 | 80 | 88.3 | 88.3 |

TABLE 61b-continued

ABUTH % Control

| Composition | 100 g a.e./ha | 150 g a.e./ha | 200 g a.e./ha | 300 g a.e./ha |
|---|---|---|---|---|
| 554 (725 g/l) | 0 | 0 | 13.3 | 25 |
| 554 (445 g/l) | 3.3 | 78.3 | 85 | 87.5 |
| 553 (360 g/l) | 63.3 | 84.2 | 91.7 | 96 |

Example 62

Aqueous concentrate compositions were prepared containing glyphosate salt and excipient ingredients as shown in Table 62a.

TABLE 62a

| Comp. | Salt | % (W/W) | Comp. 1 | % (W/W) | Comp. 2 | % (W/W) |
|---|---|---|---|---|---|---|
| 553 | IPA | 31 | BRI56 | 6.4 | ETH25 | 9.6 |
| 970A3W | K | 31 | EXP0A | 10 | | |
| 970B7U | K | 31 | EXP0B | 10 | | |
| 970C0O | K | 31 | EXP0C | 10 | | |
| 970D2S | K | 31 | EXP0A | 4 | EMUL | 6 |
| 970E5R | K | 31 | EXP0B | 4 | EMUL | 6 |
| 970F4D | K | 31 | EXP0C | 4 | EMUL | 6 |

Velvetleaf (ABUTH) and Japanese millet (ECHCF) plants were grown and treated by the standard procedures above. The compositions of Table 62a and comparative compositions 139, 360, 554 and 754 were applied. Results, averaged for all replicates of each treatment, are shown in Table 62b and Table 62c.

TABLE 62b

ABUTH % Control

| Composition | 100 g a.e./ha | 150 g a.e./ha | 200 g a.e./ha | 300 g a.e./ha |
|---|---|---|---|---|
| 970A3W | 22.5 | 51.7 | 61.7 | 69.2 |
| 970B7U | 29.2 | 55.8 | 64.2 | 69.2 |
| 970C0O | 0.8 | 18.3 | 45 | 66.7 |
| 970D2S | 12.5 | 50.8 | 54.2 | 68.3 |
| 970E5R | 20 | 52.5 | 60.8 | 70.8 |
| 970F4D | 20.8 | 47.5 | 63.3 | 68.3 |
| 554 | 0 | 13.3 | 45.8 | 55.8 |
| 360 | 42.5 | 59.2 | 73.3 | 75 |
| 139 | 58.3 | 69.2 | 75 | 80.8 |
| 754 | 38.3 | 60.8 | 66.7 | 73.3 |

TABLE 62c

ECHCF % Control

| Composition | 100 g a.e./ha | 150 g a.e./ha | 200 g a.e./ha | 300 g a.e./ha |
|---|---|---|---|---|
| 970A3W | 16.7 | 37.5 | 42.5 | 60 |
| 970B7U | 29.2 | 35.8 | 47.5 | 54.2 |
| 970C0O | 10 | 36.7 | 41.7 | 52.5 |
| 970D2S | 9.2 | 30 | 33.3 | 50 |
| 970E5R | 12.5 | 35 | 40.8 | 51.7 |
| 970F4D | 0.8 | 37.5 | 44.2 | 49.2 |
| 554 | 0 | 1.7 | 3.3 | 13.3 |
| 360 | 16.7 | 37.5 | 51.7 | 60.8 |
| 360 | 33.3 | 50.8 | 54.2 | 67.5 |
| 754 | 15.8 | 46.7 | 47.5 | 60 |

Example 63

Aqueous concentrate compositions were prepared containing glyphosate salt and excipient ingredients as shown in Table 63a.

TABLE 63a

| Comp. | Salt | % (W/W) | Comp. 1 | % (W/W) | Comp. 2 | % (W/W) |
|---|---|---|---|---|---|---|
| 553 | IPA | 31 | BRI56 | 0.4 | ETH25 | 9.6 |
| 478A2S | K | 36.9 | EXP86 | 3.6 | WIT05 | 8.4 |
| 478B4D | K | 36.9 | EXP86 | 4.8 | WIT05 | 7.2 |
| 478C8U | K | 36.9 | EXP86 | 6 | WIT05 | 6 |
| 478D6B | K | 36.9 | EXP86 | 7.2 | WIT05 | 4.8 |
| 478E2Z | K | 36.9 | EXP86 | 8.4 | WIT05 | 3.6 |
| 478F5J | K | 36.9 | EXP86 | 12 | | |
| 478G4M | K | 36.9 | | | WIT05 | 12 |

Velvetleaf (ABUTH) plants were grown and treated by the standard procedures above. The compositions of Table 63a and comparative compositions 139, 360, 554 and 754 were applied. Results, averaged for all replicates of each treatment, are shown in Table 63b.

TABLE 63b

ABUTH % Control

| Composition | 100 g a.e./ha | 150 g a.e./ha | 200 g a.e./ha | 300 g a.e./ha |
|---|---|---|---|---|
| 553 | 10.8 | 74.2 | 84.2 | 88.3 |
| 478A2S | 15.8 | 47.5 | 78.3 | 85 |
| 478B4D | 17.5 | 65 | 80.8 | 85.8 |
| 478C8U | 20.8 | 55.8 | 79.2 | 87.5 |
| 478D6B | 20.8 | 55.8 | 82.5 | 87.5 |
| 478E2Z | 14.2 | 55 | 79.2 | 84.2 |
| 478F5J | 0 | 25.8 | 56.7 | 76.7 |
| 478G4M | 3.3 | 36.7 | 59.2 | 82.5 |
| 554 (725 g/l) | 0 | 0 | 0 | 2.5 |
| 754 (445 g/l) | 0 | 19.2 | 65 | 80 |

EXP86 and WIT05 were all similar in performance for control of velvetleaf. 754 was less efficacious than WIT05 alone but more efficacious than 86B alone. All 3 were less efficacious than any blend.

Example 64

Aqueous concentrate compositions were prepared containing glyphosate salt and excipient ingredients as shown in Table 64a.

TABLE 64a

| Comp. | Salt | g/l | Comp. 1 | g/l | Comp. 2 | g/l | Comp. 3 | g/l |
|---|---|---|---|---|---|---|---|---|
| 622H7 | K | 480 | M121 | 160 | | | | |
| 560P2 | K | 540 | M121 | 135 | | | | |
| 239L8 | K | 480 | M121 | 120 | | | | |
| 676Y5 | K | 480 | ETH12 | 64 | WIT80 | 64 | INT00 | 32 |
| 677W2 | K | 480 | ETH12 | 40 | WIT80 | 48 | INT00 | 24 |
| 767K9 | K | 510 | 1816E | 5 | ARQ37 | 1.5 | | |

Velvetleaf (ABUTH) and Japanese millet (ECHCF) plants were grown and treated by the standard procedures above. The compositions of Table 64a and comparative compositions 139, 360, 554 and 754 were applied. Results, averaged for all replicates of each treatment, are shown in Table 64b and Table 64c.

TABLE 64b

ABUTH % Control

| Composition | 100 g a.e./ha | 150 g a.e./ha | 200 g a.e./ha | 300 g a.e./ha |
|---|---|---|---|---|
| 622H7 | 16.7 | 57.5 | 78.3 | 85 |
| 560P2 | 8.3 | 45 | 66.7 | 77.5 |
| 239L8 | 11.7 | 50 | 65.8 | 73.3 |
| 676Y5 | 12.5 | 60 | 71.7 | 76.7 |
| 677W2 | 5 | 56.7 | 65 | 73.3 |
| 767K9 | 18.3 | 65.8 | 80 | 83.3 |
| 139 | 0 | 17.5 | 50 | 68.3 |
| 754 | 30 | 68.3 | 80 | 90.8 |
| 360 | 23.3 | 65 | 80 | 90 |
| 554 | 0 | 0.8 | 37.5 | 55 |

TABLE 64c

ECHCF % Control

| Composition | 100 g a.e./ha | 150 g a.e./ha | 200 g a.e./ha | 300 g a.e./ha |
|---|---|---|---|---|
| 622H7 | 64.2 | 79.2 | 90 | 92.8 |
| 560P2 | 65.8 | 73.3 | 84.2 | 85 |
| 239L8 | 61.7 | 62.5 | 80 | 84.2 |
| 676Y5 | 65 | 75 | 87.5 | 93 |
| 677W2 | 63.3 | 68.3 | 88.2 | 88.8 |
| 767K9 | 61.7 | 66.7 | 67.5 | 74.2 |
| 139 | 35 | 45 | 55.8 | 65 |
| 754 | 63.3 | 77.5 | 86.7 | 92.5 |
| 360 | 66.7 | 76.7 | 92 | 93 |
| 554 | 20 | 39.2 | 49.2 | 60.8 |

No glyphosate potassium salt composition was as efficacious as compositions 754 and 360. Two potassium salt formulations, both with surfactant ratios of 3:1 were close in performance to both standards.

Example 65

Aqueous concentrate compositions were prepared containing glyphosate salt and excipient ingredients as shown in Table 65a.

TABLE 65a

| Comp. | Salt | g/l | Comp. 1 | g/l | Comp. 2 | g/l |
|---|---|---|---|---|---|---|
| 656A2D | K | 480 | VAR05 | 60 | WIT80 | 60 |
| 656B8I | K | 480 | VAR05 | 54 | WIT80 | 66 |
| 656C6Y | K | 480 | VAR05 | 48 | WIT80 | 72 |
| 271A2 | K | 480 | VAR02 | 48 | WIT80 | 48 |
| 270P0 | K | 480 | VAR02 | 61 | WIT05 | 74 |
| 239R4 | K | 480 | M117 | 120 | | |
| 460U7 | K | 480 | M121 | 135 | | |

Velvetleaf (ABUTH) and Japanese millet (ECHCF) plants were grown and treated by the standard procedures above. The compositions of Table 65a and comparative compositions 360 and 754 were applied. Results, averaged for all replicates of each treatment, are shown in Table 65b and Table 65c.

TABLE 65b

ABUTH % Control

| Composition | 100 g a.e./ha | 150 g a.e./ha | 200 g a.e./ha | 300 g a.e./ha |
|---|---|---|---|---|
| 656A2D | 22.5 | 78.3 | 85 | 87.5 |
| 656B8I | 40.8 | 80 | 87.5 | 91.7 |

TABLE 65b-continued

ABUTH % Control

| Composition | 100 g a.e./ha | 150 g a.e./ha | 200 g a.e./ha | 300 g a.e./ha |
|---|---|---|---|---|
| 656C6Y | 40.8 | 81.7 | 88.3 | 93.3 |
| 271A2 | 70 | 80 | 83.3 | 90 |
| 270P0 | 58.3 | 80.8 | 87.5 | 89.2 |
| 239R4 | 66.7 | 76.7 | 85.8 | 90.8 |
| 460U7 | 47.5 | 80 | 88.3 | 91.7 |
| 754 | 32.5 | 75 | 87.5 | 88.3 |
| 360 | 52.5 | 75.8 | 87.5 | 89.2 |
| M560 | 24.2 | 74.2 | 87.5 | 91.7 |
| M128 | 35 | 77.5 | 87.5 | 92.5 |
| 765 | 36.7 | 80.8 | 87.5 | 93 |

TABLE 65c

ECHCF % Control

| Composition | 100 g a.e./ha | 150 g a.e./ha | 200 g a.e./ha | 300 g a.e./ha |
|---|---|---|---|---|
| 656A2D | 30.8 | 58.3 | 61.7 | 66.7 |
| 656B8I | 30 | 51.7 | 62.5 | 63.3 |
| 656C6Y | 39.2 | 56.7 | 60 | 70 |
| 271A2 | 18.3 | 51.7 | 61.7 | 63.3 |
| 270P0 | 31.7 | 57.5 | 65 | 69.2 |
| 239R4 | 15.8 | 54.2 | 60 | 70.8 |
| 460U7 | 40 | 55.8 | 60.8 | 70.8 |
| 754 | 23.3 | 56.7 | 61.7 | 73.3 |
| 360 | 26.7 | 56.7 | 65.8 | 75 |
| M560 | 20 | 58.3 | 58.3 | 69.2 |
| M128 | 42.5 | 60.8 | 65.8 | 75 |
| 765 | 43.3 | 55.8 | 60 | 73.3 |

Cloud point was determined for certain liquid compositions of Examples 66–69 as follows. A sample of the composition in a test tube was heated in a water bath until it became cloudy. The test tube was then removed from the water bath and the sample stirred with a thermometer until it became clear. The temperature at which the sample became clear was recorded as the cloud point of the composition.

Percentages expressed as "%" in the following Examples are by weight/weight unless otherwise indicated.

Example 66

The surfactants used in Example 68 are Witcamine TAM-60, a Tallowamine ethoxylate with 6 moles of ethylene oxide, Witcamine TAM-80, a Tallowamine ethoxylate with 8 moles of ethylene oxide, and Witcamine TAM-105, a Tallowamine ethoxylate with 10 moles of ethylene oxide.

The aqueous concentrate compositions of Example 66 were prepared by mixing the following components:

(1) aqueous concentrate solution of glyphosate in the form of the potassium salt;

(2) surfactant as defined above; and (3) water.

The composition can be calculated to contain 360 grams/liter a.e. (29.0% a.e.) glyphosate and 90 grams/liter (7.25%) surfactant. Specific gravity of the composition at 20/15.6° C. was determined to be 1.25. The cloud point of each surfactant composition was determined as shown in the table below.

| Surfactant | Cloud Point (° C.) |
|---|---|
| Witcamine TAM-60 | >90 |
| Witcamine TAM-80 | >90 |
| Witcamine TAM-105 | <Room Temperature |

Example 67

The surfactants of Example 67 were tested at a higher potassium glyphosate loading.

An aqueous concentrate composition containing 450 grams/liter a.e. (34.6% a.e.) glyphosate potassium salt and 6.92% surfactant was prepared by a procedure similar to that of Example 66. Specific gravity of the compositions at 20/15.6° C. was determined to be 1.30. The cloud point of each surfactant composition was determined as shown in the table below.

| Surfactant | Cloud Point (° C.) |
|---|---|
| Witcamine TAM-60 | >90 |
| Witcamine TAM-80 | >55 |
| Witcamine TAM-105 | <Room Temperature |

Example 68

The surfactant used in Example 68 was Ethomeen C/15 (Ethoxylated Cocoamine (15 EO)).

An aqueous concentrate composition containing 606 grams/liter a.e. (29.0% a.e.) glyphosate potassium salt and 5.05% surfactant was prepared by a procedure similar to that of Example 66. Specific gravity of the composition at 20/15.6° C. was determined to be 1.399. The cloud point of the composition was determined to be 72° C.

Example 69

The surfactant used in Example 69 was Huntsman Surfonic AGM-550 (M121).

An aqueous concentrate composition containing 486 grams/liter a.e. (36.6% a.e.) glyphosate potassium salt, 22 grams/liter a.i. (1.66% a.i.) glufosinate ammonium salt and 9.16% surfactant was prepared by a procedure similar to that of Example 68. Specific gravity of the composition at 20/15.6° C. was determined to be 1.329. The cloud point of the composition was determined to be 70° C.

Example 70

Aqueous concentrate compositions were prepared containing glyphosate salt and excipient ingredients as shown in Table 70a.

TABLE 70a

| Comp. | Salt | g/l | Comp. 1 | g/l |
|---|---|---|---|---|
| 675A2L | K | 30 | S74 | 1.00 |
| 675B9W | K | 30 | S98 | 1.00 |
| 675C1H | K | 4.3 | S99 | 0.14 |
| 675D4G | K | 30 | S100 | 1.00 |

TABLE 70a-continued

| Comp. | Salt | g/l | Comp. 1 | g/l |
|---|---|---|---|---|
| 675E7Y | K | 30 | S101 | 1.00 |
| 675F2S | K | 30 | S102 | 1.00 |
| 675G1U | K | 30 | S103 | 1.00 |
| 675H9Q | K | 30 | S104 | 1.00 |
| 554 | | 725 | | |
| 754 | | 445 | | |
| 553 | | 360 | | |

Velvetleaf (ABUTH) and Japanese millet (ECHCF) plants were grown and treated by the standard procedures above. The compositions of Table 70a and comparative compositions 553 and 554 were applied. Results, averaged for all replicates of each treatment, are shown in Table 70b and Table 70c.

TABLE 70b

ABUTH % Control

| Comp. | 75 g a.e./ha | 150 g a.e./ha | 225 g a.e./ha | 300 g a.e./ha |
|---|---|---|---|---|
| 675A2L | 0.0 | 65.0 | 80.0 | 85.0 |
| 675B9W | 0.0 | 69.2 | 85.0 | 85.0 |
| 675C1H | 14.2 | 56.7 | 82.5 | 84.2 |
| 675D4G | 39.2 | 82.5 | 90.0 | 90.8 |
| 675E7Y | 56.7 | 82.5 | 89.2 | 90.8 |
| 675F2S | 45.0 | 79.2 | 89.2 | 90.0 |
| 675G1U | 42.5 | 78.3 | 85.0 | 90.8 |
| 675H9Q | 23.3 | 75.8 | 87.5 | 86.7 |
| 554 | 0.0 | 0.0 | 13.3 | 53.3 |
| 754 | 17.5 | 80.0 | 88.3 | 92.5 |
| 553 | 60.0 | 86.7 | 91.7 | 94.2 |

TABLE 70c

ECHCF % Control

| Comp. | 75 g a.e./ha | 150 g a.e./ha | 225 g a.e./ha | 300 g a.e./ha |
|---|---|---|---|---|
| 675A2L | 5.8 | 58.3 | 70.8 | 71.7 |
| 675B9W | 19.2 | 67.5 | 73.3 | 76.7 |
| 675C1H | 20.8 | 65.8 | 74.2 | 75.8 |
| 675D4G | 34.2 | 65.7 | 72.5 | 78.3 |
| 675E7Y | 28.3 | 67.5 | 72.5 | 75.0 |
| 675F2S | 33.3 | 65.8 | 73.3 | 75.0 |
| 675G1U | 6.7 | 55.8 | 67.5 | 72.5 |
| 675H9Q | 3.3 | 58.3 | 66.7 | 67.5 |
| 554 | 0.0 | 1.7 | 5.0 | 30.0 |
| 754 | 22.5 | 70.8 | 71.7 | 75.0 |
| 553 | 50.8 | 71.7 | 74.2 | 78.3 |

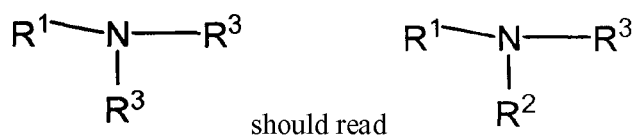

What is claimed is:

1. A formulation useful in retarding the growth of vegetation comprising an aqueous mixture containing a surfactant, glyphosate, primaraly in the form of the potassium salt thereof, and a dicarboxylic acid, the nature of said surfactant and the composition of said formulation being such that, upon application of the formulation to a plant, anisotropic aggregates comprising said surfactant are formed on the foliage of said plant.

2. A formulation as set forth in claim 1 wherein the nature of said surfactant and the composition of said formulation are such that, upon application of the formulation to a plant, liquid crystals comprising said surfactant are formed in the foliage of said plant.

3. A formulation as set forth in claim 1 wherein the glyphosate concentration is from about 400 g a.e./L to about 600 g a.e./L.

4. A formulation of claim 1 wherein the formulation has a cloud point of at least about 50° C. and a crystallization point of not higher than about 0° C.

5. A formulation of claim 4 wherein the formulation has a cloud point of at least about 60° C. and a crystallization point of not higher than about −10° C.

6. A formulation of claim 1 wherein the weight ratio of the surfactant to the dicarboxylic acid is from about 50:1.

7. A formulation of claim 1 wherein the formulation has a density of at least about 1.210 grams/liter.

8. A formulation of claim 1 wherein the formulation has a viscosity of less than about 1000 c.p. at 0° C. at 45/s shear rate.

9. A formulation of claim 8 wherein the formulation has a viscosity of less than about 250 c.p. at 0° C. at 45/s shear rate.

10. A formulation of claim 1 wherein the surfactant comprised by the formulation is not substantially antagonistic to the herbicidal activity of the glyphosate.

11. A formulation useful in retarding the growth of vegetation comprising an aqueous mixture containing a surfactant, glyphosate, predominantly in the form of the potassium salt thereof, and a dicarboxylic acid, the nature of said surfactant and the composition of said formulation being such that, upon application of the formulation to a plant, anisotropic aggregates comprising said surfactant are formed on the foliage of said plant, and wherein the growth of the plant is controlled to a greater extent than in a plant treated with a reference application mixture devoid of the dicarboxylic acid but otherwise having the same composition as said formulation.

12. A formulation as set forth in claim 11 wherein the nature of said surfactant and the composition of said formulation are such that, upon application of the formulation to a plant, liquid crystals comprising said surfactant are formed in the foliage of said plant.

13. A formulation as set forth in claim 11 wherein the glyphosate concentration is from about 400 g a.e./L to about 600 g a.e./L.

14. A formulation of claim 11 wherein the formulation has a cloud point of at least about 50° C. and a crystallization point of not higher than about 0° C.

15. A formulation of claim 14 wherein the formulation has a cloud point of at least about 60° C. and a crystallization point of not higher than about −10° C.

16. A formulation of claim 11 wherein the weight ratio of the surfactant to the dicarboxylic acid is from about 5:1 to about 50:1.

17. A formulation of claim 11 wherein the formulation has a density of at least about 1.210 grams/liter.

18. A formulation of claim 11 wherein the formulation has a viscosity of less than about 1000 c.p. at 0° C. at 45/s shear rate.

19. A formulation of claim 18 wherein the formulation has a viscosity of less than about 250 c.p. at 0° C. at 45/s shear rate.

20. A formulation of claim 11 wherein the surfactant comprised by the formulation is not substantially antagonistic to the herbicidal activity of the glyphosate.

21. A formulation useful in retarding the growth of vegetation comprising an aqueous mixture containing a surfactant, glyphosate or a salt or ester thereof, and a dicarboxylic acid, said surfactant and said dicarboxylic acid being present is a weight ratio of between about 5:1 and about 50:1, the nature of said surfactant and the composition of said formulation being such that, upon application of the formulation to a plant, anisotropic aggregates comprising said surfactant are formed on the foliage of said plant.

22. A formulation as set forth in claim 21 wherein the nature of said surfactant and the composition of said formulation are such that, upon application of the formulation to a plant, liquid crystals comprising said surfactant are formed in the foliage of said plant.

23. A formulation as set forth in claim 21 wherein the glyphosate concentration is from about 400 g a.e./L to about 600 g a.e./L.

24. A formulation of claim 21 wherein the formulation has a cloud point of at least about 50° C. and a crystallization point of not higher than about 0° C.

25. A formulation of claim 24 wherein the formulation has a cloud point of at least about 60° C. and a crystallization point of not higher than about −10° C.

26. A formulation of claim 21 wherein the formulation comprises a salt of glyphosate selected from the group consisting of potassium glyphosate, monoammonium glyphosate, diammonium glyphosate, sodium glyphosate, monoethanolamine glyphosate, n-propylamine glyphosate, ethylamine glyphosate, ethylenediamine glyphosate, hexamethylenediamine glyphosate, trimethylsulfonium glyphosate and mixtures thereof.

27. A formulation of claim 21 wherein the formulation has a density of at least about 1.210 grams/liter.

28. A formulation of claim 21 wherein the formulation has a viscosity of less than about 1000 c.p. at 0° C. at 45/s shear rate.

29. A formulation of claim 28 wherein the formulation has a viscosity of less than about 250 c.p. at 0° C. at 45/s shear rate.

30. A formulation of claim 21 wherein the surfactant comprised by the formulation is not substantially antagonistic to the herbicidal activity of the glyphosate.

31. A formulation of any one of claims 1, 11, or 21 wherein the surfactant is selected from the group consisting of:

(a) monoalkoxylated amines having the formula:

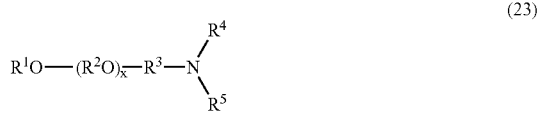

(23)

wherein $R^1$ is hydrogen or hydrocarbyl or substituted hydrocarbyl having at least 7 carbon atoms; $R^2$ in each of the x $(R^2O)$ and y $(R^2O)$ groups is independently $C_2$–$C_4$ alkylene; $R^3$ is a hydrocarbylene or substituted hydrocarbylene having from 2 to about 6 carbon atoms; $R^4$ and $R^5$ are each independently hydrogen, hydrocarbyl or substituted hydrocarbyl having from 1 to about 30 carbon atoms, $-(R^6)_n-(R^2O)_y R^7$, or $R^4$ and $R^5$, together with the nitrogen atom to which they are attached, form a cyclic or heterocyclic ring; $R^6$ is hydrocarbylene or substituted hydrocarbylene containing from 1 to about 6 carbon atoms, $R^7$ is hydrogen or a linear or branched alkyl group having 1 to about 4 carbon atoms, n is 0 or 1, and x and y are independently an average number from 1 to about 60, provided, however, that when $R^2$ and $R^3$ in each of the x $(R^2O)$ groups is ethylene, $R^1$ is other than unsubstituted alkyl or $R^4$ is other than hydrogen or unsubstituted alkyl when $R^5$ is hydrogen or unsubstituted alkyl, and when $R^2$ and $R^3$ are isopropylene and x is 1, $R^1$ is other than unsubstituted alkyl or $R^4$ is other than $-(R^2O)_y R^7$;

(b) alkoxylated poly(hydroxyalkyl)amines having the formula:

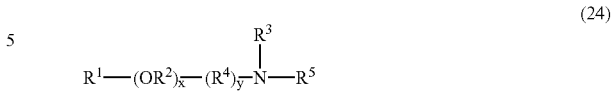

(24)

wherein $R^1$ and $R^3$ are independently hydrogen, hydrocarbyl or substituted hydrocarbyl having from 1 to about 30 carbon atoms, $R^2$ in each of the x $(R^2O)$ groups is independently $C_2$–$C_4$ alkylene; $R^4$ is hydrocarbylene or substituted hydrocarbylene having from 1 to about 30 carbon atoms, $R^5$ is hydroxyalkyl, polyhydroxyalkyl, or poly(hydroxyalkyl)alkyl; x is an average number from 0 to about 30, and y is 0 or 1;

(c) di-poly(hydroxyalkyl)amines having the formula:

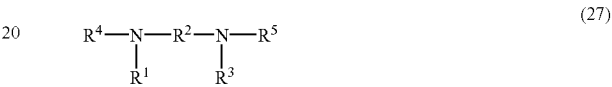

(27)

wherein $R^1$ and $R^3$ are independently hydrogen or hydrocarbyl or substituted hydrocarbyl having from 1 to about 22 carbon atoms, $R^2$ is hydrocarbylene or substituted hydrocarbylene having from 2 to about 18 carbon atoms, $R^4$ and $R^5$ are independently hydroxyalkyl, polyhydroxyalkyl, or poly(hydroxyalkyl)alkyl, provided, however, that when $R^1$ and $R^3$ are methyl, $R^2$ is other than octylene;

(d) alkoxylated triamines having the formula:

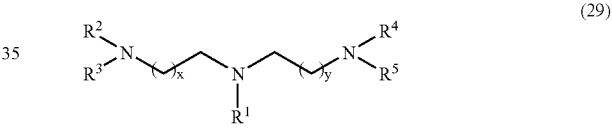

(29)

wherein $R^1$ is hydrocarbyl or substituted hydrocarbyl having from 1 to about 30 carbon atoms; $R^2$, $R^3$, $R^4$ and $R^5$ are independently hydrogen, hydrocarbyl or substituted hydrocarbyl having from 1 to about 30 carbon atoms, or $-(R^8)_s(R^7-O)_n R^6$; $R^6$ is hydrogen, or a linear or branched alkyl group having from 1 to about 4 carbon atoms; $R^7$ in each of the n $(R^7O)$ groups is independently $C_2$–$C_4$ alkylene; $R^8$ is hydrocarbylene or substituted hydrocarbylene having from 1 to about 6 carbon atoms; n is an average number from 1 to about 10; s is 0 or 1; and x and y are independently an integer from 1 to about 4; provided, however, that when $R^1$ is alkyl, $R^2$ is other than hydrogen, x is 3 or 4, or $R^4$ is other than $-(R^7-O)_n R^6$;

(e) monoalkoxylated amines having the formula:

(30)

wherein $R^1$ is a hydrocarbyl or substituted hydrocarbyl group having from 1 to about 30 carbon atoms, $R^2$ is $C_2$–$C_4$ alkylene, $R^3$ is hydrogen, or a linear or branched alkyl group having from 1 to about 4 carbon atoms, $R^4$ is a linear or branched alkynyl, aryl, or aralkyl group having from 1 to about 30 carbon atoms, and x is an average number from 1 to about 60;

(f) amine oxides having the formula:

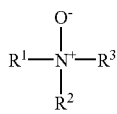 (31)

wherein $R^1$ is hydrocarbyl or substituted hydrocarbyl having from about 8 to about 30 carbon atoms, $R^2$ and $R^3$ are independently —$(R^4O)_xR^5$, $R^4$ in each of the x ($R^4O$) groups is independently $C_2$–$C_4$ alkylene, $R^5$ is hydrogen, or a hydrocarbyl or substituted hydrocarbyl having from 1 to about 30 carbon atoms, x is an average number from 1 to about 50.

(g) an alkoxylated amine oxide having the formula:

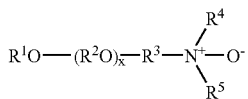 (32)

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2$–$C_4$ alkylene; $R^3$ is a hydrocarbylene or substituted hydrocarbylene having from 2 to about 6 carbon atoms; $R^4$ and $R^5$ are each independently hydrogen, hydrocarbyl or substituted hydrocarbyl having from 1 to about 30 carbon atoms, —$(R^6)_n$—$(R^2O)_yR^7$; $R^6$ is hydrocarbylene or substituted hydrocarbylene containing from 1 to about 6 carbon atoms, $R^7$ is hydrogen or a linear or branched alkyl group having 1 to about 4 carbon atoms, n is 0 or 1, and x and y are independently an average number from 1 to about 60;

(h) alkoxylated diamines having the formula:

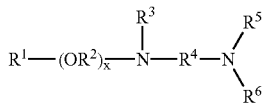 (33)

wherein $R^1$ is hydrocarbyl or substituted hydrocarbyl having from about 8 to about 30 carbon atoms; $R^2$ in each of the x ($R^2O$) groups and the y ($R^2O$) groups is independently $C_2$–$C_4$ alkylene; $R^3$, $R^5$ and $R^6$ are independently hydrogen, hydrocarbyl or substituted hydrocarbyl having from 1 to about 30 carbon atoms, or —$(R^2O)_yR^7$; $R^4$ is hydrocarbylene or substituted hydrocarbylene having from 2 to about 6 carbon atoms, —C(=$NR^{11}$)$NR^{12}R^{13}$—, —C(=O) $NR^{12}R^{13}$—, —C(=S)$NR^{12}R^{13}$—, —C(=$NR^{12}$)—, —C(S)—, or —C(O)—; $R^7$ is hydrogen, or a linear or branched alkyl group having from 1 to about 4 carbon atoms; $R^{11}$, $R^{12}$ and $R^{13}$ are hydrogen, hydrocarbyl or substituted hydrocarbyl having from 1 to about 30 carbon atoms x is an average number from 1 to about 30; and y is an average number from 1 to about 50, provided, however, that at least one of $R^3$, $R^5$ and $R^6$ is —$(R^2O)_yR^7$, at least one $R^2$ is other than ethylene, $R^4$ is other than unsubstituted propylene, $R^1$ is other than unsubstituted alkyl, or x is from 2 to about 30;

(i) dialkoxylated amines having the formula:

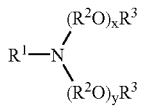 (34)

wherein $R^1$ is a hydrocarbyl or substituted hydrocarbyl having from about 6 to about 30 carbon atoms, or —$R^4SR^5$, $R^4$ and $R^2$ in each of the x ($R^2O$) and the y ($R^2O$) groups is independently $C_2$–$C_4$ alkylene, $R^3$ is hydrogen, or a linear or branched alkyl group having from 1 to about 4 carbon atoms, $R^5$ is a linear or branched alkyl group having from about 4 to about 15 carbon atoms, and x and y are independently an average number from 1 to about 40;

(j) dialkoxylated alcohols having the formula:

$$R^1(OR^2)_xO—R^3—O—(R^2O)_yR^1 \quad (35)$$

wherein $R^1$ is independently hydrogen, or a linear or branched alkyl group having from 1 to about 4 carbon atoms, $R^2$ in each of the x ($R^2O$) and the y ($R^2O$) groups is independently $C_2$–$C_4$ alkylene, $R^3$ is hydrocarbylene or substituted hydrocarbylene having from 2 to about 30 carbon atoms, and x and y are independently an average number from 1 to about 60; and (k) compounds of the formula:

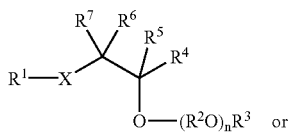 (36)

or

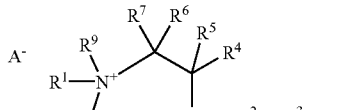 (37)

or

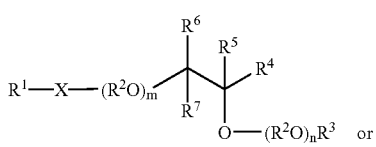 (38)

or

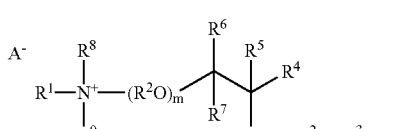 (39)

or

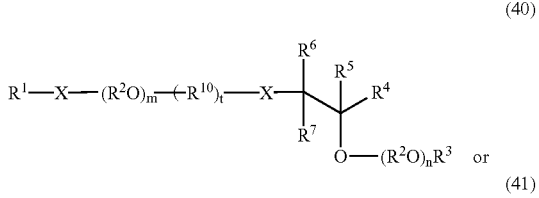 (40)

or

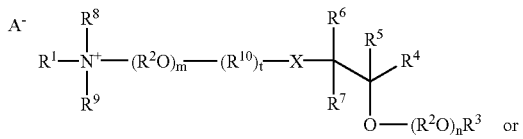 (41)

or

-continued

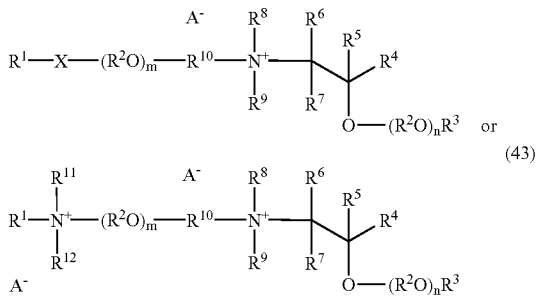

wherein $R^1$, $R^9$, and $R^{12}$ are independently hydrocarbyl or substituted hydrocarbyl having from 1 to about 30 carbon atoms, or —$(R^2O)_pR^{13}$; $R^2$ in each of the m ($R^2O$), n ($R^2O$), p ($R^2O$) and q ($R^2O$) groups is independently $C_2$–$C_4$ alkylene; $R^3$, $R^8$, $R^{11}$, $R^{13}$ and $R^{15}$ are independently hydrogen, or a hydrocarbyl or substituted hydrocarbyl having from 1 to about 30 carbon atoms; $R^4$ is —$(CH_2)_yOR^{13}$ or —$(CH_2)_yO(R^2O)_qR^3$; $R^5$, $R^6$ and $R^7$ are independently hydrogen, hydrocarbyl or substituted hydrocarbyl having from 1 to about 30 carbon atoms, or $R^4$; $R^{10}$ is hydrocarbylene or substituted hydrocarbylene having from 2 to about 30 carbon atoms; $R^{14}$ is hydrocarbyl or substituted hydrocarbyl having from 1 to about 30 carbon atoms, or —$(CH_2)_zO(R^2O)_pR^3$; m, n, p and q are independently an average number from 1 to about 50; X is —O—, —N($R^{14}$)—, —C(O)—, —C(O)O—, —OC(O)—, —N($R^{15}$)C(O)—, —C(O)N($R^{15}$)—, —S—, —SO—, or —$SO_2$—; t is 0 or 1; A- is an agriculturally acceptable anion; and y and z are independently an integer from 0 to about 30.

32. A formulation of any one of claims 1, 11 or 21 wherein the surfactant is selected from the group consisting of:

(a) aminated alkoxylated alcohol having the formula:

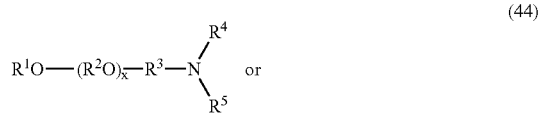

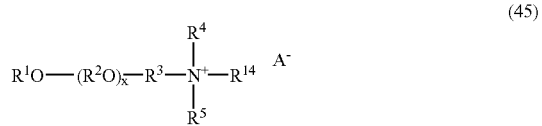

wherein $R^1$ is hydrocarbyl or substituted hydrocarbyl containing at least 7 carbon atoms; $R^2$ in each of the x ($R^2O$) and y ($R^2O$) groups is independently $C_2$–$C_4$ alkylene; $R^3$ and $R^6$ are each independently hydrocarbylene or substituted hydrocarbylene having from 1 to about 6 carbon atoms; $R^4$ is hydrogen, hydrocarbyl or substituted hydrocarbyl having from 1 to about 30 carbon atoms, hydroxy substituted hydrocarbyl, —$(R^6)_n$—$(R^2O)_yR^7$, —$C(=NR^{11})NR^{12}R^{13}$, —$C(=O)NR^{12}R^{13}$, —$C(=S)NR^{12}R^{13}$ or together with $R^5$ and the nitrogen atom to which they are attached, form a cyclic or heterocyclic ring; $R^5$ is hydrogen, hydrocarbyl or substituted hydrocarbyl having from 1 to about 30 carbon atoms, hydroxy substituted hydrocarbyl, —$(R^6)_n$—$(R^2O)_yR^7$, —$C(=NR^{11})NR^{12}R^{13}$, —$C(=O)NR^{12}R^{13}$, —$C(=S)NR^{12}R^{13}$, or together with $R^4$ and the nitrogen atom to which they are attached, form a cyclic or heterocyclic ring; $R^7$ is hydrogen or a linear or branched alkyl group having 1 to about 4 carbon atoms; $R^{11}$, $R^{12}$ and $R^{13}$ are hydrogen, hydrocarbyl or substituted hydrocarbyl, $R^{14}$ is hydrogen, hydrocarbyl or substituted hydrocarbyl having from 1 to about 30 carbon atoms, hydroxy substituted hydrocarbyl, —$(R^6)_n$—$(R^2O)_yR^7$, —$C(=NR^{11})NR^{12}R^{13}$, —$C(=O)NR^{12}R^{13}$, or —$C(=S)NR^{12}R^{13}$, n is 0 or 1, x and y are independently an average number from 1 to about 60, and A- is an agriculturally acceptable anion, provided, however, that when $R^2$ and $R^3$ are isopropylene and x is 1, $R^1$ is other than alkyl or $R^4$ is other than —$(R^2O)_yR^7$;

(b) hydroxylated amines having the formula:

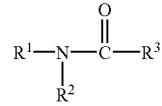

wherein $R^1$ is hydrocarbyl or substituted hydrocarbyl having from about 4 to about 30 carbon atoms, $R^2$ is hydrogen or hydrocarbyl or substituted hydrocarbyl having from 1 to about 30 carbon atoms, and $R^3$ is hydroxyalkyl, polyhydroxyalkyl, or poly(hydroxyalkyl)alkyl;

(c) diamines having the formula:

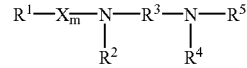

wherein $R^1$, $R^2$ and $R^5$ are independently hydrogen or hydrocarbyl or substituted hydrocarbyl having from 1 to about 30 carbon atoms or —$R^8(OR^9)_nOR^{10}$, $R^3$ is hydrocarbylene or substituted hydrocarbylene having from 2 to about 18 carbon atoms, $R^8$ and $R^9$ are individually hydrocarbylene or substituted hydrocarbylene having from 2 to about 4 carbon atoms, $R^4$ and $R^{10}$ are independently hydrogen or hydrocarbyl or substituted hydrocarbyl having from 1 to about 30 carbon atoms, m is 0 or 1, n is an average number from 0 to about 40, X is —C(O)— or —$SO_2$—, and A- is an agriculturally acceptable anion;

(d) mono- or di-ammonium salts having the formula:

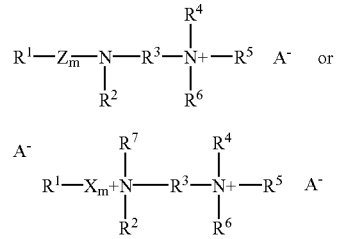

wherein $R^1$, $R^2$, $R^4$, $R^5$ and $R^7$ are independently hydrogen or hydrocarbyl or substituted hydrocarbyl having from 1 to about 30 carbon atoms or —$R^8(OR^9)_nOR^{10}$, $R^6$ is hydrocarbyl or substituted hydrocarbyl having from about 1 to about 30 carbon atoms, $R^3$ is hydrocarbylene or substituted hydrocarbylene having from 2 to about 18 carbon atoms, $R^8$, $R^9$ and $R^{11}$ are individually hydrocarbylene or substituted hydrocarbylene having from 2 to about 4 carbon atoms, $R^{10}$ is hydrogen or hydrocarbyl or substituted hydrocarbyl having from 1 to about 30 carbon atoms, m is 0 or 1, n is an average number from 0 to about 40, X is —C(O)— or —SO$_2$—, Z is —C(O)—, and A$^-$ is an agriculturally acceptable anion;

(e) poly(hydroxyalkyl)amines having the formula:

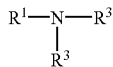

(51)

wherein R$^1$ is hydrocarbyl or substituted hydrocarbyl having from about 4 to about 30 carbon atoms or —R$^4$OR$^5$, R$^2$ is hydrogen or hydrocarbyl or substituted hydrocarbyl having from 1 to about 30 carbon atoms, R$^3$ is hydroxyalkyl, polyhydroxyalkyl, or poly(hydroxyalkyl)alkyl, R$^4$ is hydrocarbylene or substituted hydrocarbylene having from 2 to about 18 carbon atoms, and R$^5$ is hydrogen or hydrocarbyl or substituted hydrocarbyl having from about 1 to about 30 carbon atoms.

(f) di-poly(hydroxyalkyl)amine having the formula:

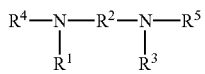

(54)

wherein R$^1$ and R$^3$ are independently hydrogen or hydrocarbyl or substituted hydrocarbyl having from 1 to about 22 carbon atoms, R$^2$ is hydrocarbylene or substituted hydrocarbylene having from 2 to about 18 carbon atoms, and R$^4$ and R$^5$ are independently hydroxyalkyl, polyhydroxyalkyl, or poly(hydroxyalkyl)alkyl;

(g) quaternary poly(hydroxyalkyl)amine salts having the formula:

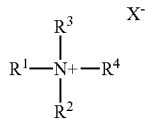

(56)

wherein R$^1$ is hydrocarbyl or substituted hydrocarbyl having from about 4 to about 30 carbon atoms, R$^2$ and R$^3$ are independently hydrogen or hydrocarbyl or substituted hydrocarbyl having from 1 to about 30 carbon atoms, and R$^4$ is hydroxyalkyl, polyhydroxyalkyl, or poly(hydroxyalkyl)alkyl;

(h) triamines having the formula:

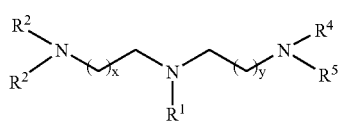

(59)

wherein R$^1$ is hydrocarbyl or substituted hydrocarbyl having from 1 to about 30 carbon atoms; R$^2$, R$^3$, R$^4$ and R$^5$ are independently hydrogen, hydrocarbyl or substituted hydrocarbyl having from 1 to about 30 carbon atoms, or —(R$^8$)$_s$(R$^7$O)$_n$R$^6$; R$^6$ is hydrogen or a linear or branched alkyl group having from 1 to about 4 carbon atoms, R$^7$ in each of the n (R$^7$O) groups is independently C$_2$–C$_4$ alkylene; R$^8$ is hydrocarbylene or substituted hydrocarbylene having from 1 to about 6 carbon atoms, n is an average number from 1 to about 10, s is 0 or 1, and x and y are independently an integer from 1 to about 4;

and mixtures thereof, wherein the pesticide is other than a bacteriocide if the composition includes a surfactant of group (a) or (d).

* * * * *

UNITED STATES PATENT AND TRADEMARK OFFICE
CERTIFICATE OF CORRECTION

| | | |
|---|---|---|
| PATENT NO. | : 7,049,270 B2 | Page 1 of 3 |
| APPLICATION NO. | : 09/926521 | |
| DATED | : May 23, 2006 | |
| INVENTOR(S) | : Lennon et al. | |

It is certified that error appears in the above-identified patent and that said Letters Patent is hereby corrected as shown below:

Column 1, line 30: "(0.16%" should read -- (1.16% --.

Column 3, line 15: "C);" should be deleted.

Column 4, line 1: "rBN" should be deleted.

Column 9, line 4: "ii;)" should be deleted.

Column 25, line 37: "-N($R^{16}$)C(O)-" should read -- -N($R^{15}$)C(O)- --.

Column 27, line 31: "($R^6$)$_n$" should read -- -($R^6$)$_n$ --.

Column 30, line 52: "M)" should be deleted.

Column 31, line 35: "1" should be deleted.

Column 41, line 37: "g" should read -- g a.e./l. --.

Column 42, line 11: "$R^8$" should read -- $R^6$ --.

Column 48, line 55: "Hexotolo™" should read -- Hexotol™ --.

Column 55, line 26: "Win" should read -- in --.

Column 55, line 67: "idle" should be deleted.

Column 57, line 3: "equipoed" should read -- equipped --.

Column 59, line 10: "$C_{16}$-$C_8$" should read -- $C_{16}$-$C_{18}$ --.

Signed and Sealed this
Eighth Day of May, 2012

David J. Kappos
*Director of the United States Patent and Trademark Office*

CERTIFICATE OF CORRECTION (continued)

Column 59, line 23: "6647" should read -- 6617 --.

Column 62, lines 65-66: "momingglory" should read -- morningglory --.

Column 64, line 43: "C16-C$_{18}$" should read -- C$_{16}$-C$_{18}$ --.

Column 66, line 32: "micelles organization" should read -- micelles are typically less organized than liquid crystals but may still have sufficient organization --.

Column 68, line 51: "weighttweight" should read -- weight/weight --.

Column 68, line 58: "surfactanttglyphosate" should read -- surfactant/glyphosate --.

Column 68, line 59: "Gside" should read -- side --.

Column 71, line 16: "(*Echinochloa crusgalii*)" should read -- (*Echinochloa crusgalli*) --.

Column 78, Surfactant I: "CAS 123714-89-9" should read -- CAS 123714-89-6 --.

Column 83, Surfactant PP:

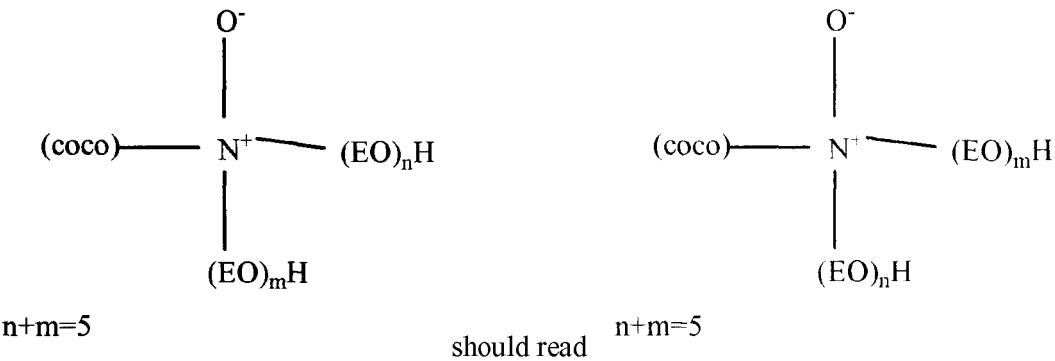

Column 95, Reaction Scheme 91:

should read

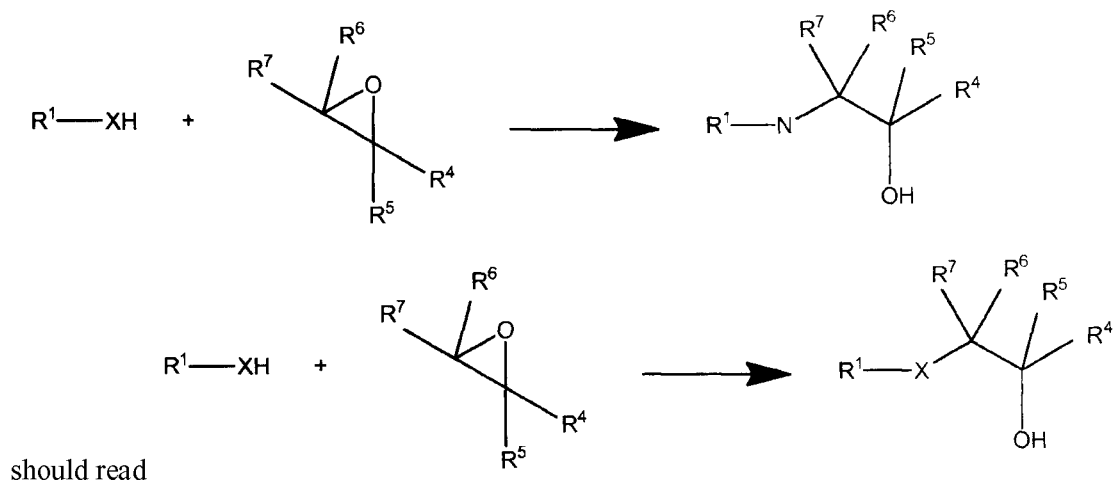

CERTIFICATE OF CORRECTION (continued)

Column 97, line 2: "or $(CH_2)_yO$" should read -- or $-(CH_2)_yO$ --.

Column 104, line 27: "Ethomeen G/12" should read -- Ethomeen C/12 --.

Column 106, IPA Glyphosate Formulation table, line 33: -- 14-15   13   NA   NT   Y   Y -- should be inserted as the first line of the table.

Column 107, line 58, x column of table: "12" should be -- 2 --.

Column 108, line 14: -- LC -- should be inserted above epi.

Column 108, line 34: "AA" should be deleted.

Column 108, line 36: "T125" should read -- T/25 --.

Column 108, line 37: "T125" should read -- T/25 --.

Column 108, line 38: "T125" should read -- T/25 --.

Column 109, line 40: "X" should read -- X⁻ --.

Column 121, line 60: "3.0 kg/m3" should read -- 3.6 kg/m3 --.

Column 136, line 56: "fective" should read -- effective --.

Column 168, Table 45b, line 24: "225 a.e./ha" should read -- 225 g a.e./ha --.

Column 168, Table 45c, line 40: "225 a.e./ha" should read -- 225 g a.e./ha --.

Column 169, Table 46b, line 21: "225 a.e./ha" should read -- 225 g a.e./ha --.

Column 169, Table 46c, line 35: "225 a.e./ha" should read -- 225 g a.e./ha --.

Column 190, claim 6, line 8: "from about 50:1." should read -- from about 5:1 to about 50:1. --.

Column 197, claim 32, Formula 51: